US008329684B2

(12) United States Patent
Cho et al.

(10) Patent No.: US 8,329,684 B2
(45) Date of Patent: Dec. 11, 2012

(54) CEPHALOSPORIN DERIVATIVES AND PHARMACEUTICAL COMPOSITIONS THEREOF

(75) Inventors: Young Lag Cho, Daejeon (KR); Joung Yul Yun, Deajeon (KR); Sang Eun Chae, Daejeon (KR); Chul Soon Park, Daejeon (KR); Hyang Sook Lee, Daejeon (KR); Kyu Man Oh, Daejeon (KR); Hye Jin Kang, Daejeon (KR); Dae Hyuck Kang, Daejeon (KR); Young Jae Yang, Daejeon (KR); Hyun Jin Kwon, Daejeon (KR); Tae Kyo Park, Daejeon (KR); Sung Ho Woo, Daejeon (KR); Young Zu Kim, Daejeon (KR)

(73) Assignee: Legochem Biosciences, Inc., Deajeon (KR)

(*) Notice: Subject to any disclaimer, the term of this patent is extended or adjusted under 35 U.S.C. 154(b) by 0 days.

(21) Appl. No.: 13/467,019

(22) Filed: May 8, 2012

(65) Prior Publication Data
US 2012/0264727 A1    Oct. 18, 2012

Related U.S. Application Data

(63) Continuation of application No. PCT/KR2012/002302, filed on Mar. 29, 2012.

(30) Foreign Application Priority Data

Mar. 30, 2011    (KR) .................. 10-2011-0028603

(51) Int. Cl.
*A61K 31/545* (2006.01)
*C07D 501/14* (2006.01)

(52) U.S. Cl. ........................................ 514/202; 540/222

(58) Field of Classification Search .................. 540/224
See application file for complete search history.

(56) References Cited

OTHER PUBLICATIONS

Kim, Yong-Zu. "The Journal of Antibiotics", vol. 49 No. 5 (May 1996), pp. 499-501.*
H. Bundgaard, "Prodrugs as a Means to Improve the Delivery of Peptide Drugs", Advanced Drug Delivery Reviews, 1992, pp. 1-38, vol. 8.
N. Nielsen et al., "Glycolamide Esters as Biolabile Prodrugs of Carboxylic Acid Agents: Synthesis, Stability, Bioconversion, and Physicochemical Properties", Journal of Pharmaceutical Sciences, 1998, pp. 285-298, vol. 77, No. 4.
N. Kakeya et al., "Studies on Prodrugs of Cephalosporins. I.", Chemical and Pharmaceutical Bulletin, 1984, pp. 692-698, vol. 32, No. 2.
R. Notari, "Theory and Practice of Prodrug Kinetics", Methods in Enzymology, 1985, pp. 309-323, vol. 112.
M. Charton, "Prodrug Lability Prediction Through the Use of Substituent Effects", Methods in Enzymology, 1985, pp. 323-340, vol. 112.
S. Nelson, "Alteration of Drug Metabolism by the Use of Prodrugs", Methods in Enzymology, 1985, pp. 340-347, vol. 112.
H. Bundgaard, "Formation of Prodrugs of Amines, Amides, Ureides, and Imides", Methods in Enzymology, 1985, pp. 347-359, vol. 112.
D. Fleisher et al., "Design of Prodrugs for Improved Gastrointestinal Absorption by Intertinal Enzyme Targeting", Methods in Enzymology, 1985, pp. 360-381, vol. 112.
N. Bodor, "Targeting of Drugs to the Brain", Methods in Enzymology, 1985, pp. 381-396, vol. 112.

* cited by examiner

*Primary Examiner* — Andrew D Kosar
*Assistant Examiner* — Laura Daniel
(74) *Attorney, Agent, or Firm* — Hyunsuk Min; SIMI Law Group, P.C.

(57) ABSTRACT

The present invention relates to novel cephalosporin derivatives represented by Chemical Formula 1.

[Chemical Formula 1]

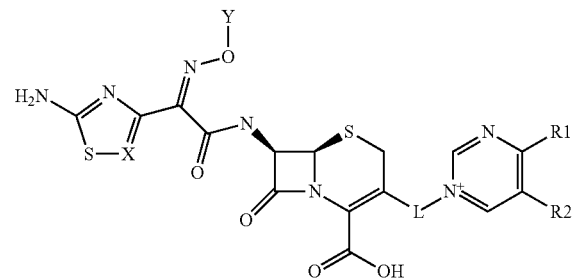

Wherein, X, Y, L, $R_1$, and $R_2$ are as same as defined in the description of the invention. The present invention also relates to pharmaceutical antibiotic compositions comprising a novel celphalosporin derivative represented by Chemical Formula 1, a prodrug thereof, a hydrate thereof, a solvate thereof, an isomer thereof, or a pharmaceutically acceptable salt thereof as an effective ingredient. Compounds of the present invention are effective ingredients for the broad spectrum of antibiotic resistance, exhibit low toxicity, particularly in Gram-negative bacteria, which can be useful with strong antimicrobial activity.

19 Claims, 2 Drawing Sheets

[Figure 1]
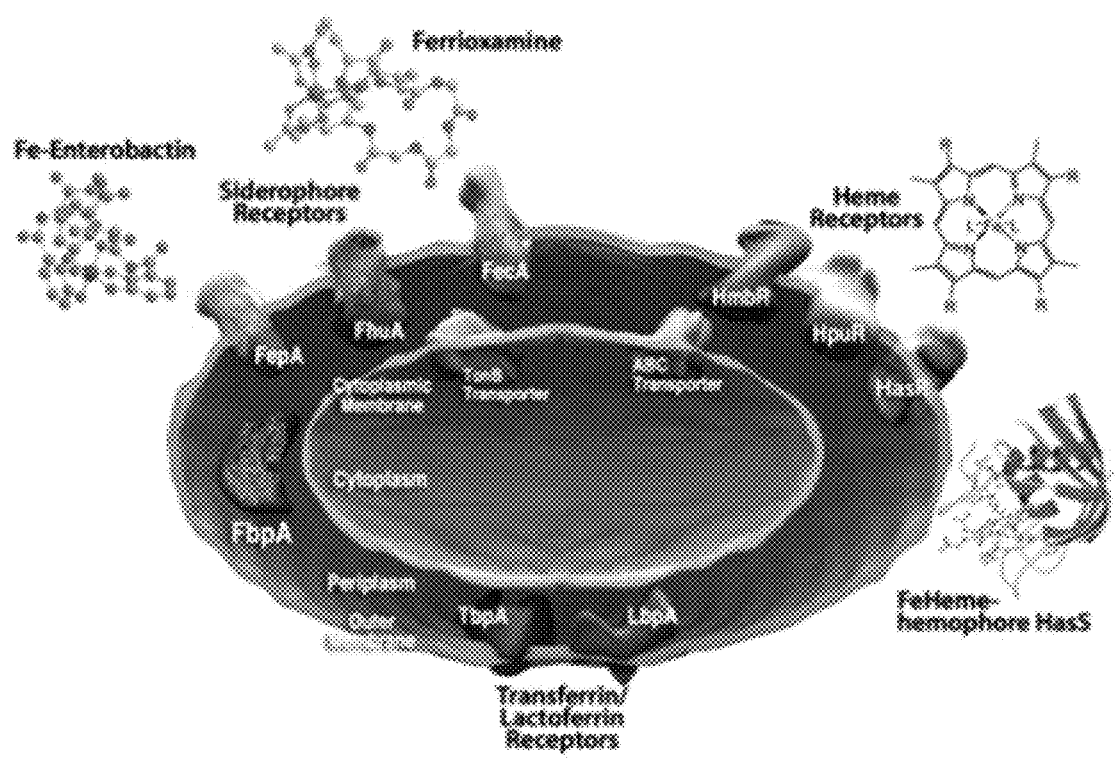

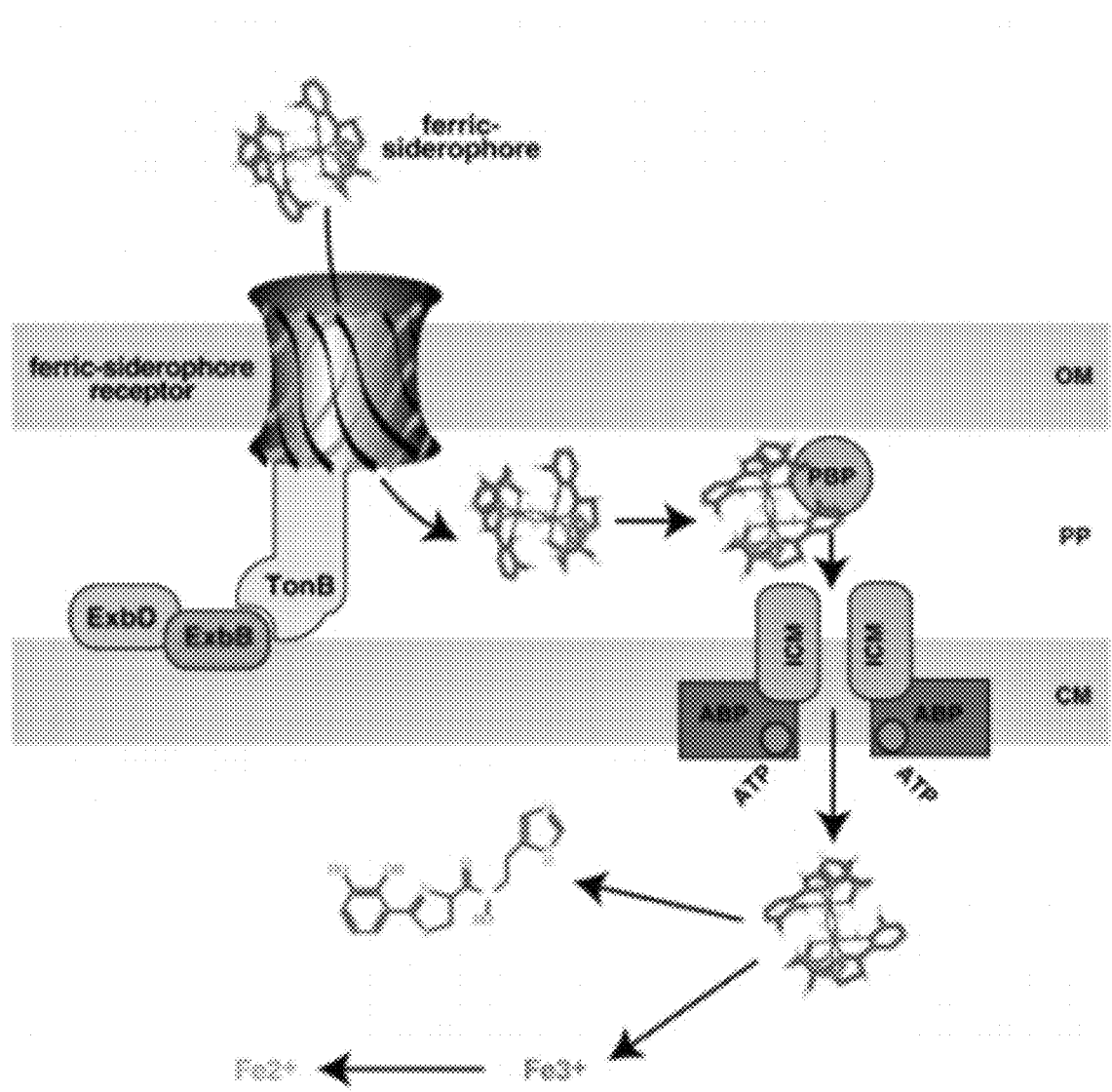
[Figure 2]

CEPHALOSPORIN DERIVATIVES AND PHARMACEUTICAL COMPOSITIONS THEREOF

CROSS-REFERENCE TO RELATED APPLICATION

This application is a continuation of PCT International Application Serial No. PCT/KR2012/002302 filed Mar. 29, 2012, which claims the benefit of Korean Patent Application No. 10-2011-0028603, filed Mar. 30, 2011, the contents of each of which are incorporated herein by reference.

TECHNICAL FIELD

The present invention relates to novel cephalosporin derivatives. The present invention also relates to pharmaceutical antibiotic compositions including novel cephalosporin derivatives, prodrug thereof, hydrate thereof, solvates thereof, isomers thereof or pharmaceutically acceptable salts thereof as an effective ingredient.

BACKGROUND

The treatment of Gram-negative bacteria has intensified with many development programs during its golden era from the 1960s through to the 1980s. However, with the increasing Gram-positive bacteria infections, such as MRSA (Methicillin-resistant Staphylococcus aureus) in the 1990s, the Gram-negative researches were overshadowed. Since late 2000, due to the growing concern of the lack of multidrug-resistant Gram-negative bacteria treatment, the Gram-negative bacteria research re-gained its interest. According to the recent publication by the Infectious Diseases Society of America (IDSA), The European Centre for Disease Prevention and Control (ECDC), and the European Medicines Agency (EMEA), there are only 8 effective drugs against Gram-negative bacteria worldwide. Especially the multidrug-resistant Gram-negative bacteria new drug discovery is extremely scarce.

In particular, the recently discovered NDM-1 (New Delhi metalo-beta-lactamase) is rapidly spreading and became a threat to international community. The NDM-1 mainly appears in Gram-negative bacteria, and currently colistin and tigecycline are the only two effective drugs. However, these drugs are not readily used due to their toxicity and side effects. Thus urgent needs to replace these two drugs are in demand. The rapid spread of these pathogens is not just a burden on few affected countries but on every country where an international join effort is a must to control such spread.

Already in 2004, the Infectious Diseases Society of America (IDSA) had published a report called the "Bad Bugs, No Drugs." A hit list was published in this report as the current global rate of resistance increases. The list is based on the morbidity, mortality with high pathogen, and absence of the effective drug therapy. Amongst the list, 3 of them are the Gram-negative bacteria: $P.$ $aeruginosa$, $A.$ $baumannii$, and $K.$ $pneumoniae$ isolates. They require government's support as they create serious disease outbreak problems. Currently, there are few classes of drug available against these bacteria, such as cephalosporins, carbapenems, aminoglycosides, and tigecyclines. However, there are no effective drugs available against the resistant stains, and especially against $acinetobacter$, tigecyclines is the only effective class of drug.

In 2006, the multidrug-resistant $K.$ $pneumoniae$ was reported in patients with XDR-KP only in the eastern part of the United States, but more recently, it spread throughout the rest of the country. In case of $acinetobacter$, the infection spread nationwide by the soldiers who were previously deployed to Middle Eastern countries. Carbapenems is mainly used as the leading treatment, but there is rapid increase in carbapenems resistant stains, thus it is left with any effective treatment.

As the demand increases for Gram-negative bacteria treatments, pharmaceutical companies are showing strong interest, but only few antibiotics are in development. Among them is β-lactam inhibitors, and some noteworthy compounds are CEF-104 and CAZ-104 from Novexel, CAX-201 from Cubist, and one compound from each of the following classes: Polymyxin, tetracycline and aminoglycoside. Among effective acinetobacters, there are PTK-0796, a tetracycline class, and CB-182,804, a polymyxin derivative. However, these two compounds are not widely used due to their toxicity issues in their safety profile.

Currently cephalosporin and carbapenem are the two most widely used Gram-negative antibiotics classes. Within carbapenem class, imipenem and meropenem are the market dominating compounds, but the predominant market leading compounds are the generic drugs. Ceftobiprole was the most promising candidate within the cephalosporin class, but unfortunately its development program was discontinued. Therefore, within the cephalosporin class, generic compounds and combi-therapy will be the main treatment options.

One of the reason why the multidrug-resistant Gram-negative bacteria causes serious problem is that most of the strains show resistance to antibiotics currently in use, leaving many strains untreatable. There are several reasons for the increase in resistant strains, but in case of $P.$ $aeruginosa$, the mutations in outer membrane and porin channel are the main causes of the resistance. Due to these mutations, many β-lactam inhibitors are an not able to enter into Gram-negative bacteria. To overcome these resistances caused by the mutations in outer membrane and in porin channel, siderophore driven antibiotic was being heavily researched. Iron ions are essential ingredient for the growth of bacteria. These iron ions have high affinity to siderosphore, and bacteria produces siderophore to bind these iron ions and internalize them into their system. Bacteria have siderophore recognizing cell membrane receptors to bind and internalize iron ions. FIG. 1 represents bacteria's binding mechanism to siderophore and iron ions using its membrane receptors.

Therefore, siderophore-mimicking moiety can be attached to an antibiotic, and bacteria's siderophore receptor can bind to antibiotic. Bacteria will then internalize the antibiotic. This internalization is much easier then the typical porin channel mediated antibiotic internalization, and it is also immune to resistancy cause by the porin channel mutation. FIG. 2 represents the internalization of iron ions by biding of siderophore to bacteria's receptor.

Although there were many research efforts that went into overcoming resistancy problems by incorporating siderophore moiety, not many have succeeded this far. One of the reasons is that catechol is mainly used for siderophore moiety, but it is rapidly transformed by catechol O-methyl transferase (COMT) and can no longer be bind to siderophore receptor. Many catechol modifications have been made to overcome this issue, but they often resulted in low efficacy and, or high toxicity. There were also dramatic variations on the location of the siderophore moiety in antibiotic. Therefore, there are critical needs to develop more potent antimicrobial activity against Gram-negative bacteria drug than currently existing cephalosporins. Especially there are urgent needs to develop cephalosporins against *P. aeruginosa* and *K. pneumonia* resistant strains.

SUMMARY OF INVENTION

The inventors of the present invention have synthesized novel cephalosporin derivatives represented by Chemical Formula 1, particularly novel cephalosporin compounds with a siderophore group. The present invention have superior antibacterial activity as compared to existing antibiotics, more effective against gram negative bacteria, and stronger antimicrobial activity against the major resistant strains.

Accordingly, first object of the present invention is to provide novel chemical compound represented by Chemical Formula 1.

Second object of the present invention is to provide pharmaceutical antibiotic compositions including novel cephalosporin derivatives, prodrugs thereof, solvates thereof, isomers thereof, or pharmaceutically acceptable salts thereof as an effective ingredient.

Third object of the present invention is to provide method of effective antibiotic treatment by providing pharmaceutical antibiotic compositions and effective amount of thereof.

DETAILED DESCRIPTION OF INVENTION

Hereinafter, the embodiments of the present invention will be described in detail. The present invention relates to novel cephalosporin derivatives represented by Chemical Formula 1, particularly novel cephalosporin compounds with a siderophore group. The present invention also relates to pharmaceutical antibiotic compositions comprising a novel cephalosporin derivative represented by Chemical Formula 1, a prodrug thereof, a hydrate thereof, a solvate thereof, an isomer thereof, or a pharmaceutically acceptable salt thereof as an effective ingredient:

[Chemical Formula 1]

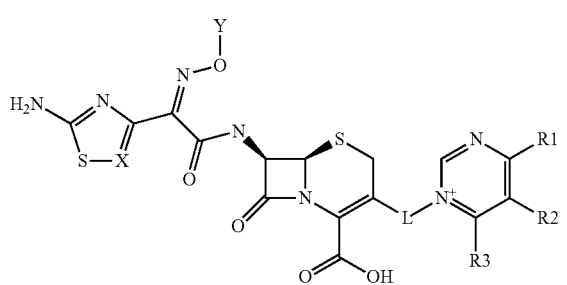

wherein,

X represents CR, N, or Cl-substituted carbon (C—Cl), and where R is hydrogen or $C_1$-$C_3$ alkyl;

Y represents $C_1$-$C_2$ alkyl, $CH(CH_3)CO_2H$, or $C(CH_3)_2CO_2H$ is;

L represents the $CH_2$ or $CH=CHCH_2$;

$R_1$ represents $NH_2$, $NHR_{11}$ or $NH(CH_2)_mNR_{11}R_{12}$ is;

$R_2$ represents $NHR_{21}$, $NH(CH_2)_nCOOH$, $NH(CH_2)nNR_{21}R_{22}$, or $NHC(=O)(CH_2)_nNR_{21}R_{22}$ is;

Here, $R_{11}$, and $R_{21}$ independently represent hydrogen, $C_1$-$C_3$ alkyl, or selected from the followings:

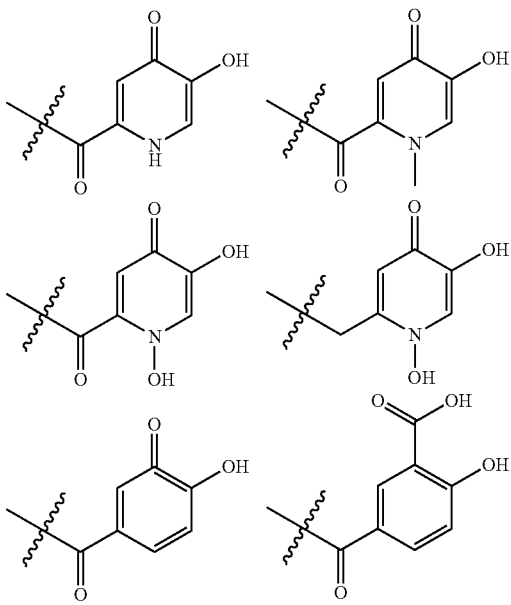

$R_{12}$ and $R_{22}$ each independently represent hydrogen or $C_1$-$C_2$ alkyl;

m and n each independently represent an integer of 1 to 6;

$R_3$ is hydrogen or $NH_2$.

Cephalosporin derivatives of the present invention have effective antibacterial activity against antibiotic resistant Gram-negative bacteria at a lower concentration. Particularly, present invention shows superior antimicrobial activity against *P. aeruginosa*, *A. baumannii*, and *K. pneumonia* as compared to currently marketed cephalosporin. When the following groups are attached to the position $R_{11}$ and $R_{12}$,

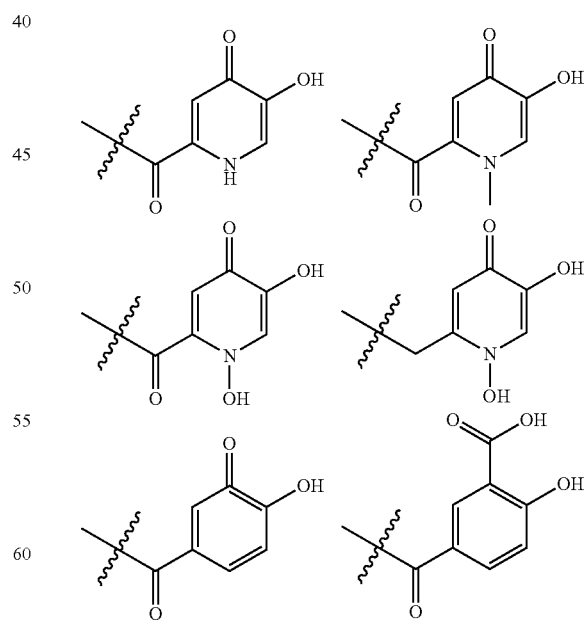

the efficacy increases substantially, and in particular, the following hydroxy piridons show excellent antibacterial activities:

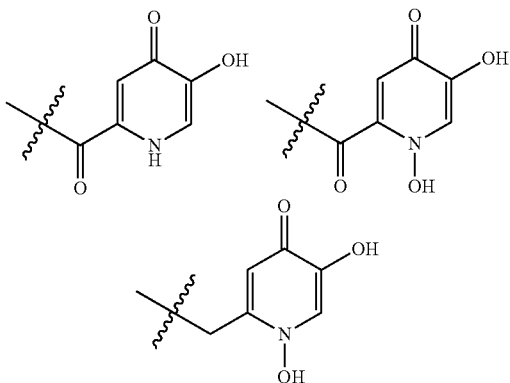

An example of the cephalosporin derivative represented by Chemical Formula 1, is represented by the compounds derived from the Chemical Formula 2.

[Chemical Formula 2]

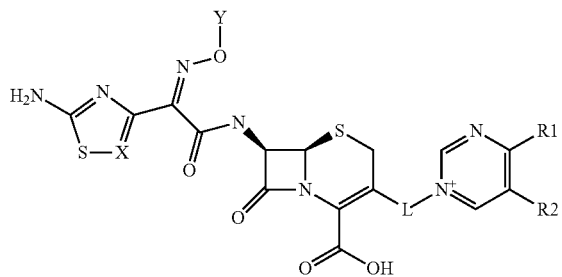

Wherein,

X represents CR, N, or Cl-substituted carbon (C—Cl), and where R represents hydrogen or $C_1$-$C_3$ alkyl;

Y represents $C_1$-$C_2$ alkyl, $CH(CH_2)CO_2H$, or $C(CH_2)_2CO_2H$;

L represents the $CH_2$ or $CH=CHCH_2$;

$R_1$ represents $NH_2$, $NHR_{11}$ or $NH(CH_2)_mNR_{11}R_{12}$;

$R_2$ represents $NHR_{21}$, $NH(CH_2)_nNR_{21}R_{22}$ or $NHC(=O)(CH_2)_nNR_{21}R_{22}$;

Here, $R_{11}$ and $R_{21}$ each independently hydrogen, $C_1$-$C_3$ alkyl, or selected from following groups;

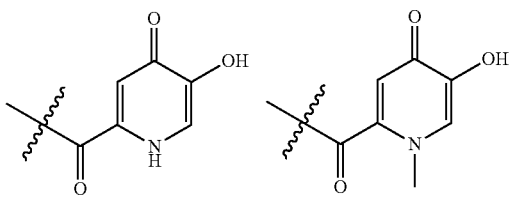

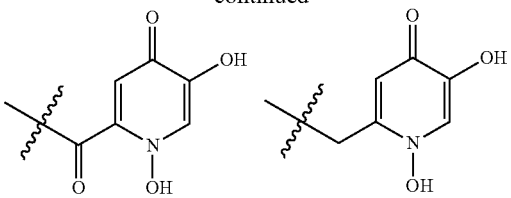

$R_{12}$ and $R_{22}$ each independently represent hydrogen or $C_1$-$C_2$ alkyl;

m and n each independently represent an integer of 1 to 6.

According to the present invention, more preferred examples of cephalosporin derivatives of Chemical Formula 2 are, X represents CR, N, or Cl-substituted carbon (C—Cl), and where R represents hydrogen or $C_1$-$C_3$ alkyl;

Y represents $CH(CH_3)CO_2H$, or $C(CH_3)_2CO_2H$;

L represents the CH2 or CH=CHCH2;

$R_1$ represents $NH_2$ or $NH(CH_2)_mNH_2$;

$R_2$ represents $NHR_{21}$, $NH(CH_2)_nNHR_{21}$ or $NHC(=O)(CH_2)_nNHR_{21}$;

$R_{21}$ is selected from the following groups;

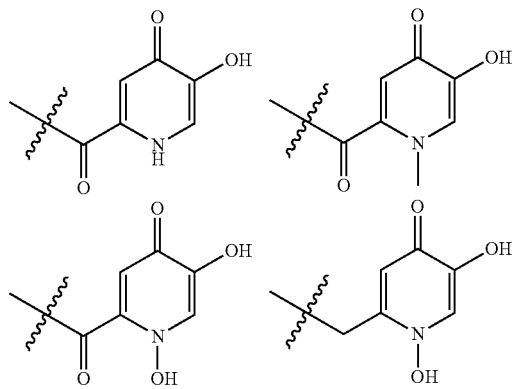

m and n independently represent integers of 1 to 6 of the compounds.

As used herein the term "alkyl" includes a structure of the linear and branch types. For example, ($C_1$-$C_6$) alkyl is methyl, ethyl, propyl, isopropyl, butyl, isobutyl, tert-butyl, pentyl and hexyl and all possible locations and isomers.

Examples of the novel cephalosporin derivatives according to the present invention, but not limited to, can be presented as the compounds below.

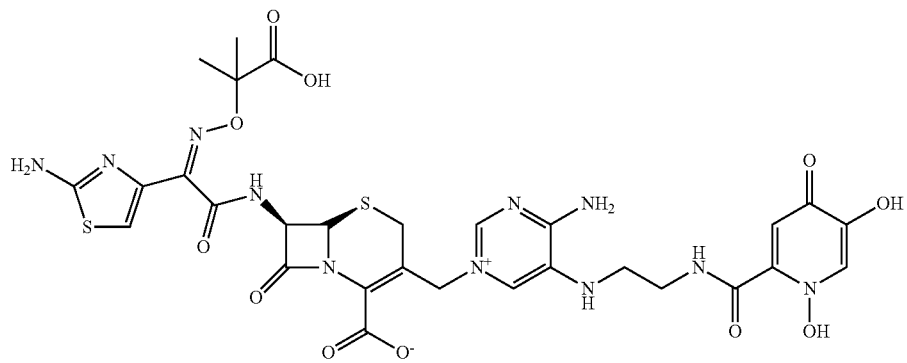

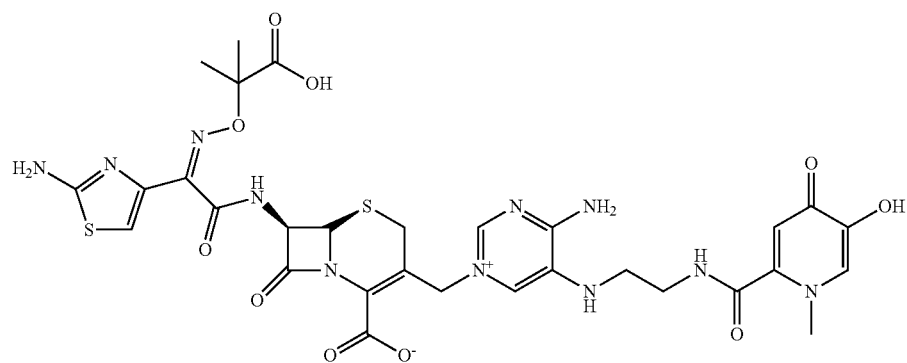
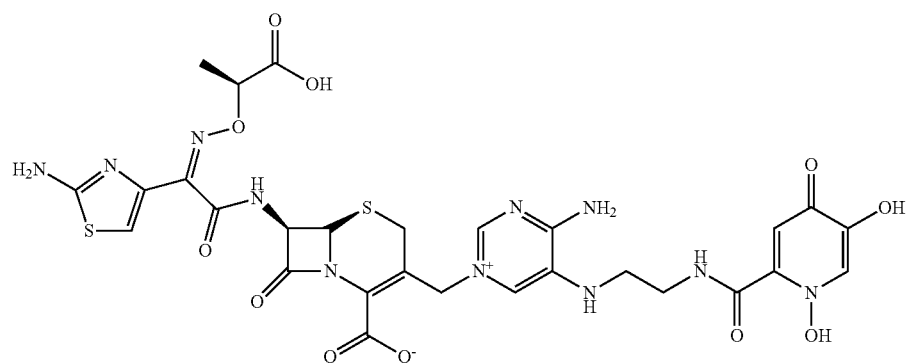
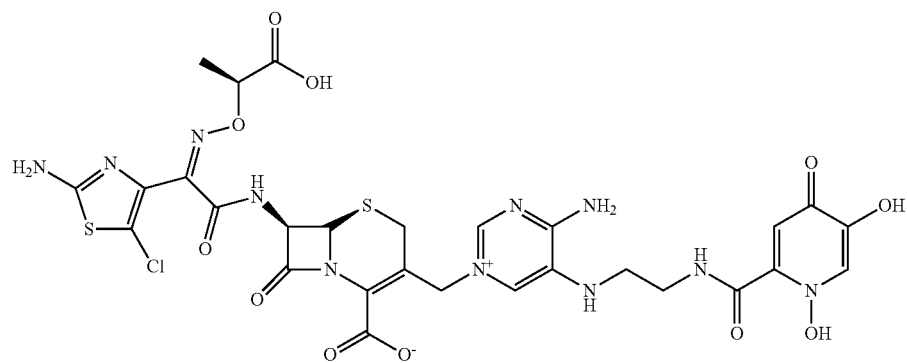
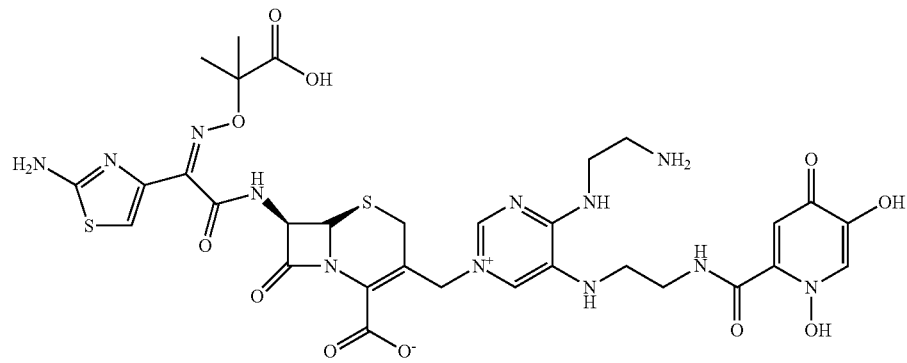

-continued
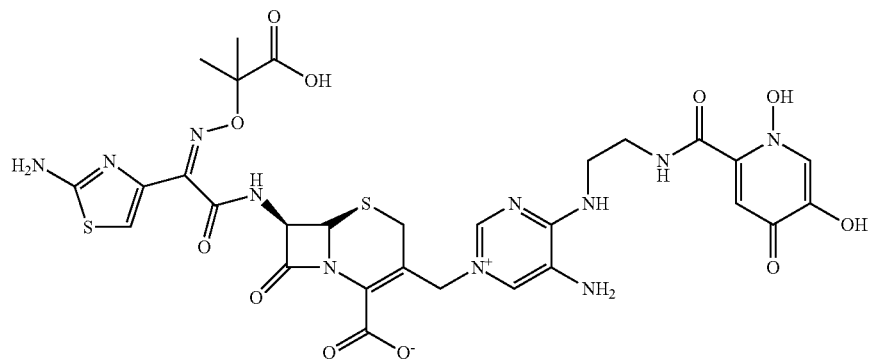
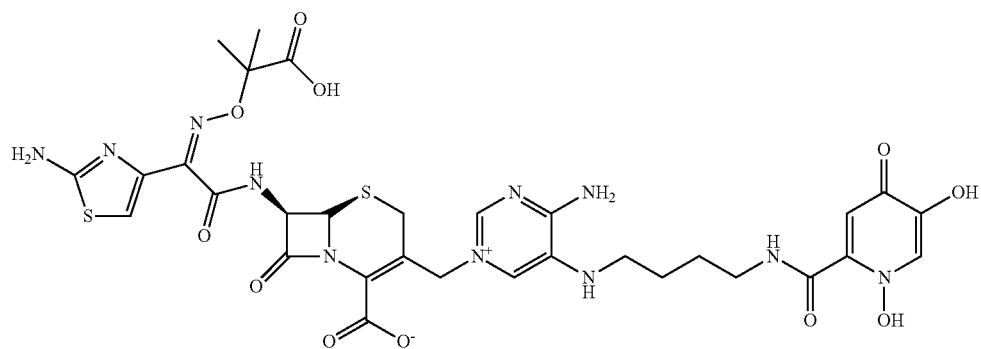
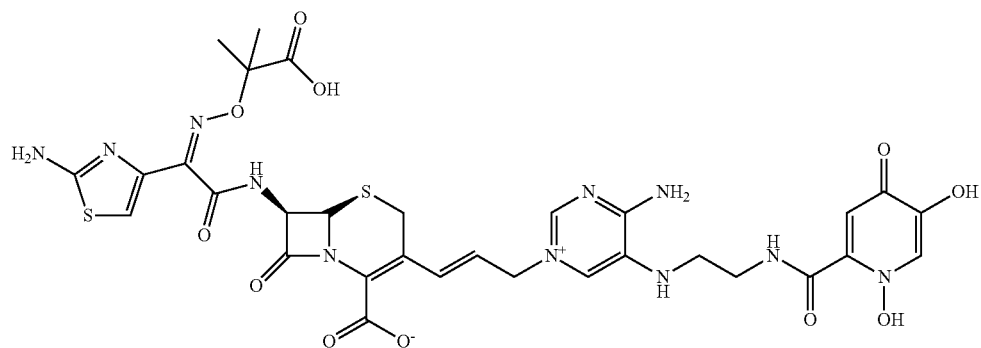
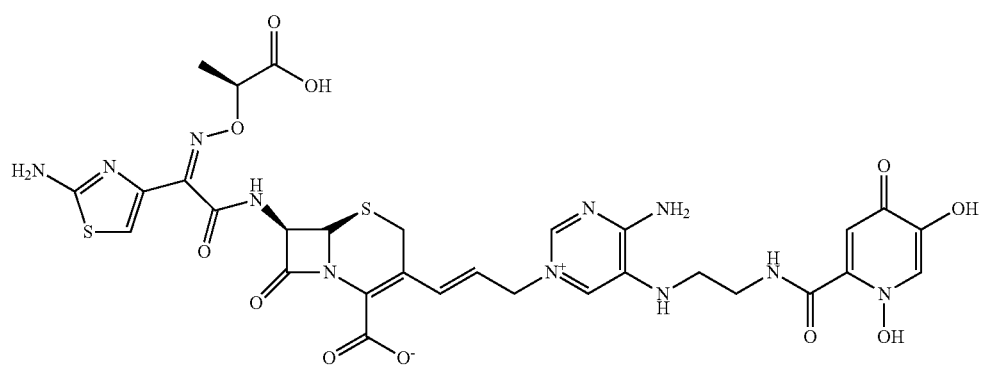

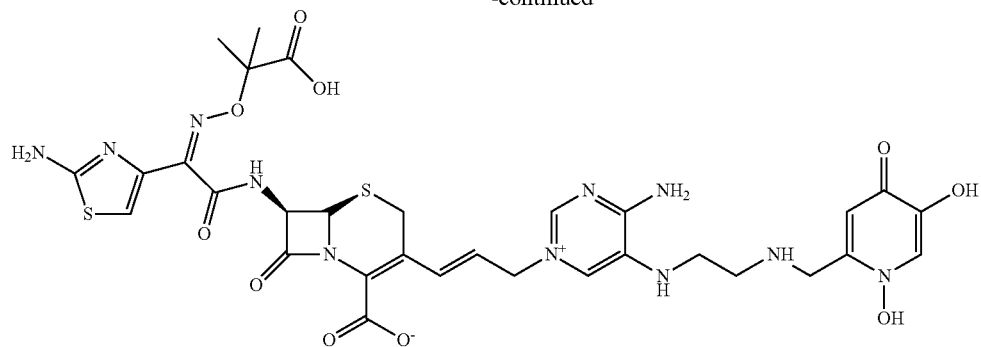
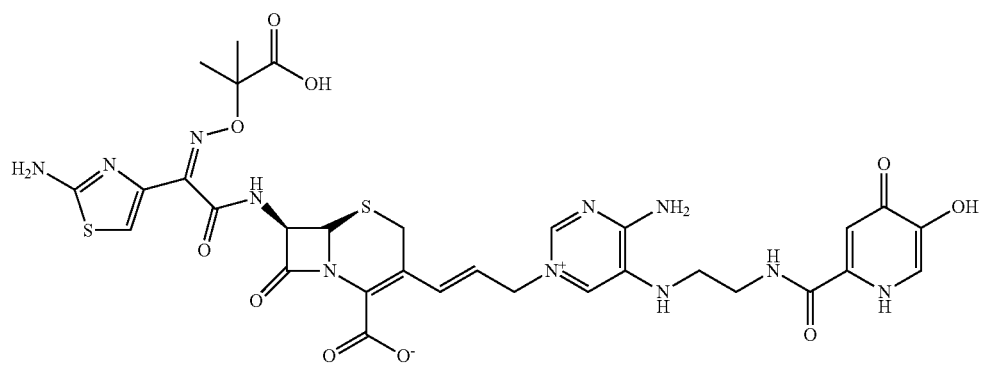
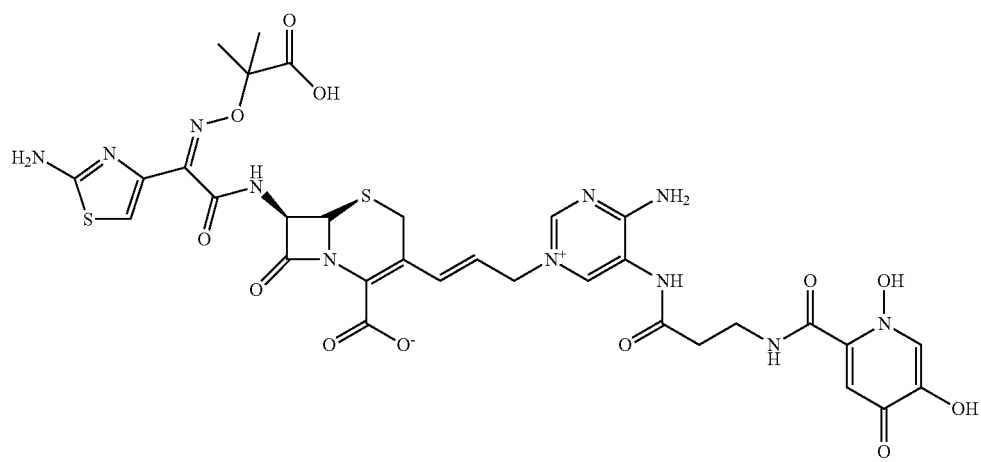
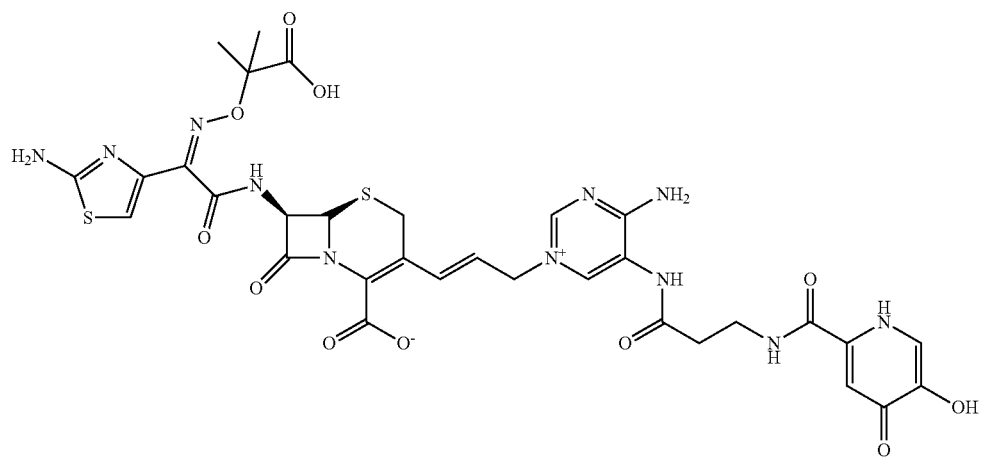

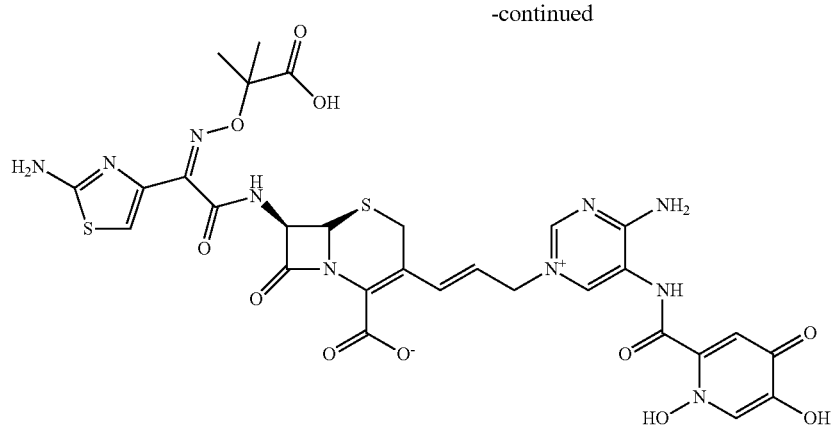
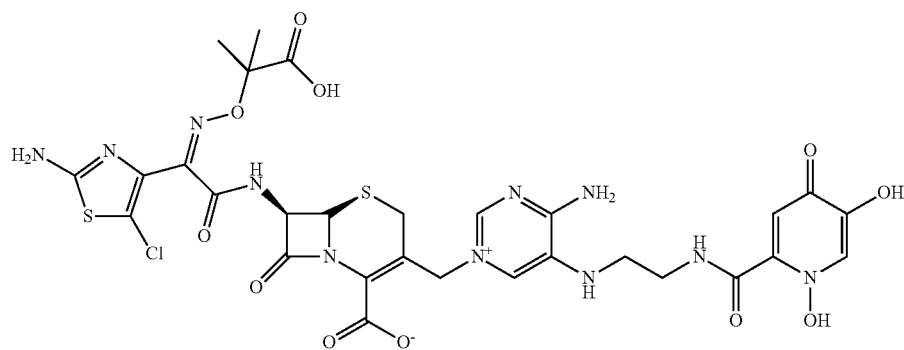
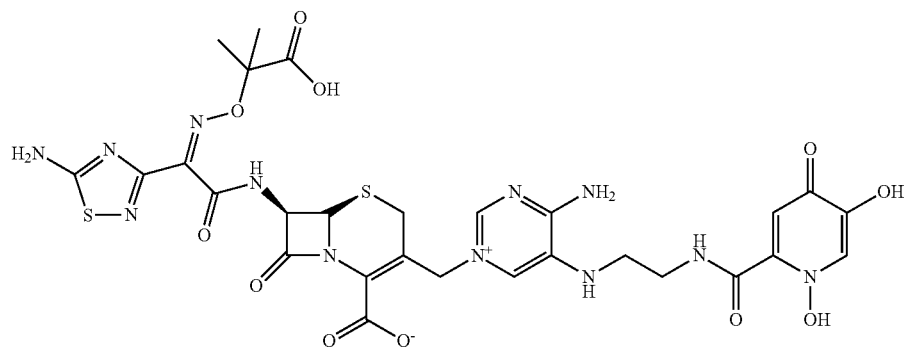
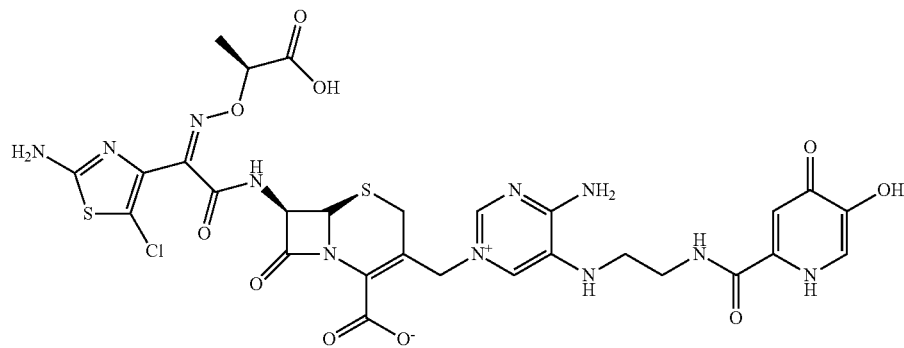

-continued
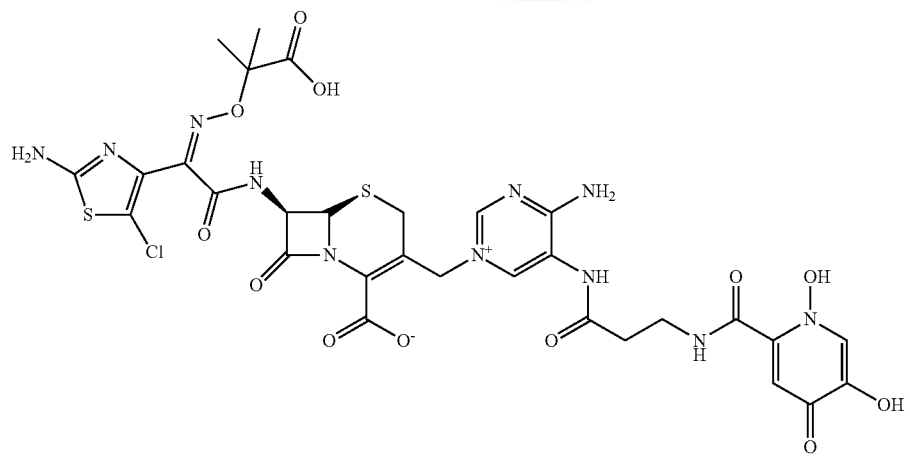
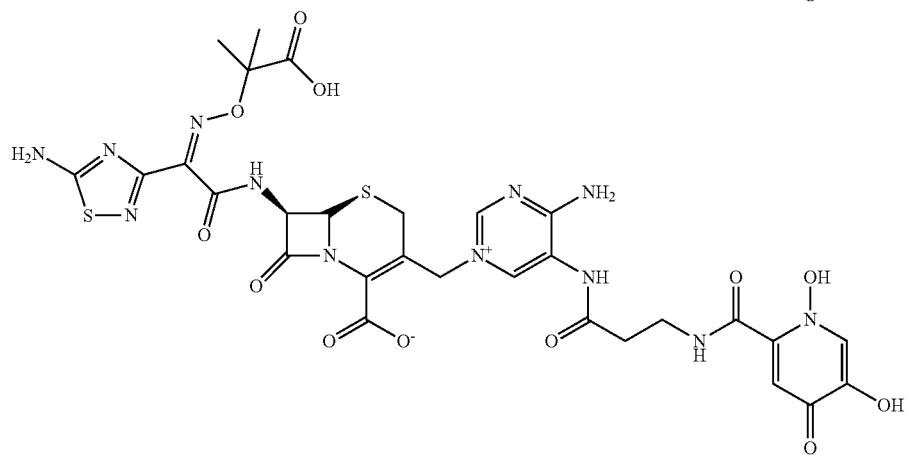
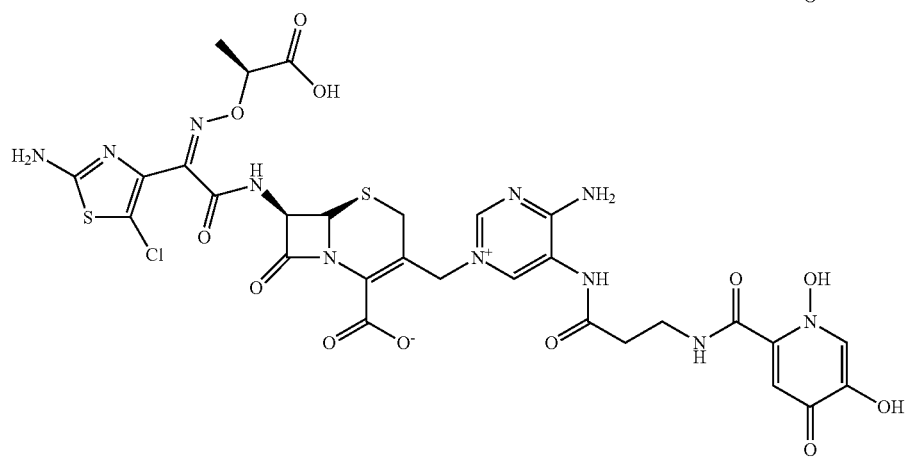
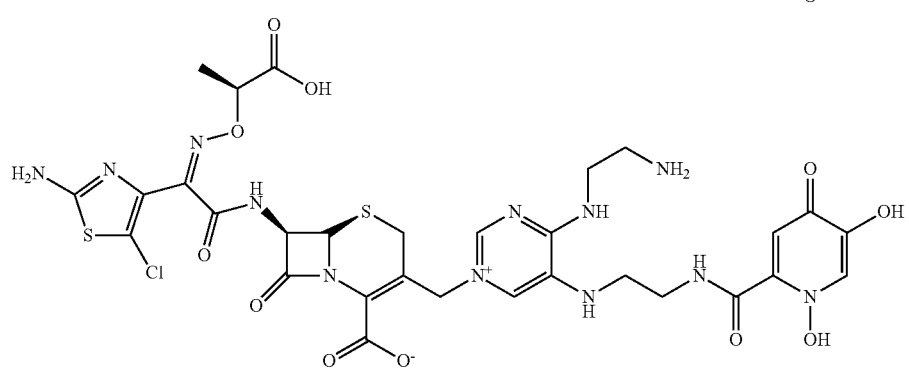

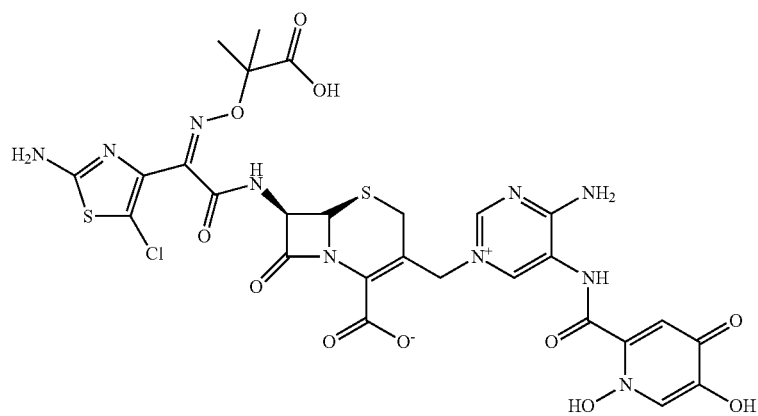
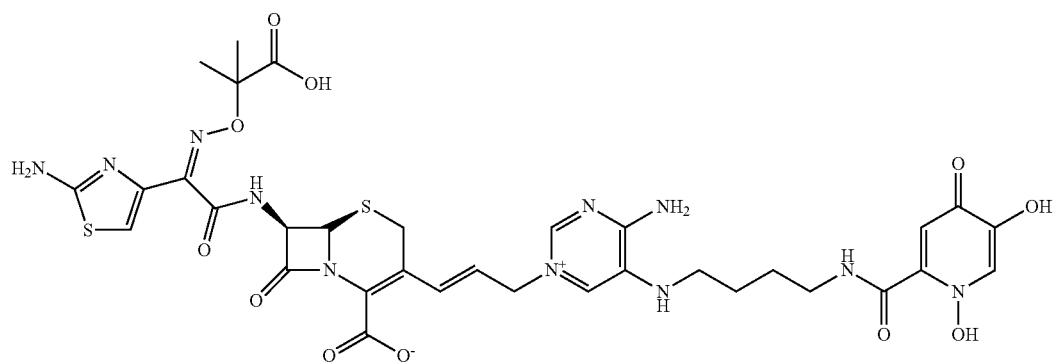
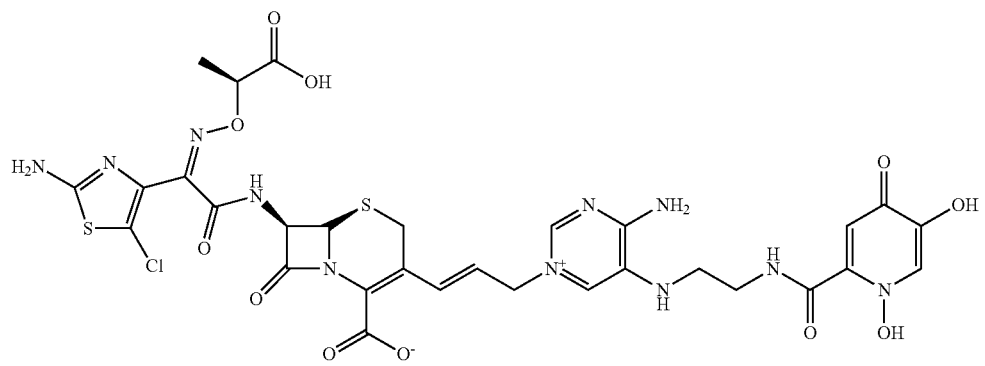

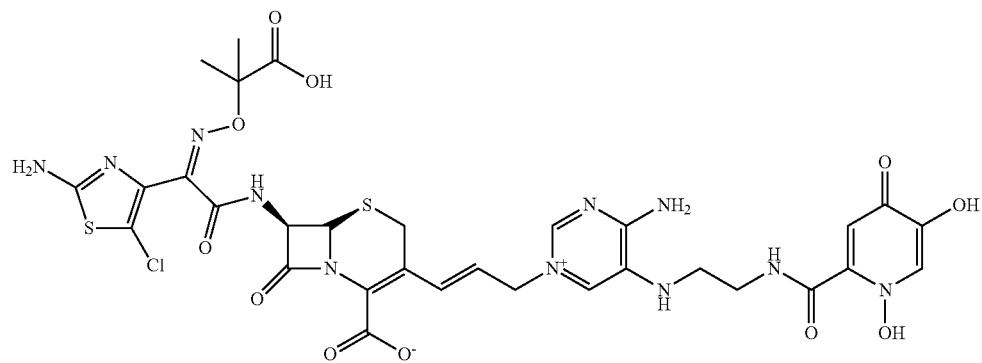
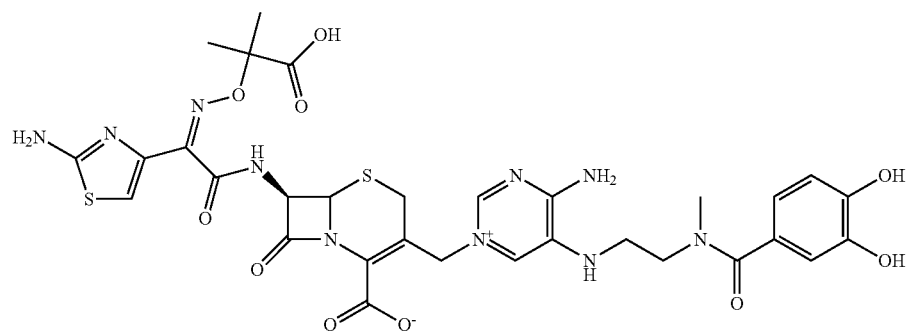
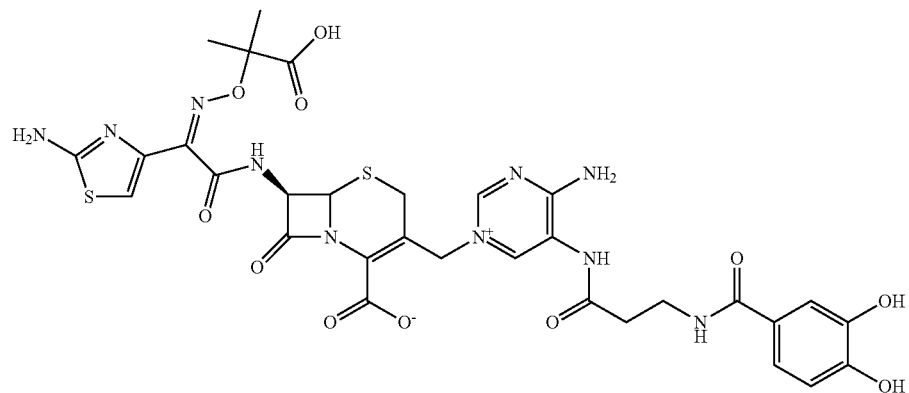
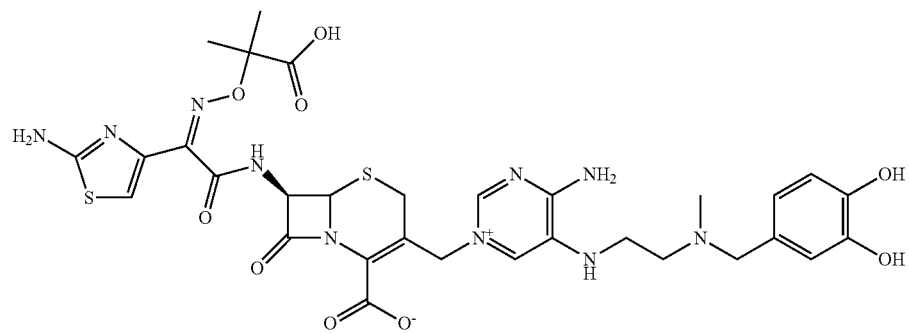

-continued
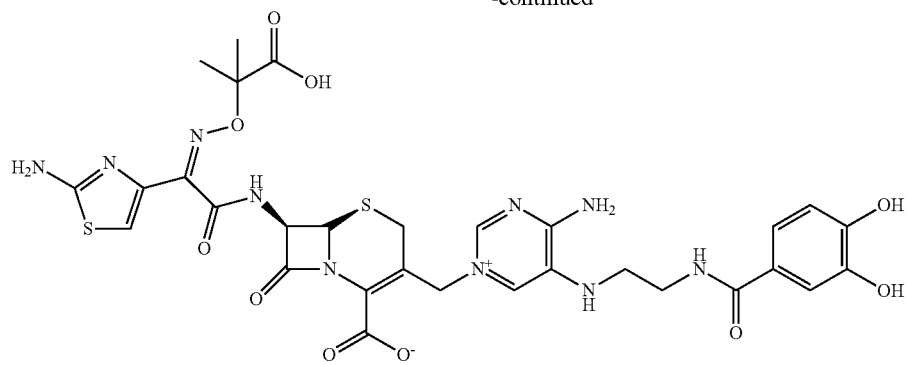
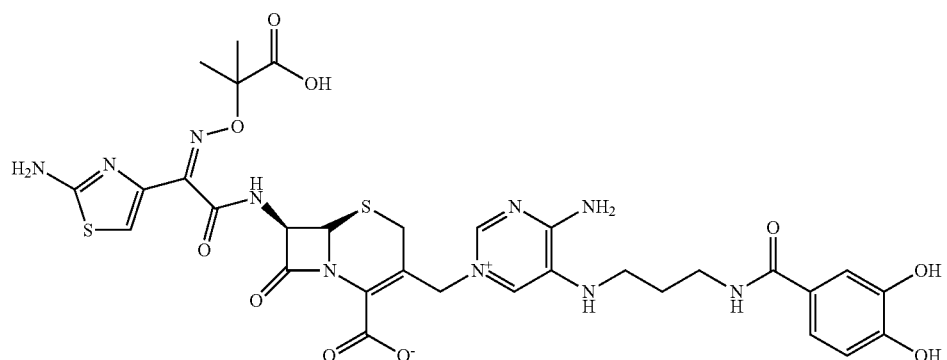
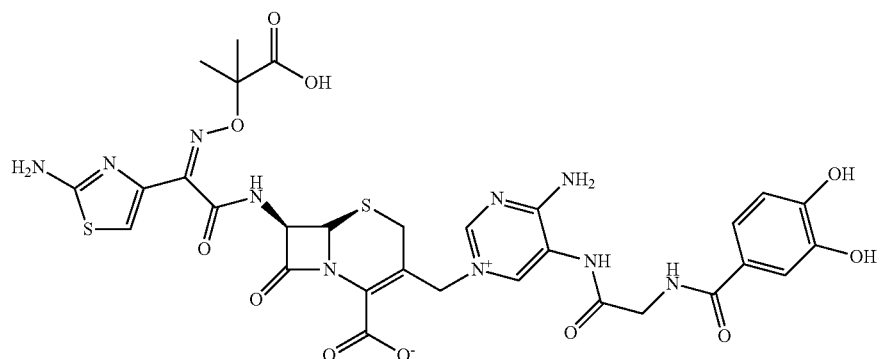
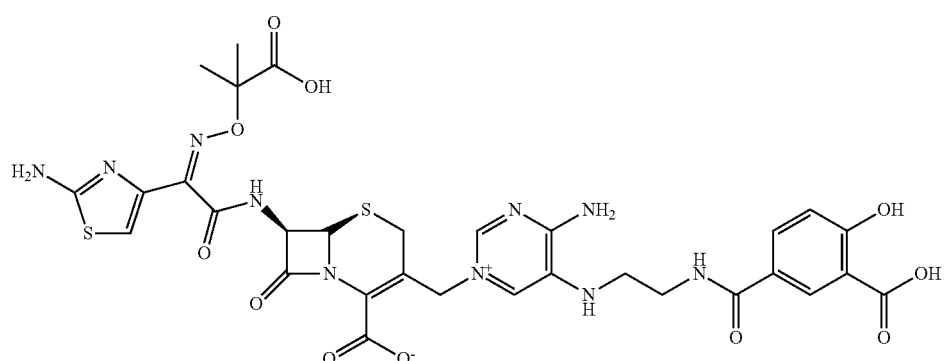

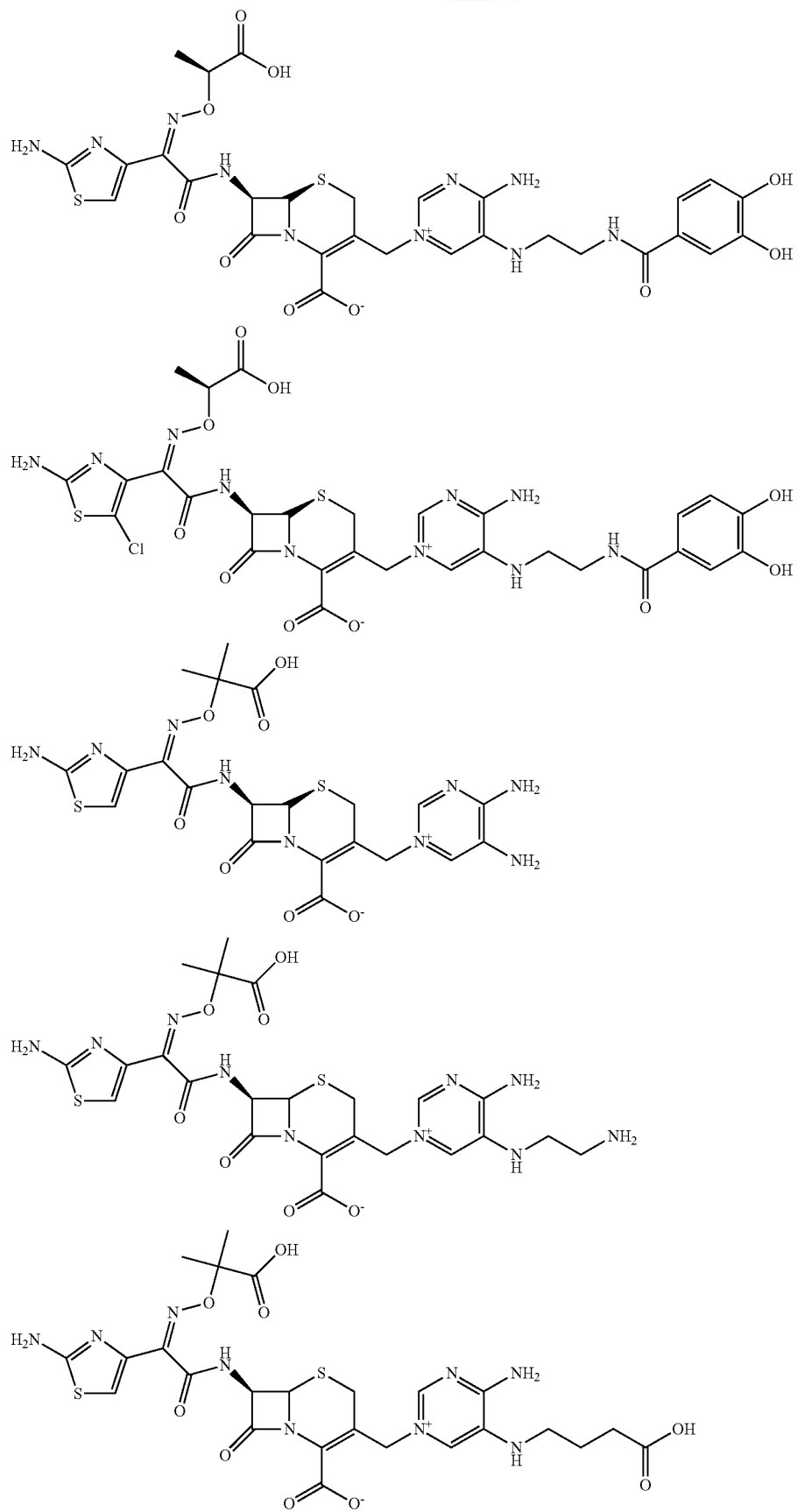

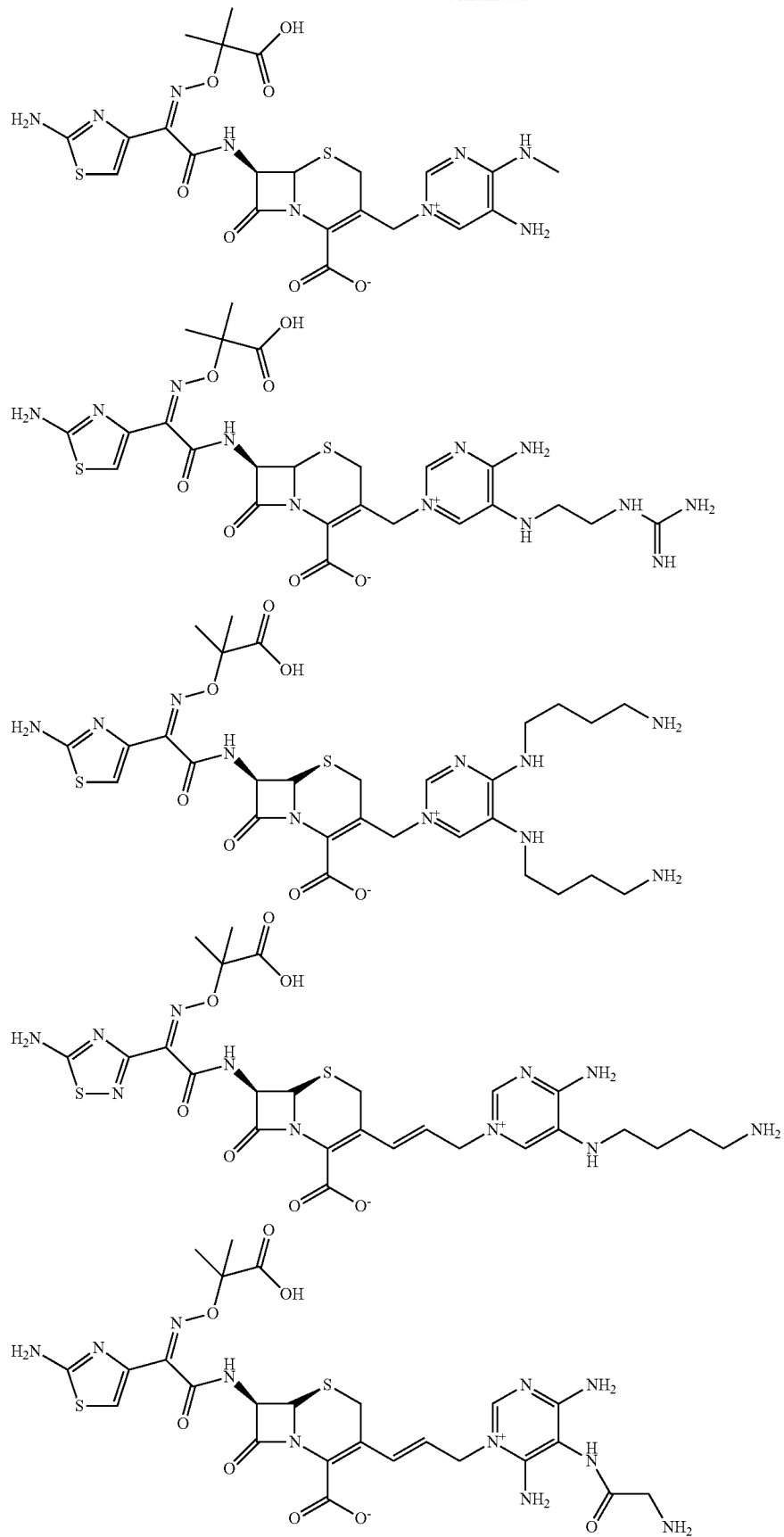

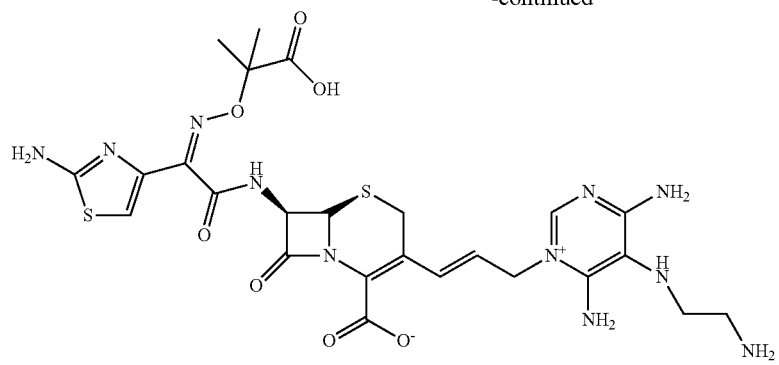
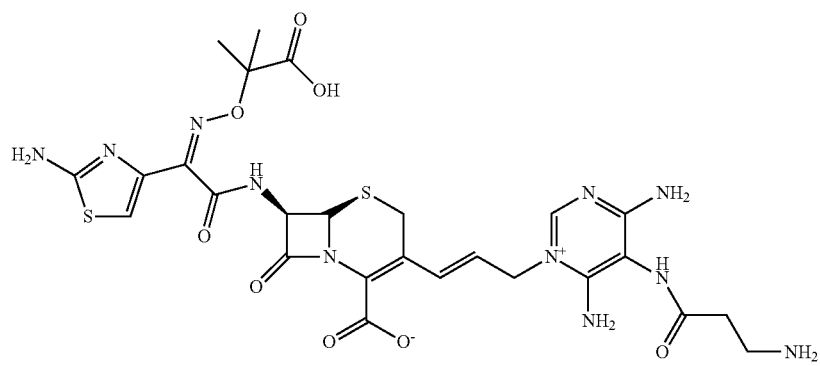
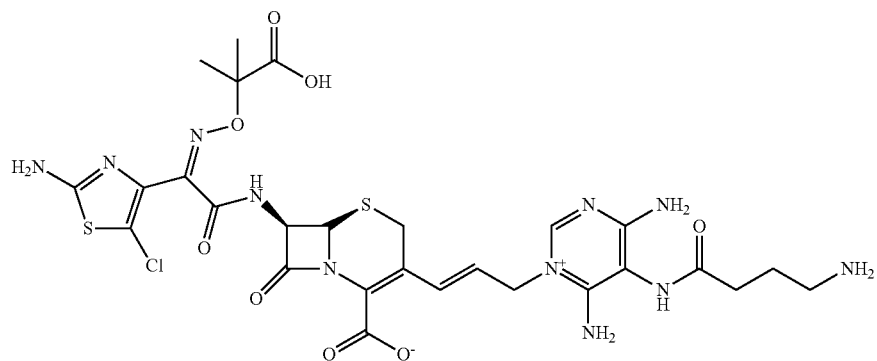
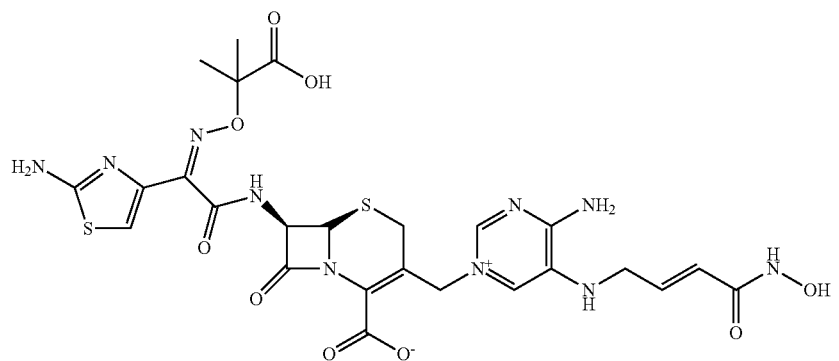

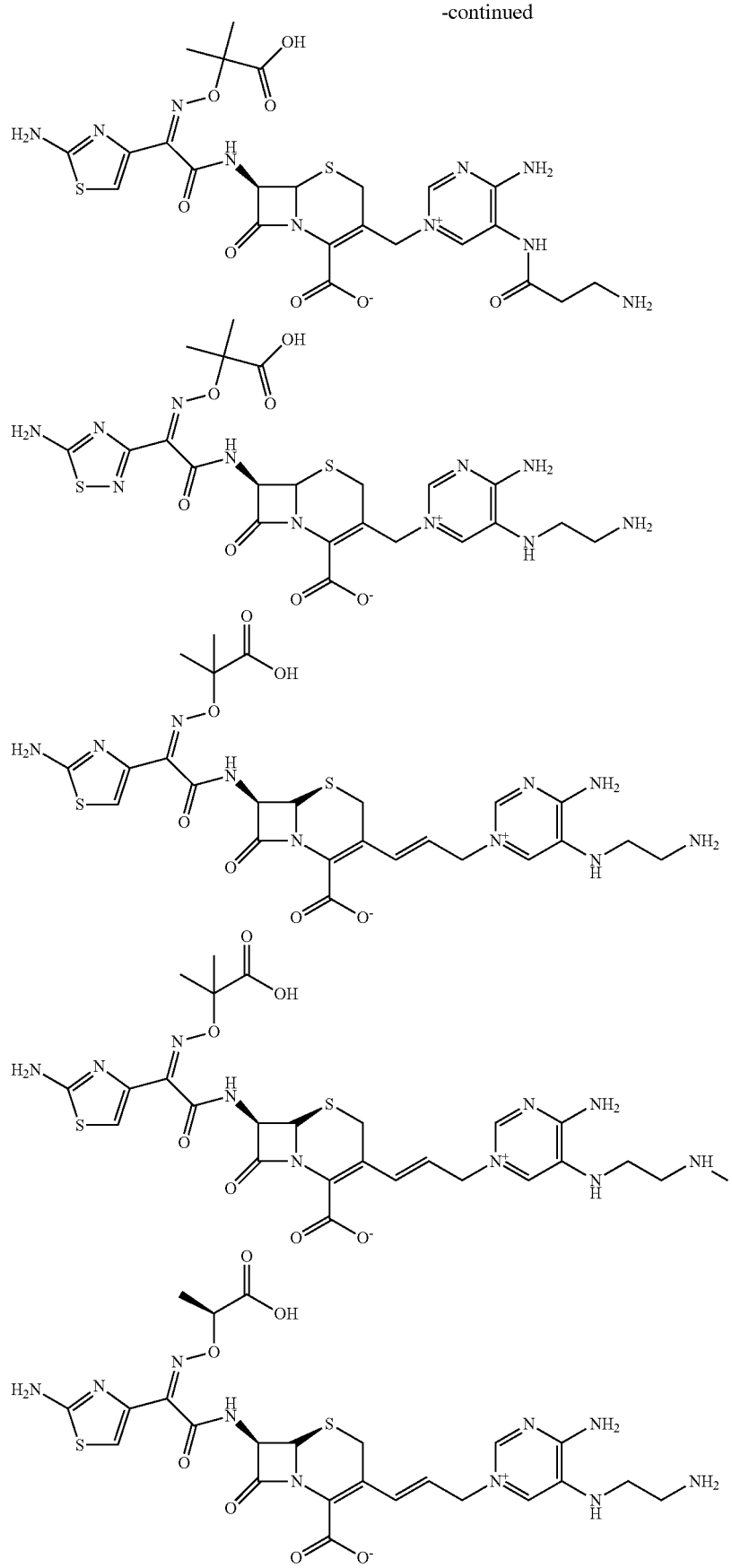

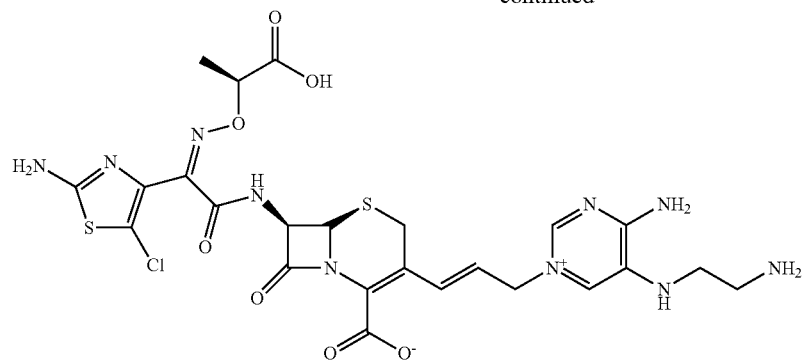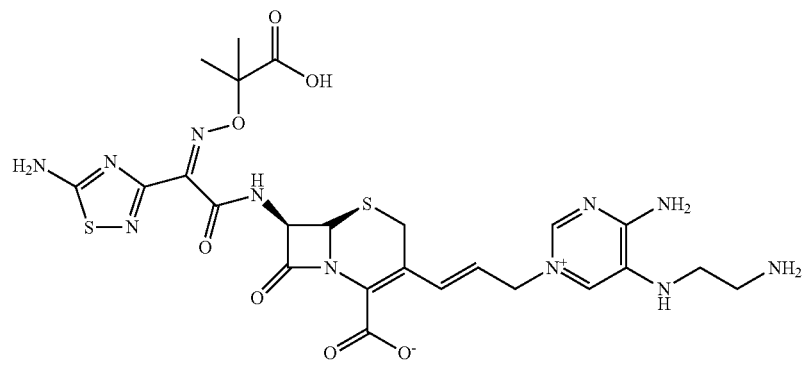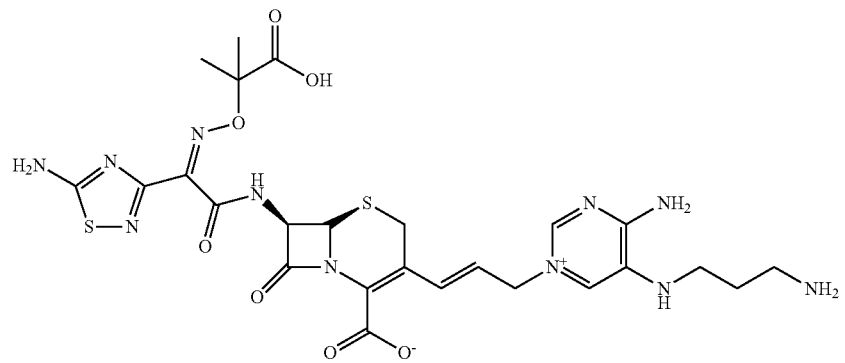

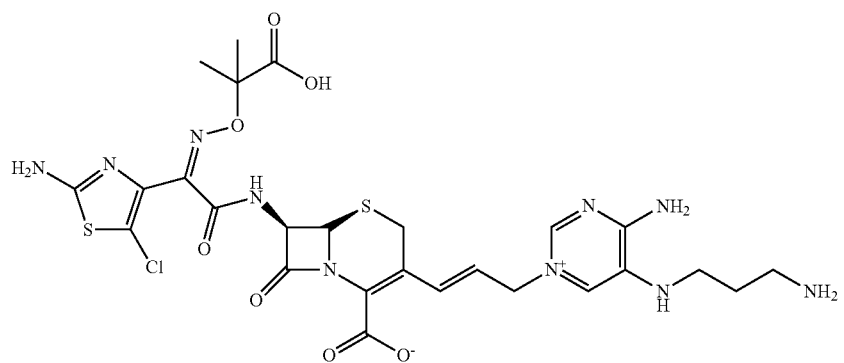
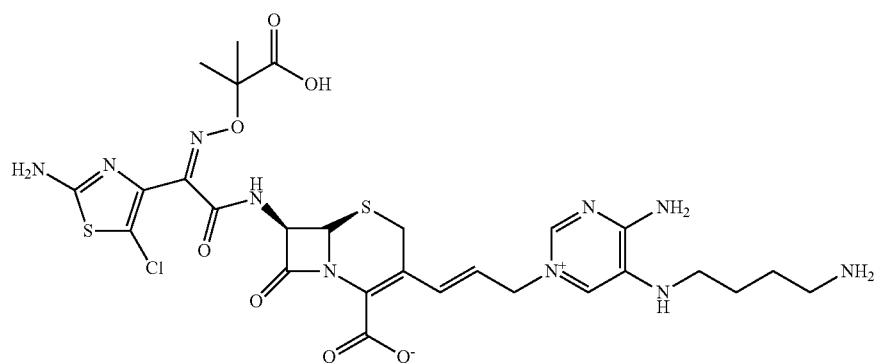
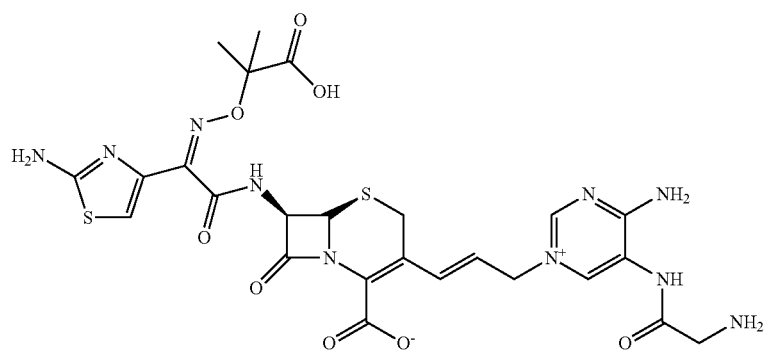
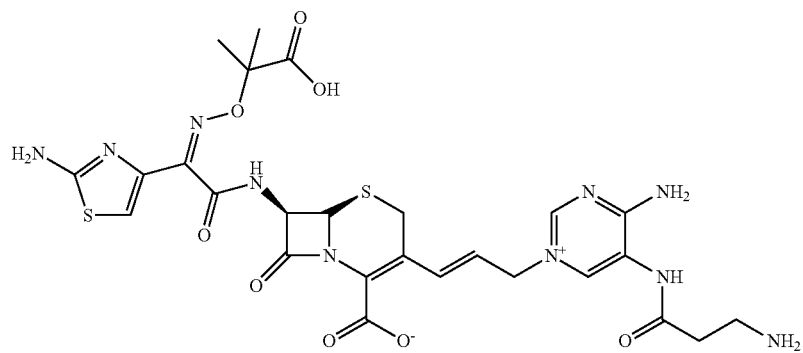

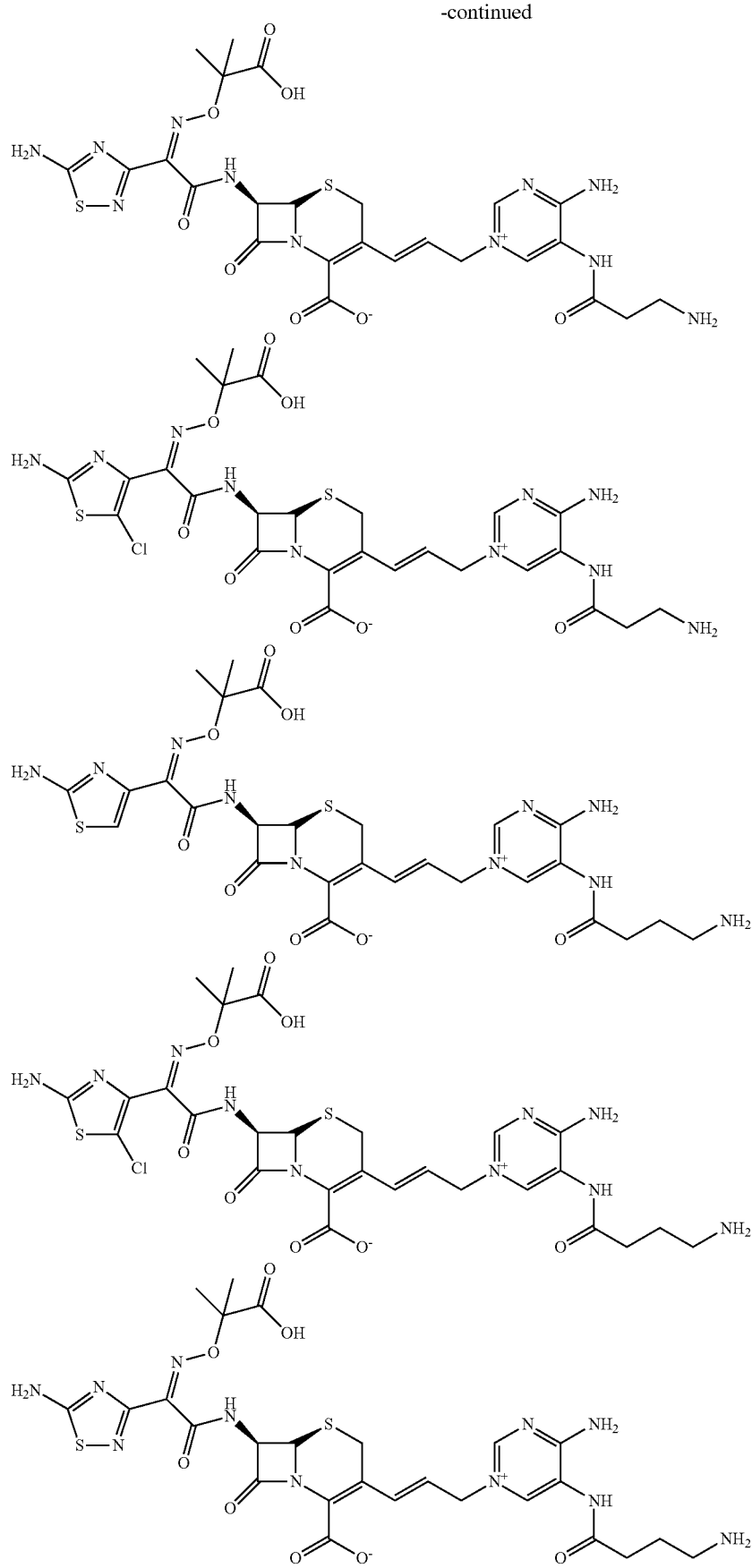

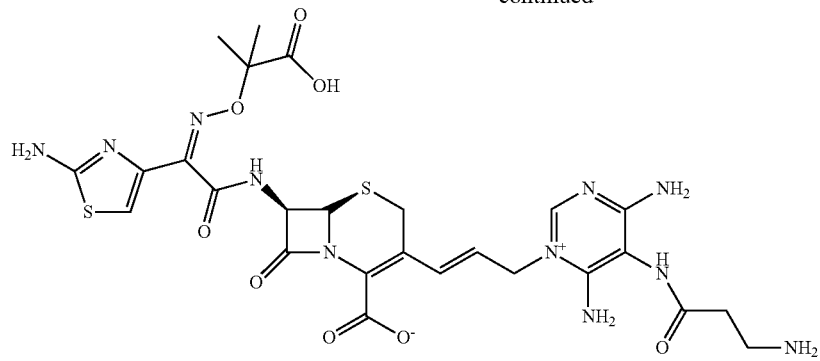
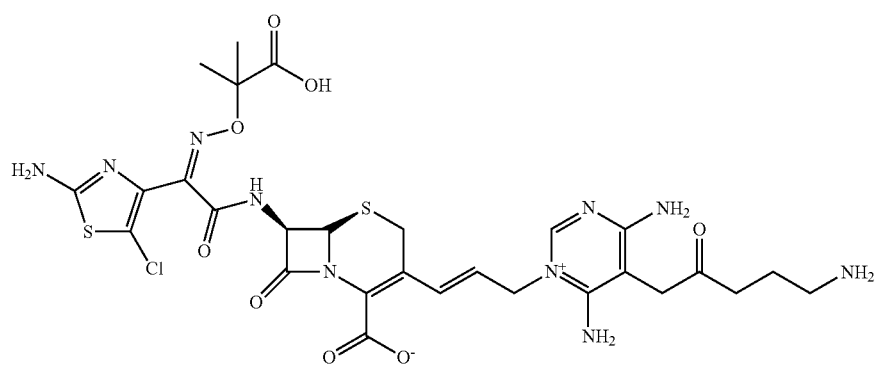
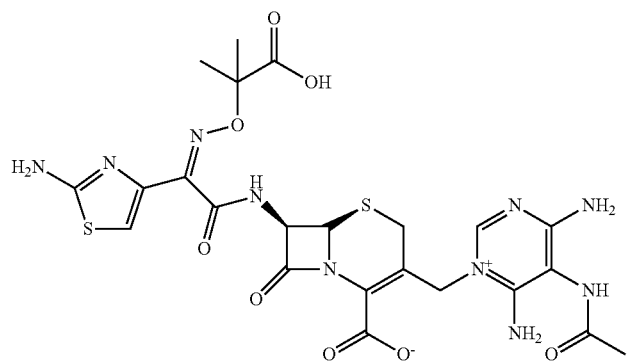
More preferred examples of the novel cephalosporin derivatives according to the present invention include the following compounds:
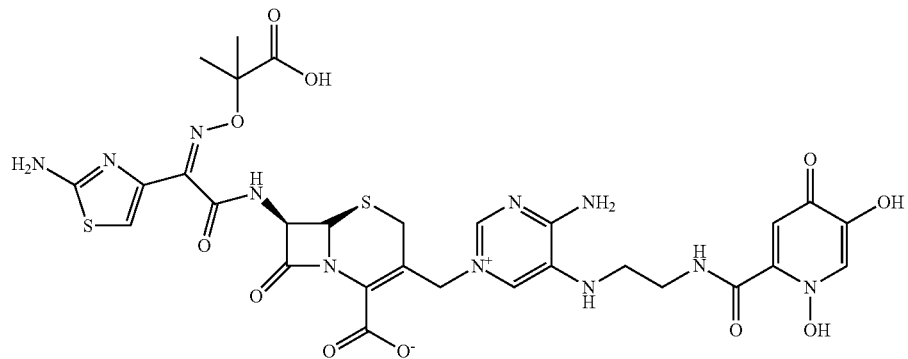

-continued
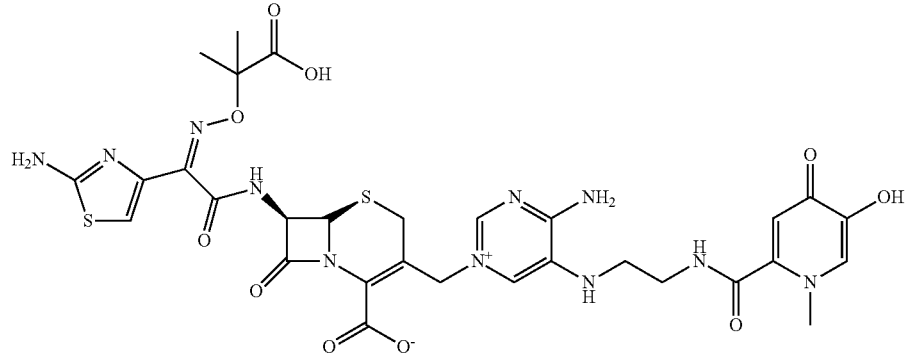
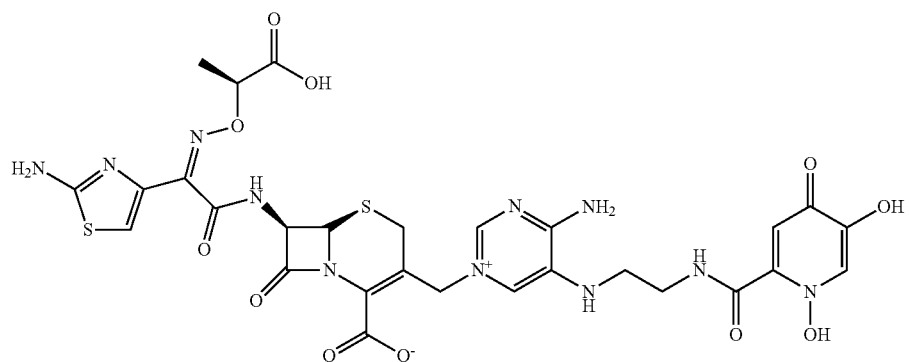
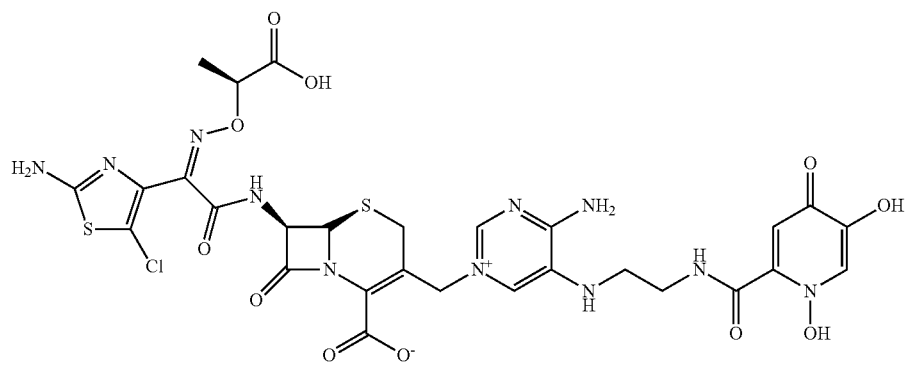
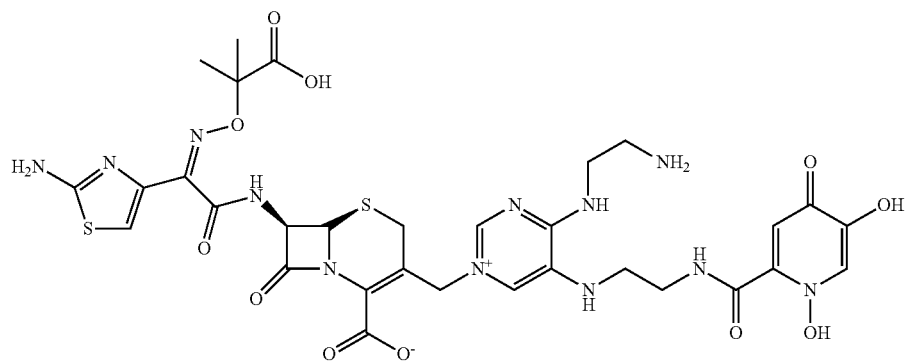

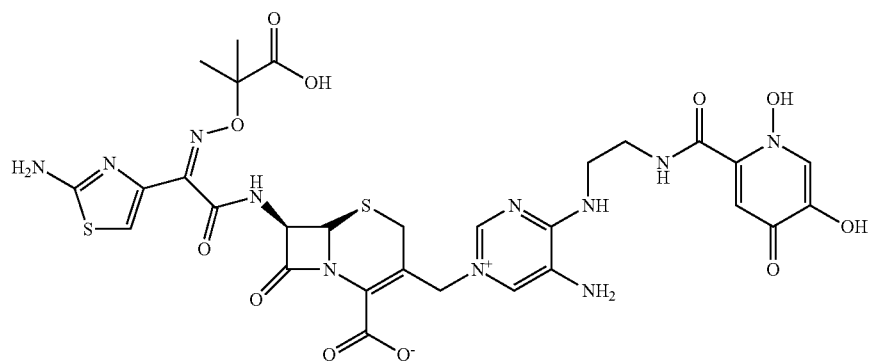
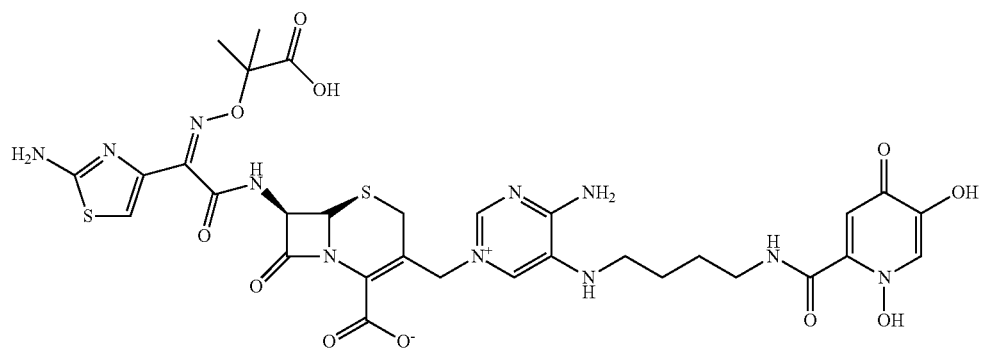
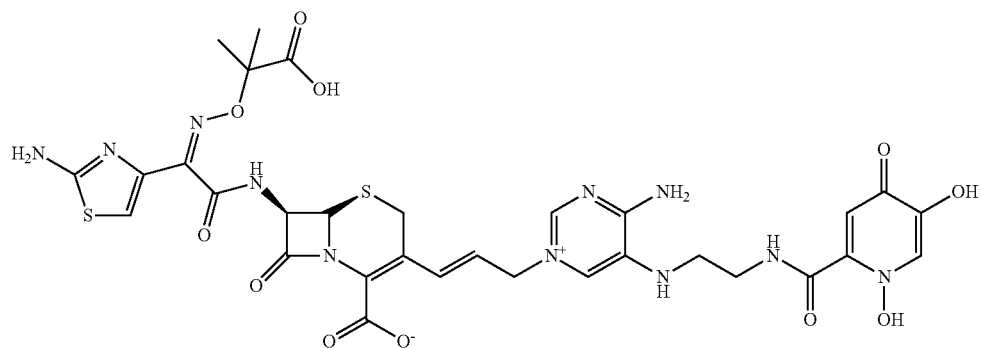
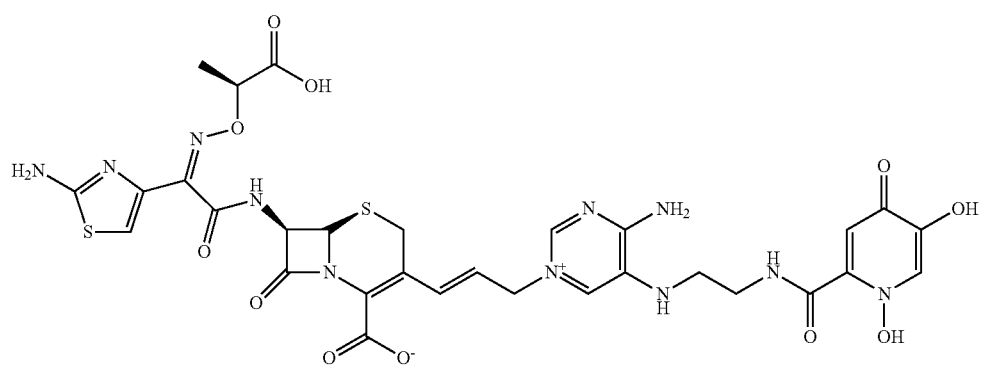

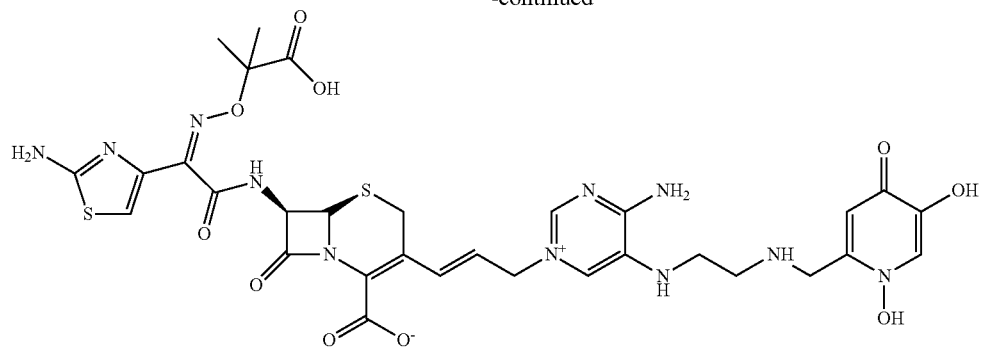
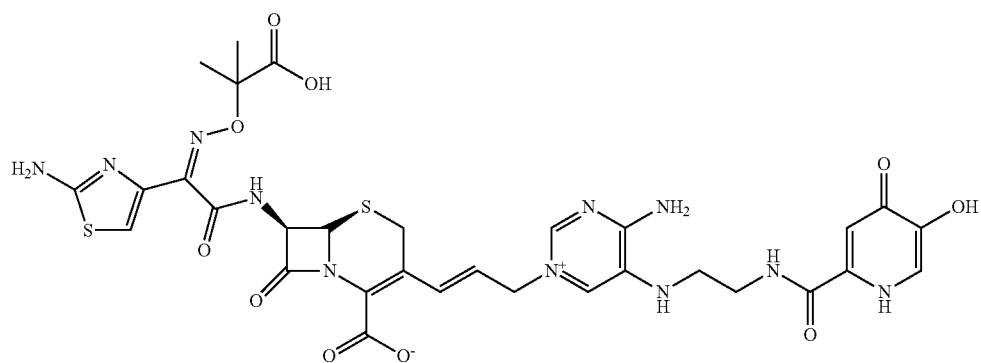
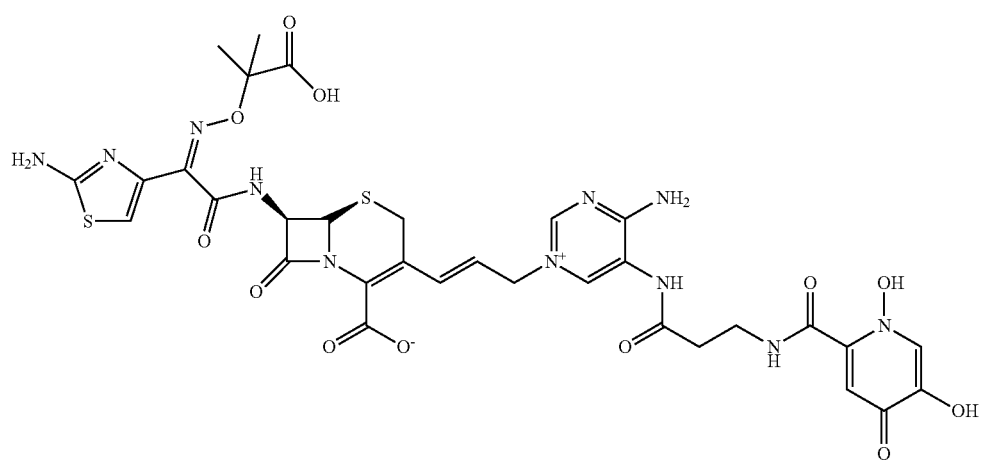
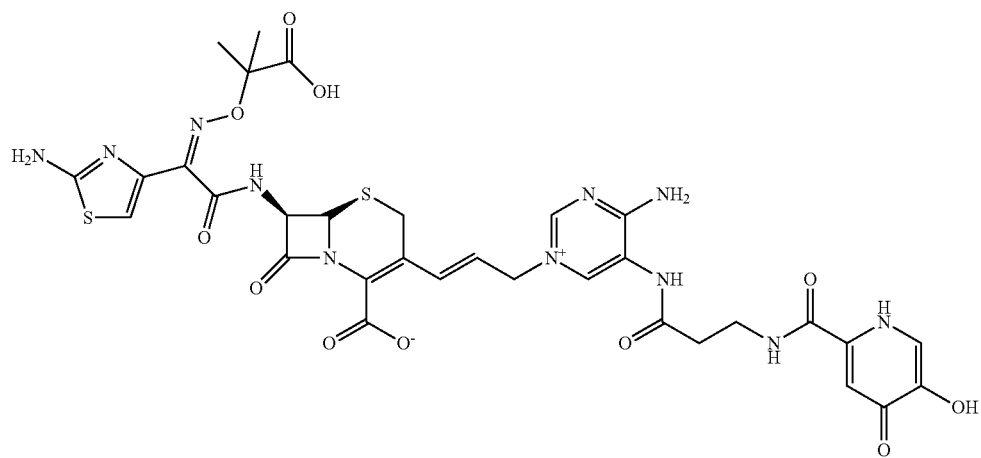

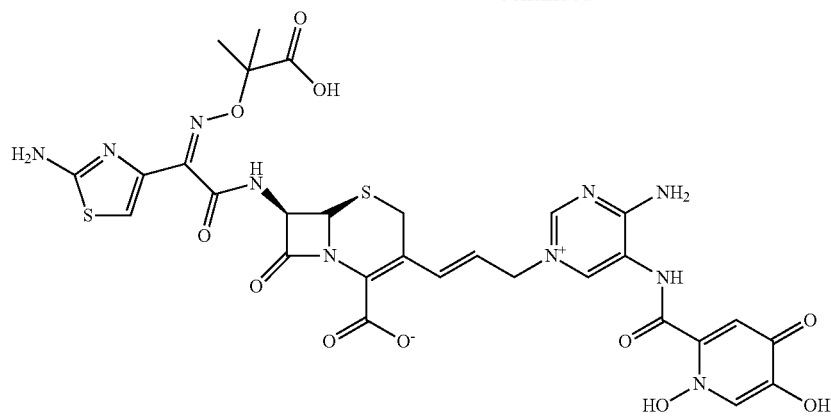
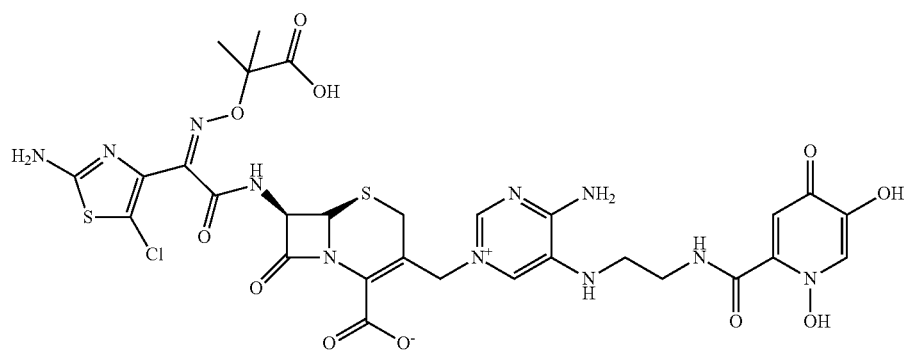
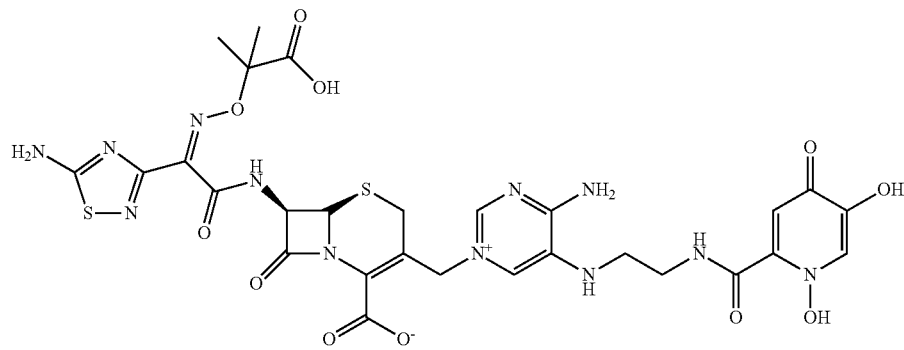
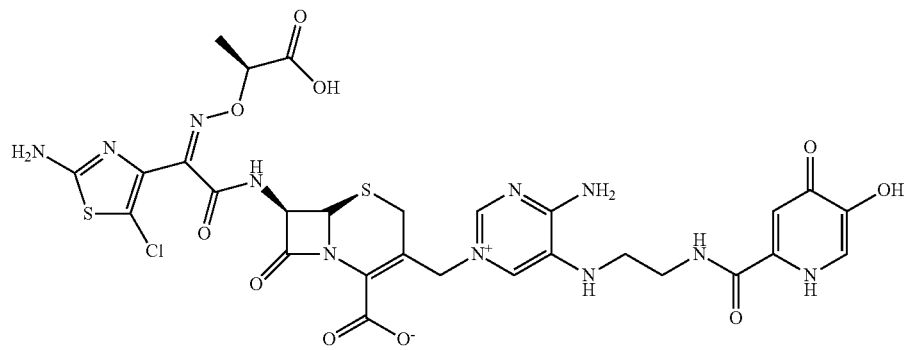

-continued
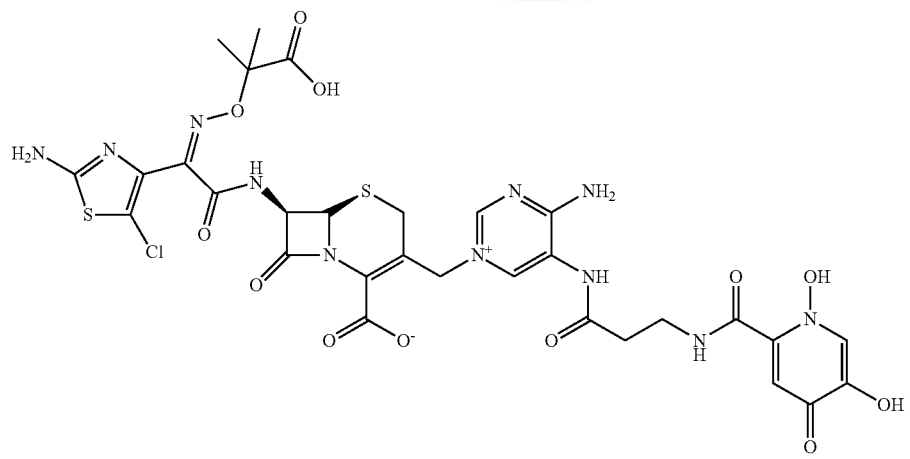
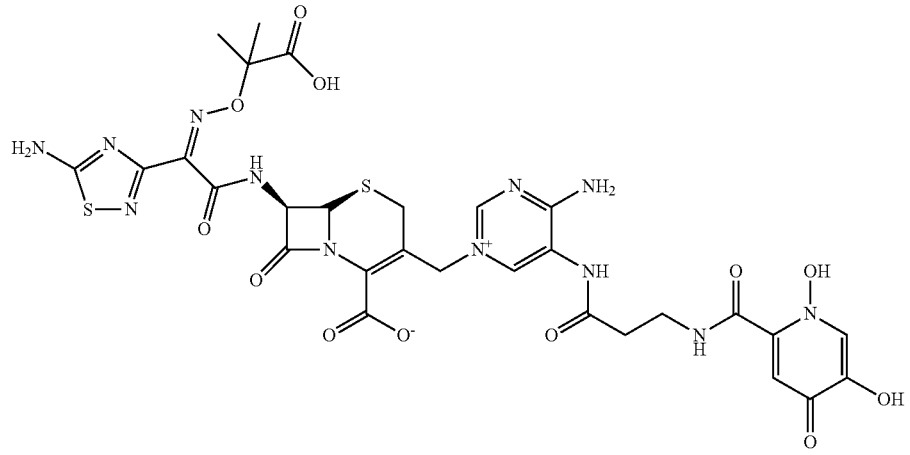
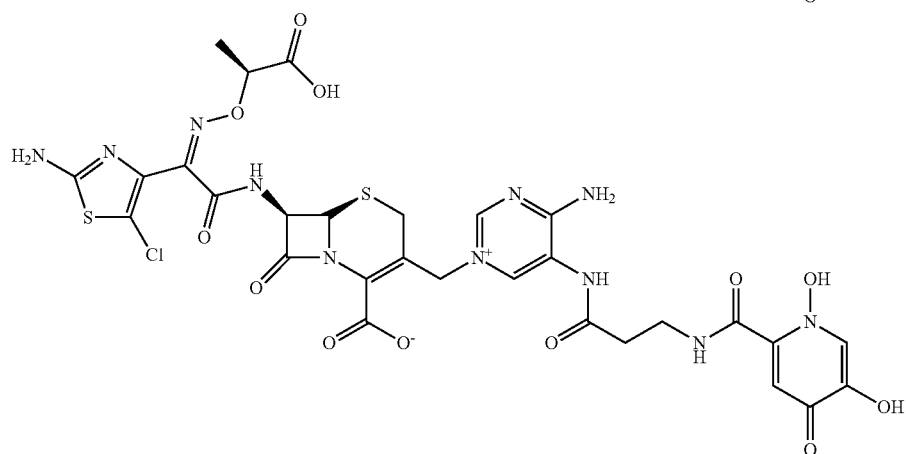
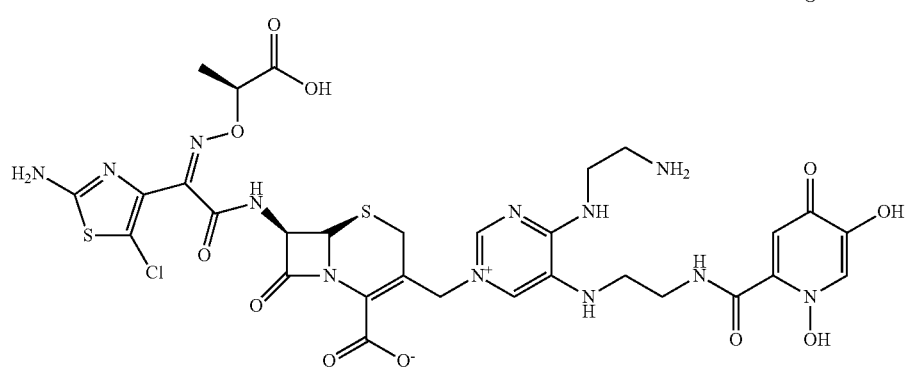

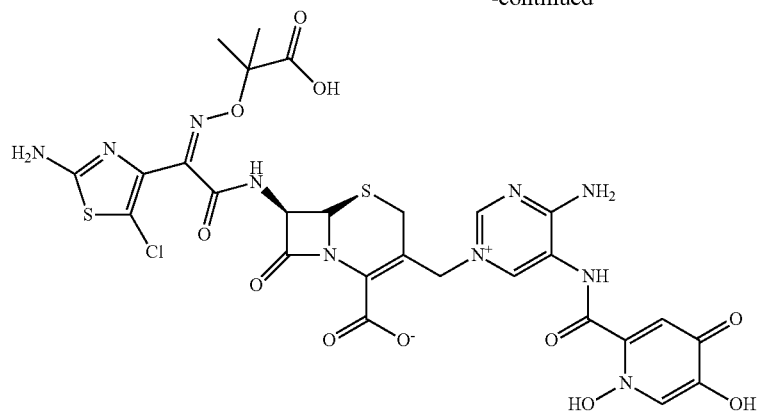
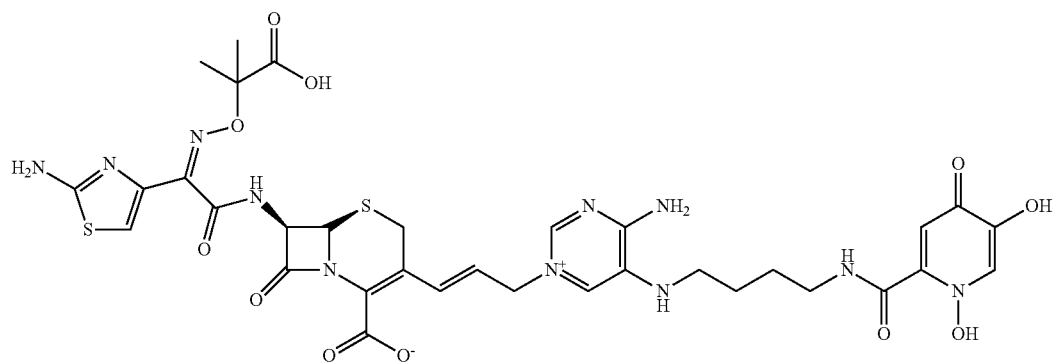
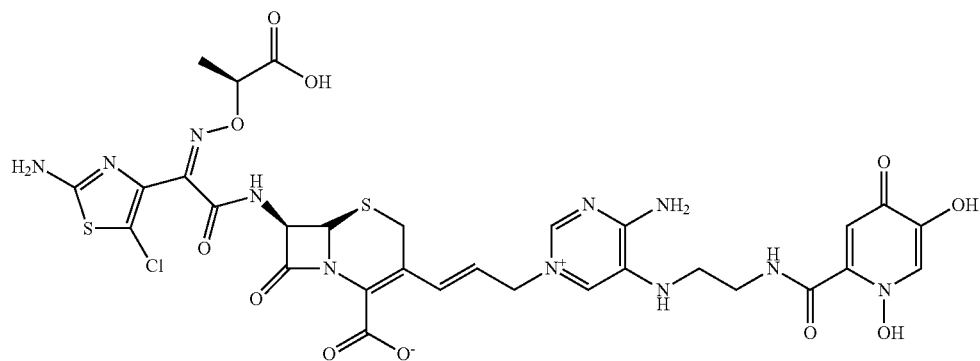
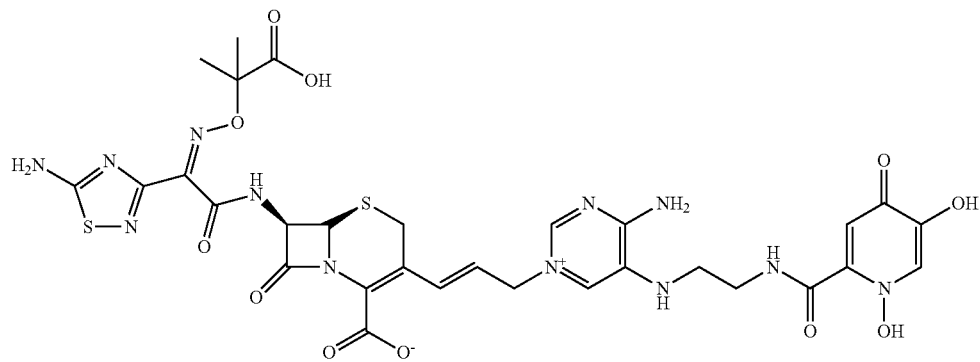

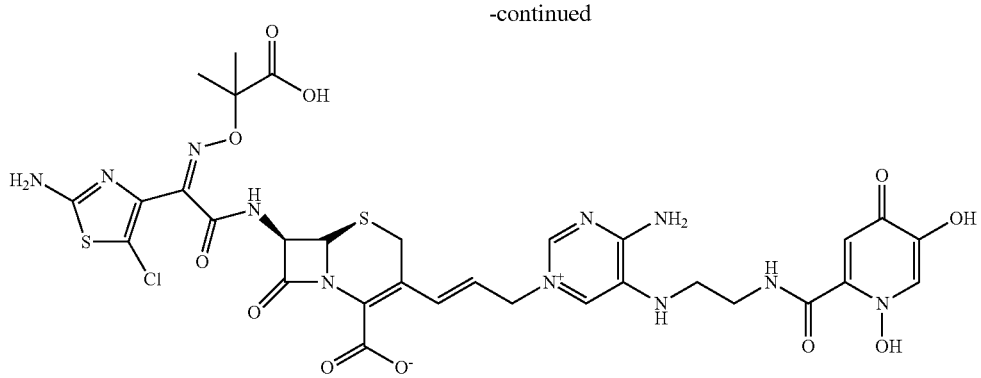

The novel cephalosporin derivatives according to the present invention can be prepared into prodrugs thereof, hydrates thereof, solvates thereof, isomers thereof or pharmaceutically acceptable salts thereof in order to improve absorption into the body or to enhance solubility. Therefore, the prodrugs thereof, hydrates thereof, solvates thereof, isomers thereof or pharmaceutically acceptable salts thereof also fall within the scope of the present invention.

The terms used herein will be described briefly.

The term "pharmaceutically acceptable salt" refers to a formulation of a compound that does not cause significant irritation to an organism to which it is administered and does not abrogate the biological activity and properties of the compound. The terms "hydrate", "solvate" and "isomer" have the same meanings as above. The pharmaceutically acceptable salt thereof can be non-toxic acid added salt containing pharmaceutically acceptable anion, for example, the acid-added salts produced by inorganic acids such as hydrochloric acid, sulfuric acid, nitric acid, phosphoric acid, hydrobromic acid and hydrolodic acid; organocarboxylic acids such as tartaric acid, formic acid, citric acid, acetic acid, trichloroacetic acid, trifluoroacetic acid, gluconic acid, benzoic acid, lactic acid, fumaric acid and maleic acid; and sulfonic acids such as methanesulfonic acid, benzenesulfonic acid, p-toluenesulfonic acid and naphthalenesulfonic acid, can be included. Also, pharmaceutically acceptable carboxylic acid salts may be obtained by allowing the compound of the present invention with bases to form with metal salts or alkaline earth metal salts bases such as lithium salt, sodium salt, potassium salt, calcium salt, and magnesium salt; salts with amino acids such as lysine, arginine, guanidine; salts with organic bases such as dicyclohexylamine, N-methyl-D-glutamine, tris (hydroxymethyl)methylamine, diethanolamine, choline, and triethylamine. The present invention according to Chemical Formula 1 can be converted to its salt forms by conventional methods.

The term "hydrate" refers to a compound of the present invention or a salt thereof, that further includes a stoichiometric or non-stoichiometric amount of water bound by non-covalent intermolecular forces. The term "solvate" as used herein means a compound of the invention or a salt thereof, that further includes a stoichiometric or non-stoichiometric amount of a solvent bound by non-covalent intermolecular forces. Preferred solvents are volatile, non-toxic, and/or acceptable for administration to humans. The term "isomer" means a compound of the present invention or a salt thereof, which has the same chemical formula or molecular formula but is optically or sterically different therefrom. Amongst these isomers structural isomer like tautomer, asymmetric carbon center R or S isomers, geometric isomers (trans, CIS), and all stereoisomers are included. The term "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. Examples of the prodrug include esters of the compounds of the present invention and pharmaceutically acceptable salts thereof that can be hydrolyzed in vivo. A further example of the prodrug might be a short peptide (polyamino acid) bonded to an acidic group, where the peptide is metabolized to reveal the active moiety.

Other terms included to describe the present invention can be interpreted typically meaning in the field.

Various types of prodrug forms are known in the related art. For example, refer to:

a) Design of Prodrugs, edited by H. Bundgaard, (Elsevier, 1985) and Methods in Enzymology, Vol. 42, p. 309-396, edited by K. Widder, et al. (Academic press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

The compounds of the present invention can represent polymorphism compounds and polymorphism compounds with antimicrobial activity.

Novel cephalosporin derivatives according to the present invention can be prepared in various ways depending on the type of substituents. For example, the composition of compounds can be prepared according to the method illustrated below. Manufacturing methods to the proposed reaction schemes are examples only, and depending on the particular substituents, the reaction schemes can be easily transformed by those skilled in the art. Thus the exemplified reaction schemes of a method for preparing cephalosporin compounds according to the present invention are not limited thereto, and unless otherwise stated, reactions of the substituents expression are the same as defined in Chemical Formula 1.

The reaction scheme of the novel cephalosporin derivatives according to the Chemical Formula 1 is shown below.

<Reaction Scheme 1>
Part A
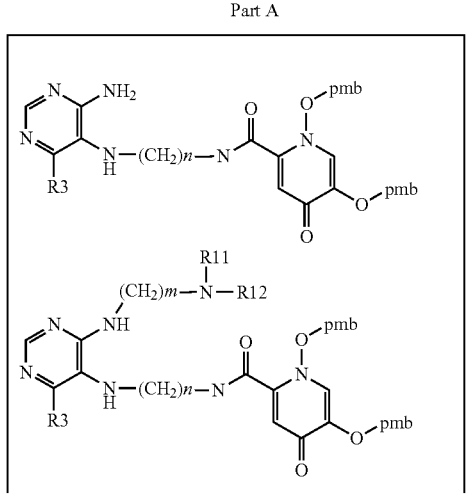
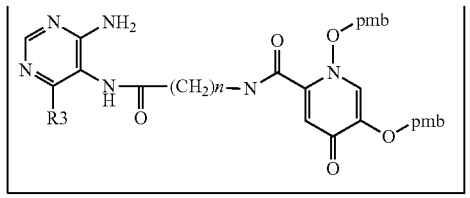
Part B
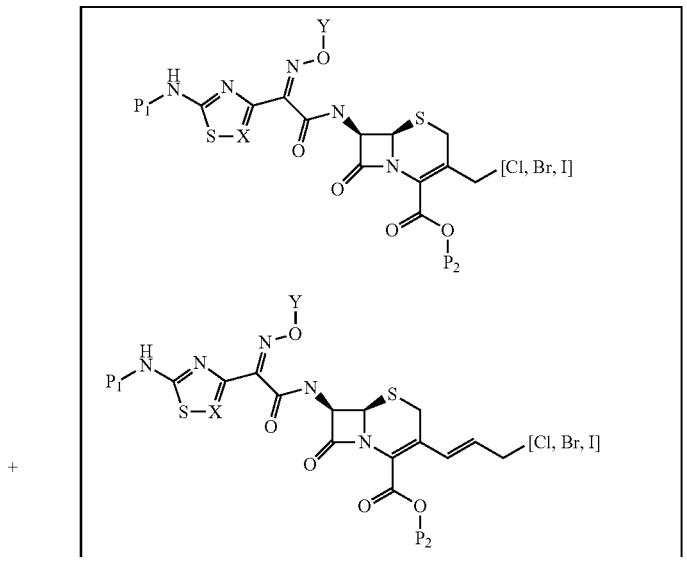
+
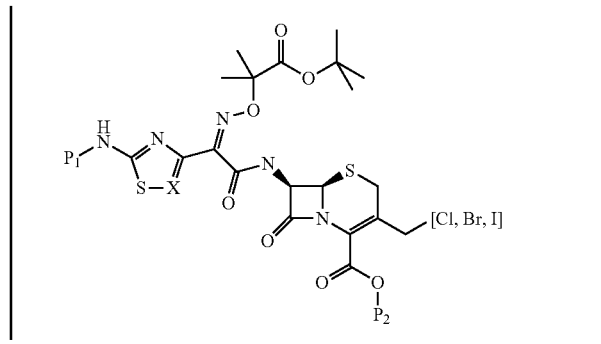
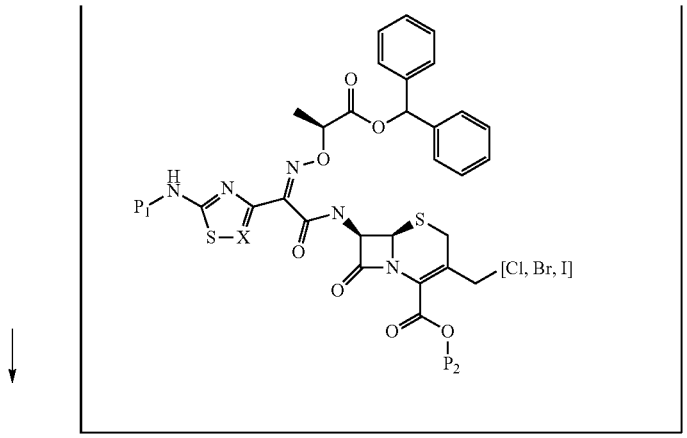
↓

-continued

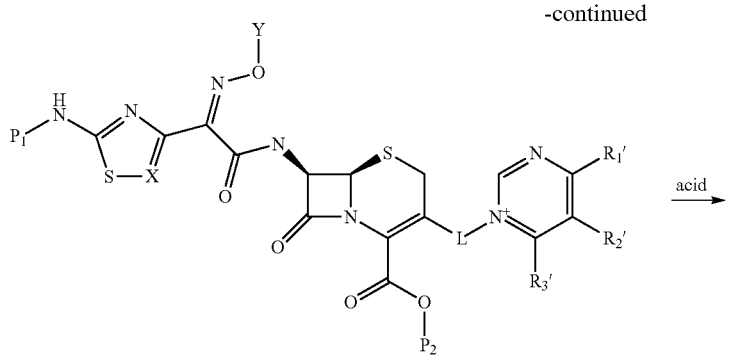

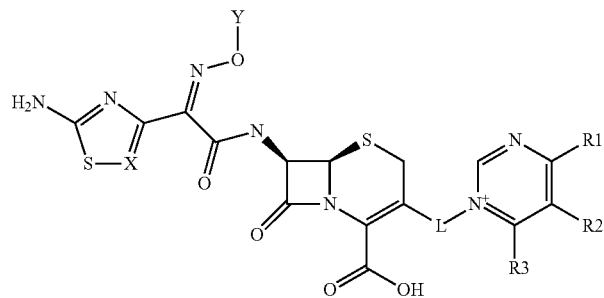

As shown in Reaction Scheme 1, pyrimidine substituted Part A of the Chemical Formula 1, and the protector (P1, P2) substituted by Part B, are reacted together and the reaction is synthesized by removing the protectors by acid.

In the Reaction Scheme 1, t-butyl, boc, or as pmb can be used as the P1 and P2 protectors, although it is not limited thereto, the halogens (Cl, Br, I, etc.) can be used as the carbon substituted leaving group in the pyrimidine reaction. Examples of Y in Part B of the Reaction Scheme 1, but not limited to, are dimethyl acetyl group protected by t-butyl, and methyl acetyl group protected by diphenyl methyl. Polar and Aprotic solvent can be used as a solvent in this reaction. Preferred example is solvent such as DMF. Amine base such as TEA or DIPEA can be used as the bases of the reaction, but more preferred reaction method is using no bases at all.

The second reaction of the above Reaction Scheme 1 is removing the protector by using acids like FTA or HCl.

In the first reaction of Reaction Scheme 1, the following isomers (Δ-2 isomer) are created as a by-product, and in order to reduce the production of isomers of these by-products following the reaction shown in Reaction Scheme 2 may be made.

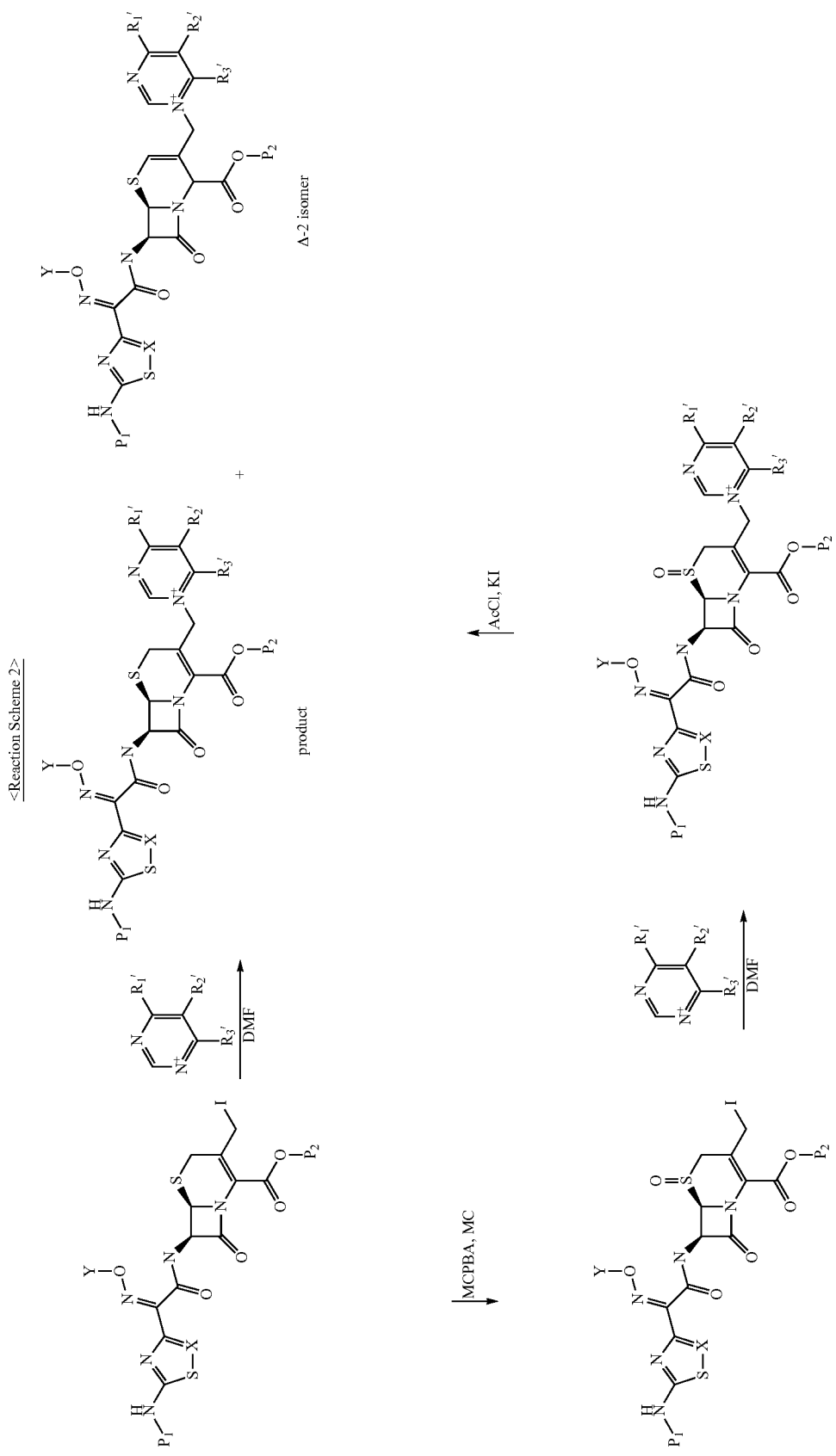
<Reaction Scheme 2>

As shown in Reaction Scheme 2, prior to reacting with pyrimidine of Part A, create sulfoxide compound by oxidating cephem compound with MCPBA first and then react with Part A. React the resulting product to conduct the reduction reaction with acetyl chloride (AcCl) and KI to obtain the desired product as the major products. In Reaction Scheme 2, methylene chloride (MC) can be used as the solvent for the MCPBA reaction, but it is not limited thereto. In addition, the reagent which can be used in oxidation and reduction reactions are not limited to MCPBA and AcCl/KI, but the oxidant and reductant with similar reactions can be used.

The invention also relates to, (a) a pharmaceutical compositions comprising a novel cephalosporin derivative represented by Chemical Formula 1, a prodrug thereof, a hydrate thereof, a solvate thereof, an isomer thereof, or a pharmaceutically acceptable salt thereof as an effective ingredient, and (b) a pharmaceutical antibiotic compositions comprising a pharmaceutically acceptable carrier thereof, diluent thereof, adjuvant thereof, or any combination thereof.

The term "pharmaceutical composition" means a mixture of the compound of the present invention with other chemical components such as diluents or carriers. The above pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, p-toluenesulfonic acid, salicylic acid and the like.

As used herein, the term "therapeutically effective amount" means the amount of active ingredient effective to alleviate or remove one or more symptoms of the disorder to be treated, or to delay clinical markers or the initiation of symptoms of the disease to be prevented. Thus, the therapeutically effective amount means the amount having the effect of (1) reversing the rate of progress of the disease, (2) prohibiting further progress of the disease and/or (3) alleviating (preferably, removing) one or more symptoms associated with the disease. Testing the compounds in vivo and in vitro model systems can empirically determine therapeutically effective amount for the treatment of the disease.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The compound used herein may be administered as the compound per se or as a pharmaceutical composition comprising the compound with other active ingredients in the combination therapy or with other suitable carriers or excipients, to the human patient. Any of the formulation and administration techniques of the compounds in this invention may be used as suitable and as understood in the art; "Remington's Pharmaceutical Sciences," Mack Publishing Co., Easton, Pa., 18th edition, 1990.

The pharmaceutical composition of the present invention may be prepared in a manner that is itself known, e.g. by means of conventional mixing, dissolving, granulating, dragee-making, powdering, emulsifying, encapsulating, entrapping or lyophilizing processes.

Thus, pharmaceutical compositions for use in accordance with the present invention may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above. In the present invention according to the composition of the Chemical Formula 1, injectable and oral formulation may be formulated for such purposes.

For injection, the agents of the present invention may be formulated in aqueous solutions or lipid emulsions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the present invention to be formulated as tablets, pills, powders, granules, dragees, capsules, liquids, gels, syrups, slurries, suspensions and the like, for oral ingestion by a patient to be treated. Preferably the formulations are in capsules, tablets, pills, powders, and granules forms, and especially, capsules and tablets forms are more useful. Tablets and pills are preferable to manufacture as the intestinal-targeted dissolving formulation. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents, such as the cross-linked polyvinyl pyrrolidone, agar, or alginic acid or a salt thereof such as sodium alginate and magnesium stearates such as lubricants and binders may be added.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Furthermore, the formulations of the present invention may be coated with enteric polymers. All formulations for oral administration should be in dosages suitable for such administration.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

In addition, an active ingredient may be for examples, a dry powder form, which can be dissolved in non-pyrogenic and non-bacterial water prior to use.

The compounds may also be formulated in rectal compositions such as suppositories or retention enemas, e.g., containing conventional suppository bases such as cocoa butter or other glycerides.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

When formulated into unit dose, the active ingredient of composition of the Chemical Formula 1 is preferably administered at a dose of from 1 to 1,500 mg. Depending on the conditions of patients, including age, body weight, sex, administration route, state of health, and severity of disease, the administration dose of the compound of the present invention is determined according to the instructions of a physician or pharmacist. Typically, the dose ranges from about 1 to 1,500 mg per one to three times a day for an adult. For example, the compounds of the present invention may be intramuscularly or intravenously injected at a dose of from 1 to 1,500 mg per one to three times a day to an adult. A higher dose may be effective from some patients.

In addition to the compounds of the present invention, the pharmaceutical compositions of the present invention may further comprise (i.e., formulated together with) one or more known drug(s) selected from clinically useful antibacterial agents (e.g., β-lactam, macrolide, quinolone or aminoglycoside) and anti-inflammatory agent (e.g., antifungal triazole or amphotericin), or may be administered in combination with one or more the known drug(s). Further, the compounds of the present invention may be formulated together with or administered in combination with a bactericidal/permeability increasing protein (BPI) product or an efflux pump inhibitor, in order to increase activity against Gram-negative bacteria and antibiotic resistant bacteria.

The compounds of the present invention may be formulated together with or administered in combination with vitamin, e.g., vitamin B, such as vitamin B2, vitamin B6 or vitamin B12, and folic acid. Further, the compounds of the present invention may be formulated together with or administered in combination with a cyclooxygenase (COX) inhibitor, particularly COX-2 inhibitor.

The present invention relates to method of antibiotic treatment using pharmaceutical antibiotic compositions comprising a novel cephalosporin derivatives presented by Chemical Formula 1, a prodrug thereof, a hydrate thereof, a solvate thereof, an isomer thereof, or a pharmaceutically acceptable salt thereof as an effective ingredient.

As described above, the present invention, a novel cephalosporin derivative, possesses superior efficacy antimicrobial activity against Gram-negative bacteria such as *P. aerugi-nosa, K. pneumonia, A. baumannii* and also against multidrug resistant Gram-negative bacteria, and especially against the most problematic multidrug resistant Gram-negative bacteria *Pseudomonas aeruginosa*. In addition, these compounds show excellent potential as drugs during the development stage by possessing excellent pharmacokinetic profile.

BRIEF DESCRIPTION OF DRAWINGS

FIG. 1 presents schematic diagram of siderophore iron (Fe) and its receptors;

FIG. 2 presents schematic view of the transportation process of iron ion and siderophore.

EXAMPLES

Hereinafter reference will now be made in detail to various Preparation Examples, Examples, and Test Examples. While the invention will be illustrated in conjunction with the Preparation Examples, Examples, and Test Examples, it will be understood that present description is not intended to limit the invention to those Preparation Examples, Examples, and Test Examples.

The following Preparation Examples describe preparation of the compounds in Part A and Part B of the Reaction Scheme 1.

Preparation Example 1

Compound A-I

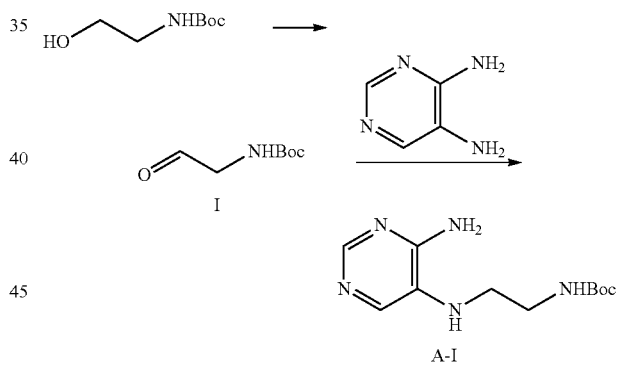

1-1) Preparation of Compound I:

Oxalyl chloride (1.3 mL, 15 mmol) was added to a reaction chamber containing methylene chloride (120 mL) at −78° C. and a solution of dimethyl sulfoxide (2.45 mL, 30 mmol) dissolved in methylene chloride (20 mL) was added. The resulting solution was stirred for 10 minutes at −78° C. A solution of N-Boc-ethanolamine (2 g, 12.4 mmol) dissolved in methylene chloride (20 mL) was slowly added and then triethylamine (8.64 ml, 62 mmol) was added. The resulting solution was stirred for 30 minutes at −78° C. and additional 30 minutes at room temperature, washed with water (100 mL) and saline (100 mL). The organic layer was dehydrated with anhydrous sodium sulfate, concentrated under reduced pressure, and applied to column chromatography (n-hex:EA=3: 1~1:1) to yield Compound I (270 mg (14%)).

$^1$H NMR (600 MHz, DMSO-d$_6$) δ=7.83 (s, 1H), 7.49 (s, 1H), 6.88 (d, J=5.4 Hz, 1H), 6.36 (br, 2H), 4.81 (br, 1H), 3.13 (m, 4H), 1.39 (s, 9H)

1-2) Preparation of Compound A-I:

4,5-diaminopyrimidine hydrochloride (2.0 g, 18.1 mmol) and Compound I (3.0 g, 18.8 mmol) were dissolved in methanol (60 mL) and then acetic acid (1.0 g, 18.1 mmol) was added. The resulting solution was stirred for 12 hours at room temperature. Sodium cyanoborochloride (2.2 g, 36.3 mmol) was added. The resulting solution was stirred for 3 hours at room temperature, concentrated under reduced pressure, and applied to column chromatography (MC:MeOH=50:1~20:1) to yield Compound A-I (1.09 g (24%)).

$^1$H NMR (600 MHz, chloroform-$d_1$) δ 8.15 (s, 1H), 7.65 (s, 1H), 5.01 (br, 2H), 3.47 (br, 2H), 3.22 (t, J=5.4 Hz, 2H), 1.46 (s, 9H)

Preparation Example 2

Compound A-II

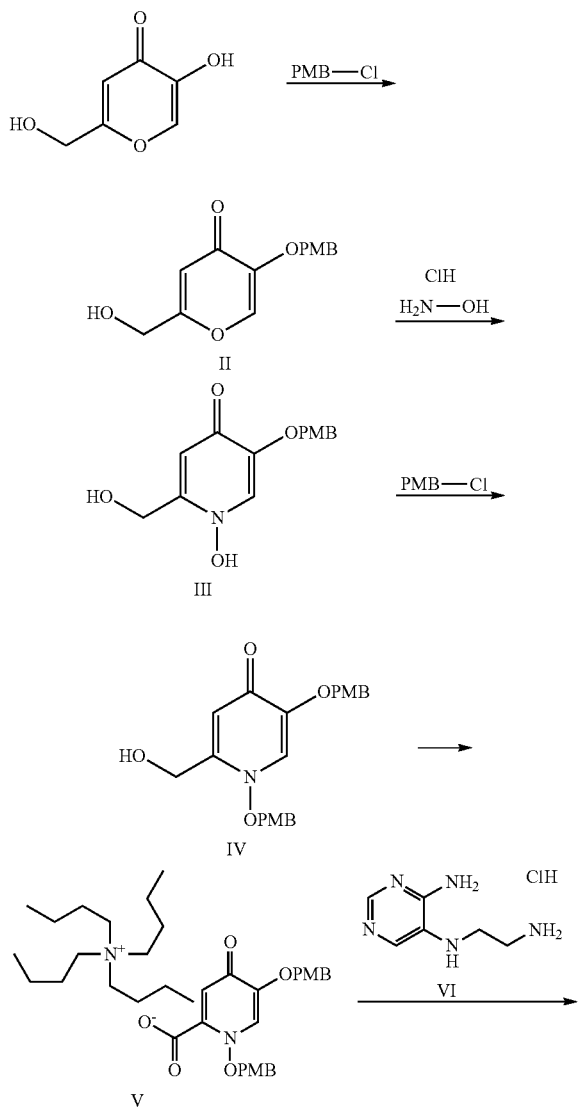

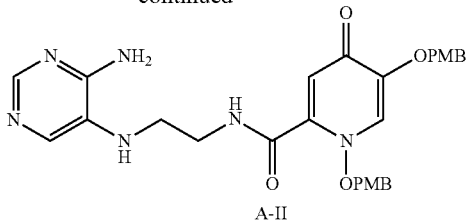

2-1) Preparation of Compound II:

Kojic acid (50 g, 0.35 mol) was dissolved in N,N-dimethylformamide (900 mL) and then potassium carbonate (58.4 g, 0.42 mol) and 4-methoxybenzyl chloride (61.7 g, 0.39 mol) were sequentially added. The resulting solution was stirred for 3 hours at 80° C., concentrated under reduced pressure, and slowly added to water (800 mL) to yield a solid. The solid was washed with ether:hexane=1:1 (800 mL) to yield Compound II (90 g (98%)).

$^1$H NMR (600 MHz, chloroform-$d_1$) δ 7.51 (s, 1H), 7.32 (d, J=8.4 Hz, 2H), 6.90 (d, J=8.0 Hz, 2H), 6.45 (s, 1H), 5.00 (s, 2H), 4.45 (s, 2H), 3.81 (s, 3H)

2-2) Preparation of Compound III:

Compound II (50 g, 0.19 mol) and hydroxylamine hydrochloride (66.2 g, 0.95 mol) were dissolved in pyridine (620 mL). The resulting solution was stirred for a hours at 70° C.~75° C., concentrated under reduced pressure, and dissolved in water (350 mL). 6N HCl (pH 1~2) was added to the resulting solution while stirring at 0° C. to yield a solid. The solid was washed with ether (300 mL) to yield Compound III (15 g (30%)).

$^1$H NMR (600 MHz, DMSO-$d_6$) δ 7.96 (s, 1H), 7.38 (d, J=8.0 Hz, 2H), 6.96 (d, J=8.0 Hz, 2H0, 6.86 (s, 1H), 5.54 (br, 1H), 5.03 (s, 2H), 4.45 (s, 2H), 3.74 (s, 3H)

2-3) Preparation of Compound IV:

Compound III (31 g, 0.11 mol) was dissolved in N,N-dimethylformamide (350 mL) and then potassium carbonate (31 g, 0.22 mol) and 4-methoxybenzyl chloride (19.3 g, 0.12 mol) were sequentially added. The resulting solution was stirred for 15 hours at room temperature, concentrated under reduced pressure, diluted with ethyl acetate (400 mL), and filtered under reduced pressure. The filtrate was washed with water (300 mL) and saline (300 mL). The organic layer was dehydrated with anhydrous sodium sulfate. The resultant was washed with ether:hexane=1:1 (400 mL) to yield Compound IV (42 g (95%)).

$^1$H NMR (600 MHz, chloroform-$d_1$) δ 7.27~7.21 (m, 5H), 6.99 (s, 1H), 6.90 (d, J=8.0 Hz, 2H), 6.86 (d, J=8.0 Hz, 2H), 6.49 (s, 1H), 5.03 (s, 2H), 4.93 (s, 2H), 4.50 (s, 2H), 3.82 (s, 3H), 3.78 (s, 3H)

2-4) Preparation of Compound V:

Compound IV (20 g, 50.3 mmol) was dissolved in methylene chloride (580 mL) and then distilled water (50 mL) was added. The resulting solution was stirred at 0° C. 1M sodium bromide (30 mL), 1M tetrabutyl ammonium bromide (55 mL), TEMPO (2.36 g, 15.1 mmol), sodium hydrocarbonate saturated solution (110 mL), and sodium hypochlorite solution (120 mL, 2.01 mol) were added sequentially. The resulting solution was stirred for 1 and a half hours at the temperature changing from 0° C. to room temperature. 1N HCl (pH6~7) was added. Then, t-butanol (380 mL) was added and 2M 2-methyl-2-butene dissolved in tetrahydrofuran (607 mL) was subsequently added. Thereafter, a solution of sodium chloride (45.5 g, 503 mmol) and sodium dihydrogen phosphate monohydrate (52 g, 377 mmol) dissolved in distilled water (170 mL) was added. The resulting solution was stirred for 1 hour at room temperature. The resulting solution was poured in a filter funnel to separate an organic layer and aqueous layer. The organic layer was washed with sodium dihydrogen phosphate saturated solution (800 mL), dehydrated with anhydrous sodium sulfate, concentrated under reduced pressure, and applied to column chromatography (MC:MeOH=50:1~8:1) to yield Compound V (40 g (61%)).

$^1$H NMR (600 MHz, chloroform-d$_1$) δ 7.35 (d, J=8.4 Hz, 2H), 7.25 (d, 8.4 Hz, 2H), 6.86 (m, 4H), 6.72 (s, 1H), 6.38 (s, 1H), 6.49 (s, 1H), 5.30 (s, 2H), 4.85 (s, 2H), 3.80 (s, 3H), 3.79 (s, 3H), 3.28 (m, 8H), 1.65 (m, 8H), 1.42 (m, 8H), 0.99 (t, J=6.6 Hz, 12H)

2-5) Preparation of Compound A-II:

Compound VI (1.89 g, 10 mmol) was dissolved in N,N-dimethylformamide (50 ml), diisopropyl ethylamine (7.2 mL, 40 mmol) and Compound V (6.52 g, 10 mmol) were sequentially added, and benzotriazol-1-yl-oxytripyrrolidino phosphononium hexafluoro phosphate (6.24 g, 12 mmol) was added. The resulting solution was stirred for 30 minutes at room temperature, diluted with ethyl acetate (300 mL), washed with water (200 mL) and saline (150 mL), dehydrated with anhydrous sodium sulfate, concentrated under reduced pressure, and applied to column chromatography (MC: MeOH=40:1~10:1) to yield Compound A-II (2.2 g (40%)).

$^1$H NMR (600 MHz, CD$_3$OD) δ 7.92 (s, 1H), 7.45 (d, J=8.4 Hz, 2H), 7.35 (s, 1H), 7.02 (d, J=12.6 Hz, 2H), 6.95 (d, J=12.6 Hz, 2H), 6.66 (d, J=13.2 Hz, 2H), 6.41 (s, 1H), 5.33 (s, 2H), 4.77 (s, 2H), 3.79 (s, 3H), 3.73 (s, 3H), 3.56 (t, J=9.0 Hz, 2H), 3.10 (t, J=9.0 Hz, 2H),

Preparation Example 3

Compound A-III

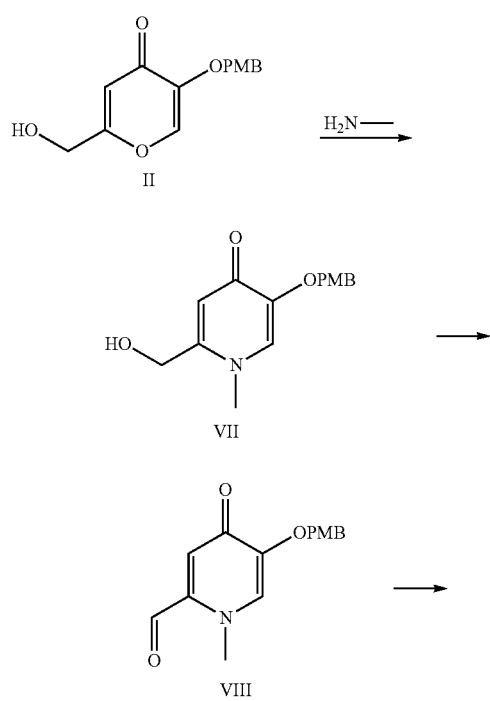

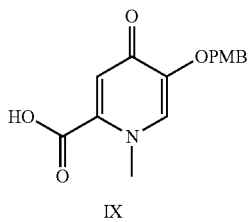

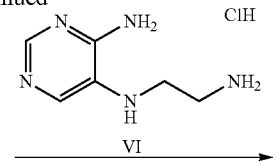

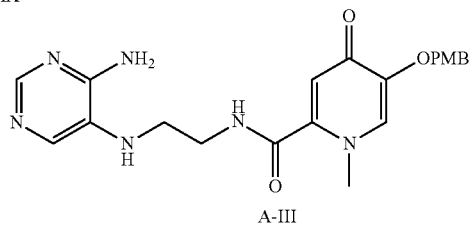

3-1) Preparation of Compound VII:

Compound II (1.0 g, 3.81 mmol) is added to 33% methylamine dissolved in ethanol (19 mL). The resulting solution was stirred for 20 hours at room temperature, creating a white solid. The resulting solution was filtered under reduced pressure to obtain the white solid. The white solid was washed with ethanol (50 mL) and ether (20 mL) to yield Compound VII (778 mg (75%)).

$^1$H NMR (600 MHz, DMSO-d$_6$) δ 7.53 (s, 1H), 7.34 (d, J=9.0 Hz, 2H), 6.94 (d, J=9.0 Hz, 2H), 6.21 (s, 1H), 5.55 (brs, 1H), 4.91 (s, 2H), 4.36 (s, 2H), 3.75 (s, 3H), 3.58 (s, 3H)

3-2) Preparation of Compound VIII:

Compound VII (778 mg, 2.83 mmol) was dissolved in dimethyl sulfoxide (7 mL) and trimethylamine (1.3 g, 12.7 mmol), methylene chloride (7 mL), sulfur trioxide complex (1.35 g, 8.48 mmol) were added. The resulting solution was stirred for 2 hours at room temperature, diluted with chloroform (150 mL), washed with water (30 mL), dehydrated with anhydrous sodium sulfate, concentrated under reduced pressure, and applied to column chromatography (MC: MeOH=30:1~10:1) to yield Compound VIII (718 mg (93%)).

$^1$H NMR (600 MHz, chloroform-d$_1$) δ 9.61 (s, 1H), 7.34 (d, J=8.4 Hz, 2H), 6.99 (s, 1H), 6.97 (s, 1H), 6.88 (d, J=8.4 Hz, 2H), 5.18 (s, 2H), 3.86 (s, 3H), 3.80 (s, 3H)

3-3) Preparation of Compound IX:

Compound VIII (718 mg, 2.63 mmol) was dissolved in a mixture of t-butanol (8.5 mL) and tetrahydrofuran (8.5 mL) and then 2M 2-methyl-2-butene (3.3 mL) dissolved in tetrahydrofuran was added. The resulting solution was stirred at room temperature. To the resulting solution, a solution of sodium chloride (1.9 g, 21.0 mmol) and sodium dihydrogen phosphate monohydrate (2.1 g, 15.2 mmol) dissolved in water (8.5 mL) was added. The resulting solution was stirred for 1 hour at room temperature, creating a white solid. The resulting solution was filtered under reduced pressure to obtain the white solid. The white solid was dissolved in water (4 mL). 1N HCl (pH 1~2) was added. The thus-obtained solid was filtered under reduced pressure and washed with ethyl acetate (50 mL) and ether (50 mL) to yield Compound IX (510 mg (67%)).

$^1$H NMR (600 MHz, DMSO-d$_6$) δ 7.79 (s, 1H), 7.37 (d, J=12.6 Hz, 2H), 6.96 (d, J=12.6 Hz, 2H), 6.71 (s, 1H), 4.97 (s, 2H), 3.83 (s, 3H), 3.76 (s, 3H), 3-4) Preparation of Compound A-III:

Compound A-III (19.mg (25%)) was prepared by a method similar to Preparation Example 2-5 by using Compound VI (34.5 mg, 0.18 mmol).

$^1$H NMR (600 MHz, CD$_3$OD) δ 7.96 (s, 1H), 7.64 (s, 1H), 7.59 (s, 1H), 7.38 (d, J=8.4 Hz, 2H), 6.91 (d, J=8.4 Hz, 2H), 6.56 (s, 1H), 5.02 (s, 2H), 3.79 (s, 3H), 3.77 (s, 3H), 3.61 (t, J=6.0 Hz, 3.39 (t, J=6.6 Hz, 2H)

Preparation Example 4

Compound XI

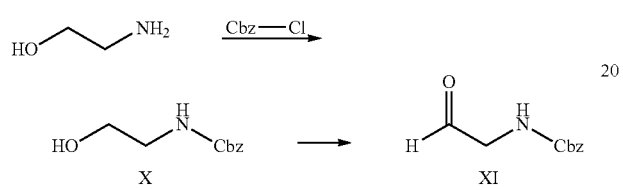

4-1) Preparation of Compound X:

2-aminoethanol (2.0 g, 32.7 mmol) was dissolved in methylene chloride (110 mL) and benzyloxycarbonyl chloride (5.07 g, 29.8 mmol) and triethylamine (4.44 g, 44.6 mmol) were sequentially added. The resulting solution was stirred for 1 hour at room temperature. Water (40 mL) was added to the resulting solution. The resultant was dehydrated with anhydrous sodium sulfate and concentrated under reduced pressure to yield Compound X (4.05 g (70%)).

$^1$H NMR (600 MHz, chloroform-d$_1$) δ=7.40 (m, 5H), 5.19 (brs, 1H), 5.11 (s, 2H), 3.73 (t, J=4.2 Hz, 2H), 3.37 (q, J=5.4 Hz, 2H), 2.23 (brs, 1H)

4-2) Preparation of Compound XI:

Compound XI (2.72 g (91%)) was prepared by a method similar to Preparation Example 3-2 by using Compound X (3 g, 15.3 mmol).

$^1$H NMR (600 MHz, chloroform-d$_1$) δ=9.66 (s, 1H), 7.39 (m, 5H), 5.44 (brs, 1H), 5.13 (s, 2H), 4.16 (d, J=4.8 Hz, 2H)

Preparation Example 5

Compound A-IV

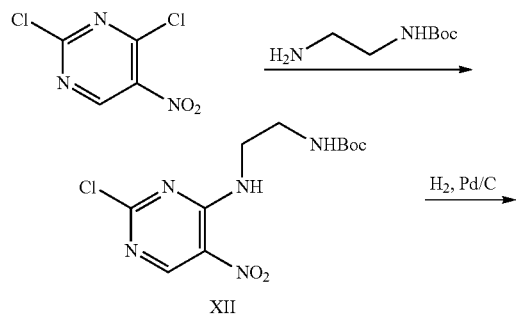

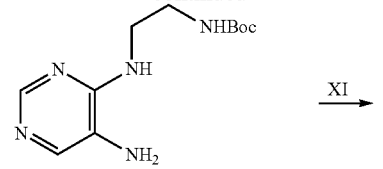

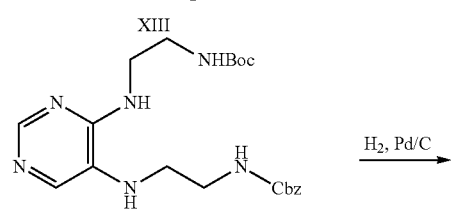

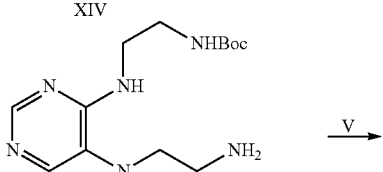

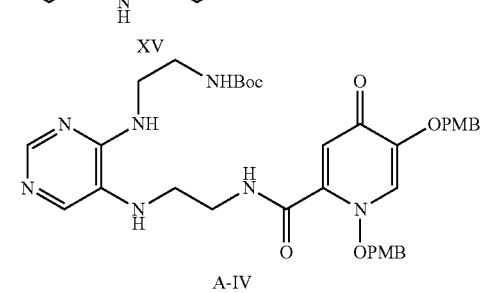

5-1) Preparation of Compound XII:

2,4-dichloro-5-nitropyrimidine (3 g, 15.4 mmol) was dissolved in tetrahydrofuran (50 mL) and isopropyl ethylamine (2.0 g, 15.4 mmol) was added. To the resulting solution, N-Boc-ethyldiamine (2.48 g, 15.4 mmol) dissolved in tetrahydrofuran (20 mL) was slowly added at −78° C. while stirring for 50 minutes and then the resulting solution was stirred for 10 minutes at room temperature. The resultant was concentrated under reduced pressure and applied to column chromatography (EA:Hex=1:4~1:3) to yield Compound XII (3.16 g (64%)).

$^1$H NMR (600 MHz, CDCl$_3$) δ 9.05 (s, 1H), 8.80 (br, 1H), 4.84 (br, 1H), 3.78 (q, J=6 Hz, 2H), 3.48 (q, J=6 Hz, 2H), 1.43 (s, 9H)

5-2) Preparation of Compound XIII:

Compound XII (3.1 g, 9.75 mmol) was dissolved in methanol (50 ml) and 10% palladium charcoal (1 g, 0.98 mmol) was added. The resulting solution was applied to hydrogen purge, stirred for 40 minutes at room temperature, filtered with celite, and concentrated under reduced pressure to yield Compound XIII (2.8 g (99%)).

$^1$H NMR (600 MHz, DMSO-d$^6$) δ 8.62 (br, 1H), 8.33 (s, 1H), 7.48 (s, 1H), 6.99 (brs, 1H), 5.88 (brs, 2H), 3.45 (br, 2H), 3.19 (br, 2H), 1.35 (s, 9H)

5-3) Preparation of Compound XIV:

Compound XIII (1.02 g, 3.52 mmol) was dissolved in 1,2-dichloroethane (34 mL) and diisopropyl ethylamine (455 mg, 3.52 mmol), Compound XI (796 mg, 4.12 mmol), and sodium triacetoxy borohydride (1.12 g, 5.28 mmol) were sequentially added. The resulting solution was stirred for 3 hours at room temperature, diluted with methylene chloride (180 mL), washed with water (100 mL) and saline (100 mL), dehydrated with anhydrous sodium sulfate, concentrated under reduced pressure, and applied to column chromatography (MC:MeOH=60:1~20:1) to yield Compound XIV (218 mg (14%)).

$^1$H NMR (600 MHz, CDCl$_3$) δ 8.22 (s, 1H), 7.60 (s, 1H), 7.34~7.30 (m, 5H), 5.77 (br, 1H), 5.46 (br, 1H), 5.18 (br, 1H), 5.11 (s, 2H), 3.58 (br, 2H), 3.54 (br, 2H), 3.38 (br, 2H), 3.20 (br, 2H), 1.39 (s, 9H)

5-4) Preparation of Compound XV:

Compound XV (150 mg (100%) was prepared by a method similar to Preparation Example 5-2 by using Compound XIV (218 mg, 0.51 mmol) and was used for next step without performing purification.

5-5) Preparation of Compound A-IV:

Compound A-IV (198 mg (57%) was prepared by a method similar to Preparation Example 5-2 by using Compound XV (150 mg, 0.51 mmol) and Compound V (330 mg, 0.51 mmol).

$^1$H NMR (600 MHz, CDCl$_3$) δ 8.22 (s, 1H), 8.44 (br, 1H), 8.09 (s, 1H), 7.55 (d, J=7.8 Hz, 2H), 7.29 (s, 1H), 7.03 (s, 2H), 6.94 (d, J=8.4 Hz, 2H), 6.67 (d, J=7.2 Hz, 2H), 6.44 (m, 3H), 5.49 (br, 2H), 4.48 (s, 2H), 4.32 (br, 1H), 3.79 (s, 3H), 3.75 (s, 3H), 3.60 (br, 2H), 3.42 (br, 2H), 3.09 (br, 2H), 2.79 (br, 2H), 1.39 (9H)

Preparation Example 6

Compound A-V

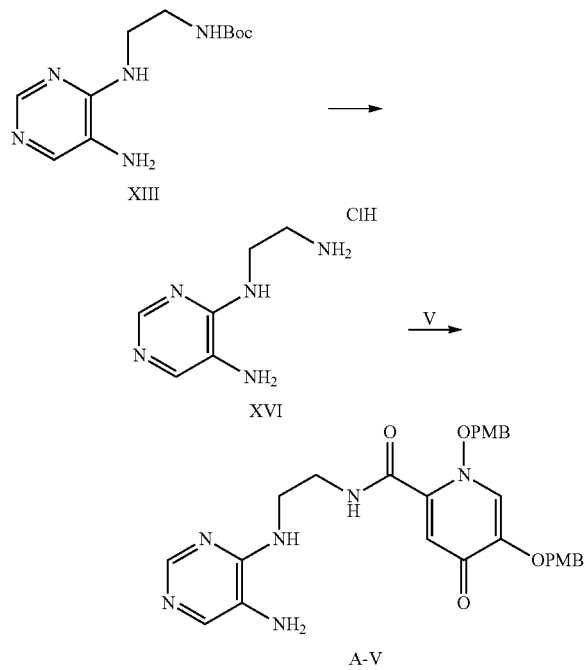

6-1) Preparation of Compound XVI:

4M HCl dissolved in 1,4-dioxane was added to Compound XIII (90 mg, 0.35 mmol). The resulting solution was stirred for 1 hour at room temperature, distilled under reduced pressure, and dried to yield Compound XVI (70 mg (100%)), which was used for next step without performing purification.

6-2) Preparation of Compound A-V:

Compound A-V (103 mg (59%)) was prepared by a method similar to Preparation Example 2-5 by using Compound XVI (60 mg, 0.31 mmol) and Compound V (206 mg, 0.31 mmol).

$^1$H NMR (600 MHz, CDCl$_3$) δ 8.55 (br, 1H), 8.05 (s, 1H), 7.48 (s, 1H), 7.40 (d, J=8.4 Hz, 2H), 7.11 (s, 1H), 6.92 (m, 4H), 6.69 (br, 1H), 6.60 (d, J=7.8 Hz, 2H), 6.33 (s, 1H), 5.35 (s, 2H), 4.48 (s, 2H), 3.80 (s, 3H), 3.73 (s, 3H), 3.44 (br, 2H), 3.34 (br, 2H)

Preparation Example 7

Compound A-VI

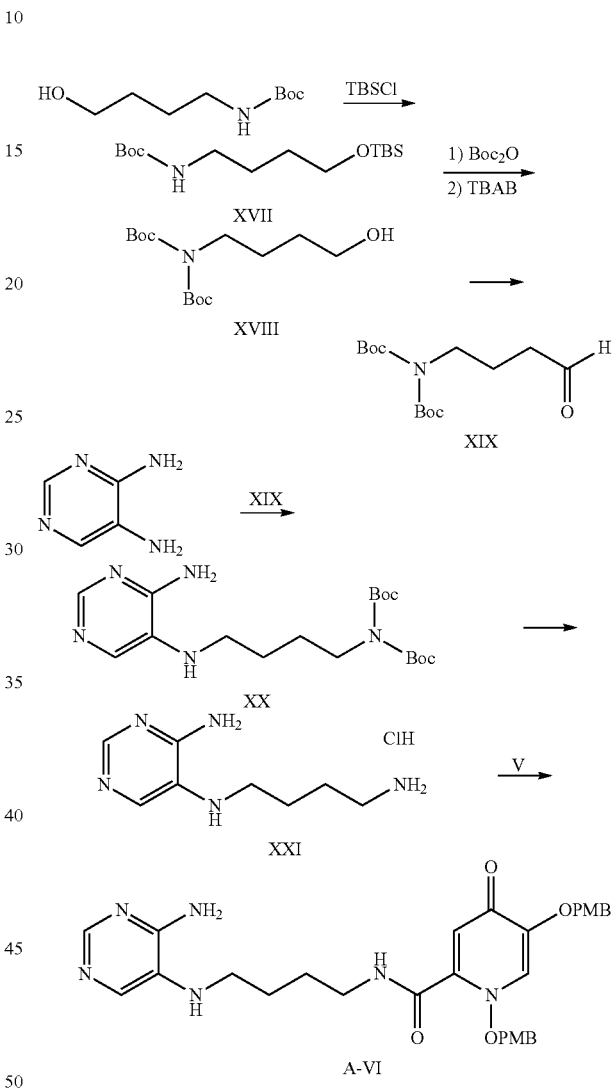

7-1) Preparation of Compound XVII:

Tert-butyl 4-hydroxybutyl carbamate (1.5 g, 7.93 mmol) was dissolved in methylene chloride (36 mL) and imidazole (1.35 g, 19.8 mmol) and tert-butyl dimethylsilyl chloride (1.43 g, 9.51 mmol) were sequentially added at 0° C. The resulting solution was diluted with ether (250 mL), washed with water (40 mL×2) and saline (40 mL×2), dehydrated with anhydrous sodium sulfate, and concentrated under reduced pressure to yield Compound XVII (2.4 g (100%)).

$^1$H NMR (600 MHz, CDCl$_3$) δ 4.68 (s, 1H), 3.63 (m, 2H), 3.13 (br, 2H), 1.54 (m, 4H), 1.43 (s, 9H), 0.88 (s, 9H), 0.04 (s, 6H)

7-2) Preparation of Compound XVIII:

Compound XVII (2.5 g, 8.23 mmol) was dissolved in tetrahydrofuran (50 mL) and 1.6 M n-butyl lithium dissolved in hexane was added at 0° C. Di-tert-butyl dicarbonate (2.15 g, 9.88 mmol) was then added. The resulting solution was stirred for 2 hours at room temperature, diluted with ether (300 mL), washed with water (30 mL) and saline (30 mL), dehydrated with anhydrous sodium sulfate, and concentrated under reduced pressure. The resultant was dissolved in tetrahydrofuran (18 mL) and 1.0M tetrabutyl ammonium bromide (14.8 mL, 14.8 mmol) dissolved in tetrahydrofuran was slowly added. The resulting solution was stirred for 4 and a half hours at room temperature, diluted with ether (150 mL), washed with water (30 mL×2) and saline (40 mL), dehydrated with anhydrous sodium sulfate, concentrated under reduced pressure, and applied to column chromatography (EA: Hex=1:4) to yield Compound XVIII (1.33 g (56%)).

$^1$H NMR (600 MHz, CDCl$_3$) δ 3.68 (m, 2H), 3.61 (t, J=7.2 Hz, 2H), 1.68 (m, 2H), 1.59 (m, 2H), 1.50 (s, 18H)

7-3) Preparation of Compound XIX:

Compound XVIII (330 mg, 1.14 mmol) was dissolved in dimethyl sulfoxide (2.5 mL) and diisopropyl ethylamine (300 mg, 2.30 mmol), methylene chloride (2.5 mL), and sulfur trioxide complex (370 mg, 2.28 mmol) were added at −20° C. The resulting solution was stirred for 30 minutes at room temperature, diluted with ethyl acetate (150 mL), washed with water (40 mL) and saline (40 mL), dehydrated with anhydrous sodium sulfate, and concentrated under reduced pressure to yield Compound XIX (333 mg (100%)).

$^1$H NMR (600 MHz, CDCl$_3$) δ 9.78 (s, 1H), 3.63 (t, J=7.2 Hz, 2H), 2.48 (t, J=7.2 Hz, 2H), 1.91 (m, 2H), 1.50 (s, 18H)

7-4) Preparation of Compound XX:

Compound XX (220 mg (35%)) was prepared by a method similar to Preparation Example 5-3 by using 4,5-diamino pyrimidine (182 mg, 1.65 mmol) and Compound XIX (948 mg, 3.30 mmol).

$^1$H NMR (600 MHz, CDCl$_3$) δ 8.09 (s, 1H), 7.63 (s, 1H), 5.84 (br, 2H), 3.65 (t, J=6.6 Hz, 2H), 3.15 (t, J=6 Hz, 2H), 1.74 (m, 2H), 1.68 (m, 2H), 1.50 (s, 18H)

7-5) Preparation of Compound XXI:

Compound XXI (111 mg (89%)) was prepared by a method similar to Preparation Example 6-1 by using Compound XX (220 mg, 0.58 mmol).

7-6) Preparation of Compound A-VI:

Compound A-VI (153 mg (53%)) was obtained by a method similar to Preparation Example 2-5 by using Compound XXI (110 mg, 0.50 mmol) and Compound V (330 mg, 0.50 mmol).

$^1$H NMR (600 MHz, CDCl$_3$) δ 8.36 (br, 1H), 7.98 (s, 1H), 7.44 (d, J=12.6 Hz, 2H), 7.33 (s, 1H), 7.11 (br, 1H), 6.94 (m, 4H), 6.65 (d, J=12.6 Hz, 2H), 6.25 (s, 1H), 5.85 (br, 2H), 5.34 (s, 2H), 4.49 (s, 2H), 3.77 (s, 3H), 3.75 (s, 3H), 3.26 (br, 2H), 2.78 (br, 2H), 1.63 (br, 2H), 1.44 (br, 2H)

Preparation Example 8

Compound A-VII

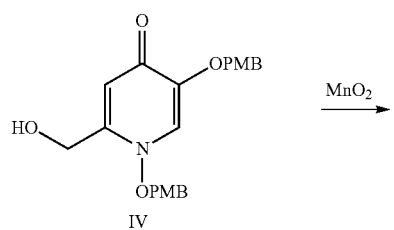

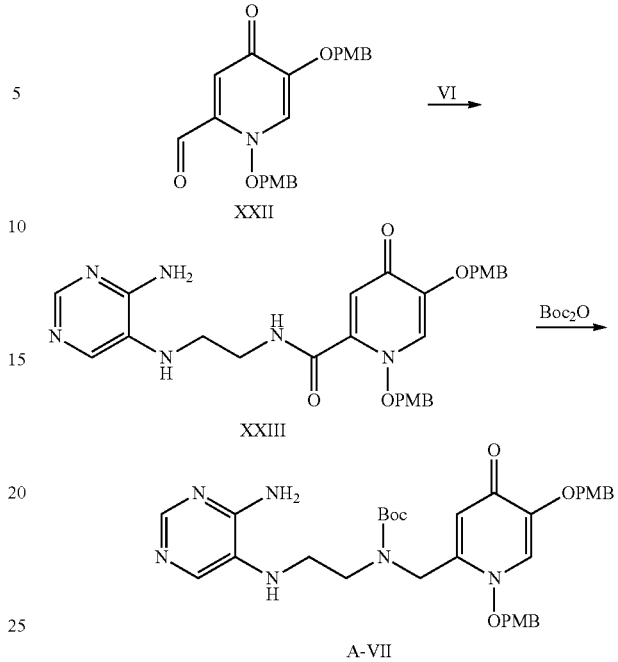

8-1) Preparation of Compound XXII:

Compound IV (1.0 g, 2.51 mmol) was dissolved in acetonitrile (13 mL). Manganese (IV) oxide (5.5 g, 63.5 mmol) was added at 50° C. The resulting solution was stirred for 7 hours, filtered with celite, concentrated under reduced pressure, and applied to column chromatography (MC:MeOH=40:1) to yield Compound XXII (0.73 g (24%)).

8-2) Preparation of Compound XXIII:

Compound VI (60 mg, 0.39 mmol) and Compound XXII (232 mg, 0.59 mmol) were dissolved in methanol (13 ml) and 10 drops of acetic acid were added. The resulting solution was stirred for 12 hours at room temperature. Sodium cyanoborohydride (370 mg, 587 mmol) was added. The resulting solution was stirred for 3 hours at room temperature, concentrated under reduced pressure, and applied to column chromatography (MC:MeOH=50:1~20:1) to yield Compound XXIII (40 mg (20%)).

$^1$H NMR (600 MHz, CD$_3$OD) δ 8.05 (s, 1H), 7.50 (s, 1H), 7.20 (d, J=8.4 Hz, 2H), 7.16 (d, J=8.4 Hz, 2H), 7.05 (s, 1H), 6.88 (d, J=8.4 Hz, 2H), 6.81 (d, J=8.4 Hz, 2H), 6.42 (s, 1H), 5.05 (s, 2H), 4.76 (s, 2H), 3.80 (s, 3H), 3.76 (s, 3H), 3.61 (s, 2H), 3.12 (br, 2H), 2.90 (br, 2H)

8-3) Preparation of Compound A-VII:

Compound XXIII (40 mg, 0.07 mmol) was dissolved in tetrahydrofuran (1 mL) and methanol (0.5 mL). Di-tert-butyl dicarbonate (18 mg, 0.08 mmol) was added. The resulting solution was stirred with reflux for 1 and a half hours, concentrated under reduced pressure, and applied to column chromatography (MC:MeOH=50:1~8:1) to yield Compound A-VII (16 mg (34%)).

$^1$H NMR (600 MHz, CDCl$_3$) δ 8.08 (s, 1H), 7.49~7.43 (br, 1H), 7.22 (Br, 2H), 7.14 (br, 2H), 7.09~7.02 (br, 1H), 6.91~6.87 (br, 2H), 6.79 (br, 2H), 6.12~6.02 (s, 1H), 5.03 (s, 1H), 4.97 (s, 1H), 4.87 (s, 1H), 4.72 (s, 1H), 4.45 (s, 1H), 4.22 (s, 1H), 3.79 (s, 3H), 3.77 (s, 3H), 3.36 (br, 2H), 3.1~3.02 (2H), 1.44~1.35 (br, 9H)

Preparation Example 9

Compound A-VIII

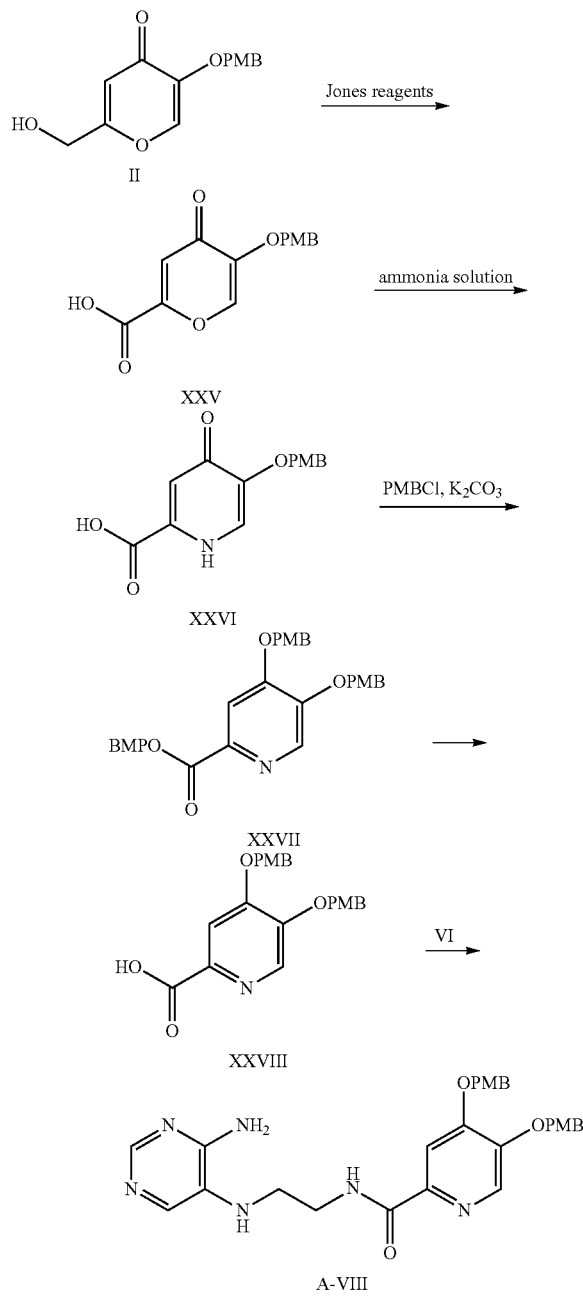

9-1) Preparation of Compound A-VIII:

Compound II (2 g, 7.63 mmol) was dissolved in acetone (100 mL) with heating and Jones reagent ($H_2SO_4$ 1.88 mL, distilled water 6 mL, $CrO_3$ 2.14 g) was slowly added at 0° C. The resulting solution was stirred for 1 hour at 0° C. and then further stirred for 1 hour at room temperature. Methanol (20 ml) was added and the resulting solution was stirred for 5 minutes at room temperature. The resulting solid was removed by filtering under reduced pressure and the filtrate was concentrated under reduced pressure. The resulting solid was washed with methanol to yield Compound XXV (560 mg (27%)).

$^1$H NMR (600 MHz, DMSO-d6) δ 8.34 (s, 1H), 7.37 (d, J=11.4 Hz, 2H), 6.97 (d, J=11.4 Hz, 2H), 6.92 (s, 1H), 4.90 (s, 2H), 3.76 (s, 3H),

9-2) Preparation of Compound XXVI:

Compound XXV (550 mg, 2 mmol) was dissolved in ammonia (15 mL) and the resulting solution was stirred for 2 hours with reflux. Ammonia (7 mL) was then added. The resulting solution was stirred for 1 hour with reflux, cooled to room temperature, and concentrated under reduced pressure to remove excessive ammonia. The resulting solution was acidified with 5N HCl solution and the resulting solid was filtered under reduced pressure to yield Compound XXVI (500 mg (91%)).

$^1$H NMR (600 MHz, DMSO-d6) δ 7.88 (br, 1H), 7.38 (d, J=8.4 Hz, 2H), 7.19 (br, 1H), 6.91 (d, J=7.8 Hz, 2H), 5.15 (s, 2H), 3.72 (s, 3H),

9-3) Preparation of Compound XXVII:

Compound XXVI (200 mg, 0.73 mmol) was dissolved in N,N-dimethylformamide (9 mL). Potassium carbonate (1 g, 7.3 mmol) and 4-methoxybenzyl chloride (570 mg, 3.64 mmol) were sequentially added. The resulting solution was stirred for 18 hours at 60° C., diluted with ethyl acetate (60 mL), and filtered under reduced pressure. The filtrate was washed with water (30 mL×3) and saline (30 mL). The organic layer was dehydrated with anhydrous sodium sulfate. The resultant was applied to column chromatography ($SiO_2$, n-hex:EA=3:1~1:1) to yield Compound XXVII (220 mg (59%)).

$^1$H NMR (600 MHz, chloroform-$d_1$) δ 8.22 (s, 1H), 7.70 (s, 1H), 7.39~7.23 (m, 6H), 6.88~6.84 (m, 6H), 5.31 (s, 2H), 5.15 (s, 2H), 5.12 (s, 2H), 3.79 (s, 3H), 3.78 (s, 3H), 3.77 (s, 3H)

9-4) Preparation of Compound XXVIII:

Compound XXVII (220 mg, 427 umol) was dissolved in tetrahydrofuran (11 mL) and 2N potassium hydroxide aqueous solution (4.4 mL) was added. The resulting solution was stirred for 1 and a half hours with reflux, cooled to room temperature, concentrated under reduced pressure to remove organic solvent, and acidified with 1N HCl solution. The resulting solid was filtered under reduced pressure to yield Compound XXVIII (160 mg (95%)).

$^1$H NMR (600 MHz, DMSO-d6) δ 8.31 (s, 1H), 7.74 (s, 1H), 7.35 (m, 4H), 6.93 (m, 4H), 5.21 (s, 2H), 5.18 (s, 2H), 3.71 (s, 3H), 3.70 (s, 3H)

9-5) Preparation of Compound A-VIII:

Compound A-VIII (110 mg (55%) was prepared by a method similar to Preparation Example 2-5 by using Compound VI (86 mg, 455 umol) and Compound XXVIII (150 mg, 380 umol).

$^1$H NMR (600 MHz, DMSO-d6) δ 8.79 (t, J=5.4 Hz, 1H), 8.25 (s, 1H), 7.84 (s, 1H), 7.73 (s, 1H), 7.56 (s, 1H), 7.39 (m, 4H), 6.97 (m, 4H), 6.40 (br, 2H), 5.22 (s, 2H), 5.20 (s, 2H), 4.97 (t, J=5.4 Hz, 1H), 3.76 (s, 3H), 3.75 (s, 3H), 3.51 (q, J=6.6 Hz, 2H), 3.21 (q, J=6 Hz, 2H)

Preparation Example 10

Compound A-IX

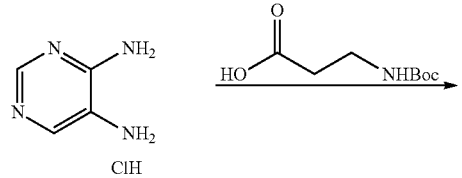

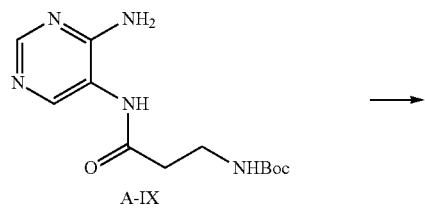

4,5-diaminopyrimidine hydrochloride (100 mg, 0.91 mmol) and 4-dimethylaminopyridine (22 mg, 0.18 mmol) were dissolved in methylene chloride (3 mL) and 3-(tert-butoxycarbonyl)propanoic acid was added. Diisopropyl carbodiimide (138 mg, 1.1 mmol) was then slowly added at 0° C. The resulting solution was stirred at room temperature, concentrated under reduced pressure, and applied to column chromatography (MC:MeOH=40:1~10:1) to yield Compound A-IX (133 mg (52%)).

$^1$H NMR (600 MHz, chloroform-d$_1$) δ=8.44 (s, 1H), 8.34 (s, 1H), 8.17 (br, 1H), 5.67 (br, 1H), 5.16 (br, 1H), 3.56 (q, J=9.0 Hz, 2H), 2.69 (t, J=9.0 Hz, 2H), 1.45 (s, 9H)

Preparation Example 11

Compound A-X

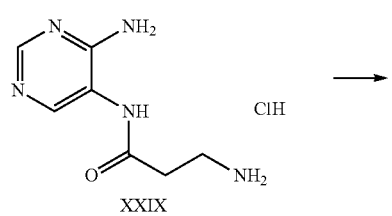

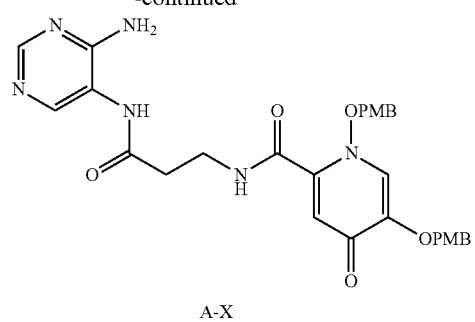

11-1) Preparation of Compound XXIX:

Compound XXIX (112 mg (100%)) was prepared by a method similar to Preparation Example 6-1 by using Compound A-IX (146 mg, 0.52 mmol).

11-2) Preparation of Compound A-X:

Compound A-X (102 mg (61%)) was prepared by a method similar to Preparation Example 2-5 by using Compound XXIX (63 mg, 0.29 mmol) and Compound V (189 mg, 0.29 mmol).

$^1$H NMR (600 MHz, CDCl$_3$) δ 8.29 (s, 1H), 8.19 (s, 1H), 7.27 (br, 2H), 7.09 (br, 2H), 6.97 (s, 1H), 6.87 (d, J=8.4 Hz, 2H), 6.77 (d, J=7.8 Hz, 2H), 6.38 (s, 1H), 5.20 (s, 2H), 4.51 (s, 2H), 3.77 (s, 3H), 3.76 (s, 3H), 3.53 (br, 2H), 2.47 (br, 2H)

Preparation Example 12

Compound A-XI

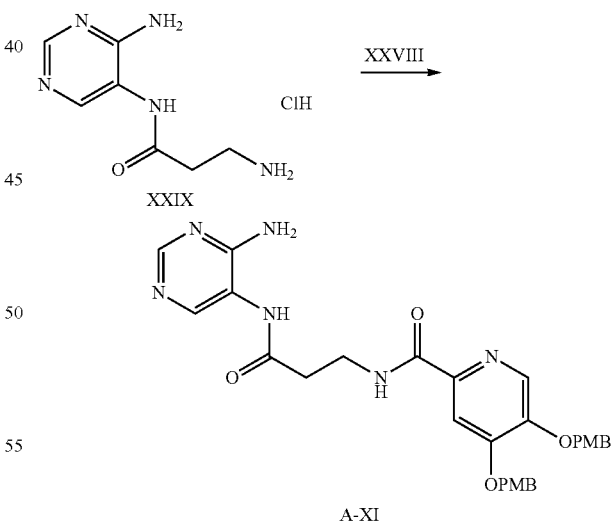

Compound A-XI (147 mg (86%)) was prepared by a method similar to Preparation Example 2-5 by using Compound XXIX (66.3 mg, 0.30 mmol) and Compound XXVIII (120 mg, 0.30 mmol).

$^1$H NMR (600 MHz, CDCl$_3$) δ 8.36 (s, 1H), 8.30 (s, 1H), 8.06 (s, 1H), 7.73 (s, 1H), 7.37 (d, J=8.4 Hz, 2H), 7.31 (d, J=8.4 Hz, 2H), 6.91 (d, J=8.4 Hz, 2H), 6.87 (d, J=8.4 Hz, 2H), 5.16 (s, 2H), 5.13 (s, 2H), 3.80 (s, 3H), 3.79 (s, 3H), 3.75 (t, J=5.4 Hz, 2H), 2.72 (t, J=6 Hz, 2H)

Preparation Example 13

Compound A-XII

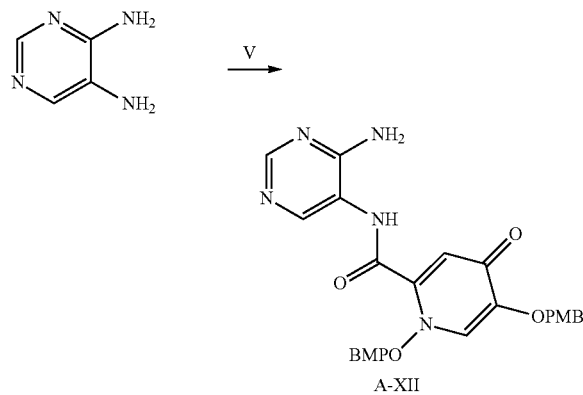

Compound A-XII (146 mg (16%)) was prepared by a method similar to Preparation Example 2-5 by using 4,5-diaminopyrimidine (200 mg, 1.81 mmol) and Compound V (1.18 g, 1.81 mmol).

$^1$H NMR (600 MHz, DMSO-d$^6$) δ 8.28 (s, 1H), 8.19 (s, 1H), 8.06 (s, 1H), 7.38 (m, 4H), 6.98 (m, 4H), 5.28 (s, 2H), 4.95 (s, 2H), 3.76 (s, 3H), 3.75 (s, 3H)

Preparation Example 14

Compound A-XIII

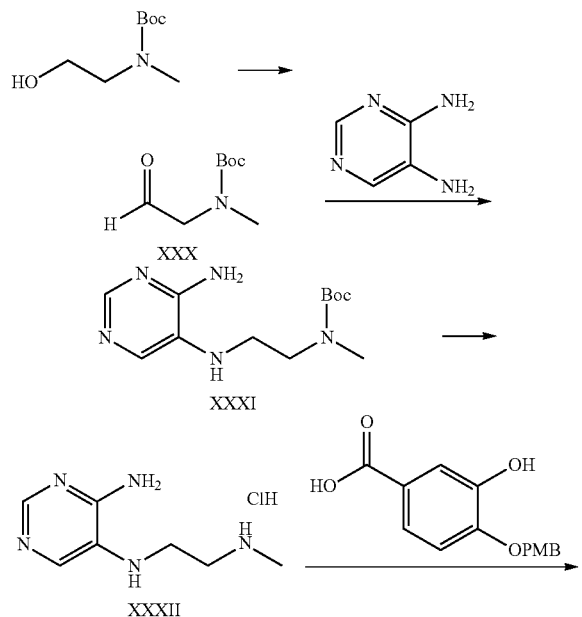

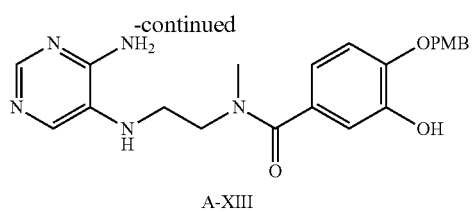

14-1) Preparation of Compound XXX:

Compound XXX (12 g (71%)) was prepared by a method similar to Preparation Example 3-2 by using tert-butyl 2-hydroxyethyl(methyl)carbamate (17 g, 97 mmol).

$^1$H NMR (600 MHz, chloroform-d$_1$) δ=9.61 (s, 1H), 3.92 (s, 2H), 2.92 (s, 3H), 1.46 (s, 9H)

14-2) Preparation of Compound XXXI:

Compound XXXI (180 mg (38%)) was prepared by a method similar to Preparation Example 8-2 by using 4,5-diaminopyrimidine (200 mg, 1.82 mmol) and Compound XXX (536 mg, 3.09 mmol).

$^1$H NMR (600 MHz, chloroform-d$_1$) δ 8.09 (s, 1H), 7.53 (s, 1H), 6.74 (br, 2H), 3.48~3.32 (m, 4H), 2.97 (s, 3H), 1.46 (s, 9H)

14-3) Preparation of Compound XXXII:

Compound XXXII was prepared by a method similar to Preparation Example 6-1 by using Compound XXXI (180 mg, 0.67 mmol) and used for next step without performing purification.

14-4) Preparation of Compound A-XIII:

Compound A-XIII (30 mg (22%)) was prepared by a method similar to Preparation Example 2-5 by using Compound XXXII (70 mg, 0.34 mmol) and 3-hydroxy-4-(4-methoxybenzyloxy)benzoic acid (103 mg, 0.38 mmol).

$^1$H NMR (600 MHz, chloroform-d$_1$) δ 8.11 (s, 1H), 7.64 (s, 1H), 7.37 (d, J=8.4 Hz, 2H), 7.03 (br, 1H), 6.93 (d, J=8.4 Hz, 2H), 6.81 (br, 1H), 5.21 (m, 3H), 3.80 (s, 3H), 3.42 (br, 5H), 3.07 (br, 2H)

Preparation Example 15

Compound A-XIV

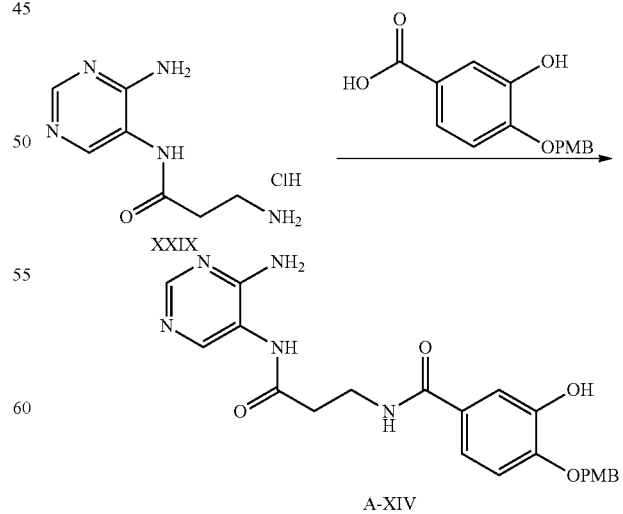

Compound A-XIV (35 mg (49%)) was prepared by a method similar to Preparation Example 2-5 by using Compound XXIX (35 mg, 0.16 mmol) and 3-hydroxy-4-(4-methoxybenzyloxy)benzoic acid (49 mg, 0.18 mmol).

¹H NMR (600 MHz, DMSO-d₆, +D₂O) δ 8.22 (s, 1H), 8.16 (s, 1H), 7.41 (d, J=8.4 Hz, 2H), 7.29 (d, J=1.8 Hz, 1H), 7.26 (dd, J=1.8 Hz, 9.4 Hz, 1H), 7.04 (d, J=8.4 Hz, 2H), 6.95 (d, J=8.4 Hz, 2H), 5.09 (s, 2H), 3.76 (s, 3H), 3.54 (t, J=7.2 Hz, 2H), 2.61 (t, J=7.2 Hz, 2H)

Preparation Example 16

Compound A-XV

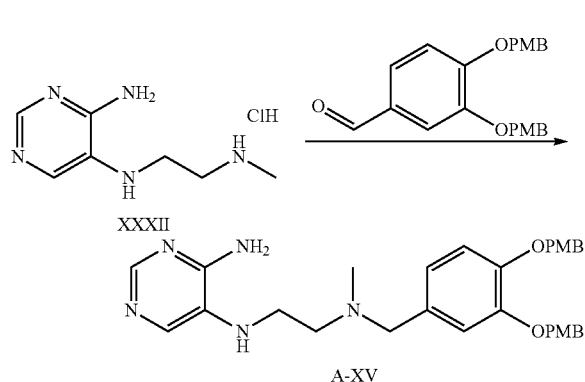

Compound A-XV (221 mg (43%)) was prepared by a method similar to Preparation Example 8-2 by using Compound XXXII (200 mg, 0.98 mmol) and 3,4-bis(4-methoxybenzyloxy)benzaldehyde (408 mg, 1.08 mmol).

¹H NMR (600 MHz, DMSO-d₆) δ 7.94 (s, 1H), 7.47 (s, 1H), 7.31 (m, 4H), 7.08 (br, 1H), 6.99 (br d, 1H), 6.90 (m, 5H), 5.94 (br, 2H), 4.97 (s, 2H), 4.94 (s, 2H), 3.71 (s, 3H), 3.70 (s, 3H), 3.30 (br, 5H), 2.85 (br, 2H), 2.41 (m, 2H), 3.02 (d, J=4.2 Hz, 3H)

Preparation Example 17

Compound A-XVI

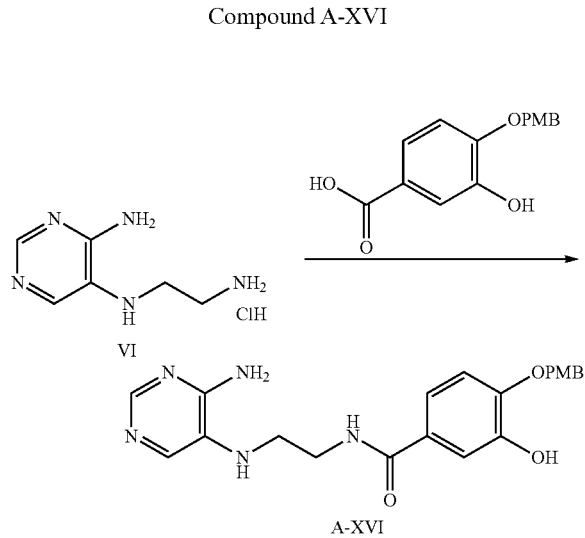

Compound A-XVI (40 mg (20%)) was prepared by a method similar to Preparation Example 2-5 by using Compound VI (95 mg, 500 umol) and 3-hydroxy-4-(4-methoxybenzyloxy)benzoic acid (165 mg, 600 umol).

¹H NMR (600 MHz, DMSO-d₆) δ 9.17 (s 1H) 8.30 (t, J=6 Hz, 1H), 7.8 (s, 1H) 7.52 (s, 1H), 7.36 (d, J=8.4 Hz, 2H), 7.28 (d, J=1.8 Hz, 1H), 7.24 (dd, J=8.4 Hz, 2.4H, 1H), 7.00 (d, J=8.4 Hz, 1H), 6.91 (d, J=9 Hz, 2H), 6.34 (br, 2H) 5.04 (s, 2H), 4.93 (br, 1H) 3.71 (s, 3H), 3.38 (q, J=6 Hz, 2H), 3.17 (q, J=6 Hz, 2H)

Preparation Example 18

Compound A-XVII

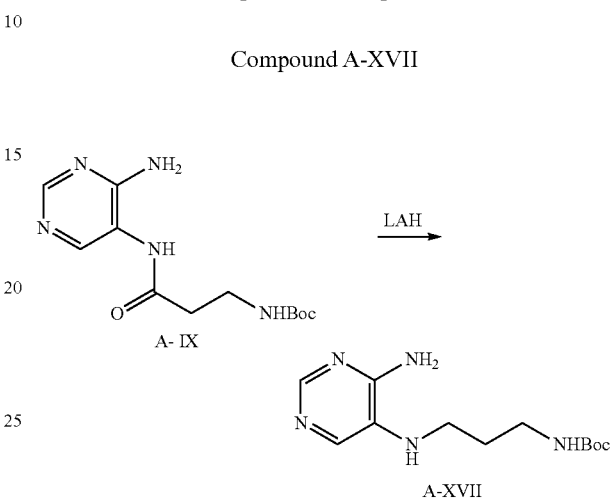

Compound A-IX (450 mg, 1.6 mmol) was dissolved in anhydrous tetrahydrofuran (12 mL) and lithium aluminium hydride (152 mg, 3.2 mmol) was slowly added at 0° C. The resulting solution was stirred for 3 hours at room temperature. 15% sodium hydroxide aqueous solution (200 uL) was then added. The resulting solution was stirred for 1 hour at room temperature. The-thus obtained solid was filtrated under reduced pressure. The filtrate was concentrated under reduced pressure. The resultant was applied to column chromatography (SiO₂, MC:MeOH=30:1~10:1) to yield Compound A-XVII 140 mg (33%).

¹H NMR (600 MHz, chloroform-d₁+CD₃OD) δ 8.01 (s, 1H), 7.44 (s, 1H), 3.23~3.12 (m, 4H), 1.85 (m, 2H), 1.48 (s, 9H), Preparation Example 19

Compound A-XVIII

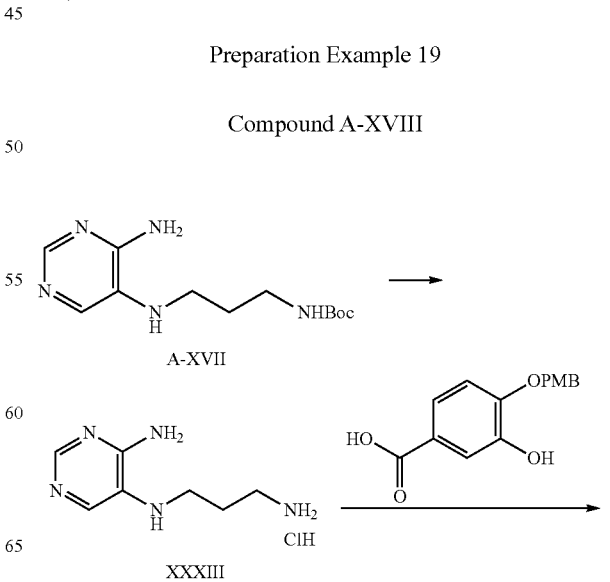

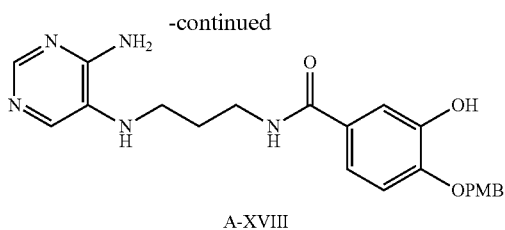

A-XVIII 19-1) Preparation of Compound XXXIII:
Compound XXXIII (110 mg (100%)) was prepared by a method similar to Preparation Example 6-1 by using Compound A-XVII (150 mg, 560 umol).

19-2) Preparation of Compound A-XVIII:
Compound A-XVIII (35 mg (41%)) was prepared by a method similar to Preparation Example 2-5 by using Compound XXXIII (50 mg, 245 umol) and 3-hydroxy-4-(4-methoxybenzyloxy)benzoic acid (92 mg, 335 umol).
$^1$H NMR (600 MHz, DMSO-$d_6$) δ 9.15 (s, 1H), 8.24 (t, J=6 Hz, 1H), 7.78 (s, 1H), 7.38 (s, 1H), 7.37 (d, J=8.4 Hz, 2H), 7.26 (d, J=2.4 Hz, 1H), 7.22 (dd, J=8.4 Hz, 2.4 Hz, 1H), 6.99 (d, J=8.4 Hz, 1H), 6.90 (d, J=8.4 Hz), 6.37 (br, 2H), 5.03 (s, 2H), 4.73 (t, J=5.4 Hz, 1H), 3.71 (s, 3H), 3.30 (m, 2H), 3.04 (q, J=6.6 Hz, 2H), 1.80 (m, 2H)

Preparation Example 20

Compound A-XIX

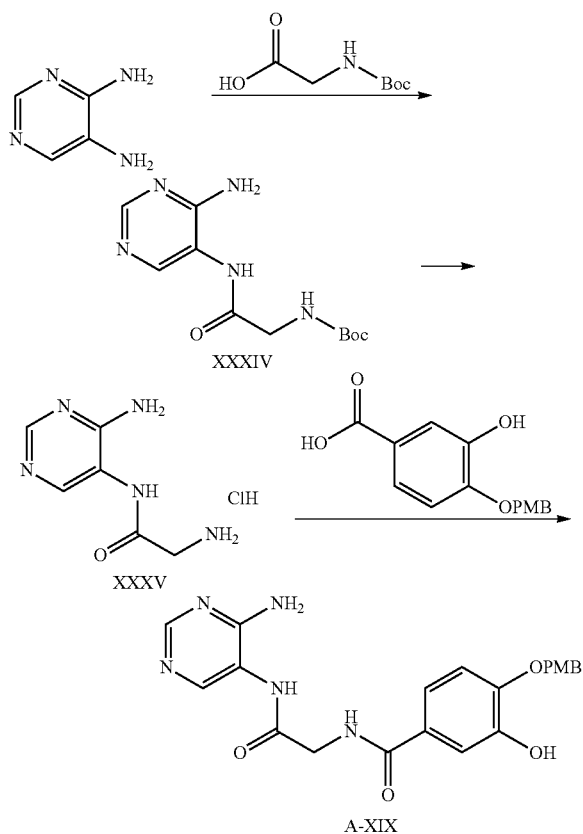

20-1) Preparation of Compound XXXIV:
Compound XXXIV (854 mg (70%)) was prepared by a method similar to Preparation Example 2-5 by using 4,5-diaminopyrimidine (500 mg, 4.54 mmol) and 2-(tert-butoxycarbonylamino)acetic acid (876 mg, 4.99 mmol).
$^1$H NMR (600 MHz, chloroform-$d_1$) δ 8.46 (s, 1H), 8.25 (br, 1H), 8.11 (br, 1H), 5.45 (br d, 3H), 3.91 (s, 2H), 1.48 (s, 9H)

20-2) Preparation of Compound XXXV:
Compound XXXV (650 mg (100%)) was prepared by a method similar to Preparation Example 6-1 by using Compound XXXIV (854 mg, 3.19 mmol).

20-3) Preparation of Compound A-XIX:
Compound A-XIX (357 mg (68%)) was prepared by a method similar to Preparation Example 2-5 by using Compound XXXV (250 mg, 1.23 mmol) and 3-hydroxy-4-(4-methoxybenzyloxy)benzoic acid (337 mg, 1.23 mmol).
$^1$H NMR (600 MHz, DMSO-$d_6$) δ 8.24 (s, 1H), 8.14 (s, 1H), 7.41 (d, J=8.4 Hz, 2H), 7.35~7.31 (m, 2H), 7.07 (d, J=8.0 Hz, 1H), 6.95 (d, J=8.4 Hz, 2H), 6.79 (br, 2H), 5.10 (s, 2H), 4.02 (d, J=6.0 Hz, 2H)

Preparation Example 21

Compound A-XX

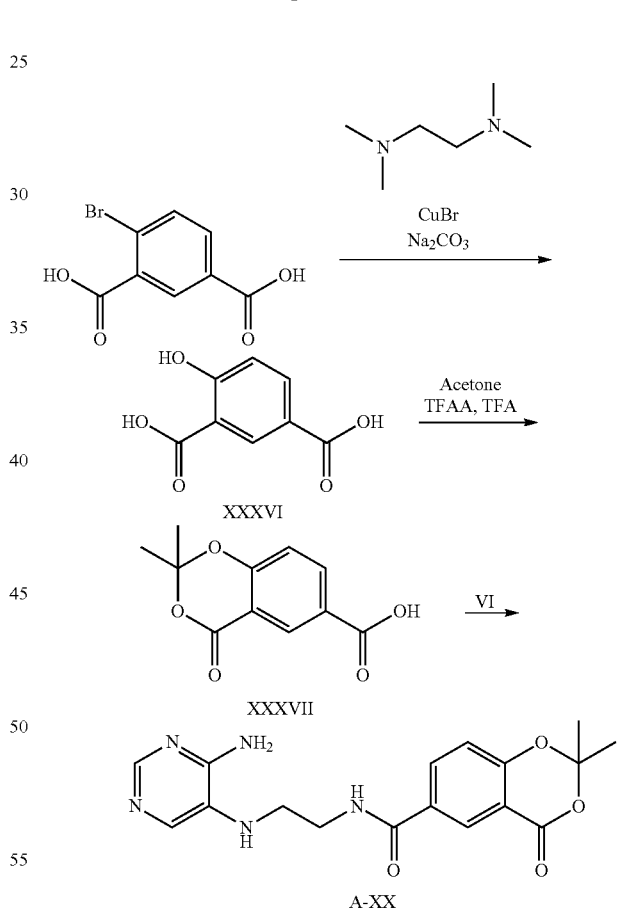

21-1) Preparation of Compound XXXVI:
4-bromoasophthalic acid (1 g, 4.1 mmol) was dissolved in distilled water (4 mL) and sodium bicarbonate (1.2 g, 11 mmol) was added. The resulting solution was stirred for 1 and a half our at 85° C. $N^1$, $N^1$, $N^2$, $N^2$-tetramethylethane-1,2-diamine (31 mg, 270 umol) and cooper bromide (18 mg, 126 umol) were dissolved in distilled water (0.5 mL). The resulting solution was stirred for 1 hour. The two resulting solutions were mixed and stirred for 18 hours at 85° C., cooled to room temperature, and acidified with 1N HCl aqueous solution. The resulting solid was filtered under reduced pressure, washed with water, and dried under reduced pressure to yield Compound XXXVI (720 mg (97%)).

¹H NMR (600 MHz, DMSO-$d_6$) δ 8.34 (t, J=3.6 Hz, 1H), 8.04 (dt, J=1.2 Hz, 13.2 Hz, 1H), 7.05 (dd, J=3.6 Hz, 12.6 Hz, 1H)

21-2) Preparation of Compound XXXVII:

Compound XXXVI (720 mg, 3.95 mmol) was dissolved in trifluoroacetic acid (4.32 mL). Acetone (2 mL) and trifluoroacetic anhydride (TFAA) (1.45 mL) were added sequentially. The resulting solution was stirred for 8 hours at 100° C., cooled to room temperature, and concentrated under reduced pressure. The resultant was dissolved in ethyl acetate (100 mL) and washed with 1N HCl aqueous solution (50 mL). The organic layer was dehydrated with anhydrous sodium sulfate and concentrated under reduced pressure. The thus-obtained solid was filtered under reduced pressure to yield Compound XXXVII (500 mg (57%)).

¹H NMR (600 MHz, chloroform-$d_1$) δ 8.76 (d, J=2.4 Hz, 1H), 8.30 (dd, J=9.0 Hz, 1.8 Hz, 1H), 7.08 (d, J=8.4 Hz, 1H), 1.78 (s, 6H)

21-3) Preparation of Compound A-XX:

Compound A-XX (90 mg (72%)) was prepared by a method similar to Preparation Example 2-5 by using Compound VI (80 mg, 416 umol) and Compound XXXVII (78 mg, 350 umol).

¹H NMR (600 MHz, CD$_3$OD) δ 8.42 (d, J=3.6 Hz, 1H), 8.13 (m, 1H), 7.94 (s, 1H), 7.61 (s, 1H), 7.14 (d, 12.6 Hz, 1H) 3.66 (t, 9.6 Hz, 2 Hz) 3.40 (t, 9.6 Hz, 2H), 1.74 (s, 6H),

Preparation Example 22

Compound A-XXI

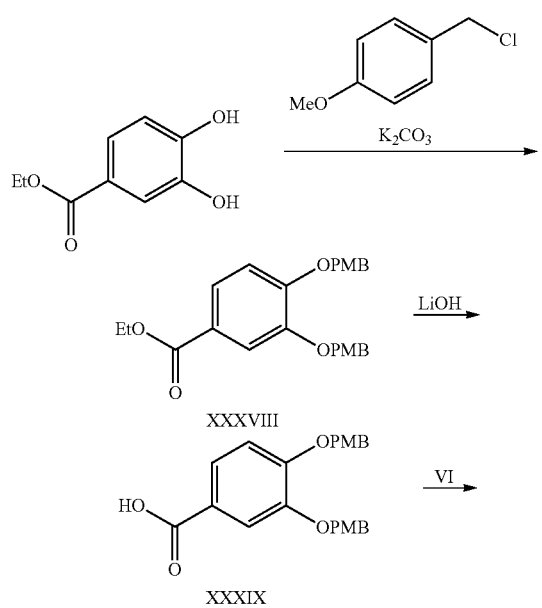

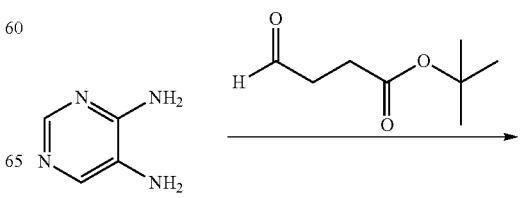

22-1) Preparation of Compound XXXVIII:

Ethyl 3,4-dihydroxybenzoate (5 g, 28 mmol) was dissolved in N,N-dimethylformamide (50 mL) and potassium carbonate (15 g, 110 mmol) was added. The resulting solution was stirred for 2 days at room temperature, diluted with ethyl acetate (400 mL), and filtered under reduced pressure. The filtrate was washed with water (300 mL×3) and saline (300 mL). The organic layer was concentrated under reduced pressure. Hexane was added to the resultant. The thus-obtained solid was filtered under reduced pressure to yield Compound XXXVIII (11 g (97%)).

¹H NMR (600 MHz, chloroform-$d_1$) δ 7.64 (d, J=1.8 Hz, 1H), 7.63 (dd, J=7.8 Hz, 2.4 Hz, 1H), 7.38 (m, 4H), 6.93 (m, 5H), 5.13 (s, 2H), 5.11 (s, 2H), 4.35 (q, J=7.2 Hz, 2H), 3.81 (s, 6H), 1.38 (t, J=7.2 Hz, 3H)

22-2) Preparation of Compound XXXIX:

Compound XXXVIII (11 g, 27 mmol) was dissolved in tetrahydrofuran (120 mL) and ethanol (130 mL). 2N lithium hydroxide aqueous solution (52 mL) was added. The resulting solution was stirred for 12 hours at room temperature, concentrated under reduced pressure, diluted with distilled water (200 mL), and washed with ethyl acetate (200 mL). The thus-obtained aqueous solution layer was acidified with 1N HCl aqueous solution. The thus-obtained solid was filtered under reduced pressure and vacuum dried to yield Compound XXXIX (8.6 g (81%)).

¹H NMR (600 MHz, DMSO-$d_6$) δ 7.50 (m, 2H), 7.34 (m, 4H), 7.11 (d, J=9.6 Hz, 1H), 6.91 (m, 4H), 5.07 (s, 2H), 5.02 (s, 2H), 3.71 (s, 6H)

22-3) Preparation of Compound A-XXI:

Compound A-XXI (300 mg (57%)) was prepared by a method similar to Preparation Example 2-5 by using Compound VI (190 mg, 1 mmol) and Compound XXXIX (410 mg, 1.1 mmol).

¹H NMR (600 MHz, DMSO-$d_6$) δ 8.46 (t, J=5.4 Hz, 1H), 7.84 (s, 1H), 7.56 (d, 11.4 Hz, 2H), 7.46 (dd, J=9.0 Hz, 2.4 Hz, 1H), 7.37 (d, J=9 Hz, 4H), 7.132 (d, J=8.4 Hz, 1H), 6.94 (d, J=9 hz, 4H), 6.37 (br, 2H) 5.09 (s, 2H), 5.06 (s, 2H), 4.99 (t, J=5.4 Hz, 1H), 3.75 (s, 6H), 3.45 (q, J=6 Hz, 2H), 3.26 (q, J=6 Hz, 2H)

Preparation Example 23

Compound A-XXII

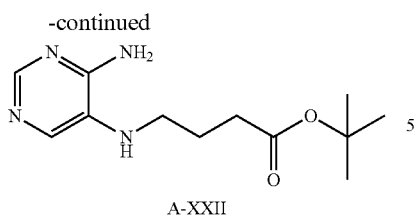

A-XXII

Compound A-XXII (135 mg (59%)) was prepared by a method similar to Preparation Example 8-2 by using 4,5-diaminopyrimidine hydrochloride (100 mg, 0.91 mmol) and tert-butyl 4-oxobutanoate (158 mg, 0.99 mmol).

$^1$H NMR (600 MHz, chloroform-$d_1$) δ=8.11 (s, 1H), 7.33 (s, 1H), 6.43 (br, 2H), 5.06 (br, 1H), 3.16 (t, J=6.6 Hz, 2H), 2.48 (t, J=6.6 Hz, 2H), 2.02 (m, 2H), 1.47 (s, 9H)

Preparation Example 24

Compound A-XXIII

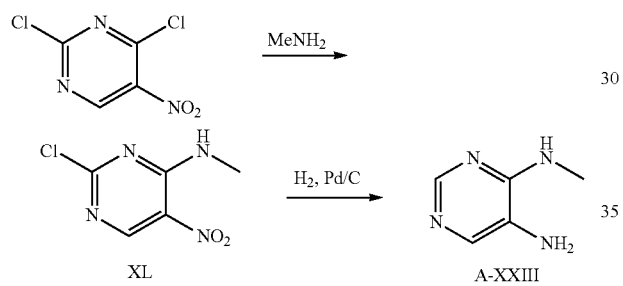

24-1) Preparation of Compound XL:

2,4-dichloro-5-nitropyrimidine (3 g, 15.4 mmol) was dissolved in tetrahydrofuran (52 mL) and 2N methylamine (15.4 mL) dissolved in tetrahydrofuran was slowly added at −78° C. The resulting solution was stirred for 10 minutes and then further stirred for 50 minutes at room temperature. The resulting solution was concentrated under reduced pressure, diluted with ethyl acetate (50 mL), and washed with water (30 mL) and saline (30 mL). The resultant was dehydrated with anhydrous sodium sulfate, concentrated under reduced pressure, and applied to column chromatography (EA:Hex=20:1~5:1) to yield Compound XL (925 mg (32%)).

$^1$H NMR (600 MHz, chloroform-$d_1$) δ 9.05 (s, 1H), 8.41 (br, 1H), 3.23 (d, J=4.8 Hz, 3H), 24-2) Preparation of Compound A-XXIII:

Compound XL (506 mg, 2.68 mmol) was dissolved in methanol (5 mL) and 10% palladium charcoal (285 mg, 0.27 mmol) was added. The resulting solution was applied to hydrogen gas purge, stirred for 2 hours at room temperature, filtered with celite, and concentrated under reduced pressure to yield Compound A-XXIII (411 mg (98%)).

$^1$H NMR (600 MHz, DMSO-$d_6$) δ 8.87 (br, 1H), 8.37 (s, 1H), 7.47 (s, 1H), 5.94 (br, 2H), 3.02 (d, J=4.2 Hz, 3H)

Preparation Example 25

Compound A-XXIV

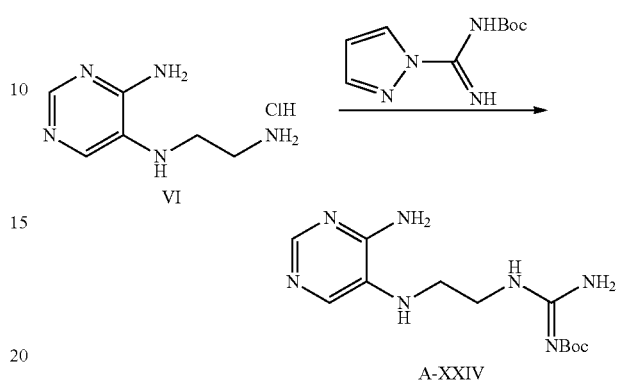

A-XXIV

Compound VI (50 mg, 0.32 mmol) was dissolved in methanol (1 mL). Triethylamine (40 mg, 0.40 mmol) and tert-butyl imino(1H-pyrazole-1-yl)methylcarbamate (69 mg, 0.32 mmol) were added. The resulting solution was stirred for 15 hours at room temperature, concentrated under reduced pressure, and applied to column chromatography (MC:MeOH=10:1~7:1) to yield Compound A-XXIV (24 mg (25%)).

$^1$H NMR (600 MHz, $CD_3OD$) δ 8.02 (br, 1H), 7.60 (br, 1H), 3.64 (t, J=5.4 Hz, 2H), 3.44 (br, 2H), 1.55 sm, 9H)

Preparation Example 26

Compound A-XXV

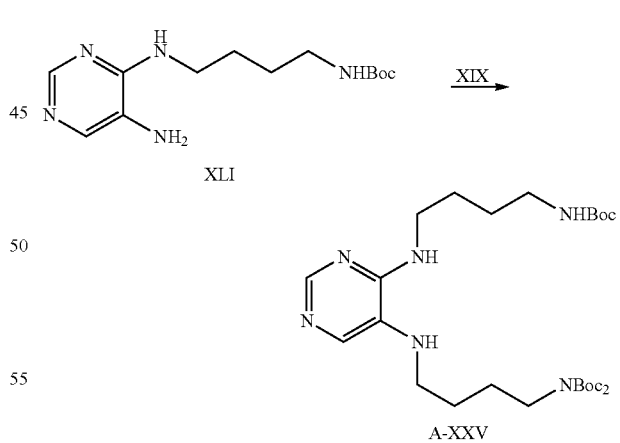

A-XXV

Compound A-XXV (189 mg (50%)) was prepared by a method similar to Preparation Example 8-2 by using Compound XLI (192 mg, 0.68 mmol) and Compound XIX (333 mg, 1.16 mmol).

$^1$H NMR (600 MHz, $CDCl_3$) δ 8.19 (s, 1H), 7.49 (s, 1H), 6.07 (br, 1H), 4.92 (br, 1H), 3.64 (t, J=7.2 Hz, 2H), 3.53 (br, 2H), 3.20 (br, 2H), 3.11 (t, J=6.6 Hz, 2H), 1.72 (m, 6H), 1.60 (m, 2H), 1.50~1.44 (m, 27H)

Preparation Example 27

Compound A-XXVI

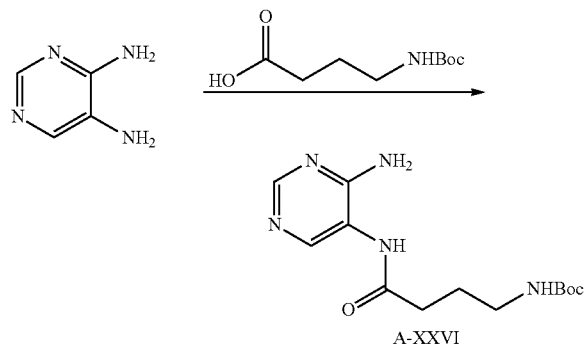

Compound A-XXVI (228 mg (59%)) was prepared by a method similar to Preparation Example 2-5 by using 4,5-diaminopyrimidine (144 mg, 1.31 mmol) and 4-(tert-butoxycarbonylamino)butanoic acid (266 mg, 1.31 mmol).

$^1$H NMR (600 MHz, CD$_3$OD) δ 8.30 (s, 1H), 8.24 (s, 1H), 3.18 (t, J=6 Hz, 2H), 2.51 (t, J=6.6 Hz, 2H), 1.89 (t, J=6.6 Hz, 2H), 1.47 (s, 9H)

Preparation Example 28

Compound A-XXVII

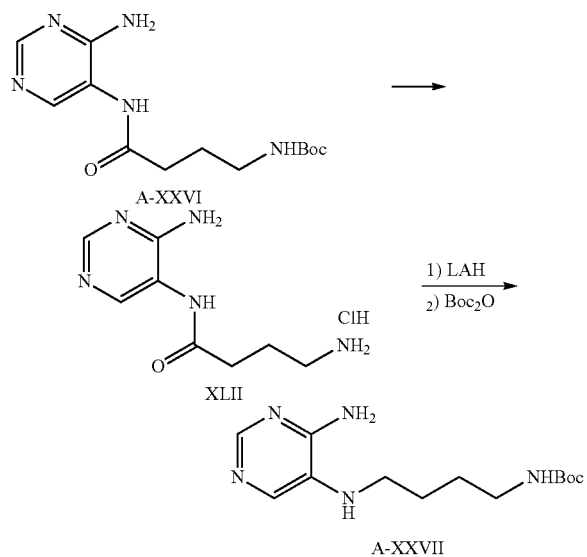

28-1) Preparation of Compound XLII:
Compound XLII (180 mg (100%)) was prepared by a method similar to Preparation Example 6-1 by using Compound A-XXVI (232 mg, 0.78 mmol).

28-2) Preparation of Compound A-XXVII:
Lithium aluminium hydride (87 mg, 2.3 mmol) was added to tetrahydrofuran (5 mL) and the resulting solution was stirred at room temperature. After adding Compound XLII (180 mg, 0.78 mmol), the resulting solution was stirred for 20 minutes with reflux. 15% sodium hydroxide aqueous solution (0.1 mL) was added. The thus-obtained solid was filtered under reduced pressure. The filtrate was concentrated under reduced pressure and dissolved in methanol (4 mL). Di-tert-butyl dicarbonate (171 mg, 0.78 mmol) was added. The resulting solution was stirred for 30 minutes with reflux, concentrated under reduced pressure, and applied to column chromatography (MC:MeOH=45:1~15:1) to yield Compound A-XXVII (25.6 mg (11%)).

$^1$H NMR (600 MHz, CDCl$_3$) δ 8.14 (s, 1H), 7.62 (s, 1H), 3.28 (br, 2H), 3.15 (br, 2H), 1.71 (m, 2H), 1.64 (m, 2H), 1.45 (s, 9H)

Preparation Example 30

Compound A-XXVIII

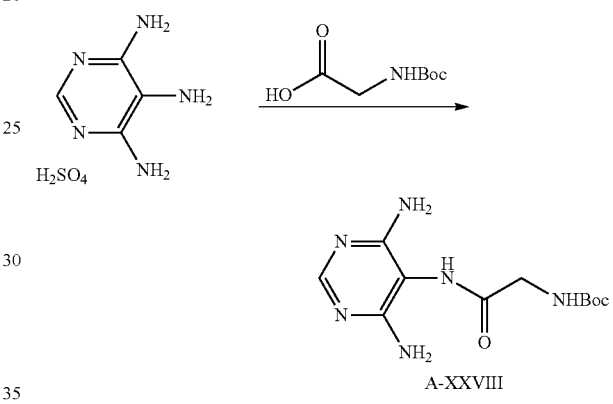

Compound A-XXVIII (135 mg (55%)) was prepared by a method similar to Preparation Example 2-5 by using 4,5,6-triaminopyrimidine sulfate (200 mg, 0.86 mmol) and 2-(tert-butoxycarbonylamino)acetic acid (166 mg, 0.95 mmol).

$^1$H NMR (600 MHz, CD$_3$OD) δ 7.83 (s, 1H), 3.82 (s, 2H), 1.46 (s, 9H)

Preparation Example 31

Compound A-XXIX

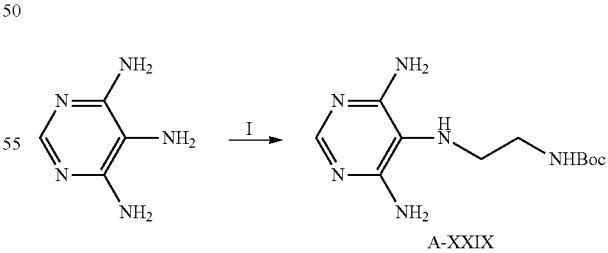

Compound A-XXIX (257 mg (62%)) was prepared by a method similar to Preparation Example 8-2 by using 4,5,6-triaminopyrimidine (193 mg, 1.54 mmol) and Compound I (370 mg, 2.31 mmol).

$^1$H NMR (600 MHz, CD$_3$OD) δ 7.89 (s, 1H), 3.19 (t, J=6 Hz, 2H), 2.90 (t, J=6 Hz, 2H), 1.42 (s, 9H)

Preparation Example 32

Compound A-XXX

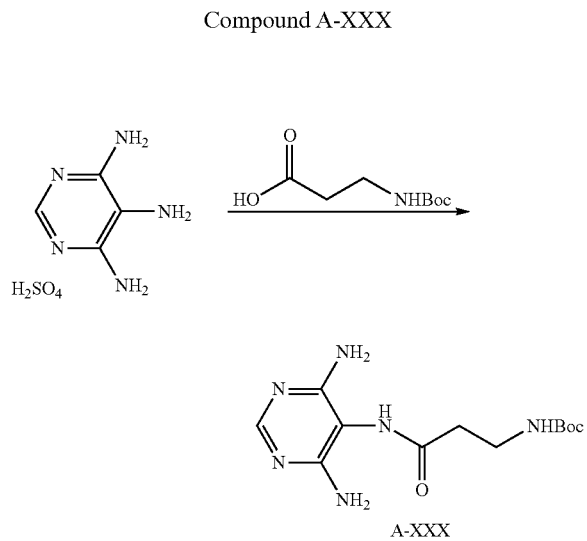

Compound A-XXX (112 mg (44%)) was prepared by a method similar to Preparation Example 2-5 by using 4,5,6-triaminopyrimidine sulfate (200 mg, 0.86 mmol) and 2-(tert-butoxycarbonylamino)acetic acid (179 mg, 0.95 mmol).

$^1$H NMR (600 MHz, CD$_3$OD) δ 7.81 (s, 1H), 3.42 (t, J=6.6 Hz, 2H), 2.60 (t, J=6 Hz, 2H), 1.43 (s, 9H)

Preparation Example 33

Compound A-XXXI

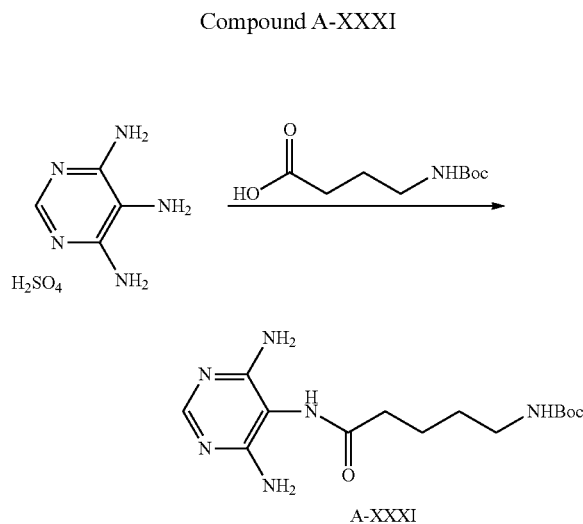

Compound A-XXXI (420 mg (60%)) was obtained as a white solid by a method similar to Preparation Example 2-5 by using 4,5,6-triaminopyrimidine sulfate (500 mg, 2.24 mmol) and 3-(tert-butoxycarbonylamino)butanoic acid (500 mg, 2.46 mmol).

$^1$H NMR (400 MHz, DMSO d-$_6$) δ 8.47 (s, 1H), 7.72 (s, 1H), 6.85 (t, J=8.4 Hz, 1H), 5.87 (brs, 4H), 2.94 (m, 2H), 2.30 (t, J=10.8 Hz, 2H), 1.64 (m, 2H), 1.39 (s, 9H)

Preparation Example 34

Compound A-XXXII

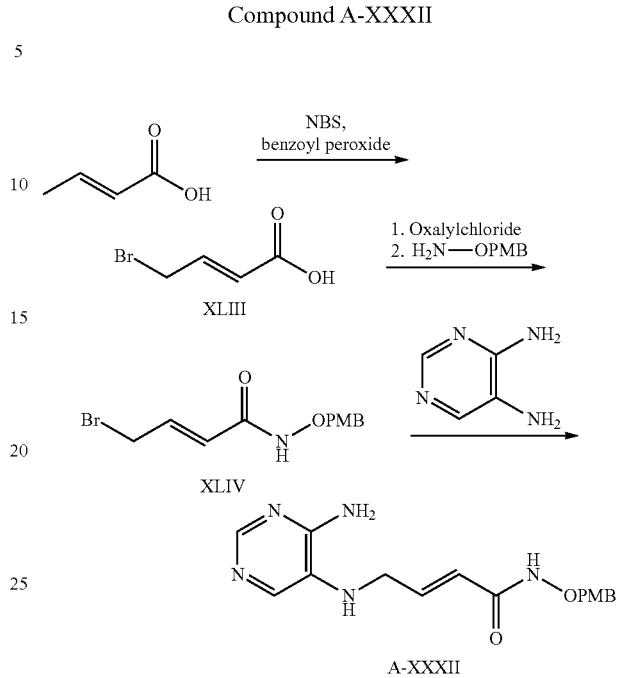

34-1) Preparation of Compound XLIII:

Crotonic acid (4 g, 47 mmol) was dissolved in CCl$_4$ (30 mL). NBS (9 g, 51 mmol) and benzoylperoxide (75 mg, 0.3 mmol) were added with reflux over 3 hours. (i.e., o hour: 4 g, 25 mg; after 1 hour: 3 g, 25 mg; after 2 hours: 2 g, 25 mg) The resulting solution was cooled to room temperature, diluted with methylene chloride (20 mL), and washed with 0.2 N HCl aqueous solution. The organic layer was dehydrated with anhydrous sodium sulfate and concentrated under reduced pressure to yield Compound XLIII (2.2 g (27%)).

$^1$H NMR (600 MHz, chloroform-d$_1$) δ=7.10 (q, J=7.2 Hz, 1H), 6.01 (dt, J=15 Hz, 1.2 Hz 1H), 4.00 (dd, J=7.2 Hz, 0.6 Hz, 2H)

34-2) Preparation of Compound XLIV:

Compound XLIII (1 g, 6.06 mmol) was dissolved in anhydrous methylene chloride (20 mL). At room temperature, oxalyl chloride (1.03 mL, 12 mmol) was added and 3 drops of N,N-dimethylformamide were added. The resulting solution was stirred for 1 hour at room temperature and distilled under reduced pressure to remove the solvent. The resultant was dissolved in tetrahydrofuran (12 mL) and cooled to 0° C. by using ice water. O-(4-methoxybenzyl)hydroxylamine (928 mg, 6 mmol) dissolved in tetrahydrofuran (20 mL) was slowly added. Diisopropylethylamine (4.1 mL, 21 mmol) was then added. The resulting solution was stirred for 30 minutes at 0° C. and for 20 minutes at room temperature. The resultant was concentrated under reduced pressure, diluted with ethyl acetate 30 ml, and washed with water 30 mL and saline 30 mL. The organic layer was dehydrated with anhydrous sodium sulfate and concentrated under reduced pressure. The resultant was applied to column chromatography (n-Hex: EA=3:1) to yield Compound XLIV (515 mg (28%)).

$^1$H NMR (600 MHz, chloroform-d$_1$) δ 7.30 (d J=7.8 Hz 2H) 7.00 (q, J=7.2 Hz, 1H), 6.96 (d, J=7.2 Hz 2H) 4.86 (br, 2H), 4.00 (d, J=11.42 Hz, 2H), 3.79 (s, 2H)

34-3) Preparation of Compound A-XXXII:

Compound XLIV (150 mg, 0.5 mmol) and 4,5-diaminopyrimidine were dissolved in N,N-dimethylformamide (1 mL). The resulting solution was stirred for 12 hours at room temperature, diluted with ethyl acetate (10 mL), and washed with water (10 ml). The organic layer was dehydrated with anhydrous sodium sulfate and concentrated under reduced pressure. The resultant was applied to column chromatography to yield Compound A-XXXII (5 mg (3%)).

$^1$H NMR (600 MHz, chloroform-d$_1$+CD$_3$OD) δ 7.98 (s, 1H) 7.30 (m 3H) 6.84 (m, 3H), 5.87 (br, 1H) 4.86 (br, 2H), 3.83~3.75 (m, 5H)

Preparation Example 35

Compound A-XXXIII

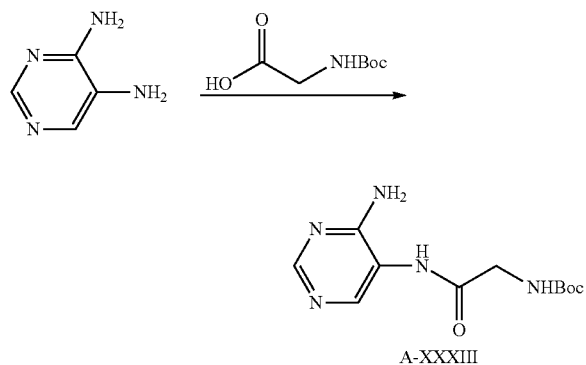

Compound A-XXXIII (854 mg (71%)) was obtained by a method similar to

Preparation Example 2-5 by using 4,5-diaminopyrimidine (500 mg, 4.54 mmol) and 2-(tert-butoxycarbonylamino)acetic acid (876 mg, 4.99 mmol).

$^1$H NMR (600 MHz, chloroform-d$_1$) δ 8.46 (s, 1H), 8.24 (s, 1H), 8.11 (s, 1H) 5.49 (br, 2H), 5.41 (s, 1H), 3.91 (s, 2H), 1.47 (s, 9H)

Preparation Example 36

Compound XLV

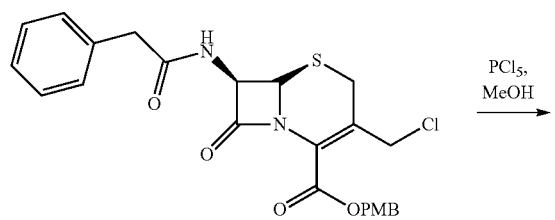

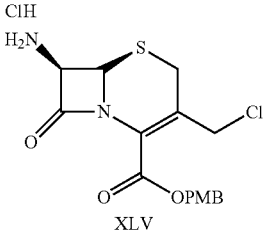

GCLE ((6S,7R)-4-methoxybenzyl 3-(chloromethyl)-8-oxo-7-(2-phenylacetamido)-5-thia-1-azabicyclo[4.2.0]oct-2-ene-2-carboxylate) (49 g, 0.1 mol) was dissolved in methylene chloride (700 mL). A solution of pyridine (15.8 g, 0.2 mol) and phosphorous pentachloride (33.3 g, 0.16 mol) dissolved in methylene chloride (350 mL) was added at 0° C. The resulting solution was stirred for 2 hours at 0° C. and cooled to −40° C. After adding methanol (80 mL), the resulting solution was stirred for 10 minutes at −40° C. and for 2 hours at 0° C., diluted with methylene chloride (400 mL), and washed with 5% sodium bicarbonate aqueous solution (800 mL×2) and 1N HCl aqueous solution (1 L). The organic layer was dehydrated with anhydrous sodium sulfate and concentrated under reduced pressure to about 200 mL. Ether (3 L) was added and the thus-obtained solid was filtered under reduced pressure to yield Compound XLV (30 g (74%)).

$^1$H NMR (600 MHz, DMSO-d6) δ 8.8 (br, 2H), 7.33 (d, J=12.6 Hz, 2H), 6.91 (d, J=12.6 Hz, 2H), 5.23 (m, 4H), 4.55 (dd, J=17.4 Hz, 57 Hz, 2H), 3.78 (dd, J=26.4 Hz, 70.8 Hz, 2H), 3.71 (s, 3H)

Preparation Example 37

Compound XLVII

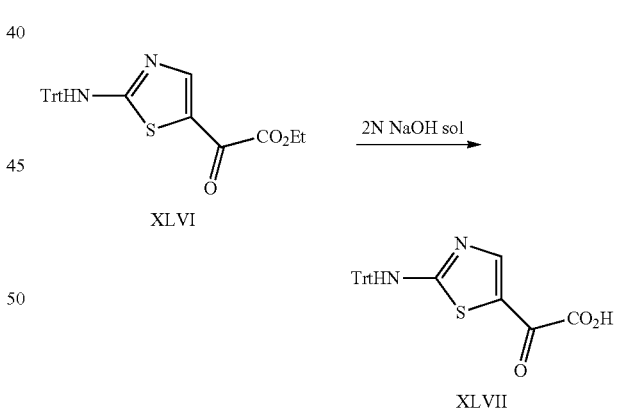

Ethyl 2-oxo-2-(2-(tritylamino)thiazol-4-yl)acetate (100 g, 230 mmol) was dissolved in methanol (95 mL). A solution of sodium hydroxide (9.4 g, 235 mmol) dissolved in methanol (235 mL) was added. The resulting solution was stirred for 10 minutes with reflux. The thus-obtained solid was filtered under reduced pressure, washed with methanol, dissolved in water (200 mL), and acidified with 2N HCl aqueous solution. The resulting solid was filtered under reduced pressure to yield Compound XLVII (84 g (84%)).

$^1$H NMR (600 MHz, DMSO-d6) δ 9.03 (s, 1H), 7.79 (s, 1H), 7.34~7.21 (m, 15)

Preparation Example 38

Compound B-1

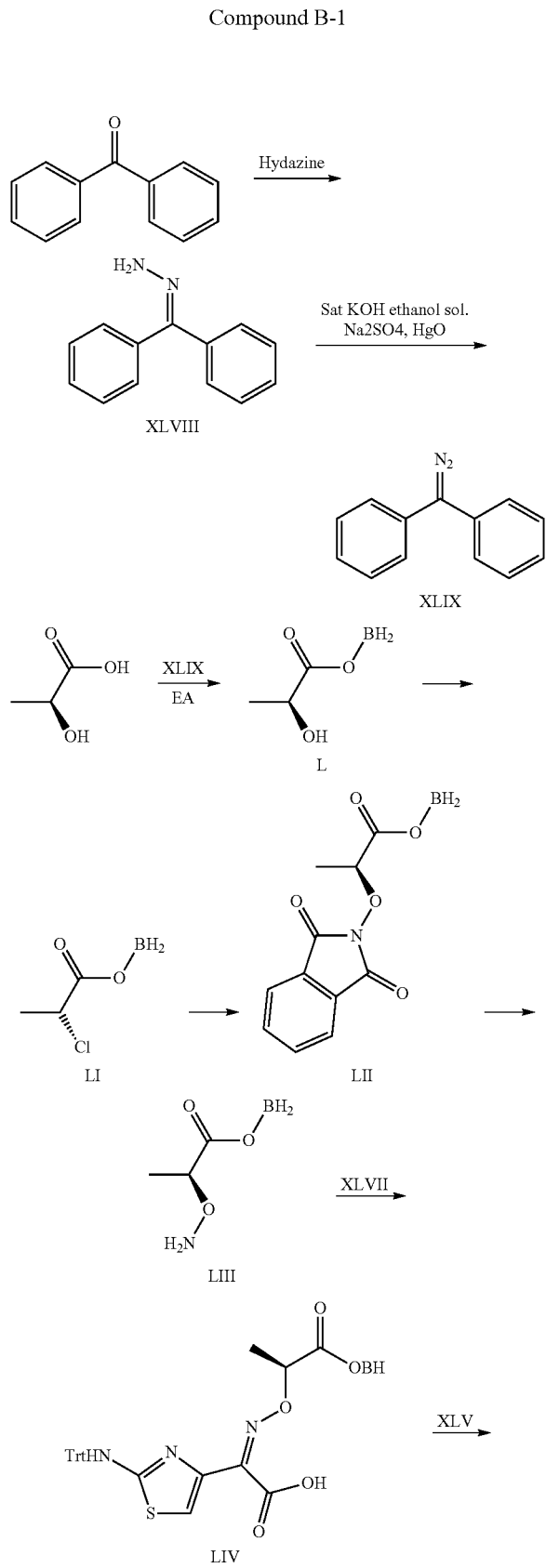

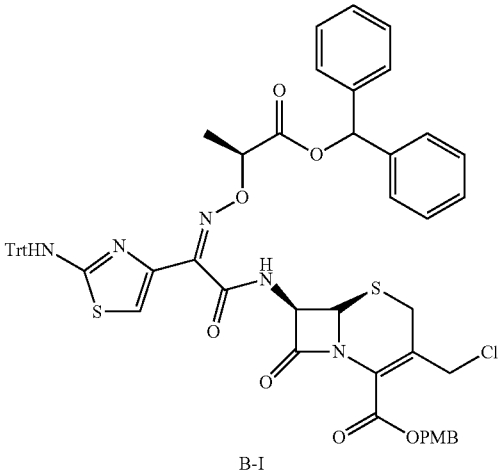

B-I 38-1) Preparation of Compound XLVIII:

Benzophenone (25 g, 137 mmol) was dissolved in ethanol (250 mL) and hydrazine monohydrate (13.7 g, 274 mmol) was added. The resulting solution was stirred for one day with reflux. Then, additional hydrazine monohydrate (13 g) was added and the resulting solution was stirred for one day with reflux. After the starting material, benzophenone, disappeared, the resulting solution was concentrated under reduced pressure to remove ethanol, diluted with ethyl acetate (500 mL), and washed with water (300 mL×2) and saline (200 mL). The organic layer was dehydrated with anhydrous sodium sulfate and concentrated under reduced pressure. The thus-obtained solid was filtered under reduced pressure to yield Compound XLVIII (20 g (75%)). The filtrate was recrystallized with ethyl acetate and hexane to yield Compound XLVIII (4 g (15%)).

$^1$H NMR (400 MHz, DMSO-d6) δ 7.55~7.17 (m, 10H), 6.20 (s, 2H)

38-2) Preparation of Compound XLIX:

Compound XLVIII (20 g, 102 mmol) was dissolved in ether (320 mL). Sodium sulfate (Na2SO4, 22 g, 153 mmol), saturated potassium hydroxide ethanol solution (8 mL, 40 g/100 mL EtOH), and mercury oxide (HgO, 55 g, 255 mmol) were sequentially added. The resulting solution was stirred at a high speed for 1 hour. The thus-created solid was filtered under reduced pressure with celite and the filtrate was concentrated under reduced pressure to yield Compound XLIX (19 g (100%)), which was used for next step without performing purification.

$^1$H NMR (400 MHz, chloroform-d$_1$) δ 7.39~7.15 (m, 10H), 38-3) Preparation of Compound L:

(+) lactic acid (85%, 9.6 g, 90 mmol) was dissolved in ethyl acetate (400 mL) and a solution of Compound XLIX (19 g, 100 mmol) dissolved in ethyl acetate (200 mL) was added at 0° C. over 20 minutes. The resulting solution was stirred for 12 hours at room temperature. The resultant was concentrated under reduced pressure and applied to column chromatography (SiO2, EA:n-hex=1:6) to yield Compound L (17 g (76%)).

$[α]_D$=−9.41 (C=5.00, CHCl$_3$)

$^1$H NMR (600 MHz, chloroform-d$_1$) δ=7.35~7.24 (m, 10H), 6.92 (s, 1H), 4.39 (m, 1H), 2.76 (d, J=5.4 Hz, 1H), 1.47 (d, J=7.2 Hz, 3H)

38-4) Preparation of Compound LI:

Compound L (10 g, 39 mmol) was dissolved in N,N-dimethylformamide (40 mL). The resulting solution was cooled to 0° C. and sulfuryl chloride (5.79 g, 42.9 mmol) was slowly added over 15 minutes. The resulting solution was stirred for 20 minutes at 0° C. and for 1 and a half hour at room temperature and diluted with ethyl acetate (200 ml). Cool sodium bicarbonate solution (100 mL) was added to end the reaction. The resulting solution was washed with saturated sodium bicarbonate solution (100 mL) and saline (100 mL). The organic layer was dehydrated with anhydrous sodium sulfate and the filtrate was concentrated under reduced pressure. The resultant was applied to column chromatography (SiO$_2$, EA:n-hex=1:9) to yield Compound LI (5.3 g (49%)).

$^1$H NMR (600 MHz, chloroform-d$_1$) δ=7.36~7.26 (m, 10H), 6.90 (s, 1H), 4.51 (q, J=6.6 Hz, 1H), 1.72 (d, J=6.6 Hz, 3H)

38-5) Preparation of Compound LII:

Compound LI (4 g, 14.6 mmol) was dissolved in N,N-dimethylformamide (30 mL). N-hydroxy phthalamide (2.45 g, 15 mmol) and potassium carbonate (2.07 g, 15 mmol) were added. The resulting solution was stirred for 12 hours at room temperature, diluted with ethyl acetate (400 mL), washed with water (200 mL) and saline (200 mL×2), and recrystallized with hexane to yield Compound LII (6 g (99%)).

[α]$_D$=−63.26 (C=5.00, CHCl$_3$)

$^1$H NMR (600 MHz, chloroform-d$_1$) δ=7.76 (m, 4H), 7.32~7.19 (m, 10H), 6.91 (s, 1H), 5.05 (q, J=6.6 Hz, 1H), 1.65 (d, J=7.2 Hz, 3H)

38-6) Preparation of Compound LIII:

Compound LII (2.5 g, 6.23 mmol) was dissolved in methylene chloride (10 mL). Methyl hydrazine (287 mg, 6.23 mmol) was added at 0° C. The resulting solution was stirred for 2 hours at 0° C. to create a solid. The solid was filtered under reduced pressure and the filtrate was concentrated under reduced pressure to yield Compound LIII, which was used for next step without performing purification.

38-7) Preparation of Compound LIV:

Compound LIII was dissolved in methylene chloride (5 mL) and methanol (20 mL). Compound XLVII (2.6 g, 6.2 mmol) was added at 0° C. The resulting solution was stirred for 30 minutes at 0° C. and 3 hours at room temperature, concentrated under reduced pressure to remove the solvent, diluted with ethyl acetate (150 mL), and washed with 0.1N HCl aqueous solution (100 mL) and saline (100 mL). The organic layer was dehydrated with anhydrous sodium carbonate, concentrated under reduced pressure to remove the solvent, and crystallized with ethyl acetate and hexane to yield Compound LIV (2.5 g (60%)).

$^1$H NMR (600 MHz, DMSO-d6) δ 8.87 (s, 1H), 7.44 (m, 25H), 6.82 (s, 2H), 4.89 (q, J=7.2 Hz, 1H), 1.41 (d, J=6.6 Hz, 3H)

38-8) Preparation of Compound B-1

Compound LIV (2.07 g, 4.03 mmol) and Compound XLV (1.8 g, 4.44 mmol) were dissolved in methylene chloride (45 mL). At 0° C., pyridine (1.47 mL, 18 mmol) and phosphoryl chloride (POCl3, 376 uL, 4.03 mmol) were added. The resulting solution was stirred for 20 minutes at 0, diluted with ethyl acetate (150 mL), washed with water (50 mL) and saline (30 mL×2). The organic layer was dehydrated with anhydrous sodium sulfate, concentrated under reduced pressure, and applied to column chromatography (SiO$_2$, n-hex:EA=6:1~2:1) to yield Compound B-1 (1.9 g (47%)).

$^1$H NMR (600 MHz, chloroform-d$_1$) δ=8.10 (d, J=8.4 Hz, 1H), 7.34~7.22 (m, 27H), 6.98 (s, 1H), 6.91 (s, 1H), 6.89 (d, J=7.8 Hz, 2H), 6.73 (s, 1H), 5.91 (dd, J=4.8 Hz, 8.4 Hz, 1H), 5.26 (m, 4H), 4.94 (d, J=5.4 Hz, 1H), 4.58 (dd, J=11.4 Hz, 94.8 Hz, 2H), 3.79 (s, 3H), 3.546 (dd, 18 Hz, 105.6 Hz, 2H), 1.61 (d, J=6.6 Hz, 3H)

Preparation Example 39

Compound B-II

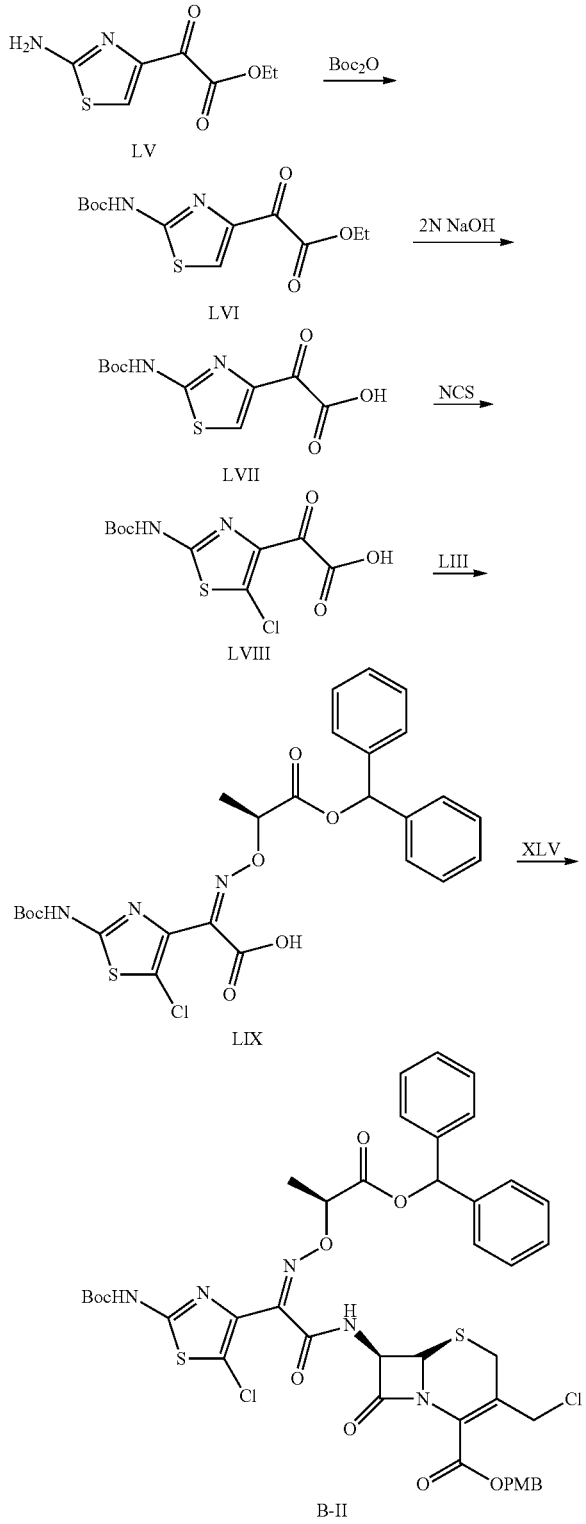

39-1) Preparation of Compound LVI:

Compound LV (30 g, 149 mmol) was dissolved in tetrahydrofuran (500 mL). Di-tert-butyl dicarbonate (33 g, 152 mmol) and 4-dimethylaminopyridine (388 mg, 3.17 mmol) were sequentially added. The resulting solution was stirred for 20 hours at room temperature, concentrated under reduced pressure, and applied to column chromatography (EA:Hex=1:7~1:5) to yield Compound LVI (17.7 g (39%)).

$^1$H NMR (600 MHz, chloroform-$d_1$) δ=8.58 (br, 1H), 8.27 (s, 1H), 4.44 (q, J=7.8 Hz, 2H), 1.54 (s, 9H), 1.42 (t, J=6.6 Hz, 3H)

39-2) Preparation of Compound LVII:

Compound LVI (17.7 g, 58.9 mmol) was dissolved in methanol (118 mL) and the resulting solution was stirred at room temperature. Sodium hydroxide (4.24 g, 106 mmol) dissolved in distilled water (40 mL) was slowly added. The resulting solution was stirred for 1 hour, concentrated under reduced pressure, dissolved in water (200 mL), and solidified with 1N HCl (pH 1~2). The thus-obtained solid was filtered under reduced pressure and washed with water (200 mL) to yield Compound LVII (16 g (100%)).

$^1$H NMR (600 MHz, DMSO-d6) δ 11.92 (s, 1H), 8.35 (s, 1H), 1.47 (s, 9H)

39-3) Preparation of Compound LVIII:

Compound LVII (16 g, 58.7 mmol) was dissolved in 1,4-dioxane (118 mL) and N-chlorosuccineimide (NCS, 8.1 g, 60.7 mmol) was added. The resulting solution was stirred for 30 minutes at room temperature and for 15 hours at 40. The resulting solution was filtered under reduced pressure and the filtrate was concentrated under reduced pressure. The resultant was filtered under reduced pressure with ether/n-hexane=2/1 (150 mL) to remove the thus-created solid and the filtrate was concentrated under reduced pressure to yield Compound LVIII (12.3 g (68%)).

$^1$H NMR (600 MHz, DMSO-d6) δ 12.19 (s, 1H), 1.43 (s, 9H)

39-4) Preparation of Compound LIX:

Compound LIX (14.2 g (63%)) was prepared by a method similar to Preparation Example 38-7 by using Compound LVIII (12.3 g, 40.1 mmol) and Compound LIII (12.8 g, 47.2 mmol).

$^1$H NMR (600 MHz, chloroform-$d_1$) δ=7.34~7.27 (m, 10H), 6.92 (s, 1H), 5.09 (q, J=6.6 Hz, 1H), 1.60 (d, J=7.2 Hz, 3H), 1.51 (s, 9H)

39-5) Preparation of Compound B-II:

Compound B-II (2.62 g (54%)) was prepared by a method similar to Preparation Example 38-8 by using Compound LIX (3.0 g, 5.35 mmol) and Compound XLV (2.82 g, 6.96 mmol).

$^1$H NMR (600 MHz, chloroform-$d_1$) δ 7.96 (br, 1H), 7.86 (d, J=9.6 Hz, 1H), 7.35 (d, J=9 Hz, 2H), 7.29~7.25 (m, 10H), 6.92~6.87 (m, 3H), 6.03 (q, J=4.8 Hz, 1H), 5.27 (d, J=11.4 Hz, 1H), 5.21 (d, J=11.4 Hz, 1H), 5.10 (q, J=7.2 Hz, 1H), 4.98 (d, J=5.4 Hz, 1H), 4.60 (d, J=12 Hz, 1H), 4.44 (d, J=12 Hz, 1H), 3.81 (s, 3H), 3.59 (d, J=18.6 Hz, 1H), 3.41 (d, J=18 Hz, 1H), 1.64 (d, J=7.2 Hz, 3H), 1.52 (s, 9H)

Preparation Example 40

Compound B-III

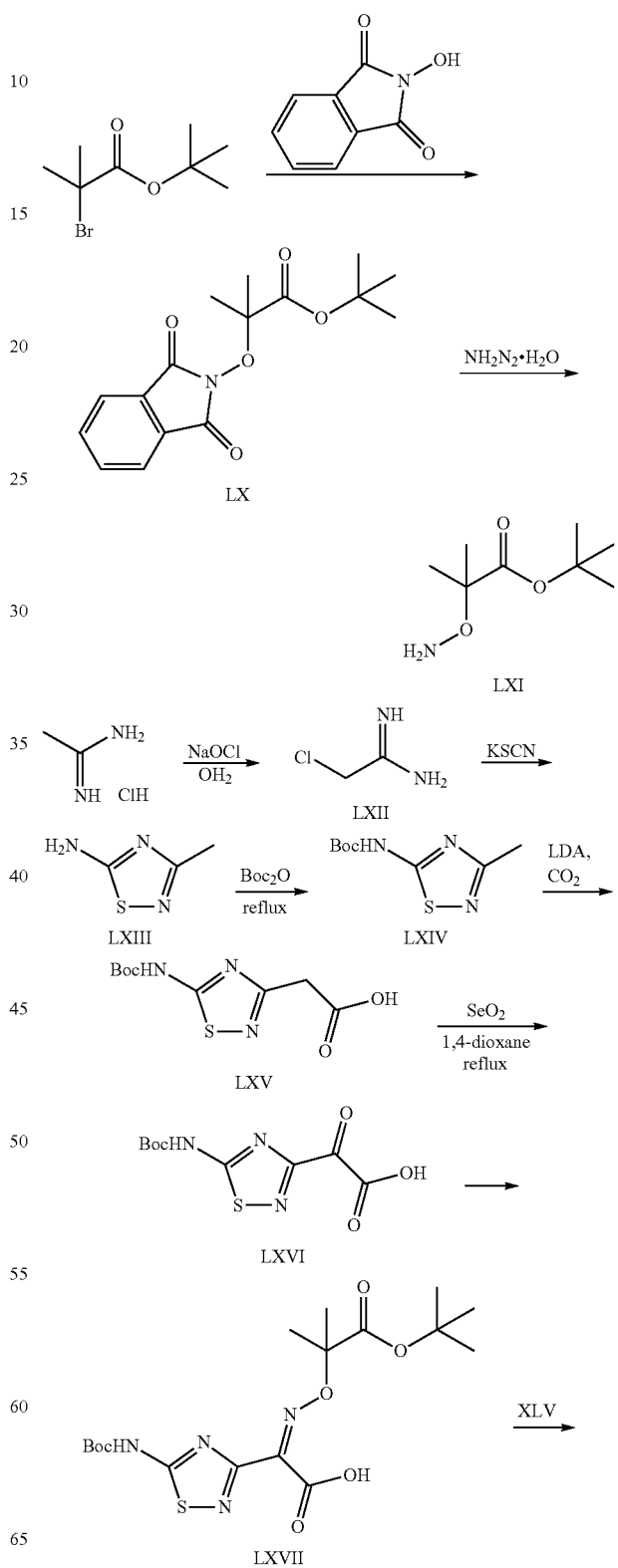

-continued

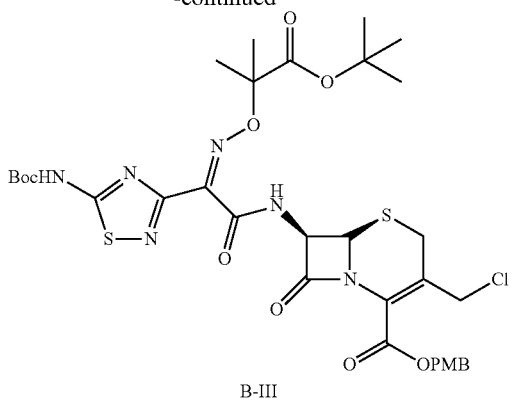

B-III 40-1) Preparation of Compound LX:

Tert-butyl 2-bromo-2-methylpropanoate (100 g, 0.6 mol), N-hydroxy phthalamide (136 g, 0.6 mol), and triethylamine (93 g, 0.9 mol) were stirred for 24 hours at 80° C. The resultant was diluted with ethyl acetate (1 L×2), washed with water (1 L), 1N HCl (800 mL), and 0.5N sodium hydroxide (500 mL), dehydrated with anhydrous sodium sulfate, and concentrated under reduced pressure. The thus-obtained white solid was washed with n-hexane (800 mL) and filtered under reduced pressure to yield Compound LX (91 g (49%)).

$^1$H NMR (600 MHz, chloroform-$d_1$) δ 7.85 (q, J=3 Hz, 2H), 7.76 (q, J=3 Hz, 2H), 1.59 (s, 6H), 1.52 (s, 9H)

40-2) Preparation of Compound LXI:

Compound LX (2.63 g, 8.6 mmol) was dissolved in methylene chloride (11 mL) and methanol (2 mL). Hydrazine monohydrate (1.7 mL) was added. The resulting solution was stirred for 1 and a half hour at room temperature. The thus-obtained solid was filtered under reduced pressure. The filtrate was diluted with ethyl acetate (20 mL) and washed with distilled water (20 mL×2) and saline (20 mL). The organic layer was dehydrated with anhydrous sodium sulfate and concentrated under reduced pressure to yield Compound LXI (1.4 g, (93%)), which was used for next step without performing purification.

40-3) Preparation of Compound LXII:

Acetamidine hydrochloride (6 g, 64 mmol) was dissolved in distilled water (75 mL) and the resulting solution was cooled to 0° C. Sodium hyperchloride (4% chlorine available sol, 95 mL) was added over 1.5 hours and the resulting solution was stirred for 1 hour. Excessive amount of sodium chloride was added and the resultant was extracted with ethyl acetate (150 mL×2). The organic layer was dehydrated with anhydrous sodium sulfate and concentrated under reduced pressure to yield Compound LXII (5.1 g (87%)), which was used for next step without performing purification.

40-4) Preparation of Compound LXIII:

Compound LXII (5.1 g, 55 mmol) was dissolved in methanol (250 mL) and the resulting solution was cooled to 0° C. Potassium thiocyanate (5.3 g, 55 mmol) was then added. The resulting solution was stirred for 12 hours at room temperature, concentrated under reduced pressure, diluted with ethyl acetate (200 mL), and filtered under reduced pressure to remove a solid. The filtrate was concentrated under reduced pressure, creating a solid which was filtered under reduced pressure to yield Compound LXIII (2 g (32%)). The filtrate was further concentrated and applied to column chromatography (SiO2, n-hex:EA=4:1) to yield Compound LXIII (2 g (32%)).

$^1$H NMR (600 MHz, CD$_3$OD) δ 3.27 (s, 3H)

40-5) Preparation of Compound LXIV:

Compound LXIII (2 g, 17.4 mmol) was added to Boc$_2$O (6 mL). The resultant was stirred for 12 hours with reflux, concentrated under reduced pressure, and applied to column chromatography (SiO2, n-hex:EA=4:1) to yield Compound LXIV (2 g (53%)).

$^1$H NMR (600 MHz, chloroform-$d_1$) δ=10.97 (br, 1H), 2.55 (s, 3H), 1.55 (s, 9H)

40-6) Preparation of Compound LXV:

Diisopropylamine (11.37 mL, 82 mmol) was dissolved in anhydrous tetrahydrofuran (50 mL) and the resulting solution was cooled to −78. Butyl lithium (1.6 M n-hex sol., 56.1 mL, 90 mmol) was added and the resulting solution was stirred for 10 minutes at the same temperature to prepare LDA solution.

To the LDA solution, a solution of Compound LXIV (4.39 g, 20.4 mmol) dissolved in anhydrous tetrahydrofuran (20 mL) was slowly added at −78° C. Carbonic acid gas was introduced in the resulting solution −40° C. The resulting solution was stirred for 1 hour at −40° C., 30 minutes at 0° C., and 4 hours at room temperature. Distilled water (5 mL) was added to end the reaction. The resulting solution was concentrated under reduced pressure. By adding distilled water (200 mL) and extracting with ether (150 mL×3), remaining starting material was recovered (2 g). The resulting aqueous solution was acidified with 1N HCl aqueous solution and extracted with ethyl acetate (250 mL). The organic layer was dehydrated with anhydrous sodium sulfate and concentrated under reduced pressure to yield Compound LXV (2.2 g (40%)).

$^1$H NMR (600 MHz, DMSO-d6) δ 12.34 (s, 1H), 3.74 (s, 2H), 1.50 (s, 9H)

40-7) Preparation of Compound LXVI:

Compound LXV (2.2 g, 8.5 mmol) was dissolved in 1,4-dioxane (33 mL) and selenium dioxide (SeO2, 1.87 g, 17 mmol) was added. The resulting solution was stirred at 100° C., cooled to room temperature, filtered under reduced pressure, washed with 1,4-dioxane. The filtrate was concentrated under reduced pressure to yield Compound LXVI, which was used for next step without performing purification.

40-8) Preparation of Compound LXVII:

Compound LXVII (12.9 g (64%)) was prepared by a method similar to Preparation Example 38-7 by using Compound LXVI (12.8 g, 47.1 mmol) and Compound LXI (10.2 g, 58.2 mmol).

$^1$H NMR (600 MHz, DMSO-d$_6$) δ 1.49 (s, 9H), 1.44 (s, 6H), 1.36 (s, 9H)

40-9) Preparation of Compound B-III:

Compound B-III (4.12 g (39%)) was prepared by a method similar to Preparation Example 38-8 by using Compound LXVII (5.85 g, 13.6 mmol) and Compound XLV (7.16 g, 17.6 mmol).

$^1$H NMR (600 MHz, chloroform-$d_1$) δ=8.75 (br, 1H), 8.05 (br, 1H), 7.35 (d, J=7.8 Hz, 2H), 6.96 (d, J=9 Hz, 2H), 6.09 (dd, J=4.8 Hz, 1H), 5.26 (d, J=11.4 Hz, 1H), 5.21 (d, J=11.4 Hz, 1H), 5.05 (d, J=4.8 Hz, 1H), 4.53 (d, J=11.4 Hz, 1H), 4.47 (d, J=11.4 Hz, 1H), 3.82 (s, 3H), 3.65 (d, J=18 Hz, 1H), 3.49 (d, J=18 Hz, 1H), 1.66 (s, 3H), 1.63 (s, 3H), 1.54 (s, 9H), 1.40 (s, 9H)

Preparation Example 41

Compound LXXII

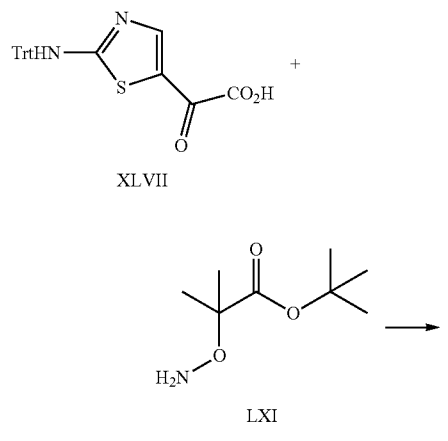

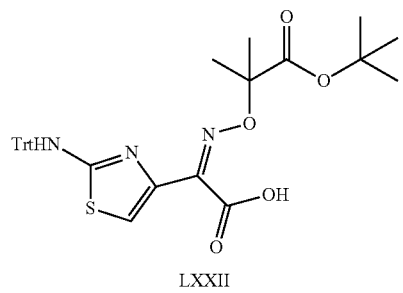

Compound LXXII was prepared by a method similar to Preparation Example 38-7 by using Compound XLVII and Compound LXI.

Preparation Example 42

Compounds B-IV and B-V

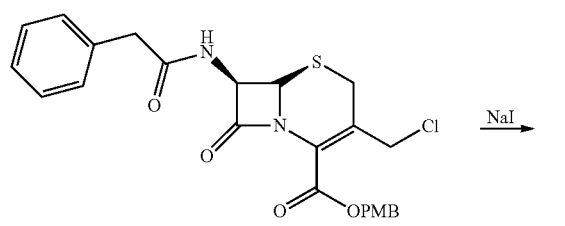

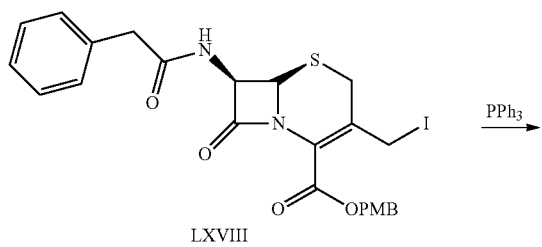

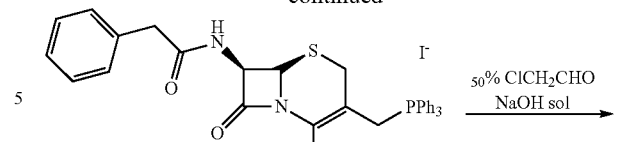

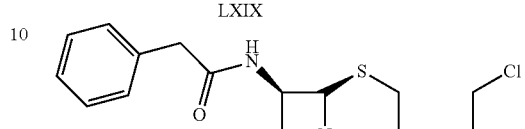

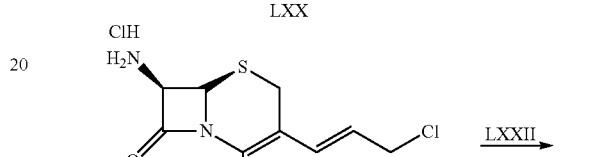

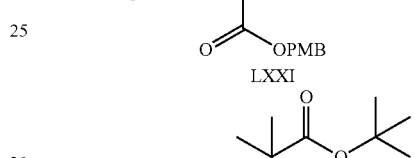

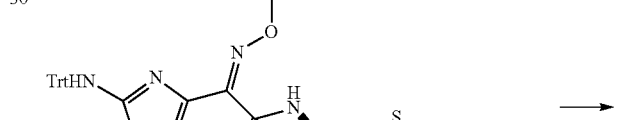

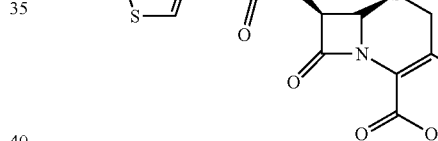

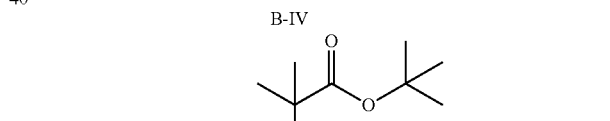

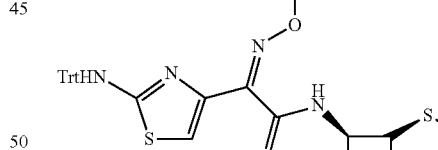

42-1) Preparation of Compound LXVIII:

GCLE (49 g, 0.1 mol) was dissolved in acetone (1 L) and sodium iodide (45 g, 0.3 mol) was added. The resulting solution was stirred for 2 hours at room temperature, concentrated under reduced pressure, diluted with ethyl acetate (1.2 L), and washed with water (500 ml), 10% sodium thiosulfate ($Na_2S_2O_3 \cdot 5H_2O$) aqueous solution (1 L), and saline (500 mL×2). The organic layer was washed with anhydrous sodium sulfate and concentrated under reduced pressure to yield Compound LXVIII (57 g (99%)), which was used for next step without performing purification.

42-2) Preparation of Compound LXIX:

Compound LXVIII (57 g, 0.1 mol) was dissolved in ethyl acetate (1 L) and triphenylphosphine (52 g, 0.2 mol) was added at room temperature. The resulting solution was stirred for 2 hours. The thus-created solid was filtered under reduced pressure and washed with ethyl acetate and dried to yield Compound LXIX (80 g (95%)).

$^1$H NMR (600 MHz, chloroform-$d_1$) δ=7.80~7.64 (m, 15H), 7.35~7.26 (m, 5H), 7.16 (d, J=7.8 Hz, 2H), 7.65 (d, J=7.8 Hz, 2H), 6.46 (d, J=3.0 Hz, 1H), 5.66 (dd, J=5.4 Hz, 9 Hz, 1H), 5.62 (t, J=15 Hz, 1H) 5.16 (t, J=15 Hz, 1H), 4.58 (m, 3H), 4.05 (dd, 4.8 Hz, 18.6 Hz, 1H), 3.80 (s, 3H), 3.66 (s, 2H), 3.37 (d, 18.6 Hz, 1H)

42-3) Preparation of Compound LXX:

Compound LXIX (40 g, 48 mmol) was dissolved in methylene chloride (450 ml) and distilled water (150 mL). The resulting solution was cooled to 0° C. and chloroacetaldehyde (50% aq sol, 30 mL, 238 mmol) was added. Then, 2N sodiumhydroxide aqueous solution (29 mL) was added and the resulting solution was stirred for 30 minutes at the same temperature. The organic layer was washed with water (200 mL) and saline (250 mL), dehydrated with anhydrous sodium sulfate, concentrated under reduced pressure, and applied to column chromatography (SiO2, n-hex:EA:MC=2:1:1) to yield Compound LXX (9.1 g (37%)).

$^1$H NMR (600 MHz, chloroform-$d_1$) δ=7.63 (m, 7H), 6.86 (d, J=9 Hz, 2H), 6.20 (d, J=11.4 Hz, 1H), 6.01 (d, J=8.4 Hz, 1H), 5.82 (dd, 4.8 Hz, 9 Hz, 1H), 5.72 (m, 1H), 5.14 (m, 2H), 4.98 (d, J=4.8 Hz, 1H), 3.91 (dd, J=8.4 Hz, 12.6 Hz, 1H), 3.78 (s, 3H), 3.72 (dd, J=7.2 Hz, 12 Hz, 1H), 3.67 (q, J=16.2 Hz, 2H), 3.47 (dd, J=18.6 Hz, 124.8 Hz, 2H)

42-4) Preparation of Compound LXXI:

Compound LXXI (15 g (50%)) was prepared by a method similar to Preparation Example 36 by using Compound LXX (36 g, 70.2 mmol).

$^1$H NMR (600 MHz, chloroform-$d_1$) δ=7.31 (d, J=9.0 Hz, 2H), 6.87 (d, J=9 Hz, 2H), 6.23 (d, J=11.4 Hz, 1H), 5.70 (m, 1H), 5.16 (m, 1H), 4.92 (d, J=4.8 Hz, 1H), 4.74 (d, J=4.8 Hz, 1H), 3.93 (dd, J=9.6 Hz, 11.4 Hz, 1H), 3.78 (s, 3H), 3.72 (dd, J=7.2 Hz, 12 Hz, 1H), 3.51 (dd, J=18.6 Hz, 124.8 Hz, 2H)

42-5) Preparation of Compound B-IV:

Compound B-IV (17 g (47%)) (E/Z mixture 2:8) was prepared by a method similar to Preparation Example 38-8 by using Compound LXXII (19.7 g, 34.5 mmol) and Compound LXXI (14.9 g, 34.5 mmol).

$^1$H NMR (600 MHz, chloroform-$d_1$) δ=8.18 (d, J=9 Hz, 1H), 7.33~7.24 (m, 17H), 6.89 (m, 3H), 6.71 (s, 1H), 6.27 (d, J=10.8 Hz, 1H), 5.98 (m, 1H), 5.74 (m, 1H), 5.73 (m, 3H), 3.94 (dd, J=7.8 Hz, 9 Hz, 1H), 3.79 (s, 3H), 3.75 (dd, J=7.8 Hz, 9 Hz, 1H), 3.47 (dd, J=18.Hz, 124.8 Hz, 2H), 1.62 (d, J=27 Hz, 6H), 1.39 (s, 9H)

42-6) Preparation of Compound B-V:

Compound B-V (18 g (95%)) was prepared by a method similar to Preparation Example 42-1 by using Compound B-IV (17 g, 17.9 mmol) and used for next step without performing purification.

Preparation Example 43

Compounds B-VI and B-VII

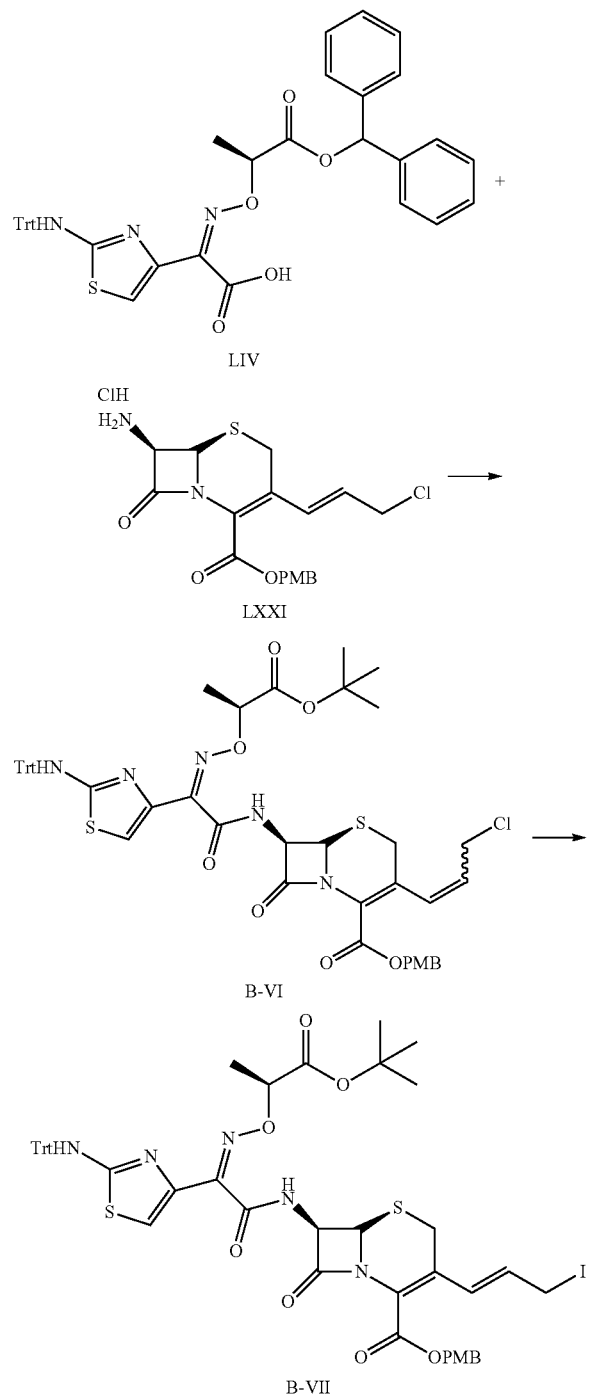

43-1) Preparation of Compound B-VI:

Compound B-VI (2 g (52%)) (E/Z mixture 2:8) was prepared by a method similar to Preparation Example 38-8 by using Compound LIV (2.5 g, 3.7 mmol) and Compound LXXI (1.73 g, 3.7 mmol).

¹H NMR (600 MHz, chloroform-d₁) δ=8.16 (d, J=8.4 Hz, 1H), 7.35~7.26 (m, 27H), 6.98 (s, 1H), 6.91 (m, 3H), 6.75 (s, 1H), 6.33 (d, J=10.8 Hz, 1H), 5.92 (dd, J=4.8 Hz, 8.4 Hz, 1H), 5.78 (m, 1H), 5.20 (m, 3H), 5.78 (d, J=4.8 Hz, 1H), 3.93 (dd, J=8.4 Hz, 12 Hz, 1H), 3.81 (s, 3H), 3.75 (dd, J=8.4 Hz, 12 Hz, 1H), 3.47 (dd, J=18 Hz, 89.4 Hz, 2H), 1.69 (d, J=7.8 Hz, 3H)

43-2) Preparation of Compound B-VII:

Compound B-VII (1.1 g (99%)) was prepared by a method similar to Preparation Example 42-1 by using Compound B-VI (1 g, 0.96 mmol) and used for next step without performing purification.

Preparation Example 44

Compound B-VIII

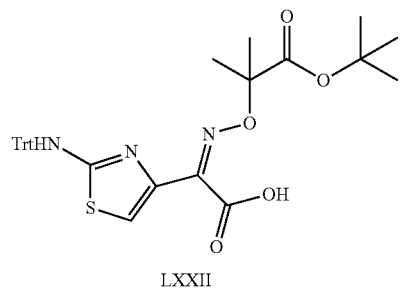

LXXII

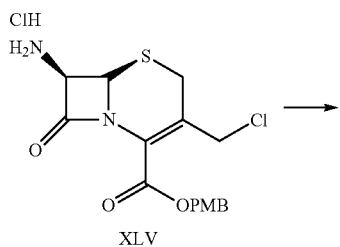

XLV

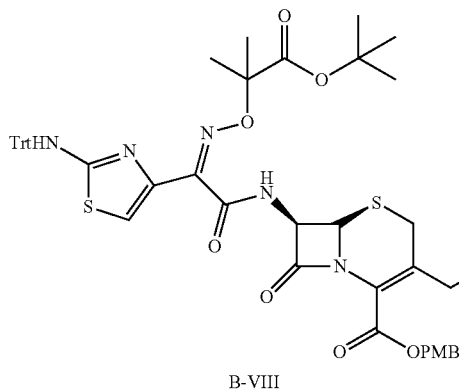

B-VIII

Compound B-VIII (5.3 g (52%)) was prepared by a method similar to Preparation Example 38-8 by using Compound LXXII (6.8 g, 10 mmol) and Compound XLV (4.86 g, 12 mmol).

¹H NMR (600 MHz, chloroform-d₁) δ=8.23 (d, J=3.6 Hz, 1H), 7.33 (m, 17H), 7.00 (s, 1H), 6.90 (m, 3H), 6.70 (s, 1H), 5.96 (dd, J=4.8 Hz, 8.4 Hz, 1H), 5.24 (dd, J=11.4 Hz, 34.8 Hz, 2H), 5.00 (d, J=5.4 Hz, 1H), 5.51 (dd, J=12 Hz, 50.4 Hz, 2H), 3.79 (s, 3H), 3.60 (d, J=18 Hz, 1H), 3.44 (d, J=18 Hz, 1H), 1.61 (s, 3H), 1.59 (s, 3H), 1.39 (s, 9H)

Preparation Example 45

Compound B-IX

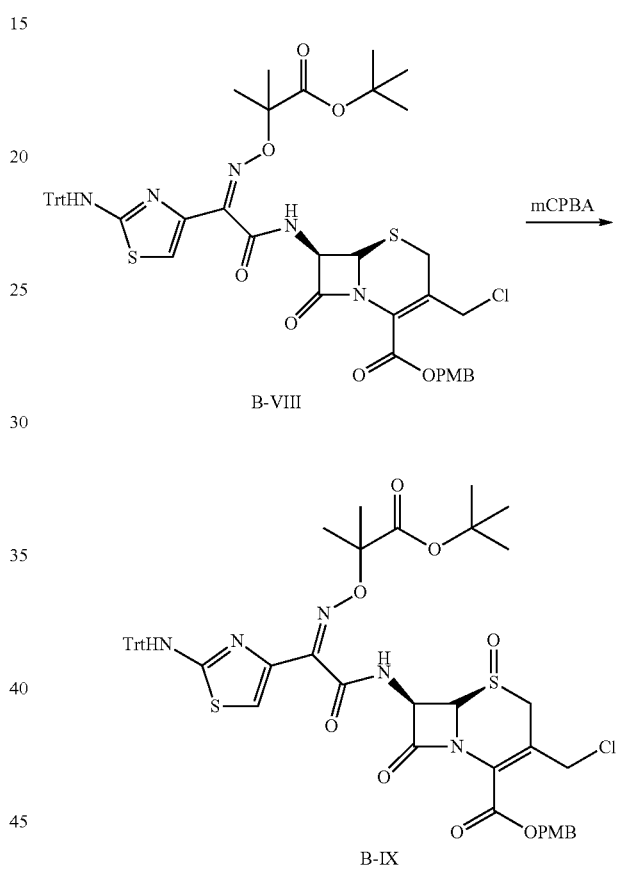

Compound B-VIII (5.0 g, 5.42 mmol) was dissolved in methylene chloride (50 mL) and m-chloroperbenzoic acid (0.84 g, 4.88 mmol) was added at −20° C. The resulting solution was stirred for 1 hour at 10° C. Sodium thiosulfate saturated aqueous solution (30 mL) was then added. The resulting solution was ⅓ concentrated under reduced pressure, extracted with ethyl acetate (100 mL×2), dehydrated with anhydrous sodium sulfate, concentrated under reduced pressure, and applied to column chromatography (EA: Hex=1:3-1:2) to yield Compound B-IX (3.73 g (73%)).

¹H NMR (600 MHz, CDCl₃) δ 7.87 (d, J=9.6 Hz, 1H), 7.36 (d, J=8.4 Hz, 2H), 7.31~7.27 (m, 15H), 7.03 (s, 1H), 6.92 (d, J=9 Hz, d), 6.69 (s, 1H), 6.21 (q, J=4.8 Hz, 1H), 5.29 (d, J=11.4 Hz, 1H), 5.24 (d, J=11.4H), 5.07 (d, J=12 Hz, 1H), 4.55 (d, J=4.8 Hz), 4.22 (d, J=12.6 Hz, 1H), 3.82 (s, 3H), 3.74 (d, J=19.2 Hz, 1H), 3.39 (d, J=18.6 Hz, 1H), 1.58 (d, J=15 Hz, 6H), 1.41 (s, 9H)

Preparation Example 46

Compound B-X

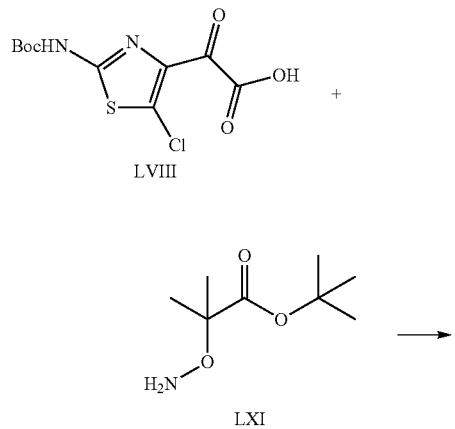

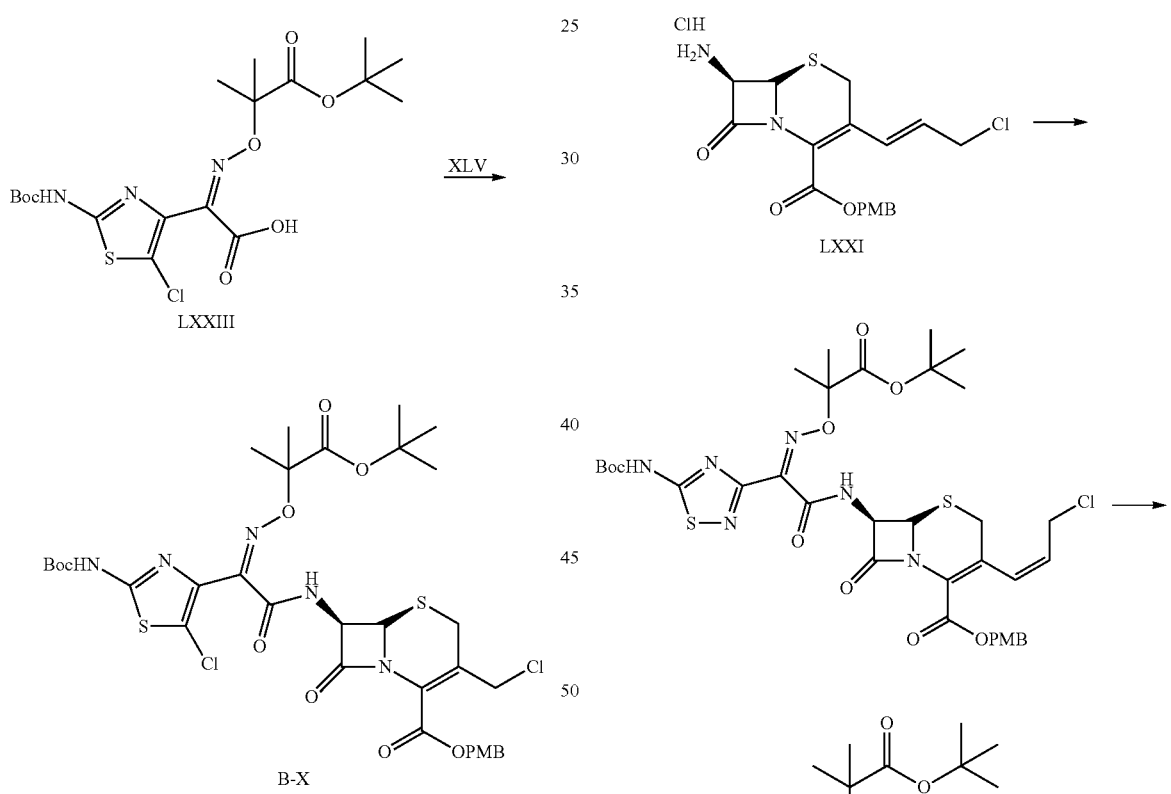

46-1) Preparation of Compound LXXIII:
Compound LXXIII was prepared by a method similar to Preparation Example 38-7 by using Compound LVIII and Compound LXI.

46-2) Preparation of Compound B-X:
Compound B-X (4 g (25%)) was prepared by a method similar to Preparation Example 38-8 by using Compound LXXIII (9.2 g, 19.8 mmol) and Compound XLV (10.45 g, 25.8 mmol).

$^1$H NMR (600 MHz, chloroform-$d_1$) δ=7.92 (d, J=9.0 Hz, 1H), 7.87 (brs, 1H), 7.36 (d, J=9.6 Hz, 2H), 6.92 (d, J=9.6 Hz, 2H), 6.05 (dd, J=5.4 Hz, 9.6 Hz, 1H), 5.28 (dd, J=11.4 Hz, 36.6 Hz, 2H), 5.04 (d, J=5.4 Hz, 1H), 4.56 (dd, J=12 Hz, 56.4 Hz, 2H), 3.82 (s, 3H), 3.66 (dd, J=18 Hz, 97.8 Hz, 2H), 1.62 (s, 3H), 1.60 (s, 3H), 1.42 (s, 9H)

Preparation Example 47

Compound B-XI

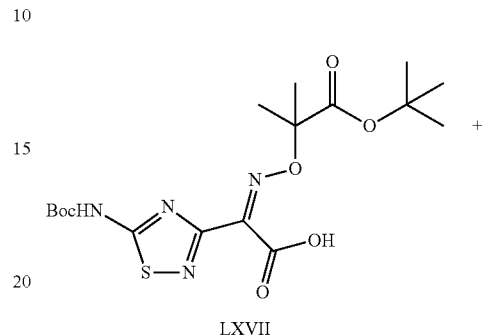

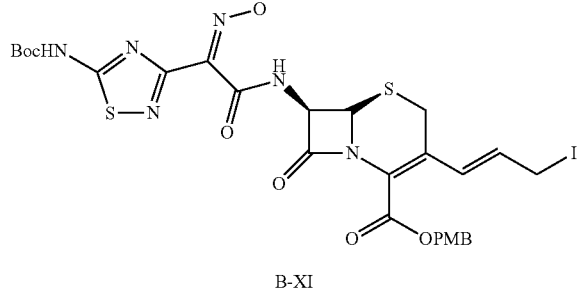

Compound B-XI was prepared by a method similar to Preparation Example 43 by using Compound LXVII and Compound LXXI.

$^1$H NMR (600 MHz, chloroform-$d_1$) δ=8.98 (brs, 1H), 8.06 (d, J=9.0 Hz, 1H), 7.31 (d, J=8.4 Hz, 2H), 6.87 (d, J=8.4 Hz, 1H), 6.27 (d, J=11.4 Hz, 1H), 6.07 (m, 1H), 5.74 (m, 1H), 5.14 (m, 3H), 3.93~3.71 (m, 2H), 3.52 (m, 2H), 1.62 (s, 3H), 1.60 (s, 3H), 1.52 (s, 9H): NMR of allylchloride.

Preparation Example 48

Compound B-XII

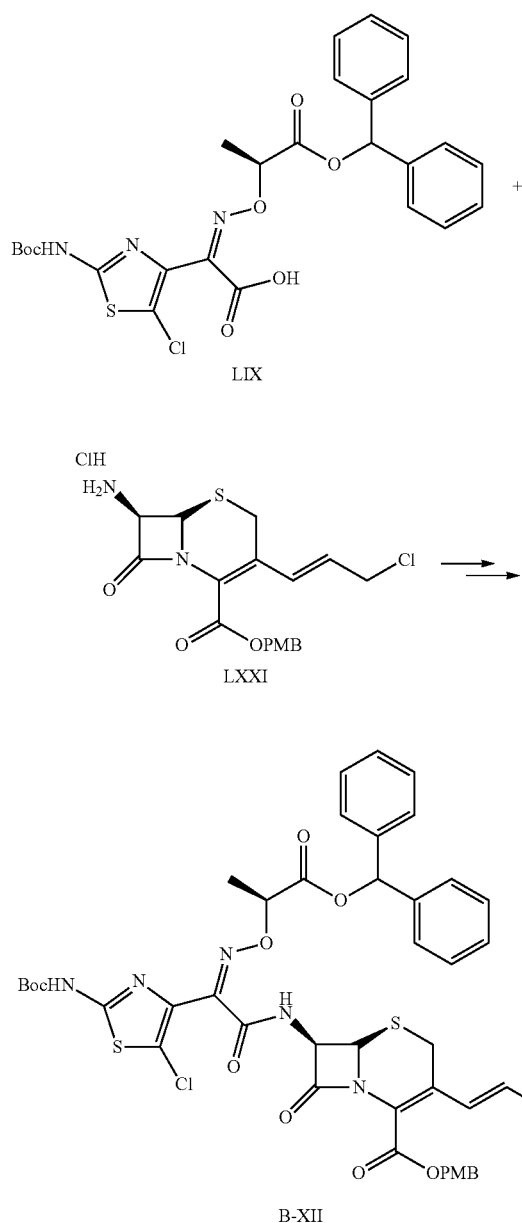

B-XII

Compound B-XII was prepared by a method similar to Preparation Example 43 by using Compound LIX and Compound LXXI.

$^1$H NMR (600 MHz, chloroform-$d_1$) δ=7.99 (brs, 1H), 7.85 (d, J=9.0 Hz, 1H), 7.36~7.12 (m, 12H), 6.92 (d, J=8.4 Hz, 1H), 6.31 (d, J=11.4 Hz, 1H), 6.04 (m, 1H), 5.78 (m, 1H), 5.15~4.99 (m, 3H), 3.94~3.72 (m, 2H), 3.45 (m, 2H), 1.66 (t, J=3 Hz, 3H), 1.52 (s, 9H): NMR of allylchloride.

Preparation Example 49

Compound B-XIII

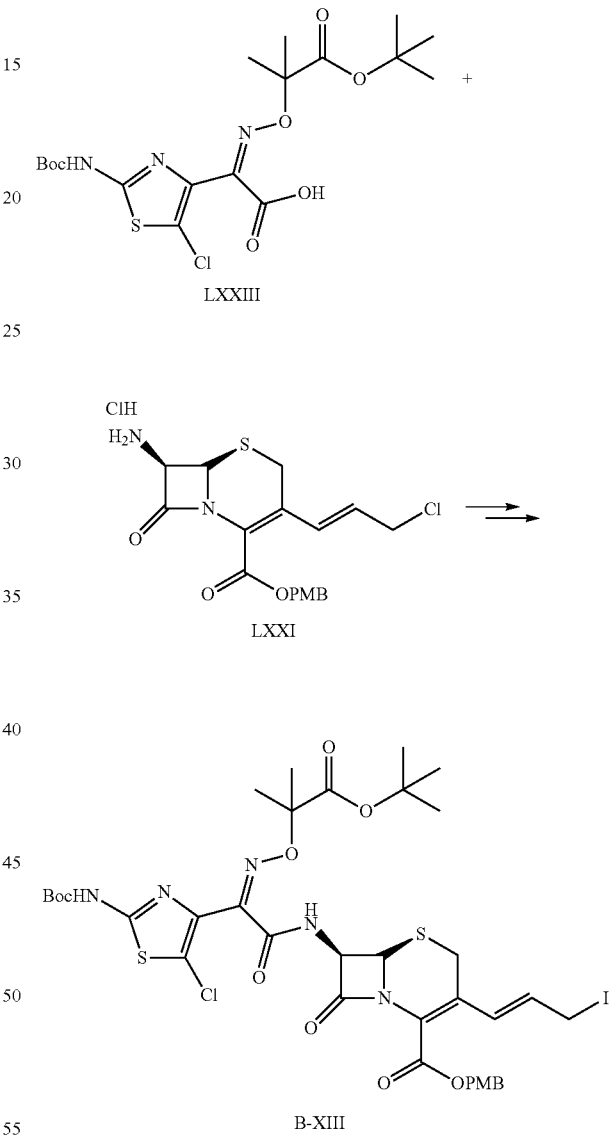

B-XIII

Compound B-XIII was prepared by a method similar to Preparation Example 43-3 by using Compound LXXIII and Compound LXXI.

$^1$H NMR (600 MHz, chloroform-$d_1$) δ=7.91 (m, 2H), 7.36 (d, J=8.4 Hz, 2H), 6.91 (d, J=8.4 Hz, 1H), 6.30 (d, J=11.4 Hz, 1H), 6.06 (m, 1H), 5.77 (m, 1H), 5.20 (dd, J=12 Hz, 22.8 Hz, 2H), 5.10 (d, J=4.8 Hz, 1H), 3.96~3.74 (m, 2H), 3.55 (dd, J=18 Hz, 99.6 Hz, 2H), 1.62 (s, 3H), 1.60 (s, 3H), 1.42 (s, 9H): NMR of allylchloride.

Example 1

Compound 1

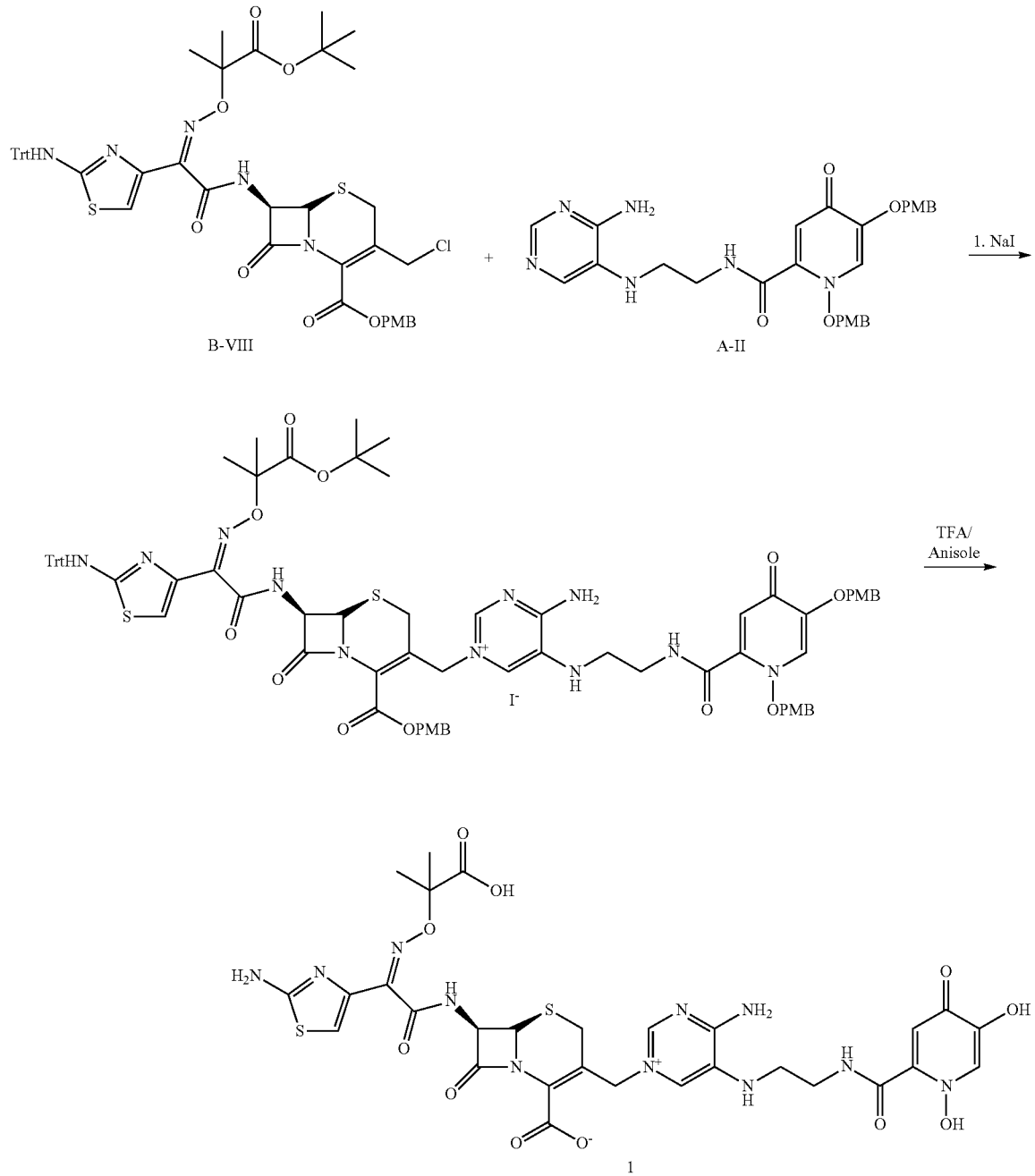

Compound B-VIII (193 mg, 0.21 mmol) was dissolved in N,N-dimethylformamide (0.5 mL) and sodium iodide (31 mg, 0.21 mmol) was added. The resulting solution was stirred for 30 minutes at room temperature. Compound A-II (86 mg, 0.21 mmol) was added. Then, the resulting solution was stirred for 4 hours at room temperature, diluted with ethyl acetate (5 mL), washed with water (3 mL) and saline (3 mL), dehydrated with anhydrous sodium sulfate, concentrated under reduced pressure, and applied to column chromatography (MC:MeOH=50:1~10:1) to yield a quaternary salt compound (67 mg (22%)).

The quaternary salt compound (67 mg, 40 umol) was dissolved in methylene chloride (0.5 mL). Anisole (0.2 mL) and trifluoroacetic acid (0.5 mL) were sequentially added. The resulting solution was stirred for 4 hours at room temperature. Isopropyl ether (5 mL) was added. The thus-created solid was filtered under reduced pressure to yield Compound 1 (34 mg (94%)).

$^1$H NMR (600 MHz, DMSO-$d_6$+D2O) δ 8.36 (s, 1H), 7.86 (s, 1H), 7.61 (s, 1H), 7.58 (s, 1H), 6.77 (s, 1H), 5.90 (d, J=4.8 Hz, 1H), 5.21 (d, J=4.8 Hz, 1H), 5.09 (dd, J=15 Hz, 33.6 Hz, 2H), 3.60 (m, 4H), 3.28 (m, 2H), 1.43 (s, 3H), 1.42 (s, 3H)

Example 2
Compound 2
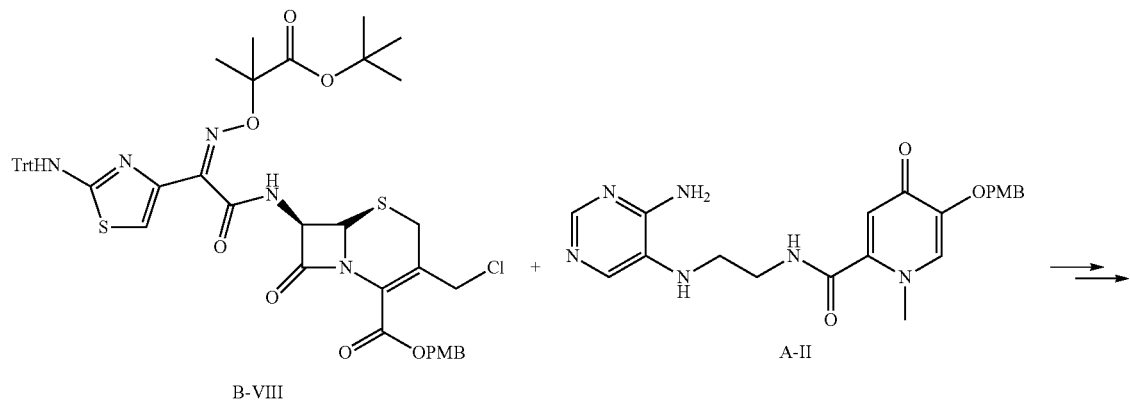
B-VIII
A-II
2
Compound 2 (2.6 mg, 8%) was prepared by a method similar to Example 1 by using Compound B-VIII and Compound A-II.
$^1$H NMR (600 MHz, CD$_3$OD) δ 8.40 (s, 1H), 7.90 (s, 1H), 7.83 (s, 1H), 7.34 (s, 1H), 7.03 (s, 1H), 5.95 (d, J=4.8 Hz, 1H), 5.29 (m, 3H), 3.93 (s, 3H), 3.66~3.37 (m, 6H), 1.61 (s, 3H), 1.60 (s, 3H)
Example 3
Compound 3
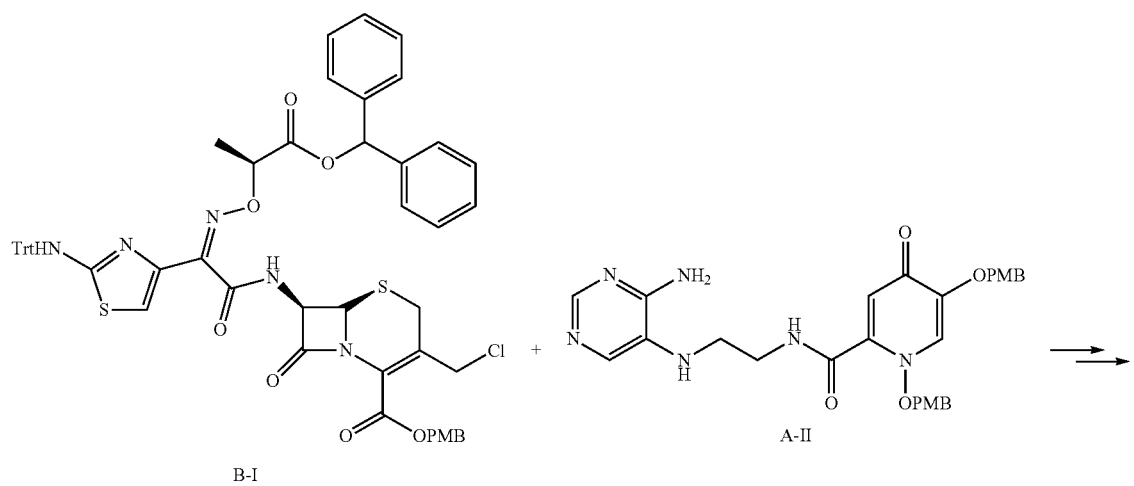
B-I
A-II

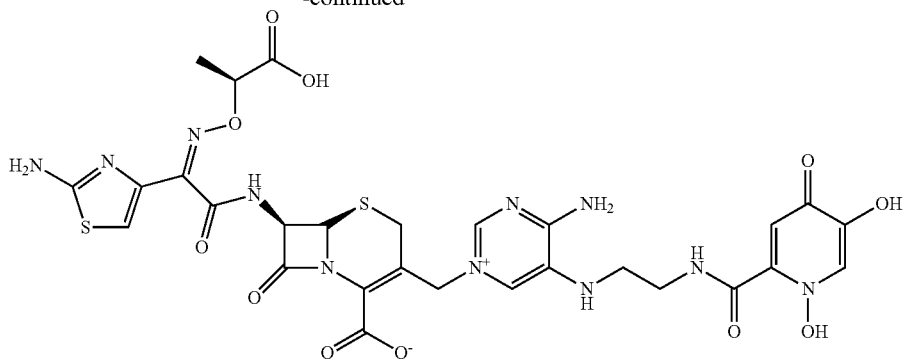
3
Compound 3 (25 mg, 41%) was prepared by a method similar to Example 1 by using Compound B-I and Compound A-II.
$^1$H NMR (600 MHz, DMSO-$d_6$+D2O) δ 8.33 (s, 1H), 7.79 (s, 1H), 7.59 (s, 1H), 7.53 (s, 1H), 6.72 (s, 1H), 5.87 (d, J=4.8 Hz, 1H), 5.14 (d, J=4.8 Hz, 1H), 5.05 (m, 2H), 4.54 (q, J=7.2 Hz, 1H), 3.54~3.22 (m, 6H), 1.35 (s, 3H), 1.32 (s, 3H)
Example 4
Compound 4
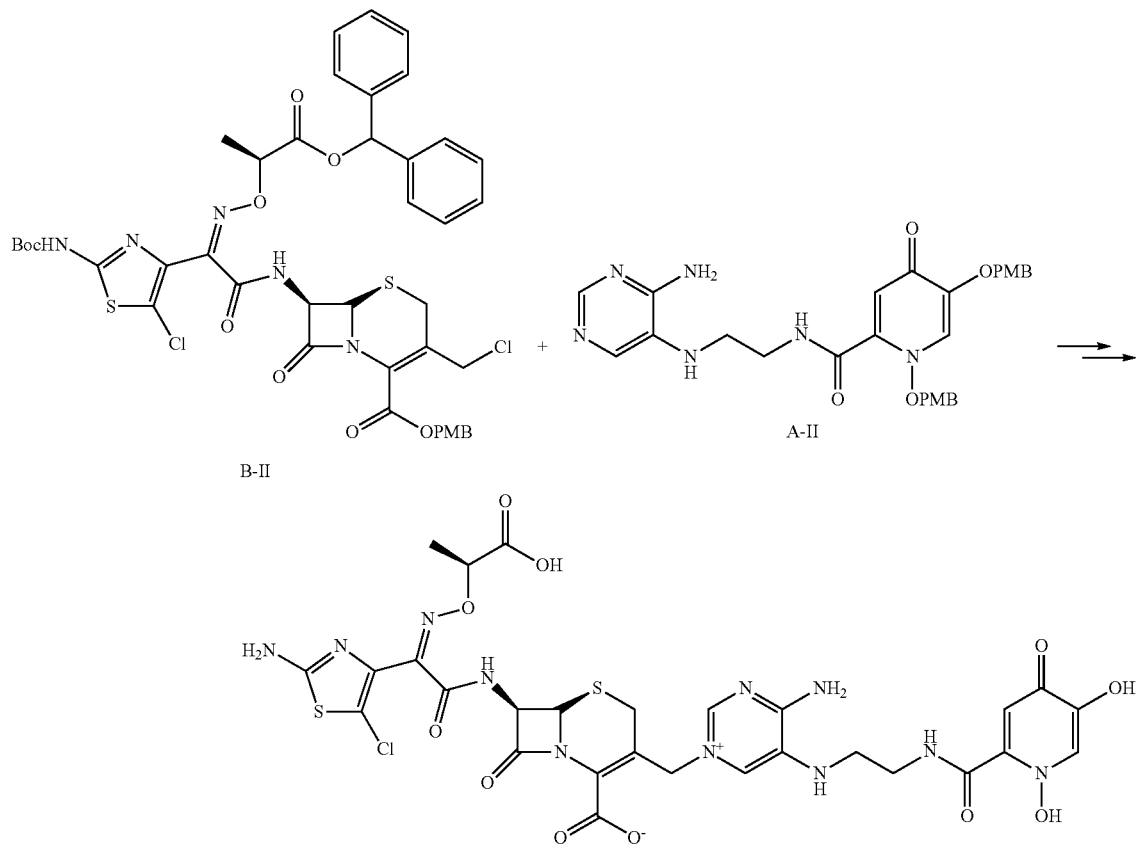

Compound 4 (10 mg, 28%) was prepared by a method similar to Example 1 by using Compound B-II and Compound A-II.

$^1$H NMR (600 MHz, DMSO-d$_6$+D2O) δ 8.41 (s, 1H), 7.85 (s, 1H), 7.71 (s, 1H), 7.60 (s, 1H), 5.87 (d, J=5.4 Hz, 1H), 5.16 (d, J=4.8 Hz, 1H), 5.08 (m, 2H), 4.58 (q, J=7.2 Hz, 1H), 3.59~3.26 (m, 6H), 1.41 (d, J=7.2 Hz, 3H)

Example 5

Compound 5

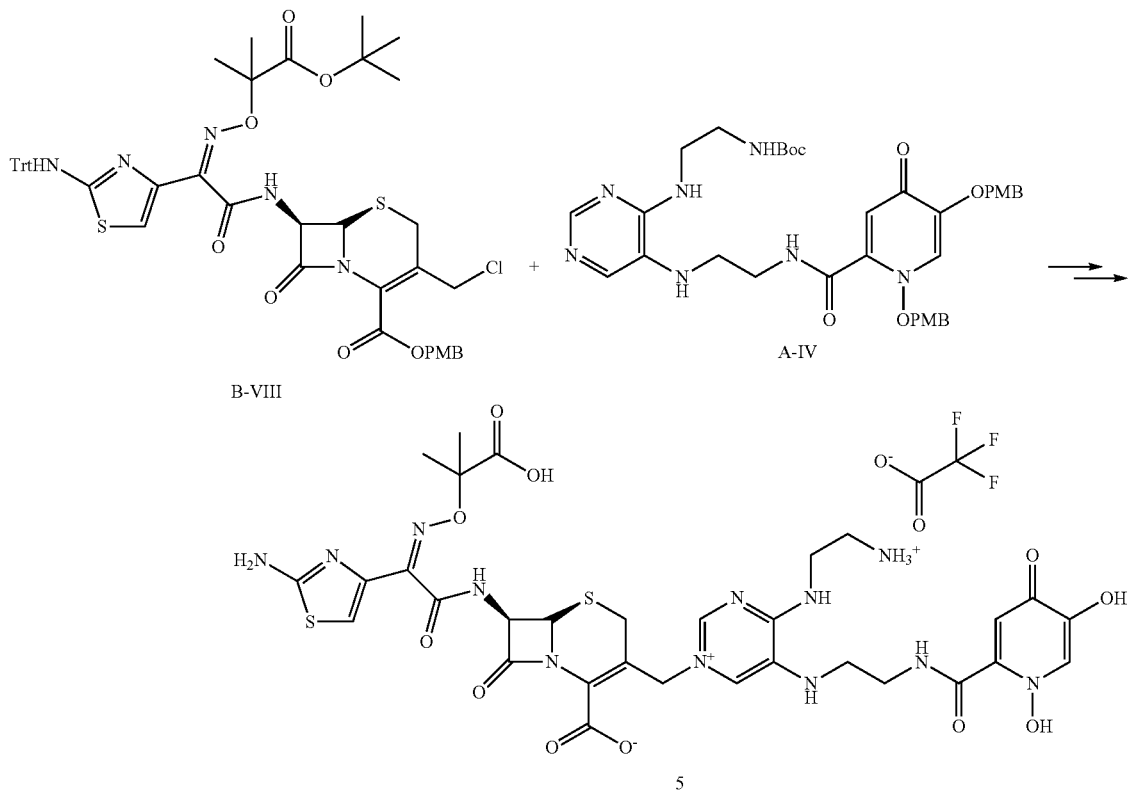

Compound 5 (7.6 mg, 24%) was prepared by a method similar to Example 1 by using Compound B-VIII and Compound A-IV.

$^1$H NMR (600 MHz, CD$_3$OD) δ 8.52 (s, 1H), 7.88 (s, 1H), 7.86 (s, 1H), 7.61 (s, 1H), 7.06 (s, 1H), 5.97 (d, J=5.4 Hz, 1H), 5.32 (d, J=14.4 Hz, 1H), 5.26 (d, J=5.4 Hz, 1H), 5.17 (d, J=14.4 Hz, 1H), 3.98 (m, 2H), 3.70 (m, 2H), 3.44 (m, 2H), 3.36~3.28 (m, 4H), 1.58 (s, 3H), 1.56 (s, 3H)

Example 6

Compound 6

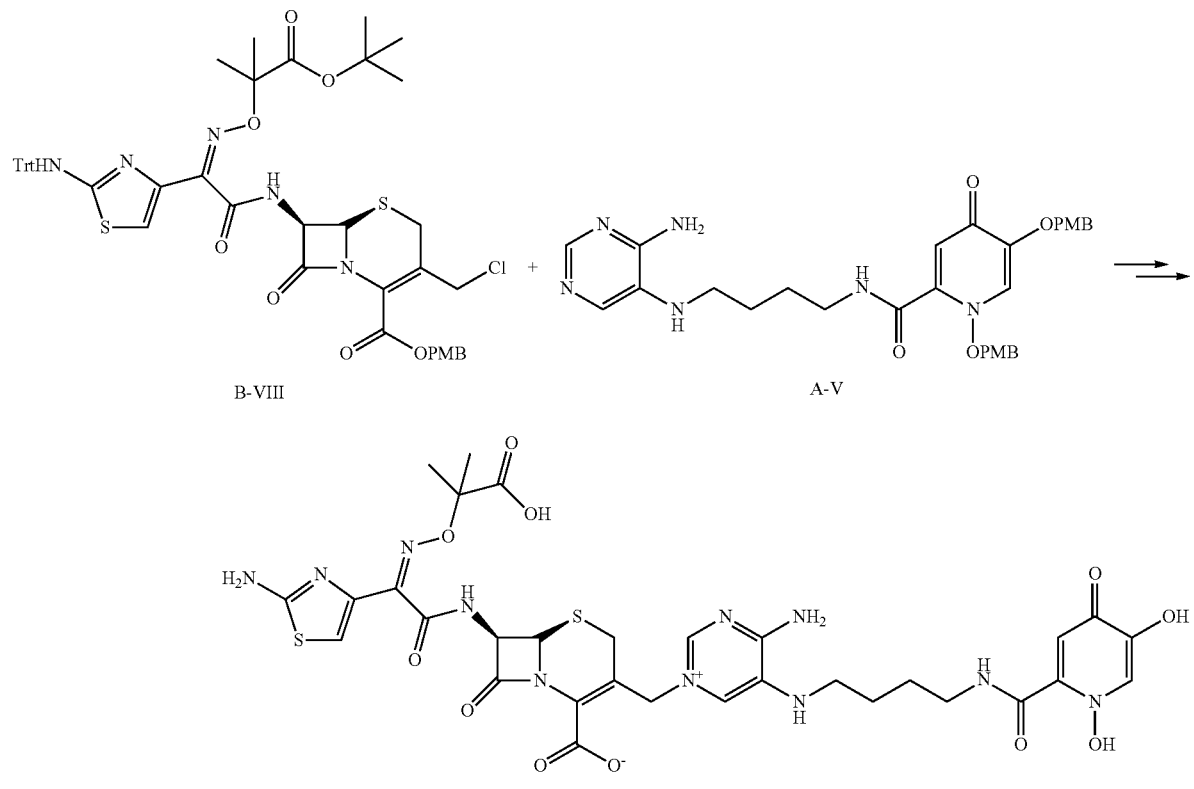

Compound 6 (12 mg, 17%) was prepared by a method similar to Example 1 by using Compound B-VIII and Compound A-V.

$^1$H NMR (600 MHz, DMSO-d$^6$) δ 11.72 (s, 1H), 11.05 (s, 1H), 10.88 (s, 1H), 9.48 (d, J=8.4 Hz, 1H), 8.67 (br, 1H), 8.48 (s, 1H), 7.79 (s, 1H), 7.55 (s, 1H), 7.31 (br, 2H), 6.70 (s, 1H), 5.98 (br, 1H), 5.93 (dd, J=4.8 Hz, 5.4 Hz, 1H), 5.21 (d, J=4.8 Hz, 1H), 5.12 (d, J=14.4 Hz, 1H), 4.94 (d, J=15 Hz, 1H), 3.75 (m, 2H), 3.60 (m, 2H), 3.42 (m, 2H), 1.41 (s, 3H), 1.40 (s, 3H)

Example 7

Compound 7

Compound 7 (38 mg, 39%) was prepared by a method similar to Example 1 by using Compound B-VIII and Compound A-VI.

$^1$H NMR (600 MHz, DMSO-d$^6$+D$_2$O) δ 8.36 (s, 1H), 7.84 (s, 1H), 7.57 (s, 1H), 7.51 (s, 1H), 6.73 (s, 1H), 5.91 (d, J=4.8 Hz, 1H), 5.20 (d, J=4.8 Hz, 1H), 5.08 (q, J=15.6 Hz, 2H), 3.54~3.41 (m, 2H), 3.37 (br, 2H), 3.05 (br, 2H), 1.64 (br, 4H), 1.43 (s, 3H), 1.41 (s, 3H)

Example 8

Compound 8

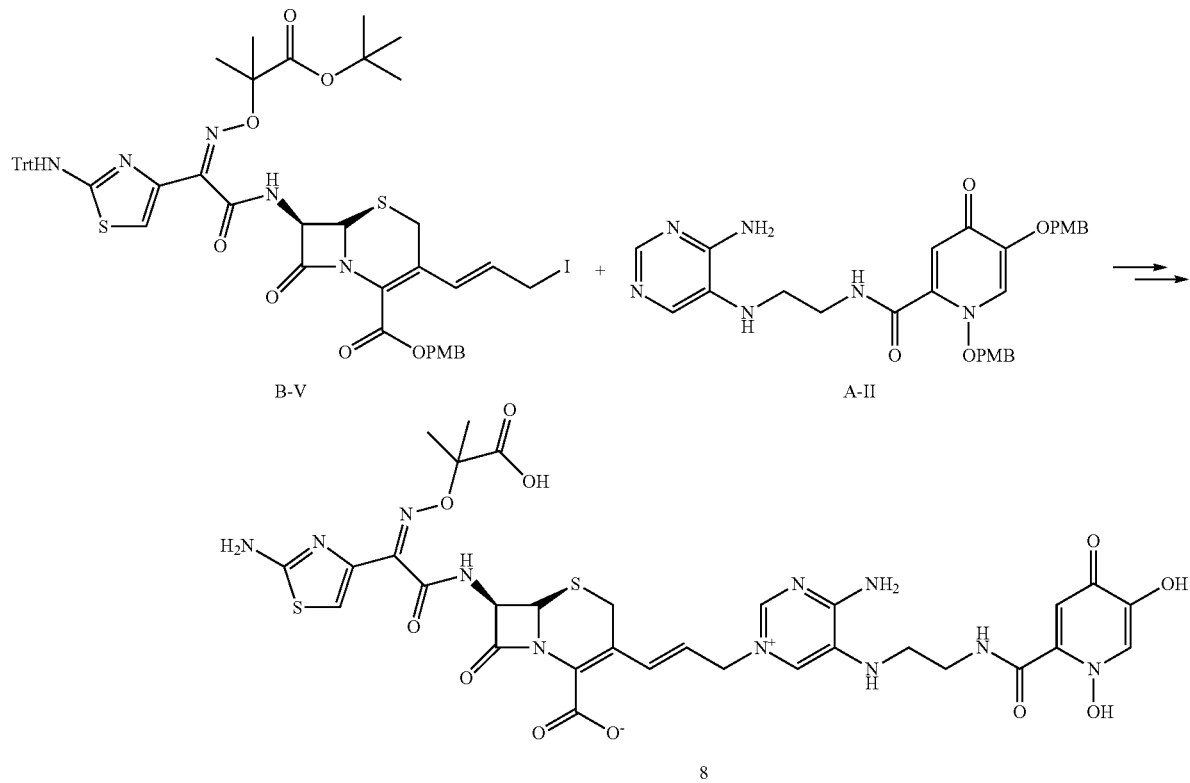

Compound B-V (371 mg, 0.39 mmol) and Compound A-II (200 mg, 0.36 mmol) were dissolved in N,N-dimethylformamide (2 mL). The resulting solution was stirred for 3 hours at room temperature, diluted with ethyl acetate (15 mL), washed with water (20 mL) and saline (10 mL), dehydrated with anhydrous sodium sulfate, concentrated under reduced pressure, and applied to column chromatography (MC:MeOH=50:1~10:1) to yield a quaternary salt compound (323 mg (60%)).

The quaternary salt compound (323 mg, 0.22 mmol) was dissolved in methylene chloride (4 mL). Anisole (0.5 mL) and trifluoroacetic acid (4 mL) were sequentially added. The resulting solution was stirred for 3 hours at room temperature. Isopropyl ether (20 mL) was added and the thus-created solid was filtered under reduced pressure to yield Compound 8 (176 mg, 100%).

$^1$H NMR (600 MHz, DMSO-d$^6$+D$_2$O) δ 8.40 (s, 1H), 7.85 (s, 1H), 7.67 (s, 1H), 7.58 (s, 1H), 6.91 (d, J=16.2 Hz, 1H), 6.77 (s, 1H), 6.31 (m, 1H), 5.84 (d, J=4.8 Hz, 1H), 5.22 (d, J=4.8 Hz, 1H), 4.92 (m, 2H), 3.85 (d, J=18 Hz, 1H), 3.74 (d, J=18 Hz, 1H), 3.57 (m, 2H), 3.30 (br, 2H), 1.45 (s, 3H), 1.43 (s, 3H)

Example 9

Compound 9

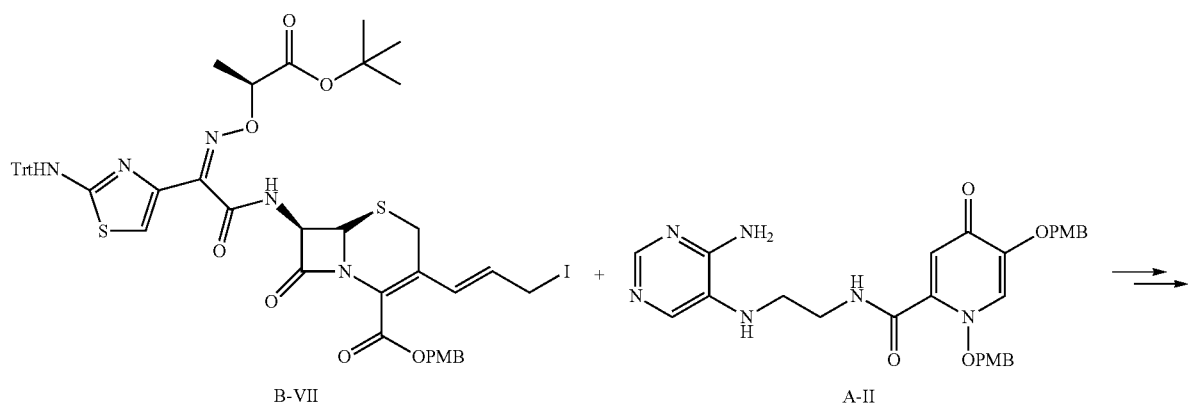

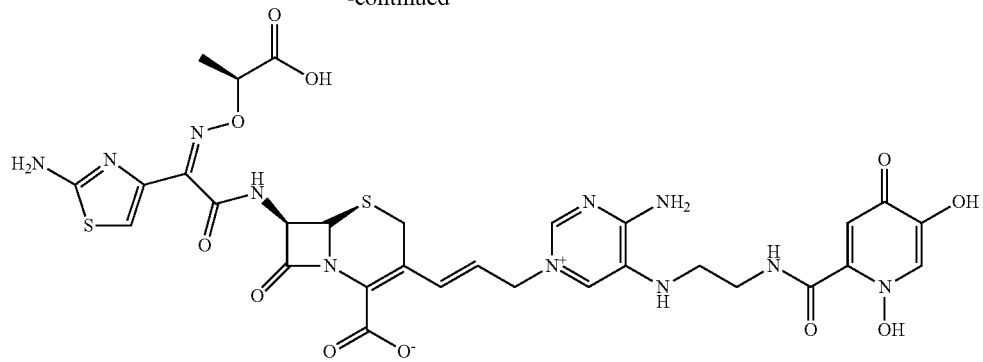

9

Compound 9 (35 mg, 28%) was prepared by a method similar to Example 8 by using Compound B-VII and Compound A-II.

¹H NMR (600 MHz, DMSO-d6) δ 11.78 (t, J=6.6 Hz, 1H), 11.03 (br d, 2H), 9.54 (d, J=8.4 Hz, 1H), 9.00 (s, 1H), 8.42 (s, 1H), 8.09 (br, 1H), 7.82 (s, 1H), 7.70 (s, 1H) 7.57 (s, 1H) 7.34 (br, 2H) 6.93 (d, J=15.6 Hz), 6.78 (s, 1H), 6.31 (m, 1H), 6.04 (br, 1H), 5.87 (dd, J=4.8 Hz, 8.4 Hz, 1H), 5.22 (d, J=4.8 Hz, 1H), 4.93 (m, 1H), 4.62 (q, J=6.6 Hz, 1H), 3.83~3.29 (m, 6H), 1.4 (d, J=7.2 Hz, 3H)

Example 10

Compound 10

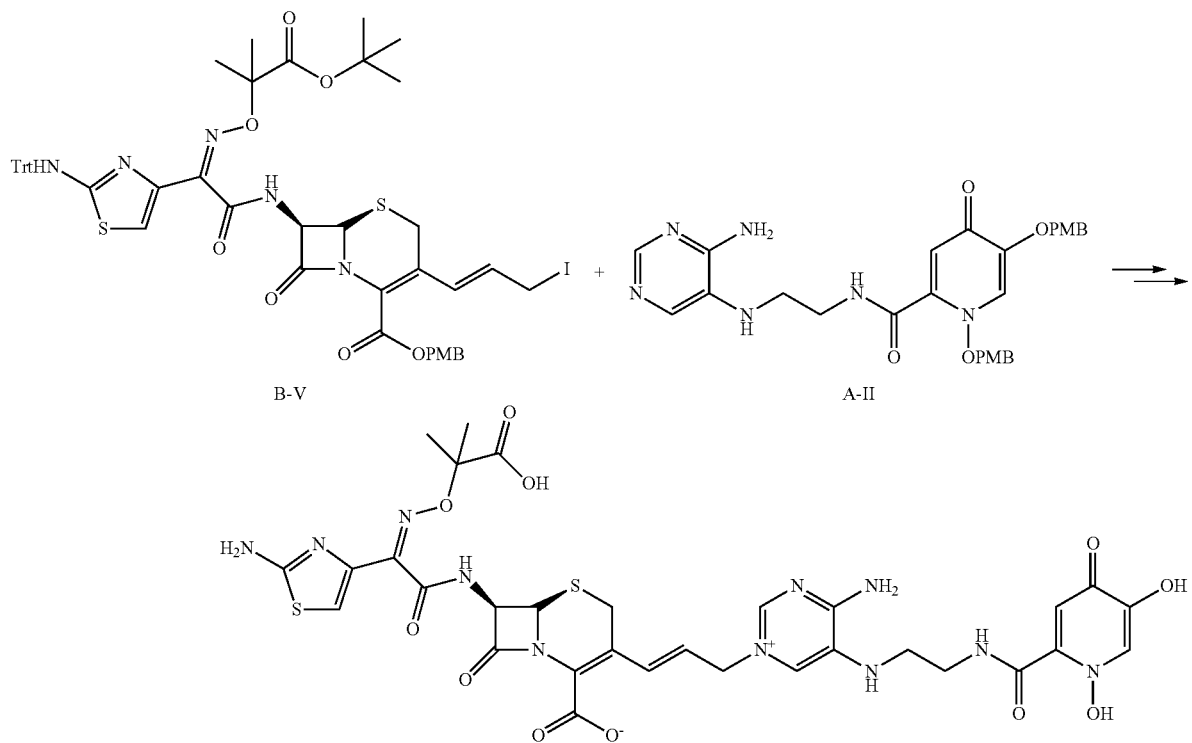

Compound 10 (8 mg, 3.2%) was prepared by a method similar to Example 8 by using Compound B-V and Compound A-II.

¹H NMR (600 MHz, CD₃OD) δ 8.34 (s, 1H), 7.93 (s, 1H), 7.58 (s, 1H), 7.10 (s, 1H), 7.02 (s, 1H), 6.97 (d, J=16.2 Hz, 1H), 6.23 (m, 1H), 5.92 (d, J=4.8 Hz, 1H), 5.21 (d, J=4.8 Hz, 1H), 4.96 (m, 2H), 4.42 (s, 2H), 3.83 (d, J=18 Hz, 1H), 3.66~3.61 (m, 3H), 3.41 (t, J=5.4 Hz), 1.62 (s, 3H), 1.59 (s, 3H)

Example 11
Compound 11
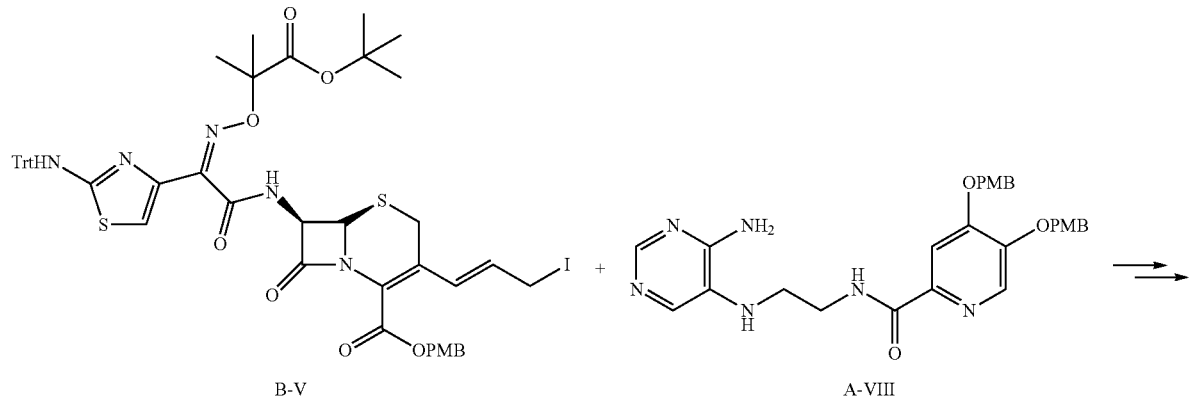
Compound 11 (51 mg, 30%) was prepared by a method similar to Example 8 by using Compound B-V and Compound A-VIII.
$^1$H NMR (600 MHz, DMSO-d6) δ 9.44 (d, J=9 Hz, 1H), 8.97 (br, 1H), 8.67 (br, 1H), 8.39 (s, 1H), 8.01 (br, 1H), 7.90 (s, 1H), 7.63 (s, 1H), 7.41 (s, 1H), 7.34 (br, 2H), 6.89 (d, J=15.6 Hz, 1H), 6.69 (s, 1H), 6.27 (m, 1H), 5.93 (br, 1H), 5.81 (dd, J=4.8 Hz, 8.4 Hz, 1H), 5.18 (d, J=4.8 Hz, 1H), 4.89 (m, 2H), 3.81 (d, J=17.4 Hz, 1H), 3.55~3.21 (m, 5H), 1.40 (s, 3H), 1.39 (s, 3H)
Example 12
Compound 12
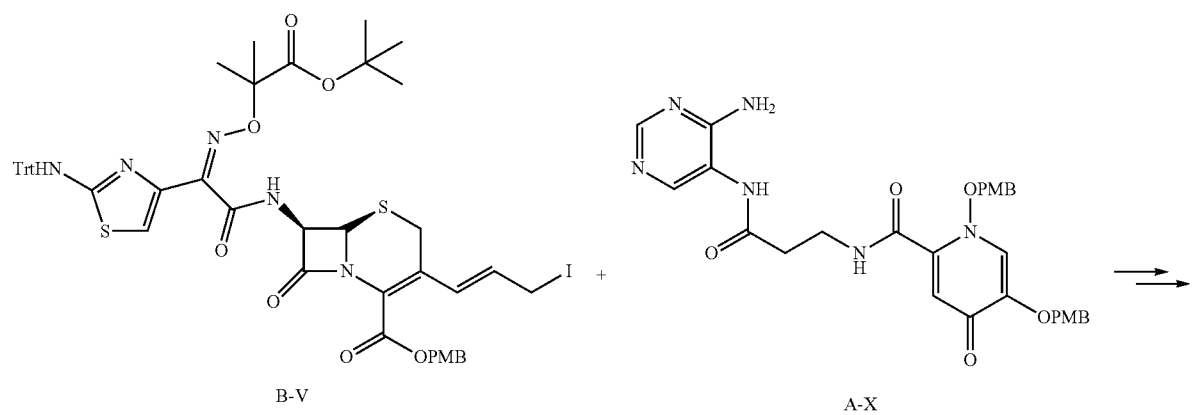

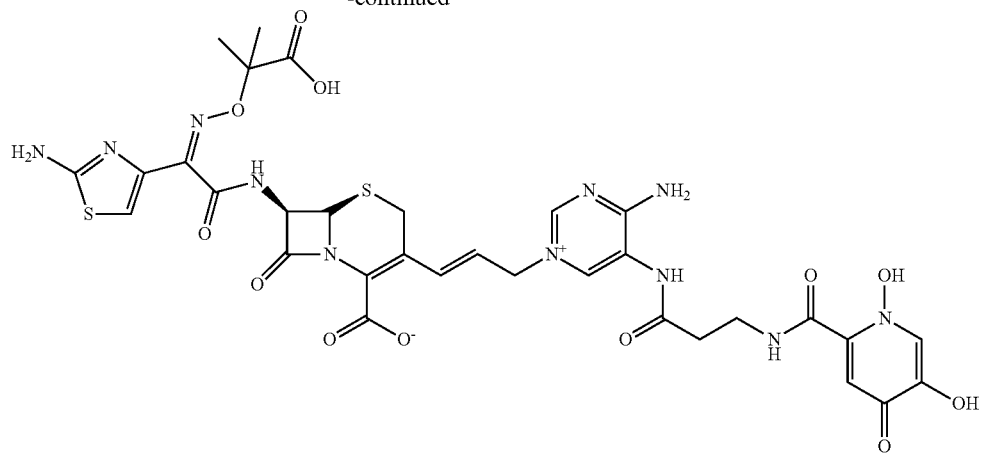
12
Compound 12 (40 mg, 39%) was prepared by a method similar to Example 8 by using Compound B-V and Compound A-X.
¹H NMR (600 MHz, CD₃OD) δ 8.66 (s, 1H), 8.60 (s, 1H), 7.90 (s, 1H), 7.65 (s, 1H), 7.19 (d, J=15.6 Hz, 1H), 6.99 (s, 1H), 6.22 (m, 1H), 5.92 (d, J=4.8 Hz, 1H), 5.23 (d, J=4.8 Hz, 1H), 4.93 (m, 2H), 3.82~3.77 (m, 3H), 3.68 (d, J=18 Hz, 1H), 2.80 (t, J=6 Hz, 2H), 1.61 (s, 3H), 1.60 (s, 3H)
Example 13
Compound 13
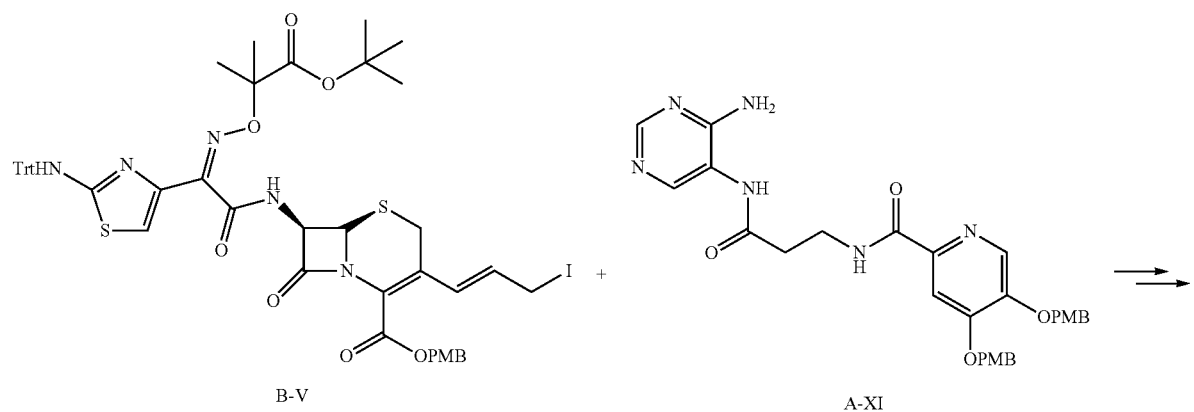
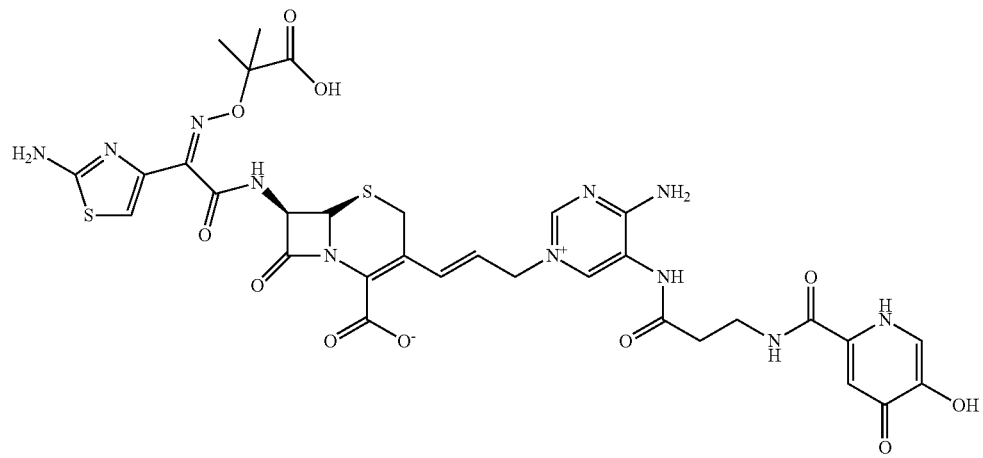
13

Compound 13 (70 mg, 69%) was prepared by a method similar to Example 8 by using Compound B-V and Compound A-XI.

$^1$H NMR (600 MHz, CD$_3$OD) δ 8.62 (s, 1H), 8.60 (s, 1H), 7.90 (s, 1H), 7.45 (s, 1H), 7.21 (d, J=16.2 Hz, 1H), 7.06 (s, 1H), 6.22 (m, 1H), 5.94 (d, J=4.8 Hz, 1H), 5.23 (d, J=4.8 Hz, 1H), 4.90 (m, 2H) 3.83~3.65 (m, 4H), 2.80 (m, 2H), 1.63 (s, 3H), 1.61 (s, 3H)

Example 14

Compound 14

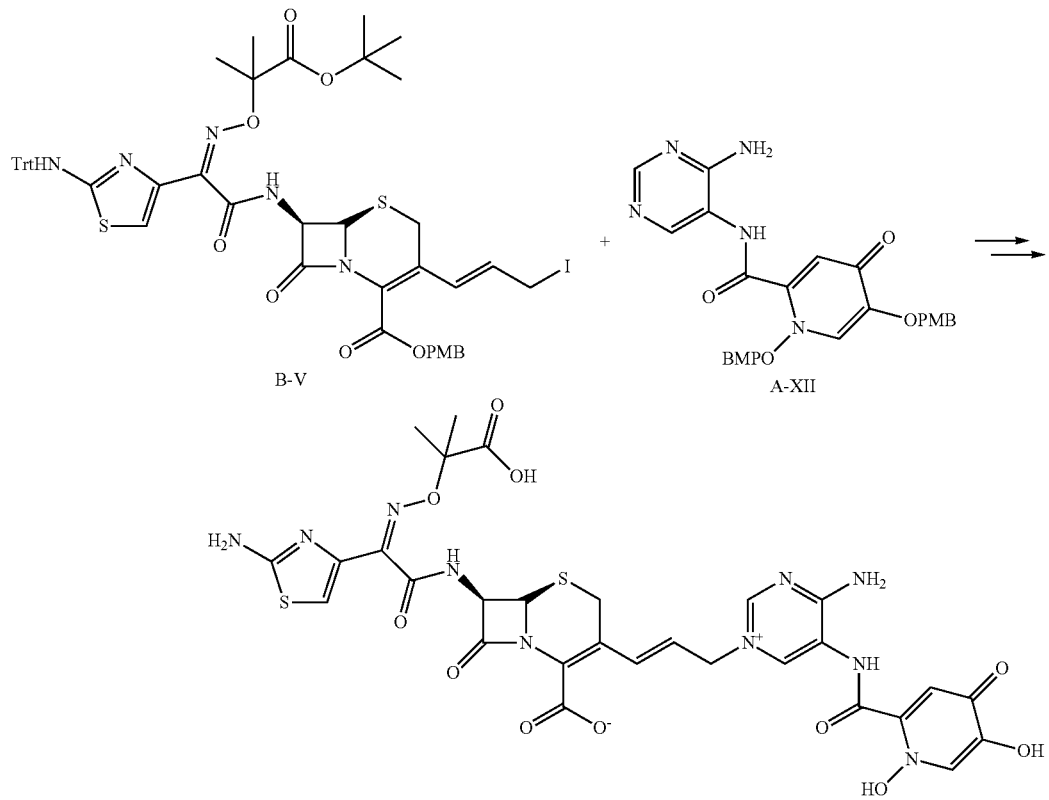

Compound 14 (88 mg, 42%) was prepared by a method similar to Example 8 by using Compound B-V and Compound A-XII.

$^1$H NMR (600 MHz, CD$_3$OD) δ 8.66 (s, 1H), 8.65 (s, 1H), 7.97 (s, 1H), 7.69 (s, 1H), 7.23 (d, J=16.2 Hz, 1H), 7.03 (s, 1H), 6.25 (m, 1H), 5.94 (d, J=4.2 Hz, 1H), 5.23 (d, J=4.8 Hz, 1H), 4.92 (m, 2H), 3.85 (d, J=18 Hz, 1H), 3.69 (d, J=17.4 Hz), 1.62 (s, 3H), 1.61 (s, 3H)

Example 15

Compound 15

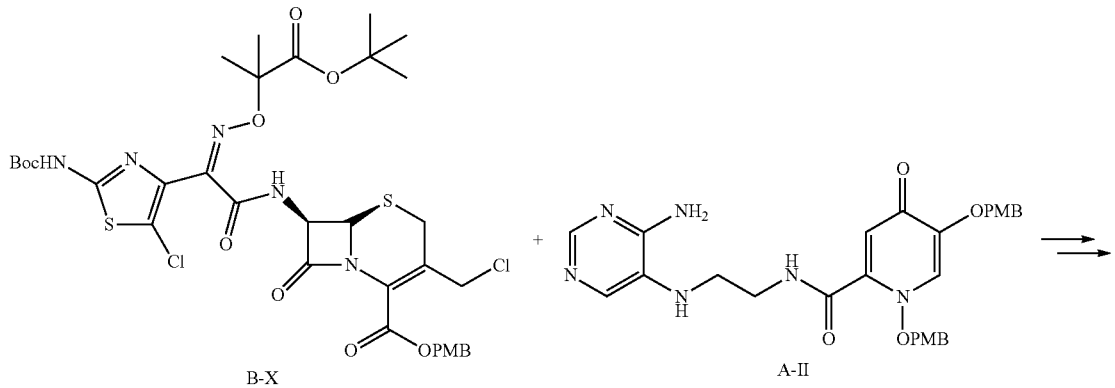

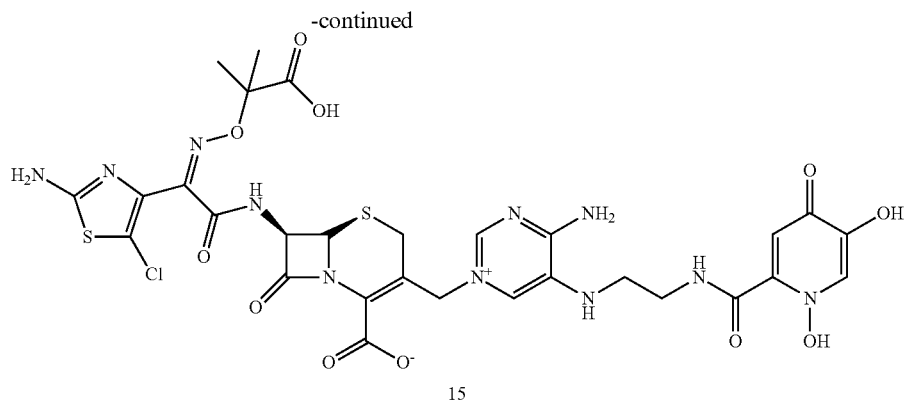
15
Compound 15 (65 mg, 12%) was prepared by a method similar to Example 1 by using Compound B-X and Compound A-II.
$^1$H NMR (600 MHz, CD$_3$OD) δ 8.37 (s, 1H), 8.28 (s, 1H), 7.87 (s, 1H), 7.65 (s, 1H), 5.95 (d, J=4.8 Hz, 1H), 5.28 (d, J=14.4 Hz, 1H), 5.24 (d, J=5.4 Hz, 1H), 5.10 (d, J=15 Hz, 1H), 3.69 (m, 3H), 3.43~3.33 (m, 3H), 1.56 (s, 3H), 1.55 (s, 3H)
Example 16
Compound 16
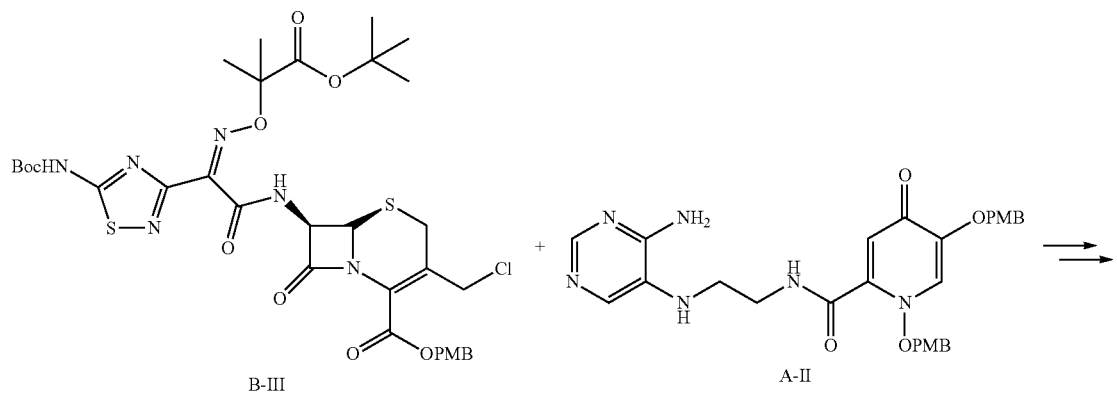
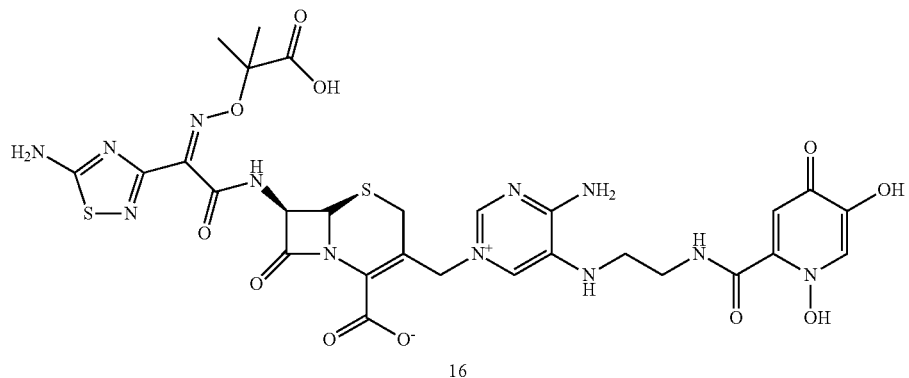
16
Compound 16 (25 mg, 9%) was prepared by a method similar to Example 1 by using Compound B-III and Compound A-II.
$^1$H NMR (600 MHz, DMSO-d$_6$+D$_2$O) δ 8.31 (s, 1H), 7.80 (s, 1H), 7.79 (s, 1H), 7.52 (s, 1H), 5.84 (d, J=4.8 Hz, 1H), 5.12 (d, J=4.8 Hz, 1H), 5.05 (m, 2H), 3.55~3.20 (m, 6H), 1.37 (s, 6H)

Example 17
Compound 17
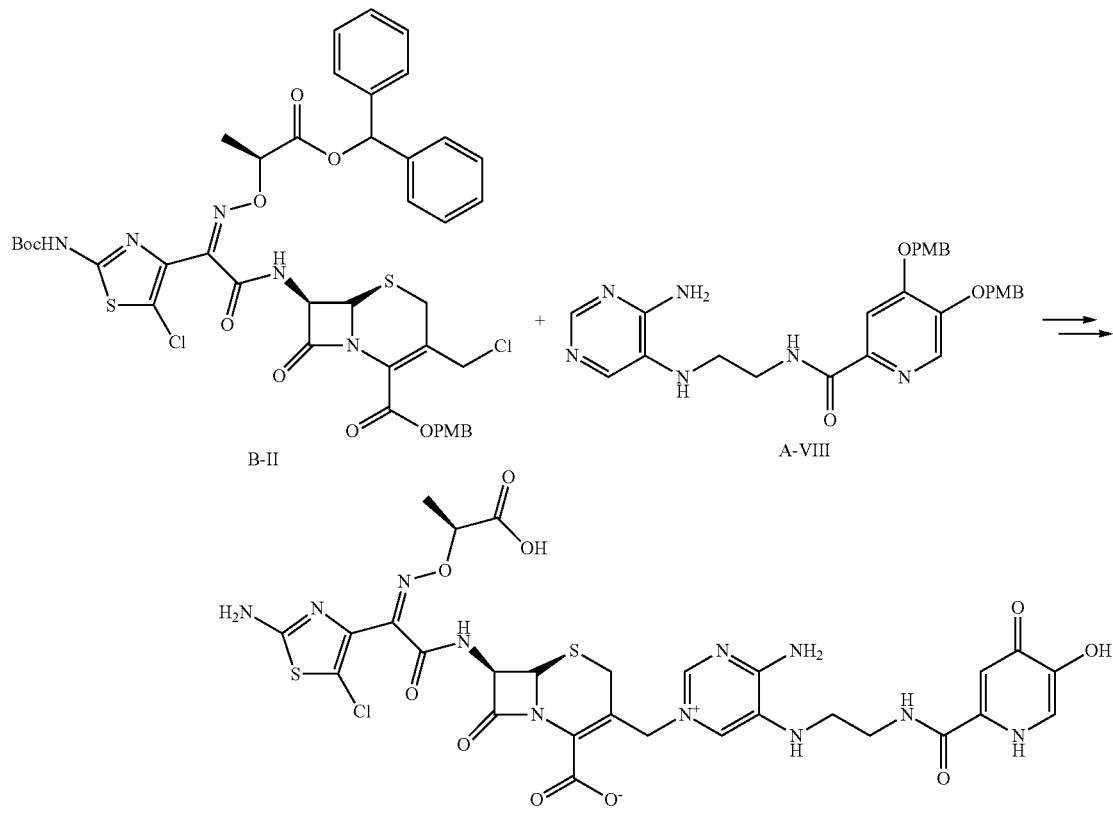
Compound 17 (30 mg, 16%) was prepared by a method similar to Example 1 by using Compound B-II and Compound A-VIII.
$^1$H NMR (600 MHz, CD$_3$OD) δ 8.39 (d, J=1.8 Hz, 1H), 8.00 (s, 1H), 7.89 (d, J=1.8 Hz, 1H), 7.60 (s, 1H), 5.96 (d, J=4.8 Hz, 1H), 5.34 (d, J=14.4 Hz, 1H), 5.24 (d, J=4.8 Hz, 1H), 4.97 (d, J=15 Hz, 1H), 4.81 (q, J=7.2 Hz, 1H), 3.65~3.33 (m, 6H), 1.51 (d, J=7.8 Hz, 3H)
Example 18
Compound 18
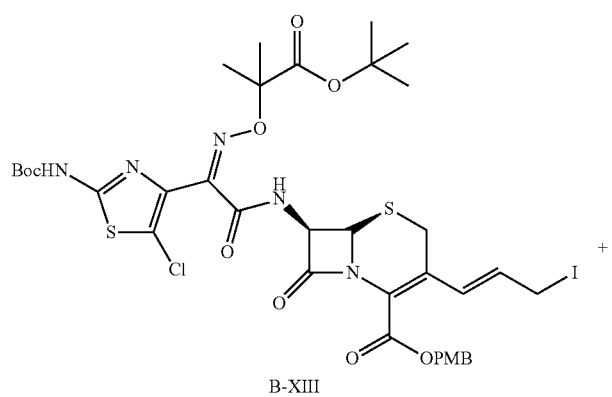

-continued
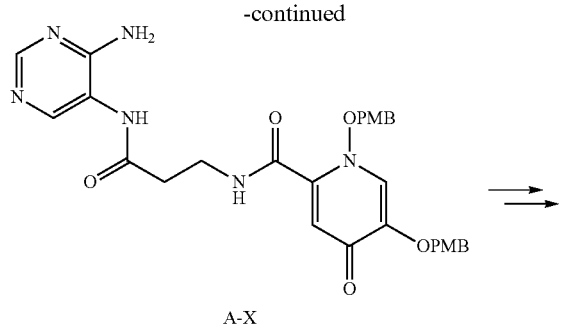
A-X
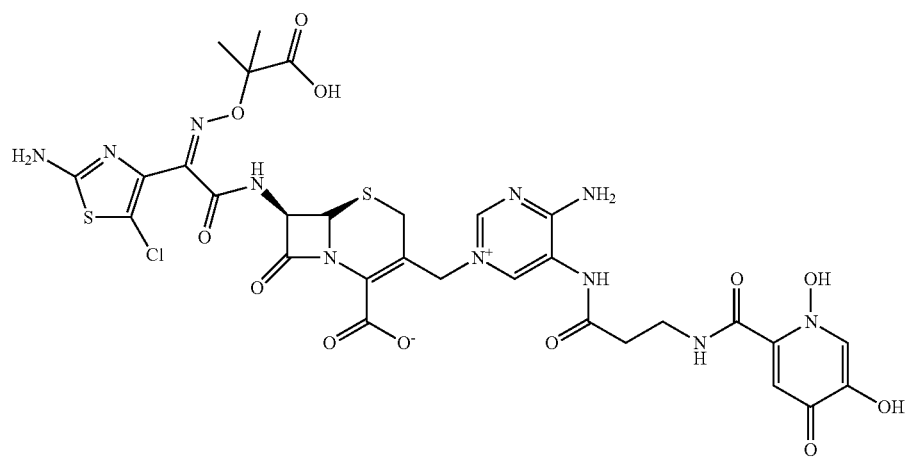
18
Compound 18 (69 mg, 20%) was prepared by a method similar to Example 1 by using Compound B-X and Compound A-X.
$^1$H NMR (600 MHz, CD$_3$OD) δ 8.78 (s, 1H), 8.67 (s, 1H), 7.91 (s, 1H), 7.65 (s, 1H), 5.95 (d, J=4.8 Hz, 1H), 5.31 (d, J=15 Hz, 1H), 5.24 (d, J=4.8 Hz), 5.14 (d, J=15.6 Hz, 1H), 3.80 (m, 2H), 3.70 (d, J=18 Hz, 1H), 3.14 (d, J=18 Hz, 1H), 2.78 (m, 2H), 1.59 (s, 3H), 1.57 (s, 3H)
Example 19
Compound 19
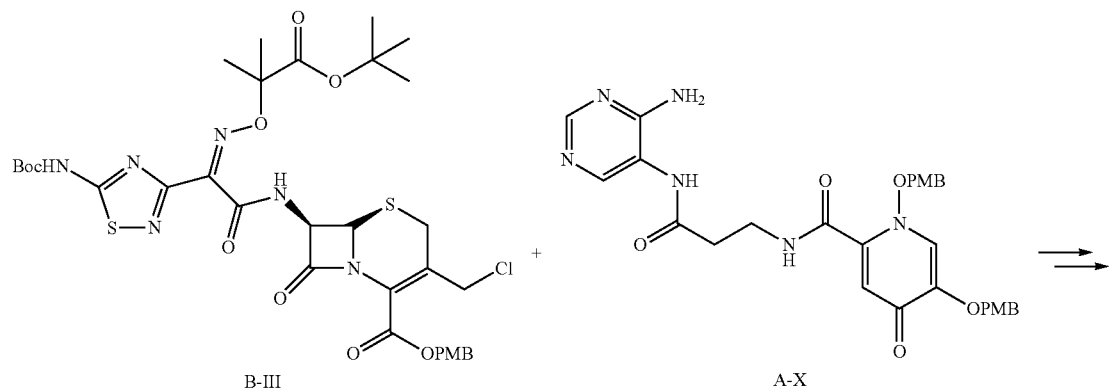

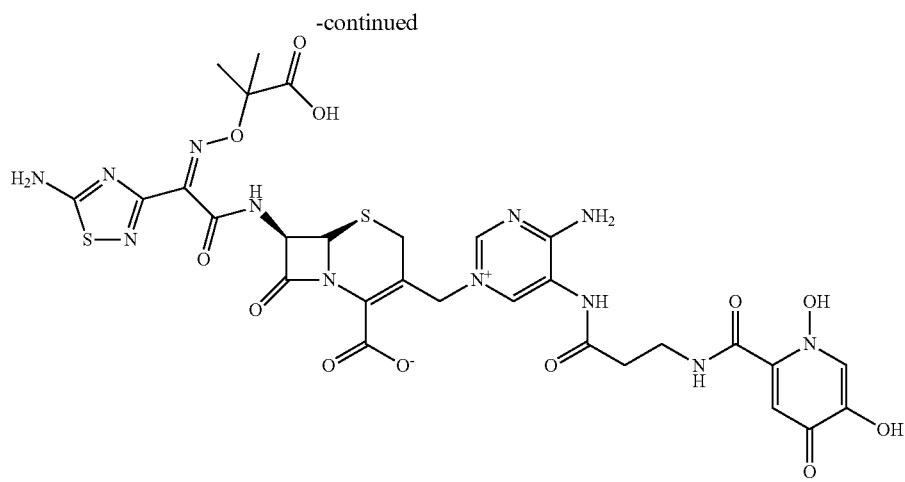
19
Compound 19 (134 mg, 48%) was prepared by a method similar to Example 1 by using Compound B-III and Compound A-X.
$^1$H NMR (600 MHz, DMSO-$d_6$+D2O) δ 8.77 (s, 1H), 8.64 (s, 1H), 7.82 (s, 1H), 7.56 (s, 1H), 5.91 (d, J=4.8 Hz, 1H), 5.20~4.97 (m, 3H), 3.56 (m, 4H), 2.69 (m, 2H), 1.43 (s, 6H)
Example 20
Compound 20
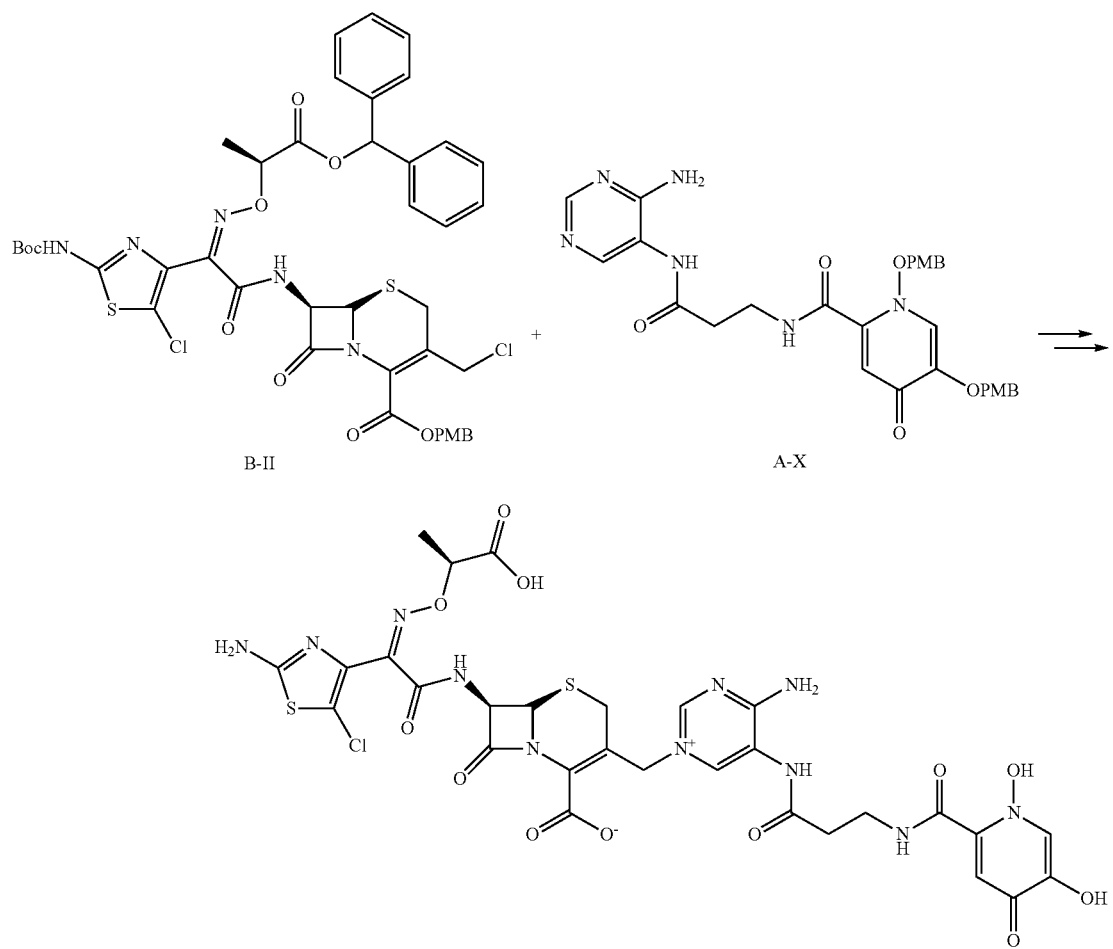
20

Compound 20 (120 mg, 20%) was prepared by a method similar to Example 1 by using Compound B-II and Compound A-X.

$^1$H NMR (600 MHz, DMSO-d$_6$+D2O) δ 8.76 (s, 1H), 8.66 (s, 1H), 7.82 (s, 1H), 7.53 (s, 1H), 5.65 (d, J=4.2 Hz, 1H), 5.09 (d, J=14.4 Hz, 1H), 4.92 (d, J=4.8 Hz, 1H), 4.86 (d, J=4.8 Hz, 1H), 4.58 (q, J=14.4 Hz, 1H), 3.56 (m, 2H), 3.41 (d, J=18 Hz, 1H), 3.20 (d, J=17.4 Hz, 1H), 1.36 (s, 3H), 1.35 (s, 3H)

Example 21

Compound 21

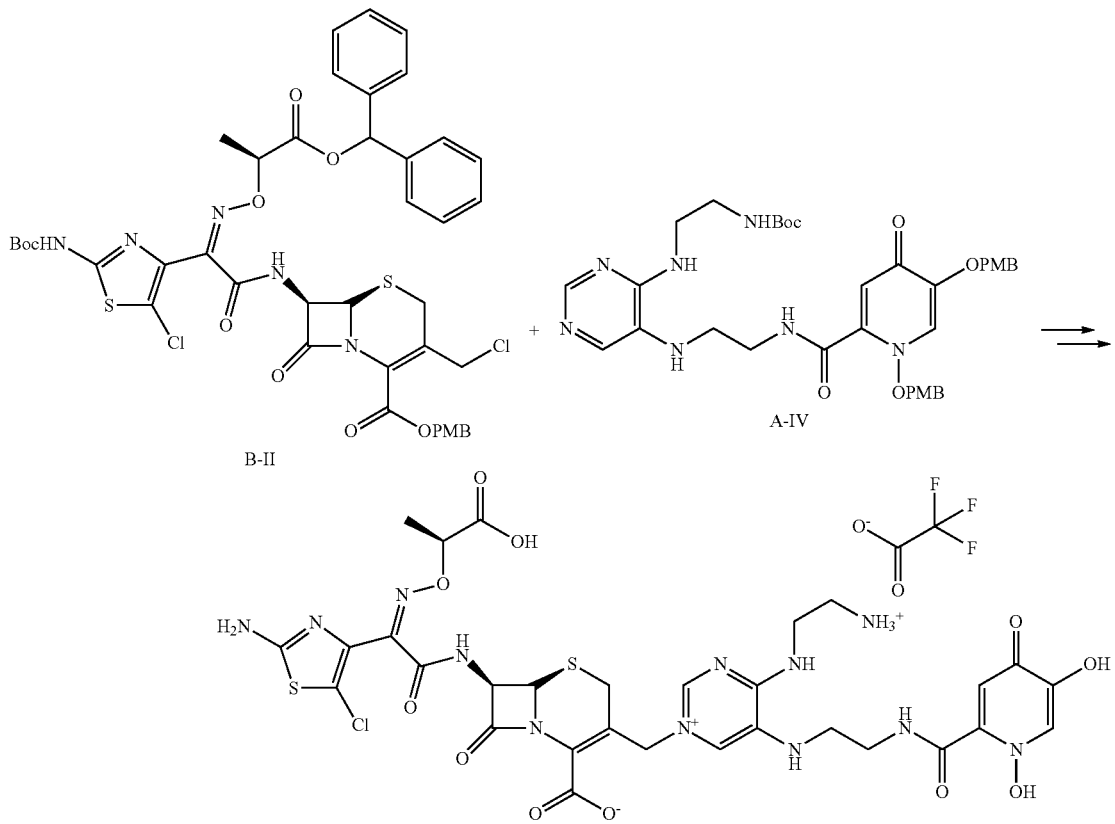

Compound 21 (145 mg, 53%) was prepared by a method similar to Example 1 by using Compound B-II and Compound A-IV.

$^1$H NMR (600 MHz, CD$_3$OD) δ 8.45 (s, 1H), 7.93 (s, 1H), 7.86 (s, 1H), 7.61 (s, 1H), 5.98 (d, J=4.8 Hz, 1H), 5.33 (d, J=14.4 Hz, 1H), 5.24 (d, J=4.8 Hz, 1H), 5.18 (d, J=15 Hz, 1H), 4.81 (q, J=7.2 Hz, 1H), 4.12~3.33 (m, 10H), 1.53 (d, J=3.6 Hz, 3H)

Example 22

Compound 22

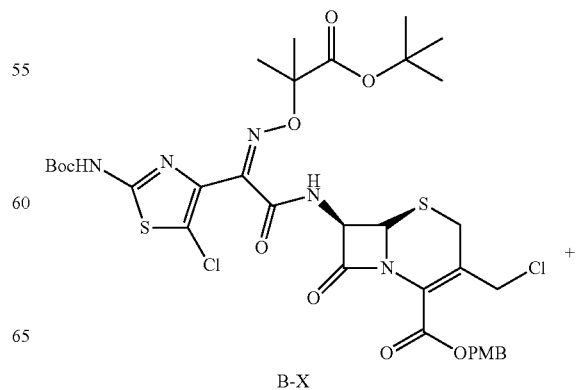

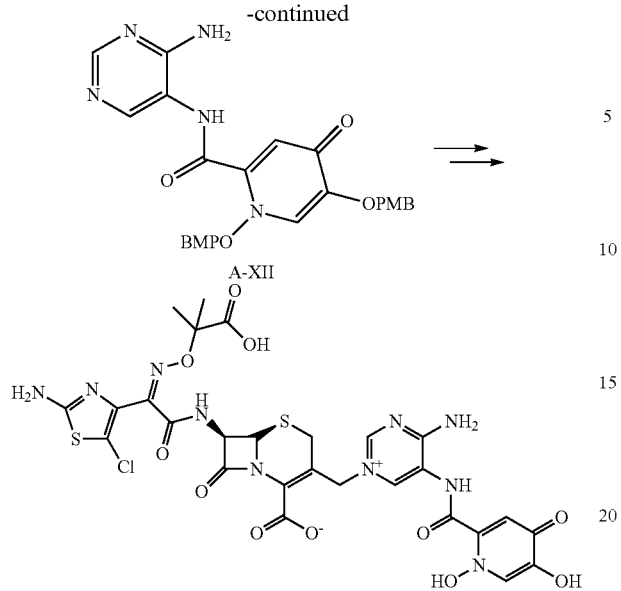
Compound 22 (33 mg, 8%) was prepared by a method similar to Example 1 by using Compound B-X and Compound A-XII.
$^1$H NMR (600 MHz, CD$_3$OD) δ 8.81 (s, 1H), 8.75 (s, 1H), 7.97 (s, 1H), 7.70 (s, 1H), 5.97 (d, J=4.8 Hz), 5.35 (d, J=14.4 Hz, 1H), 5.24 (d, J=5.4 Hz, 1H), 5.01 (m, 1H), 3.49~3.43 (m, 2H), 1.60 (br, 6H)
Example 23
Compound 23
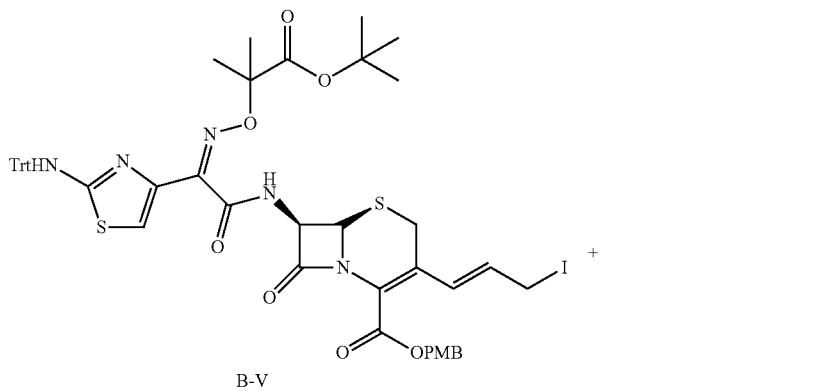
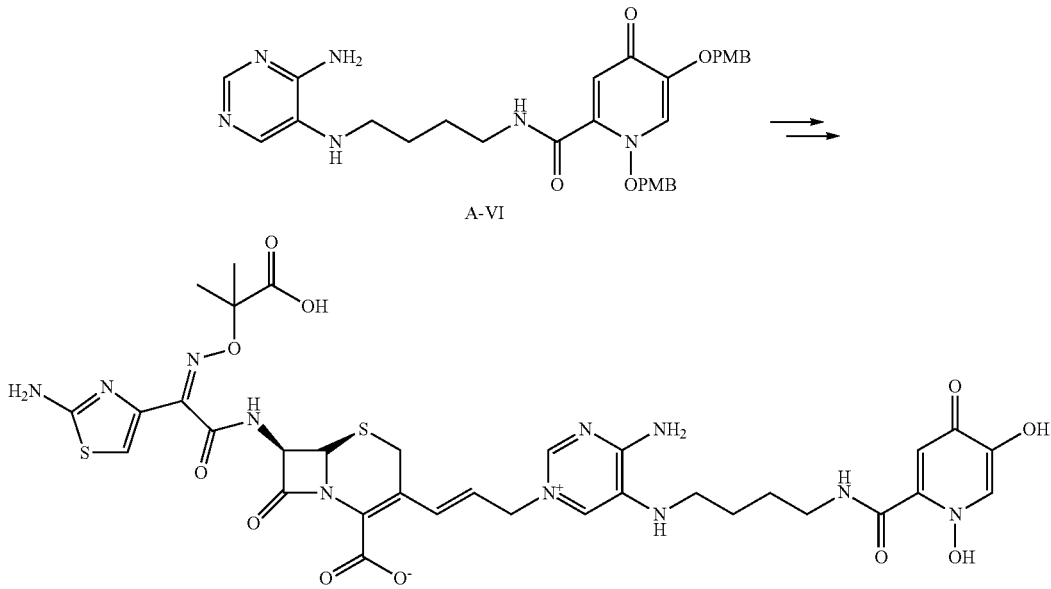

Compound 23 (11 mg, 28%) was prepared by a method similar to Example 8 by using Compound B-V and Compound A-VI.

$^1$H NMR (600 MHz, DMSO-d6) δ 11.72 (t, J=6.6 Hz, 1H), 11.03 (br, 1H), 10.83 (br, 1H), 9.48 (d, J=8.4 Hz, 1H), 8.98 (s, 1H), 8.58 (s, 1H), 8.15 (br, 1H), 7.81 (s, 1H), 7.56 (s, 1H) 7.51 (s, 1H) 7.33 (br, 2H) 6.85 (d, J=15.6 Hz, 1H), 6.74 (s, 1H), 6.28 (m, 1H), 5.87 (dd, J=5.4 Hz, 8.4 Hz, 1H), 5.79 (br, 1H), 5.23 (d, J=4.8 Hz, 1H), 4.93 (m, 2H), 3.84 (d, J=17.4 Hz, 1H), 3.62 (d, J=7.8 Hz 1H), 3.5~3.09 (m, 4H), 1.66 (m, 4H), 1.44 (s, 3H) 1.43 (s, 3H)

Example 24
Compound 24

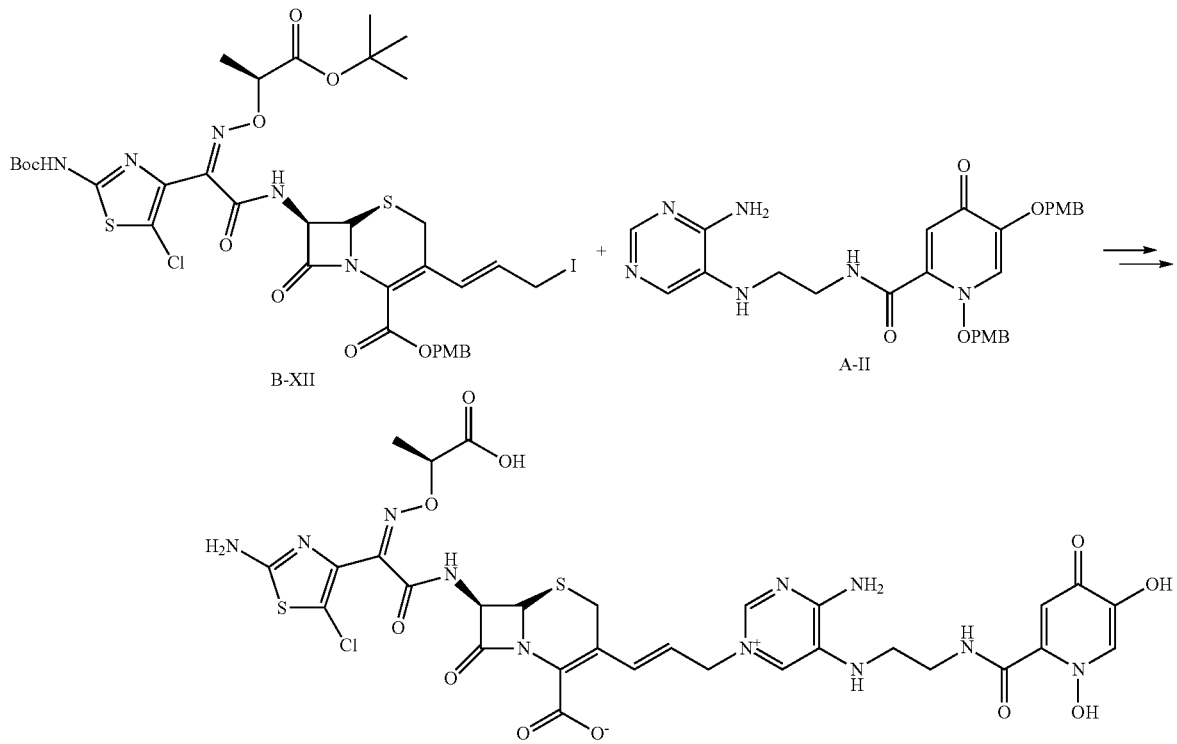

Compound 24 (49 mg, 38%) was prepared by a method similar to Example 8 by using Compound B-XII and Compound A-II.

$^1$H NMR (600 MHz, DMSO-d$^6$) δ 11.76 (t, J=5.4 Hz, 1), 11.05 (s, 1H), 10.90 (s, 1H), 9.53 (d, J=8.4 Hz, 1H), 9.00 (s, 1H), 8.42 (s, 1H), 8.09 (s, 1H), 7.82 (s, 1H), 7.69 (s, 1H), 7.57 (s, 1H), 7.42 (br, 2H), 7.12 (t, J=7.2 Hz, 1H), 6.91 (d, J=16.2 Hz, 1H), 6.30 (m, 1H), 6.05 (br, 1H), 5.84 (dd, J=4.8 Hz, 5.4 Hz, 1H), 5.20 (d, J=4.8 Hz, 1H), 4.91 (m, 2H), 4.63 (q, J=7.2 Hz, 1H), 3.82 (d, J=18 Hz, 1H), 3.58 (m, 3H), 3.30 (m, 2H), 1.42 (d, J=6.6 Hz, 3H)

Example 25
Compound 25

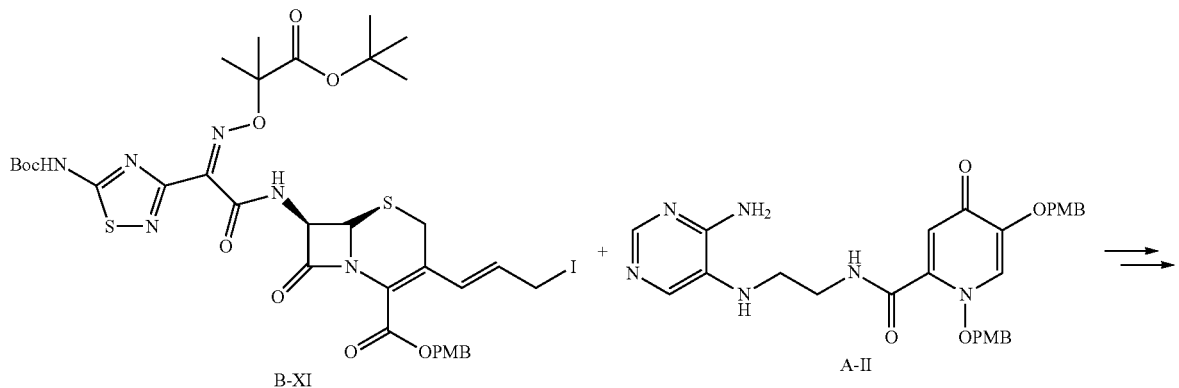

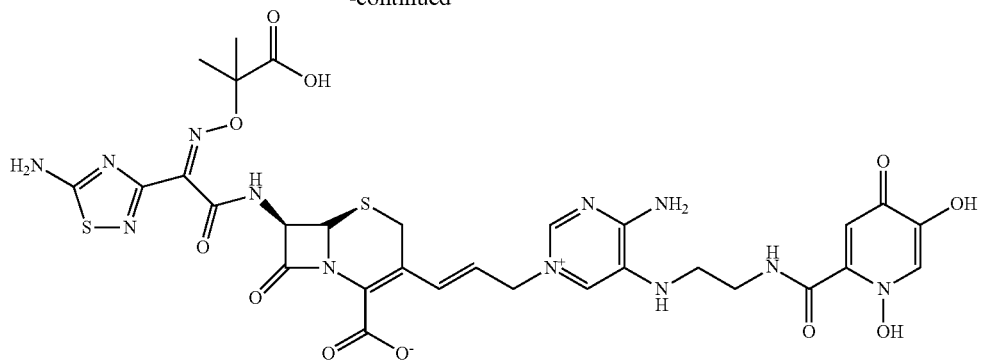

25

Compound 25 (26 mg, 36%) was prepared by a method similar to Example 8 by using Compound B-XI and Compound A-II.

$^1$H NMR (600 MHz, DMSO d-$_6$) δ 11.74 (t, J=5.4 Hz, 1H), 9.52 (d, J=7.8 Hz, 1H), 8.97 (bs, 1H), 8.44 (s, 1H), 8.20 (bs, 2H), 8.06 (bs, 2H), 7.81 (s, 1H), 7.63 (s, 1H), 7.11 (m, 1H), 6.15 (bs, 2H), 5.75 (m, 1H), 5.07 (m, 1H), 4.94 (m, 1H), 4.80 (m, 1H), 3.73 (m, 2H), 3.55 (m, 4H), 1.46 (s, 3H), 1.45 (s, 3H)

Example 26

Compound 26

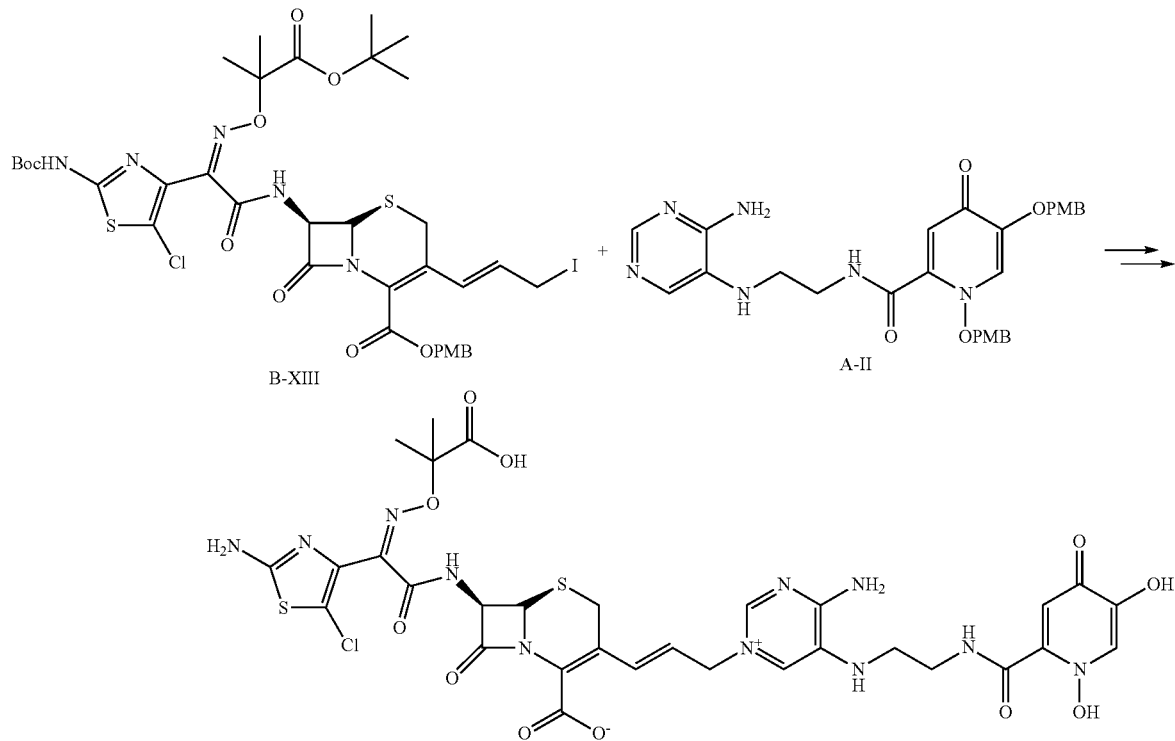

Compound 26 (22 mg, 29%) was prepared by a method similar to Example 8 by using Compound B-XIII and Compound A-II.

$^1$H NMR (600 MHz, DMSO d-$_6$) δ 11.77 (t, J=5.4 Hz, 1H), 11.04 (bs, 1H), 10.91 (bs, 1H), 9.45 (d, J=8.4 Hz, 1H), 9.00 (bs, 1H), 8.42 (s, 1H), 8.09 (bs, 1H), 7.82 (s, 1H), 7.70 (s, 1H), 7.57 (s, 1H), 7.42 (s, 1H), 6.90 (d, J=16.2 Hz, 1H), 6.29 (m, 1H), 6.05 (t, J=4.8 Hz, 1H), 5.82 (dd, J$_1$=8.4 Hz, J$_2$=5.4 Hz, 1H), 5.20 (d, J=5.4 Hz, 1H), 4.88 (m, 2H), 3.83 (d, J=18.0 Hz, 1H), 3.58 (m, 3H), 3.29 (m, 2H), 1.47 (s, 3H), 1.45 (s, 3H)

Example 27
Compound 27
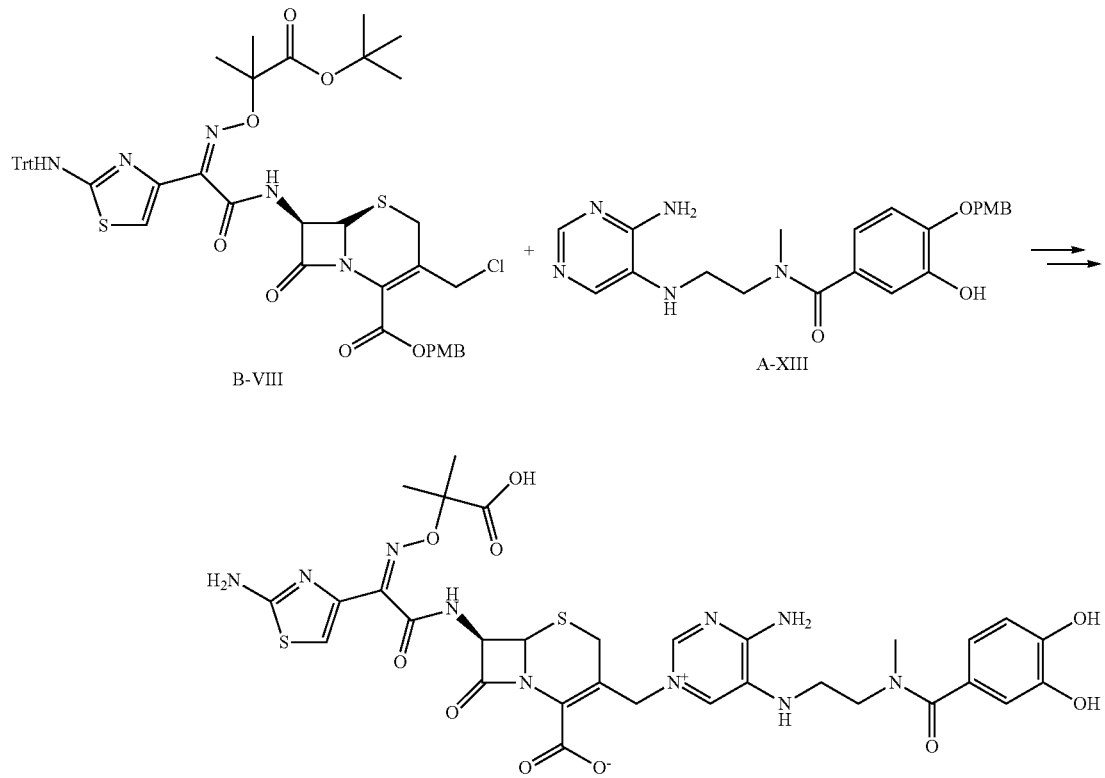
Compound 27 (6 mg, 8%) was prepared by a method similar to Example 1 by using Compound B-VIII and Compound A-XIII.
$^1$H NMR (600 MHz, CD$_3$OD) δ=8.37 (br, 1H), 7.91 (br, 1H), 7.34 (br, 1H), 6.79 (br, 1H), 6.60 (br, 1H), 5.95 (d, 1.8 Hz, 1H), 5.25 (m, 2H), 4.94 (br, 1H), 3.73~3.23 (m, 6H), 3.10 (d, J=6.6 Hz, 3H), 1.66 (d, J=3.6 Hz, 6H)
Example 28
Compound 28
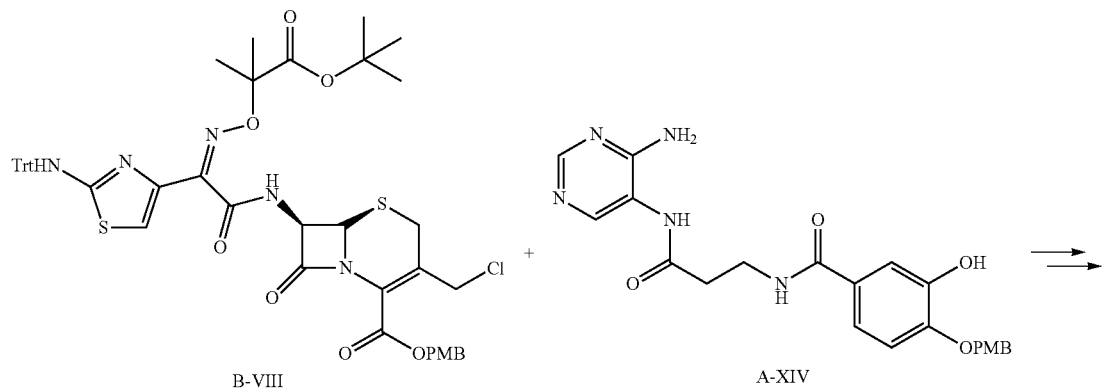

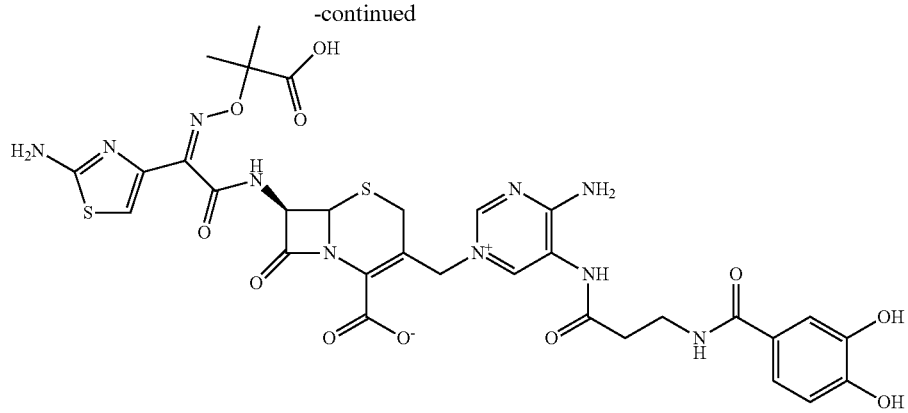

28

Compound 28 (17 mg, 33%) was prepared by a method similar to Example 1 by using Compound B-VIII and Compound A-XIV.

$^1$H NMR (600 MHz, CD$_3$OD) δ 8.76 (s, 1H), 8.66 (s, 1H), 7.25 (d, J=2.4 Hz, 1H), 7.18 (dd, J=2.4 Hz, 8.4 Hz, 1H), 7.04 (s, 1H), 6.77 (d, J=8.4 Hz, 1H), 5.95 (d, J=5.4 Hz, 1H) 5.29 (d, J=15.6 Hz, 1H), 5.21 (d, J=4.8 Hz, 1H), 4.94 (d, J=15.6 Hz, 1H), 3.69 (m, 3H), 3.41 (d, J=18.6 Hz, 1H), 2.72 (t, J=6.6 Hz, 2H), 1.61 (s, 6H)

Example 29

Compound 29

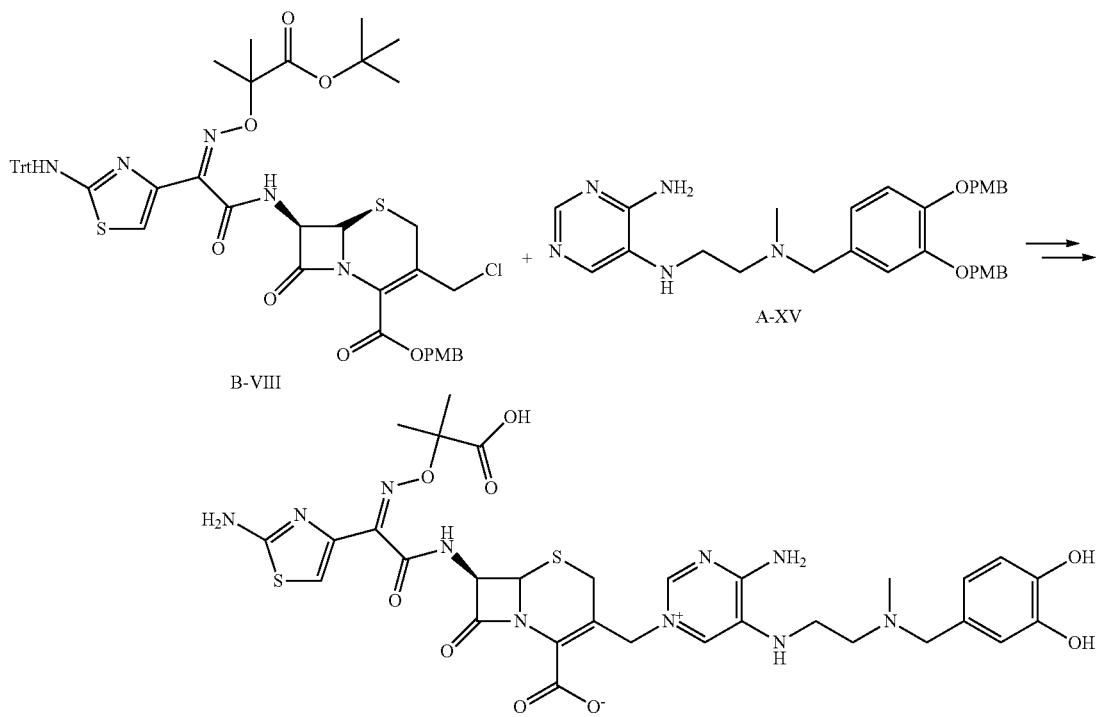

29

Compound 29 (42 mg30%) was prepared by a method similar to Example 1 by using Compound B-VIII and Compound A-XV.

$^1$H NMR (600 MHz, DMSO-d$_6$) δ=9.62 (br, 1H), 9.48 (d, J=6.6 Hz, 1H), 9.23 (s, 1H), 8.43 (s, 1H), 8.23 (br, 1H), 7.61 (s, 1H), 7.37 (br, 1H), 6.87 (s, 1H), 6.79~6.74 (m, 3H), 6.70 (s, 1H), 6.17 (br, 1H), 5.91 (m, 1H), 5.18 (d, J=4.8 Hz, 1H), 5.06 (br, 2H), 4.25 (br, 2H), 4.10 (br, 2H), 3.48 (br, 2H), 3.34 (br, 1H), 3.23 (br, 1H), 2.71 (s, 3H), 1.42 (d, J=6.6 Hz, 6H)

Example 30
Compound 30
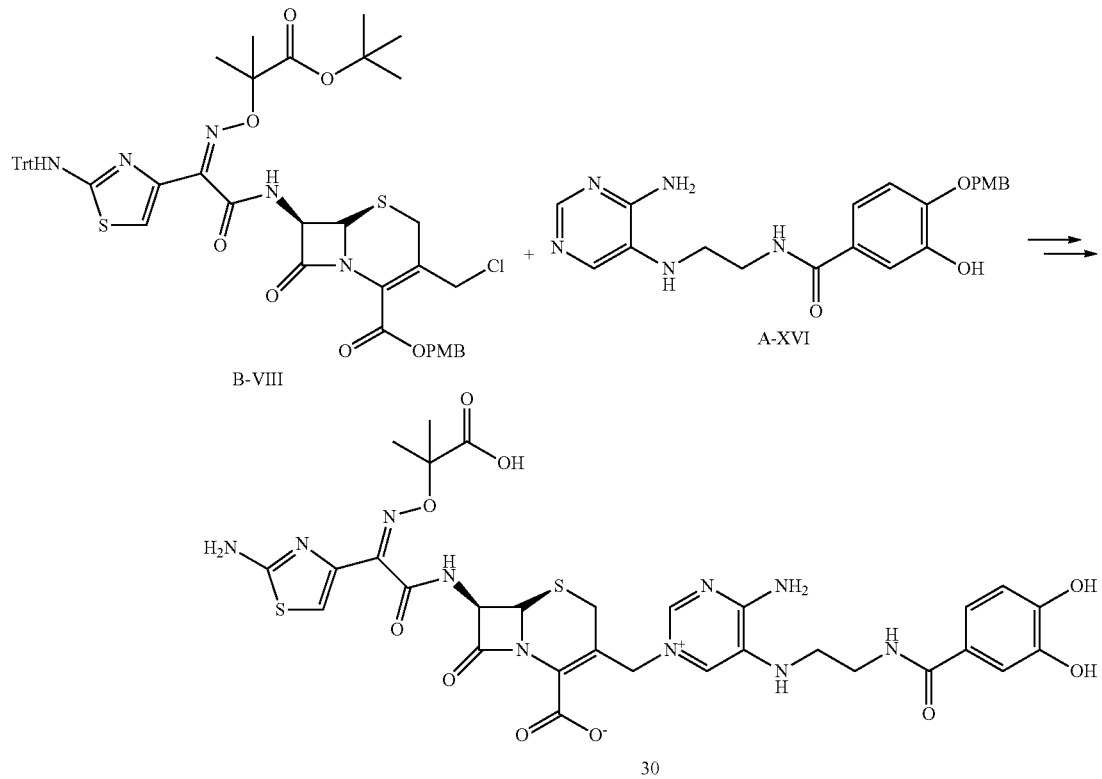
Compound 30 (12 mg, 14%) was prepared by a method similar to Example 1 by using Compound B-VIII and Compound A-XVI.
$^1$H NMR (600 MHz, DMSO-$d_6$) δ 9.51 (br, 1H), 9.46 (d, J=8.4 Hz, 1H), 8.35 (s, 1H), 8.25 (t, J=4.2 Hz, 1H), 8.13 (s, 1H), 7.61 (s, 1H), 7.35 (br, 2H), 7.26 (d, J=6.6 Hz, 1H), 7.15 (dd, J=2.4 Hz, 7.8 Hz, 1H), 6.73 (d, J=8.4 Hz, 1H), 6.675 (s, 1H), 5.94 (br, 1H), 5.86 (dd, J=8.4 Hz, 5.4 Hz, 1H), 5.15 (d, J=5.4 Hz, 5.07 (m, 2H), 3.5~3.34 (m, 4H), 3.18 (m, 2H), 1.38 (s, 3H), 1.36 (s, 3H)
Example 31
Compound 31
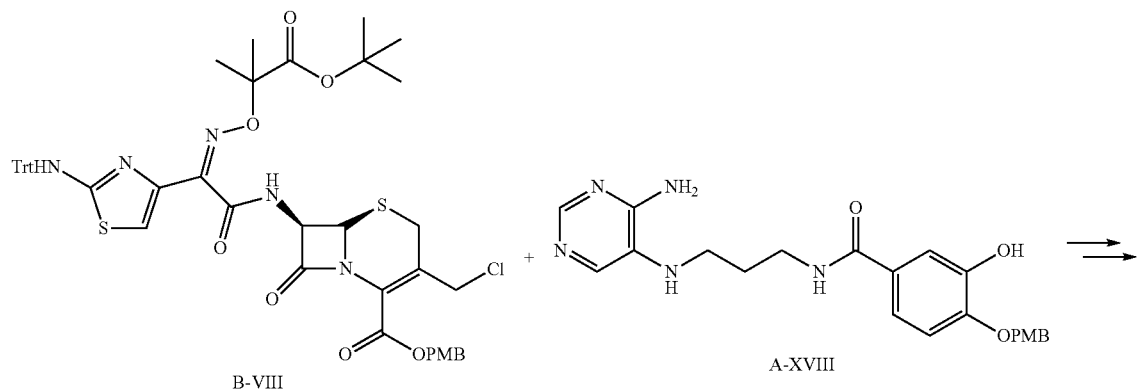

-continued

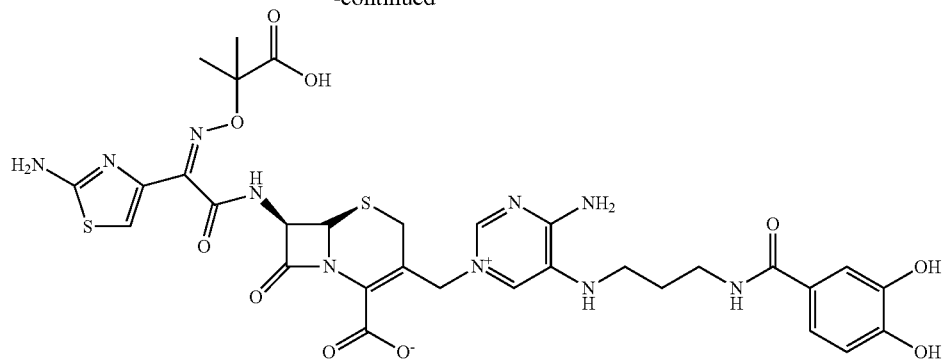

31

Compound 31 (10 mg, 16%) was prepared by a method similar to Example 1 by using Compound B-VIII and Compound A-XVIII.

$^1$H NMR (600 MHz, DMSO-$d_6$) δ 9.49 (d, J=8.4 Hz, 1H), 9.09 (br, 1H) 8.38 (s, 1H), 8.25 (br, s) 8.25 (t, J=5.4 Hz, 1H), 7.54 (s, 1H), 7.34 (br, 2H), 7.27 (d, J=1.8 Hz, 1H), 7.15 (dd, J=1.8 Hz, 6.6 Hz, 1H), 6.76 (d, J=7.8 Hz, 1H), 6.71 (s, 1H), 5.92 (dd, J=4.8 Hz, 8.4 Hz, 1H), 5.84 (br, 1H), 5.19 (d, J=4.8 Hz, 5.05 (m, 2H), 3.5~3.32 (m, 4H), 3.07 (m, 2H), 1.88 (m, 2H), 1.42 (s, 3H), 1.41 (s, 3H)

Example 32

Compound 32

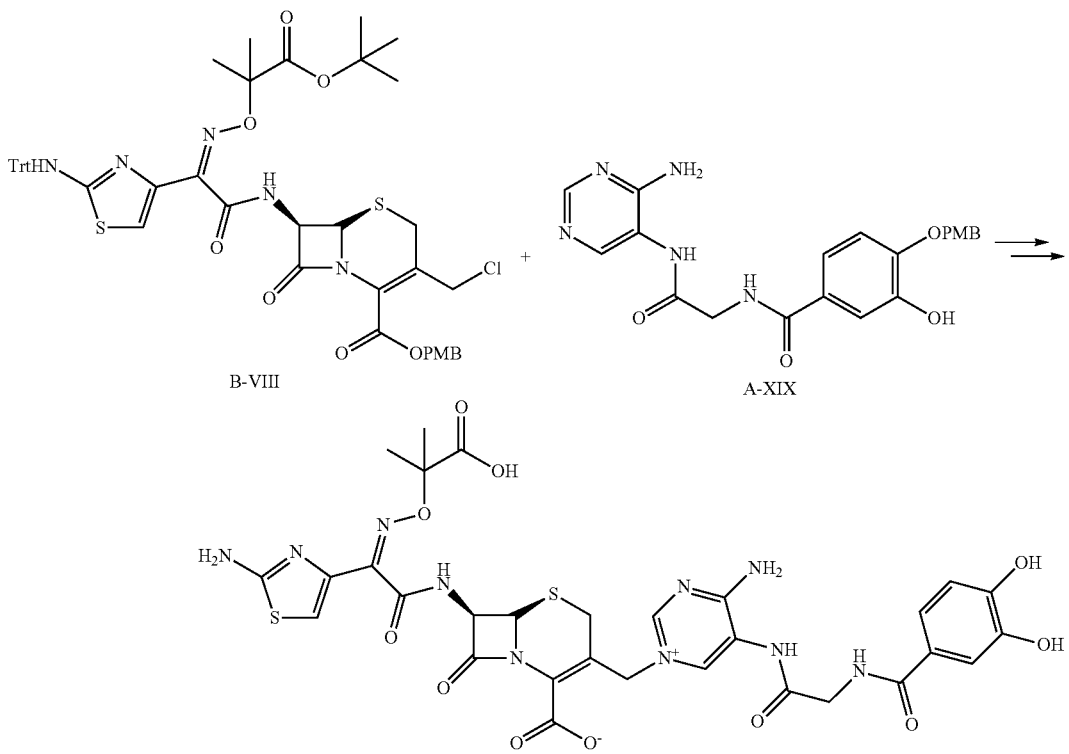

32

Compound 32 (65 mg, 24%) was prepared by a method similar to Example 1 by using Compound B-VIII and Compound A-XIX.

$^1$H NMR (600 MHz, DMSO-$d_6$+D2O) δ 8.76 (s, 1H), 8.73 (s, 1H), 7.30 (d, J=2.4 Hz, 1H), 7.25 (dd, J=2.4 Hz, 8.4 Hz, 1H), 6.83 (dd, J=1.2 Hz, 7.8 Hz, 6.76 (s, 1H), 5.90 (4.2 Hz, 1H), 5.20 (d, J=4.8 Hz, 1H), 5.14 (d, J=15 Hz, 1H), 4.99 (d, J=15 Hz, 1H), 4.08 (s, 2H), 3.60 (dd, J=18 Hz, 59.4 Hz, 2H), 1.46 (s, 3H), 1.44 (s, 3H)

Example 33
Compound 33
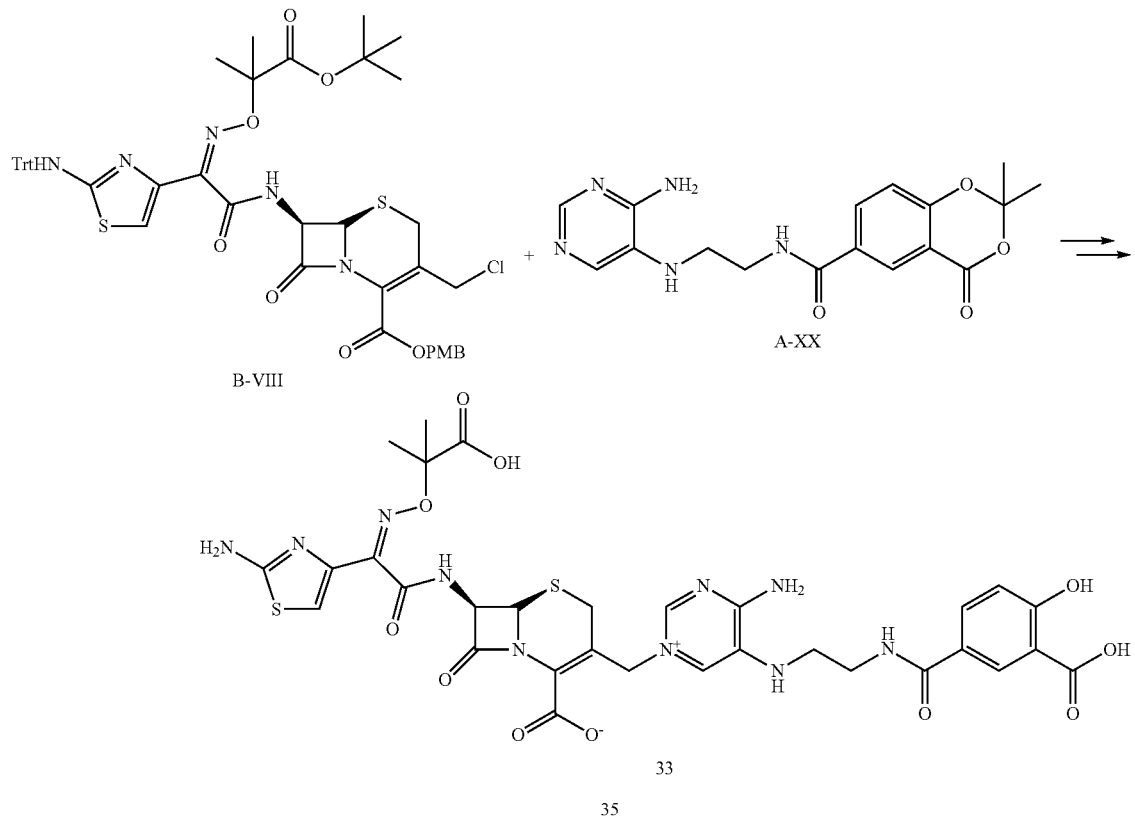
Compound 33 (15 mg, 12%) was prepared by a method similar to Example 1 by using Compound B-VIII and Compound A-XX.
$^1$H NMR (600 MHz, DMSO-d$_6$, D$_2$O) δ 8.34 (s, 1H), 8.21 (br, s, 1H) 7.77 (d, J=6 Hz, 1H), 7.73 (s, 1H), 6.81 (d, J=8.4 Hz, 1H), 6.67 (s, 1H), 5.77 (d, J=4.2 Hz, 1H), 5.10 (d, J=4.2 Hz, 1H), 5.04~4.86 (m, 2H), 3.55~3.20 (m, 6H), 1.39 (s, 3H), 1.37 (s, 3H)
Example 34
Compound 34
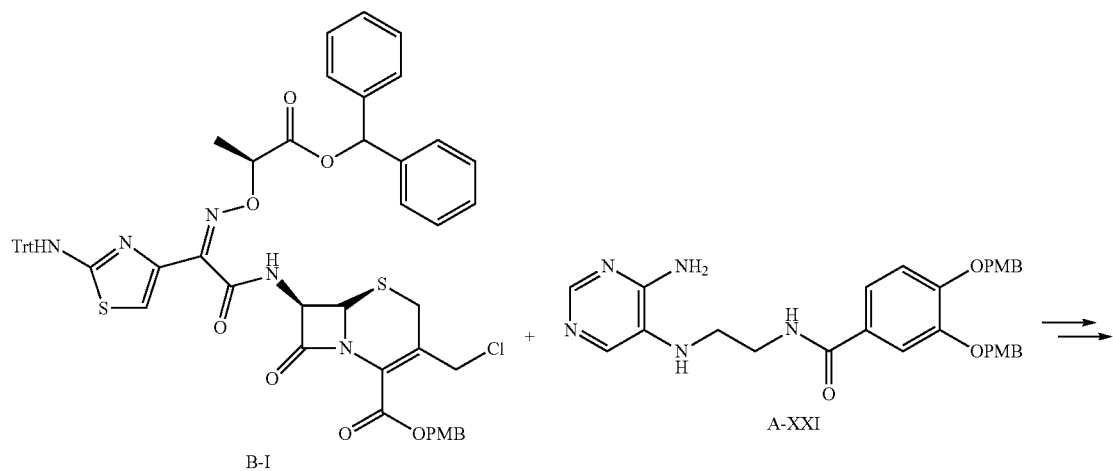

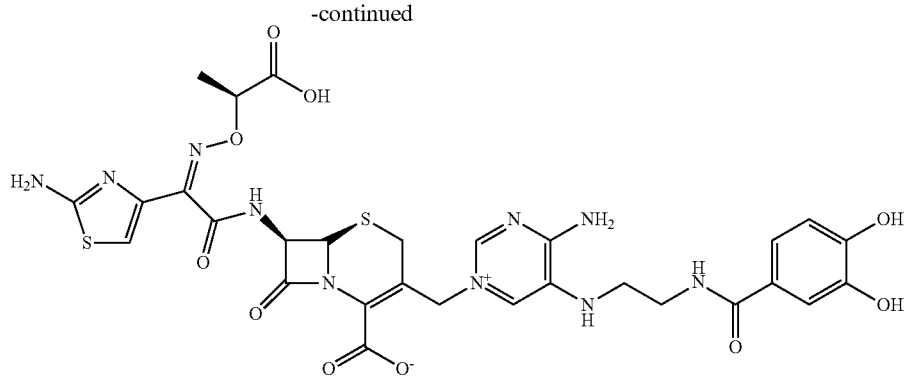
34
Compound 34 (10 mg, 9%) was prepared by a method similar to Example 1 by using Compound B-I and Compound A-XXI.
$^1$H NMR (600 MHz, CD3OD) δ 8.33 (s, 1H), 7.83 (s, 1H), 7.25 (s, 1H), 7.20 (d, J=7.8 Hz, 1H), 6.97 (s, 1H), 6.79 (d, J=8.4 Hz, 1H), 5.92 (d, J=4.8 Hz, 1H), 5.21~(m, 2H), 4.92 (m, 2H), 3.72~3.67 (m, 6H), 1.51 (2, J=7.2 Hz, 3H)
Example 35
Compound 35
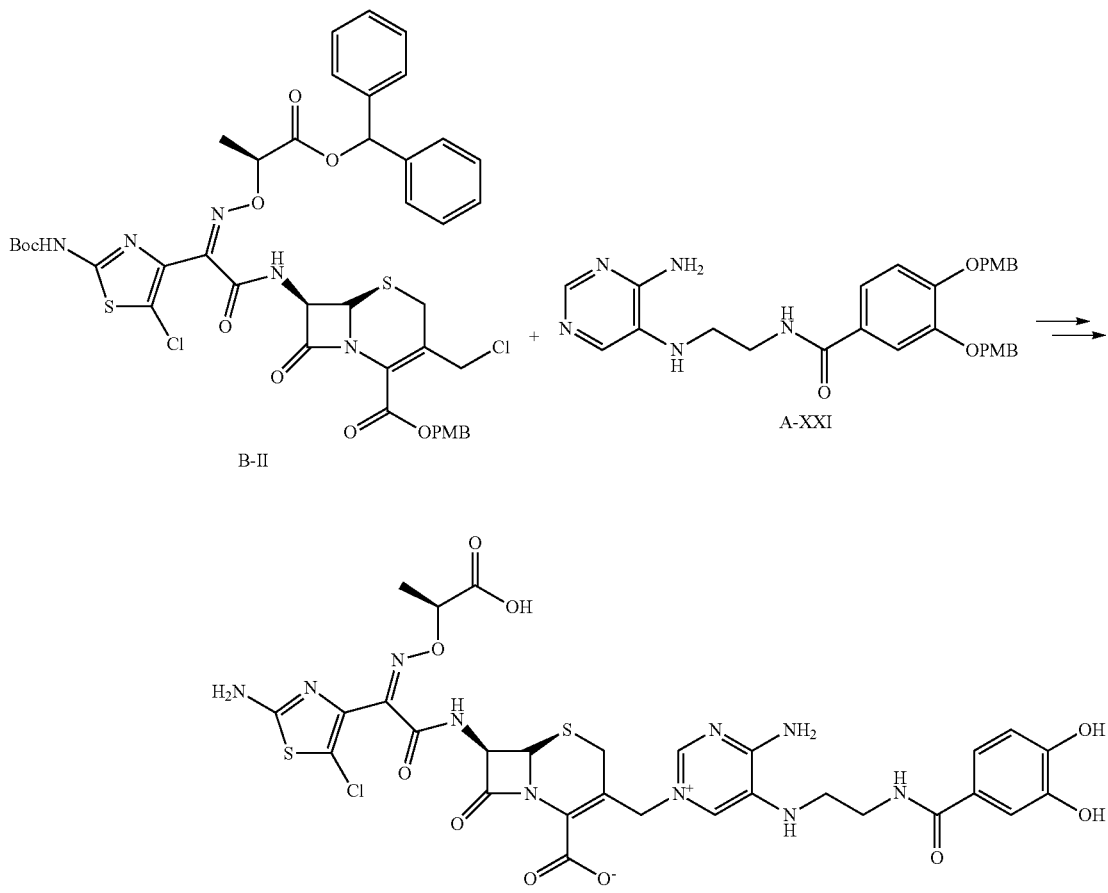

Compound 35 (49 mg, 31%) was prepared by a method similar to Example 1 by using Compound B-II and Compound A-XXI.

$^1$H NMR (600 MHz, DMSO-$d_6$) δ 9.54 (m, 2H) 9.14 (s, 1H), 9.06 (s, 1H), 8.36 (s, 1H), 8.30 (t, J=5.4 Hz, 1H), 8.15 (s, 1H), 7.75 (s, 1H), 7.42 (s, 1H), 7.32 (s, 1H), 7.19 (dd, J=1.8 Hz, 7.8 Hz, 1H), 6.76 (d, J=7.8 Hz, 1H), 5.98 (t, J=5.4 Hz, 1H), 5.87 (dd, J=5.4 Hz, 7.8 Hz, 1H), 5.15 (d, J=4.8 Hz, 1H), 5.08 (m, 2H), 4.60 (q, J=7.2 Hz, 1H), 3.52~3.20 (m, 6H), 1.40 (d, J=6.6 Hz, 3H)

Example 36

Compound 36

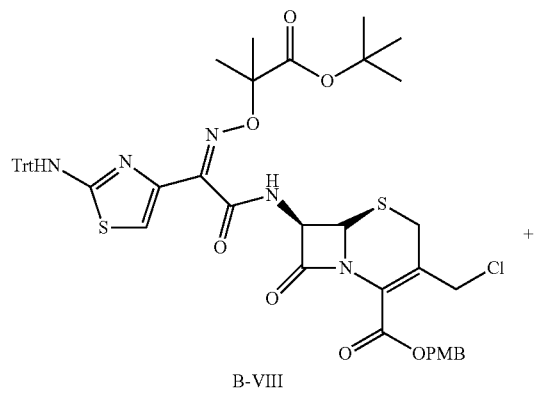

B-VIII

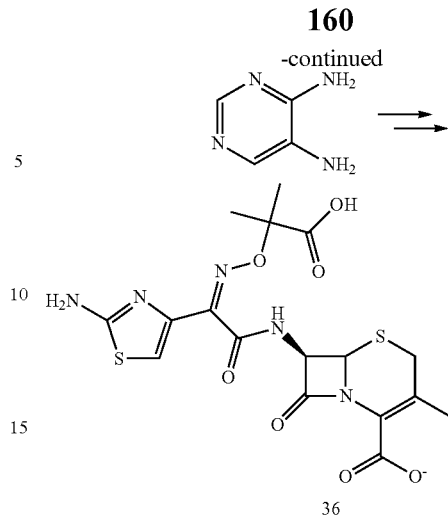

36

Compound 36 (12 mg, 52%) was prepared by a method similar to Example 1 by using Compound B-VIII and 4,5-diaminopyrimidine.

$^1$H NMR (600 MHz, CD$_3$OD) δ 8.34 (d, J=1.8 Hz, 1H), 7.78 (d, J=1.8 Hz, 1H), 7.02 (s, 1H), 5.99 (d, J=4.8 Hz, 1H) 5.30~4.90 (m, 3H), 3.65 (d, J=18 Hz, 1H), 3.34 (d, J=18 Hz, 1H), 1.60 (s, 6H)

Example 37

Compound 37

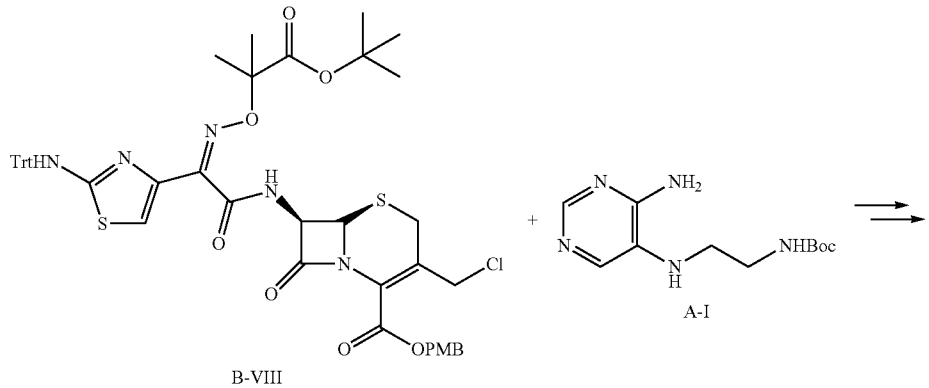

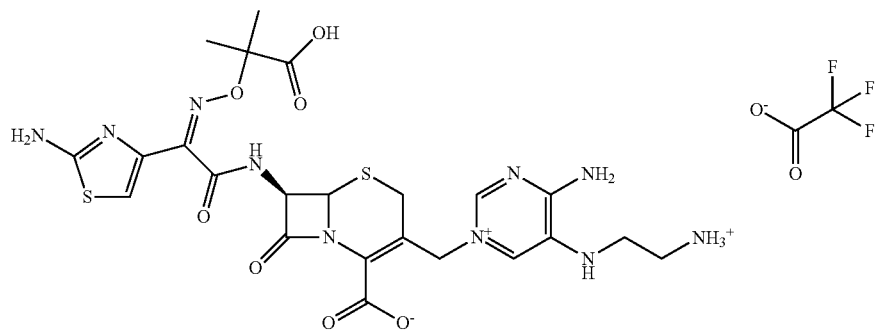

37

Compound 37 (19 mg, 31%) was prepared by a method similar to Example 1 by using Compound B-II and Compound A-I.
$^1$H NMR (600 MHz, CD$_3$OD) δ 8.43 (s, 1H), 7.94 (s, 1H), 7.04 (s, 1H), 5.90 (d, J=4.8 Hz, 1H), 5.25~4.8 (m, 3H), 3.70 (d, J=18.6 Hz, 1H), 3.49 (t, J=6 Hz, 1H), 3.30~3.25 (m, 3H), 1.62 (s, 6H)
Example 38
Compound 38
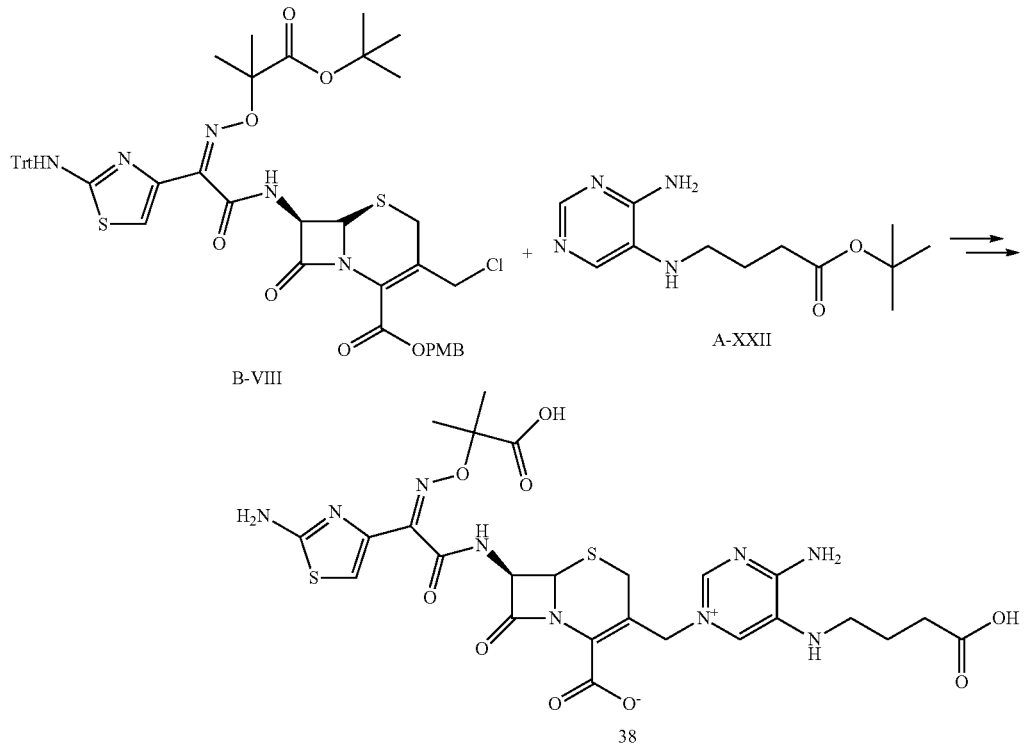
Compound 38 (7 mg, 9%) was prepared by a method similar to Example 1 by using Compound B-VIII and Compound A-XXII.
$^1$H NMR (600 MHz, CD$_3$OD) δ=8.36 (s, 1H), 7.70 (s, 1H), 7.04 (s, 1H), 5.98 (d, J=4.8 Hz, 1H), 5.27~4.8 (m, 3H), 3.70~3.50 (m, 2H), 3.49 (m, 2H), 2.45 (m, 2H), 1.98 (m, 2H), 1.62 (s, 6H)
Example 39
Compound 39
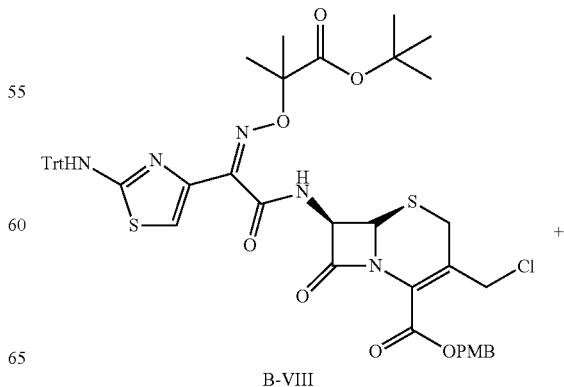

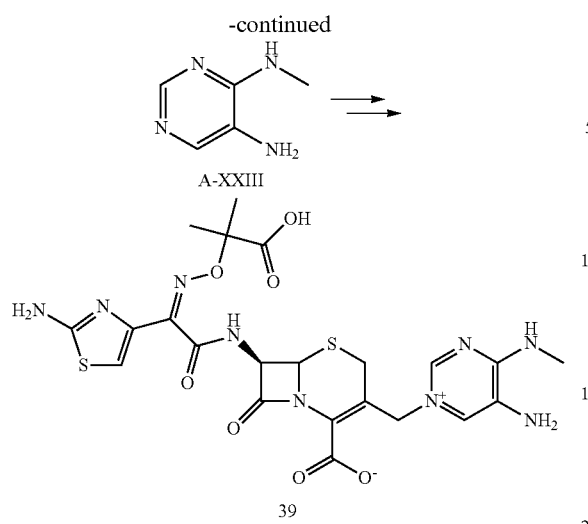
Compound 39 (2 mg, 2%) was prepared by a method similar to Example 1 by using Compound B-VIII and Compound A-XXIII.
$^1$H NMR (600 MHz, CD$_3$OD) δ 8.42 (d, J=1.8 Hz, 1H), 7.70 (d, J=1.8 Hz, 1H), 6.99 (s, 1H), 5.92 (d, J=4.8 Hz, 1H) 5.27~4.90 (m, 3H), 3.63 (d, J=18 Hz, 1H), 3.34 (d, J=18 Hz, 1H), 3.15 (d, J=3.6 Hz, 3H), 1.62 (s, 6H)
Example 40
Compound 40
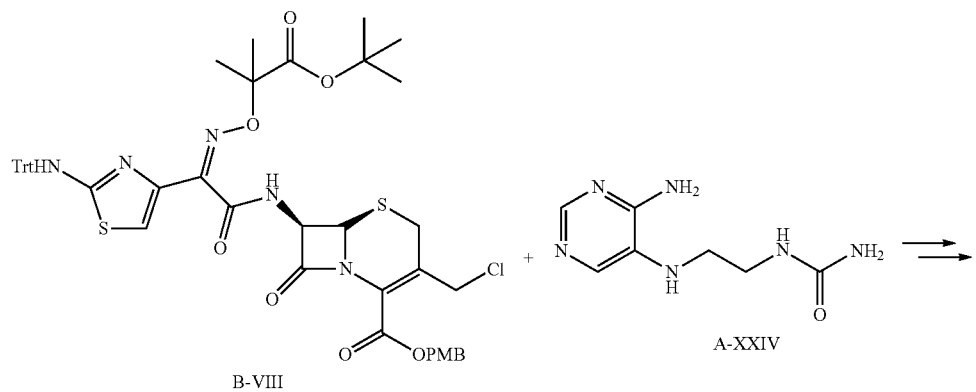
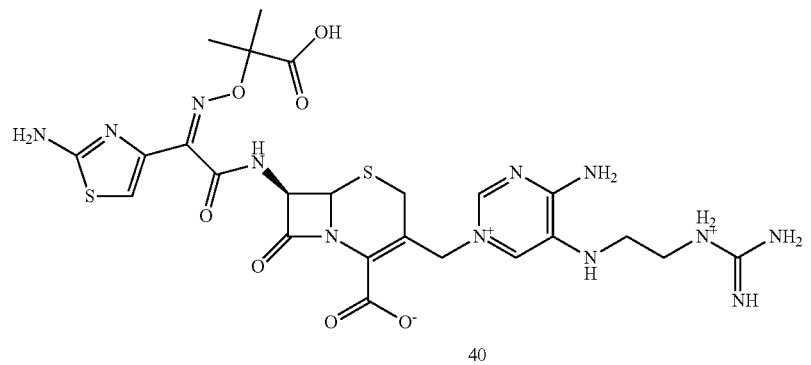
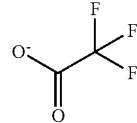
Compound 40 (12 mg, 18%) was prepared by a method similar to Example 1 by using Compound B-VIII and Compound A-XXIV.
$^1$H NMR (600 MHz, CD$_3$OD) δ 8.41 (d, J=1.8 Hz, 1H), 7.98 (d, J=1.8 Hz, 1H), 7.03 (s, 1H), 5.91 (d, J=4.8 Hz, 1H), 5.23~4.90 (m, 3H), 3.68~3.37 (m, 6H), 1.60 (s, 6H)

Example 41
Compound 41
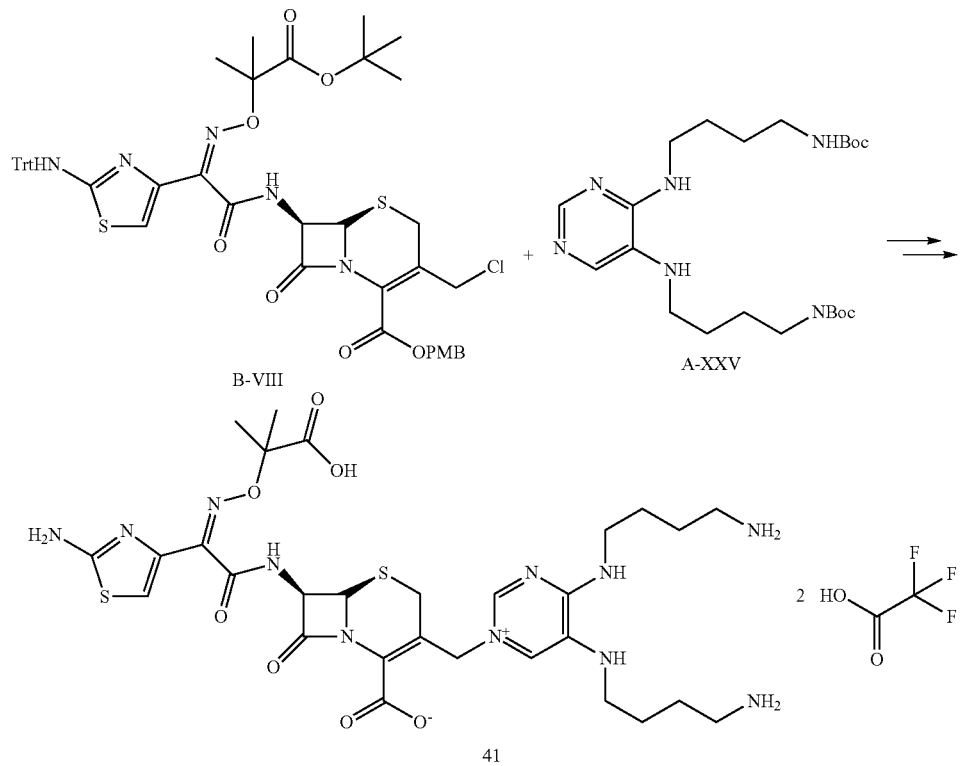
Compound 41 (70 mg, 40%) was prepared by a method similar to Example 1 by using Compound B-VIII and Compound A-XXVI.
$^1$H NMR (600 MHz, DMSO-d$^6$+D$_2$O) δ 8.46 (s, 1H), 7.49 (s, 1H), 6.74 (s, 1H), 5.90 (d, J=4.2 Hz, 1H), 5.20 (d, J=4.8 Hz, 1H), 5.10 (q, J=15.6 Hz, 2H), 3.62~3.40 (m, 6H), 3.03 (br, 2H), 2.83 (br, 4H), 1.66~1.59 (m, 8H), 1.44 (s, 3H), 1.43 (s, 3H)
Example 42
Compound 42
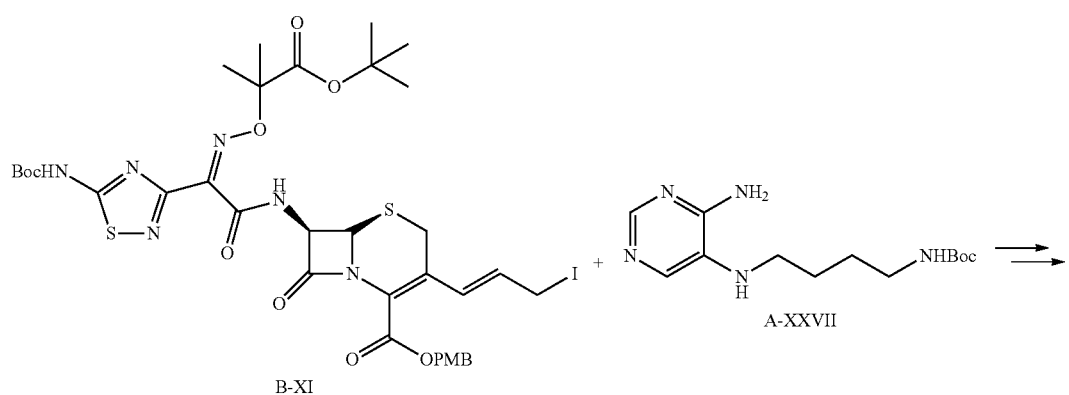

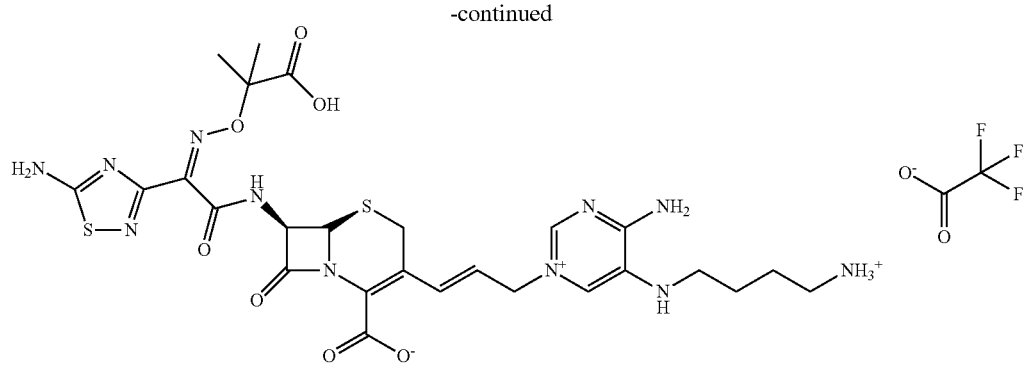
42
Compound 42 (6.2 mg, 28%) was prepared by a method similar to Example 8 by using Compound B-XII and Compound A-XXVII.
$^1$H NMR (600 MHz, CD$_3$OD) δ 8.26 (s, 1H), 7.41 (s, 1H), 7.09 (d, J=16.2 Hz, 1H), 6.25 (m, 1H), 5.91 (d, J=4.8 Hz, 1H), 5.21 (d, J=4.8 Hz, 1H), 3.82 (d, J=18 Hz, 1H), 3.66 (d, J=18 Hz, 1H), 3.21 (br, 2H), 2.99 (br, 2H), 1.80 (br, 4H), 1.62 (s, 3H), 1.61 (s, 3H)
Example 43
Compound 43
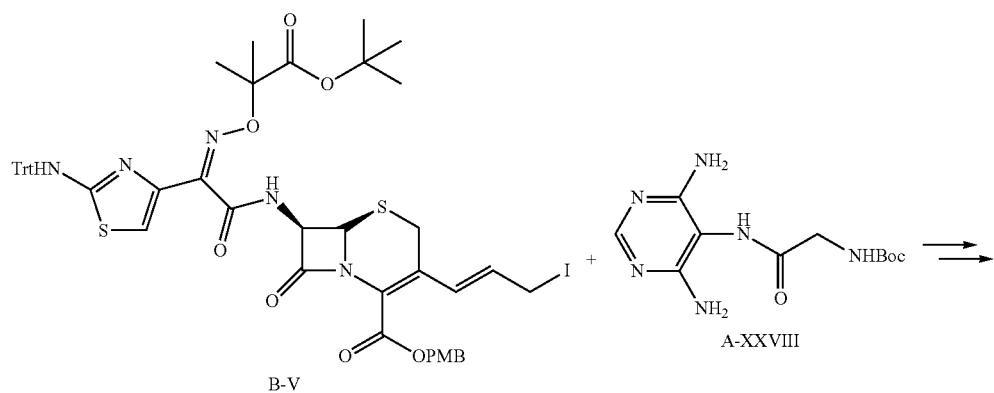
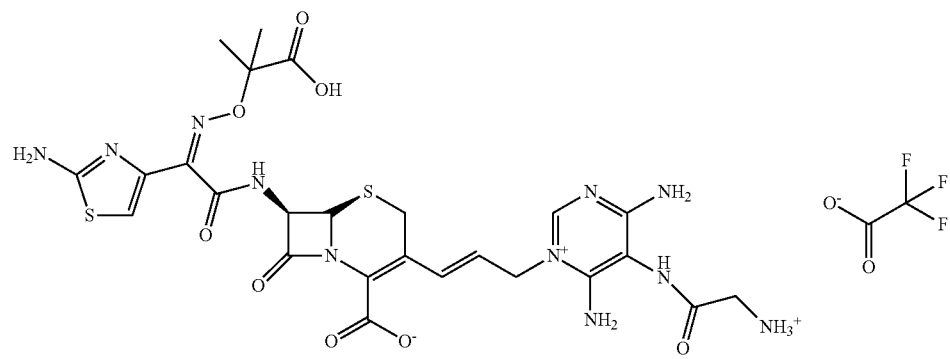
43

Compound 43 (38.7 mg, 38%) was prepared by a method similar to Example 8 by using Compound B-V and Compound A-XXVIII.

$^1$H NMR (600 MHz, CD$_3$OD) δ 8.25 (s, 1H), 7.04 (s, 1H), 6.16 (m, 1H), 5.92 (d, J=4.8 Hz, 1H), 5.22 (d, J=4.8 Hz, 1H), 4.87 (m, 2H), 3.98 (s, 2H), 3.83 (d, J=18 Hz, 1H), 3.68 (d, J=18 Hz, 1H), 1.63 (s, 3H), 1.61 (s, 3H)

Example 44

Compound 44

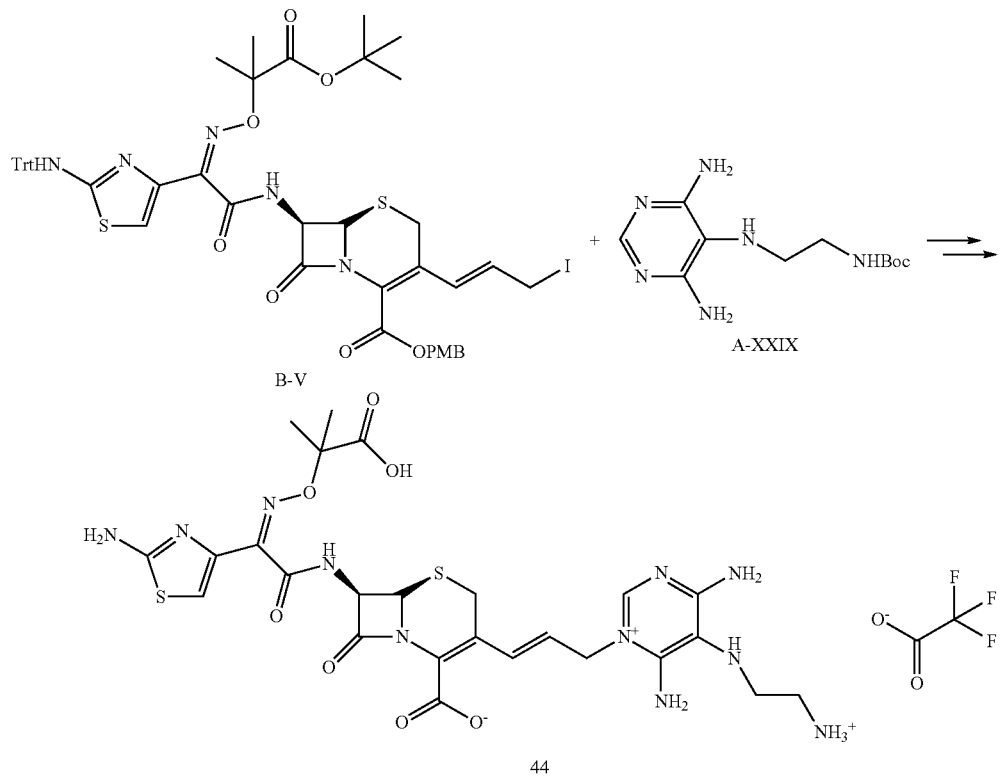

Compound 44 (11.4 mg, 13%) was prepared by a method similar to Example 8 by using Compound B-V and Compound A-XXIX.

$^1$H NMR (600 MHz, CD$_3$OD) δ 8.11 (s, 1H), 7.00 (s, 1H), 6.76 (d, J=16.8 Hz, 1H), 6.10 (d, J=15.6 Hz, 1H), 5.87 (br, 1H), 5.20 (br, 1H), 4.88 (m, 2H), 3.78 (d, J=17.4 Hz, 1H), 3.67 (d, J=16.8 Hz, 1H), 3.11 (m, 4H), 1.62 (s, 3H), 1.60 (s, 3H)

Example 45

Compound 45

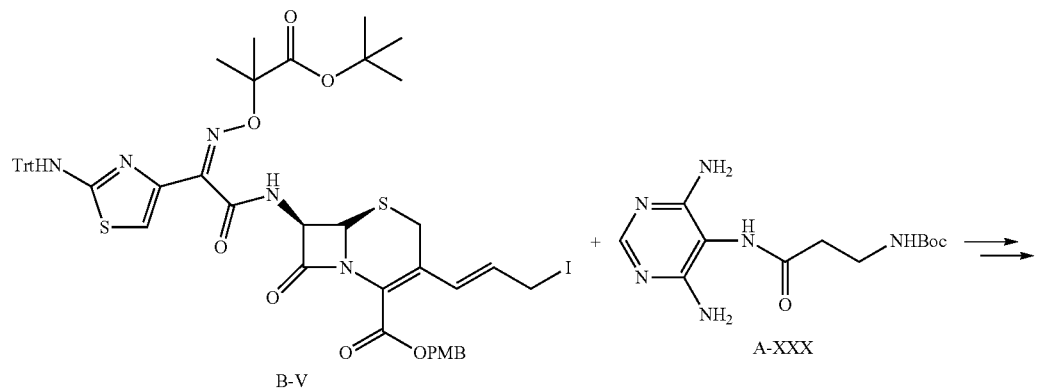

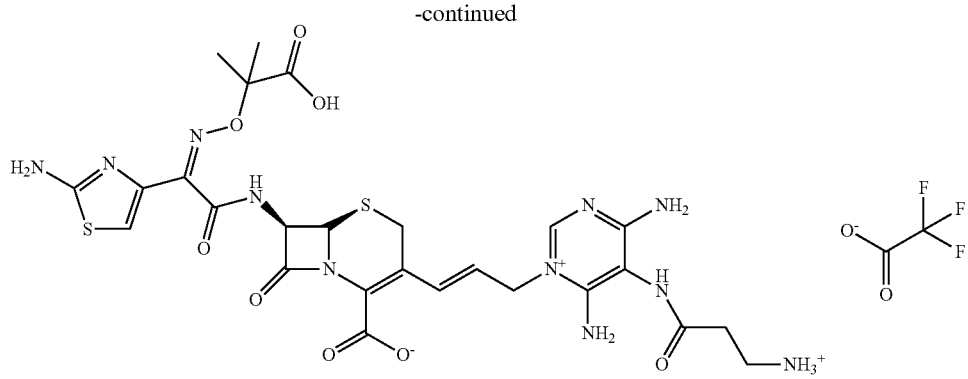
45
Compound 45 (30 mg, 30%) was prepared by a method similar to Example 8 by using Compound B-V 와 Compound A-XXX.
$^1$H NMR (600 MHz, CD$_3$OD) δ 8.23 (s, 1H), 7.03 (d, J=16.8 Hz, 1H), 6.98 (s, 1H), 6.13 (m, 1H), 5.91 (d, J=5.4 Hz, 1H), 5.21 (d, J=4.8 Hz, 1H), 4.90 (m, 2H), 3.81 (d, J=17.4 Hz, 1H), 3.66 (d, J=17.4 Hz, 1H), 3.29 (t, J=6 Hz, 2H), 2.93 (t, J=6 Hz, 2H), 1.62 (s, 3H), 1.60 (s, 3H)
Example 46
Compound 46
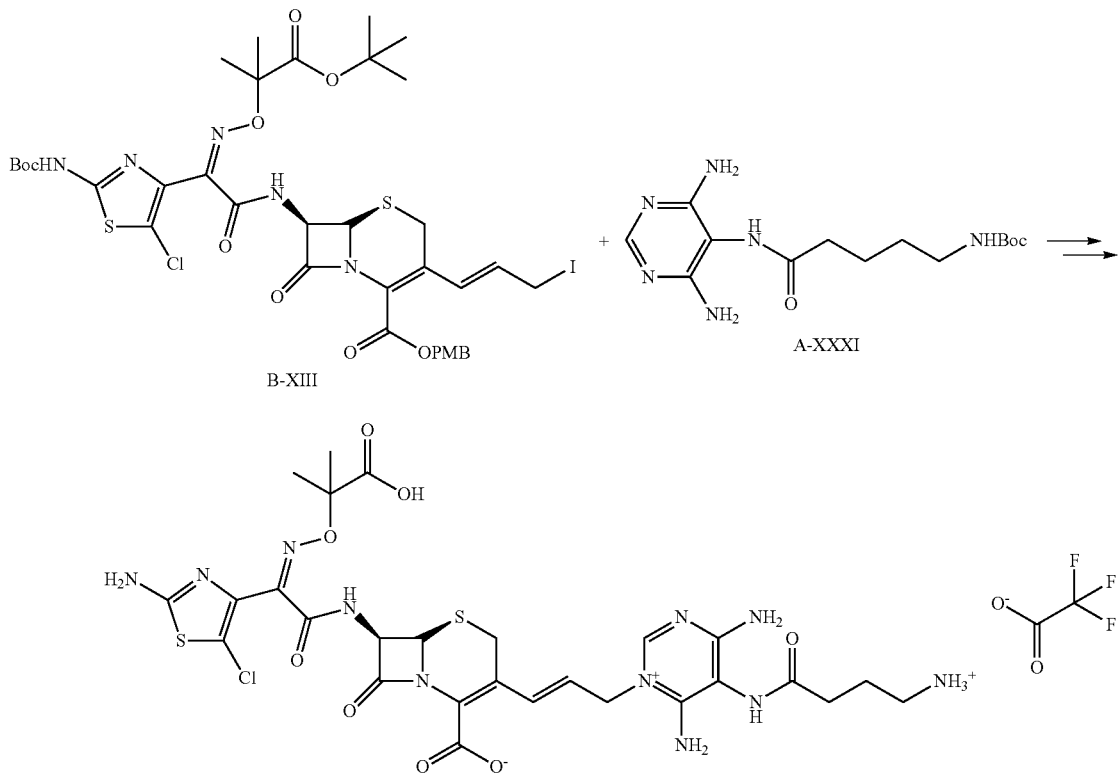
46

Compound 46 (20 mg, 18%) was prepared by a method similar to Example 8 by using Compound B-XIII and Compound A-XXXI.

$^1$H NMR (600 MHz, DMSO d-$_6$) δ 9.48 (m, 1H), 8.93 (bs, 1H), 8.36 (s, 1H), 7.97 (bs, 1H), 7.76 (bs, 1H), 7.75 (bs, 2H), 7.47 (bs, 1H), 7.42 (s, 1H), 6.92 (d, J=16.2 Hz, 1H), 6.08 (m, 1H), 5.80 (m, 1H), 5.19 (d, J=4.8 Hz, 1H), 4.82 (m, 2H), 3.80 (d, J=18.0 Hz, 1H), 3.55 (d, J=18.0 Hz, 1H), 2.83 (m, 2H), 2.44 (m, 2H), 1.82 (m, 2H), 1.48 (s, 3H), 1.46 (s, 3H)

Example 47

Compound 47

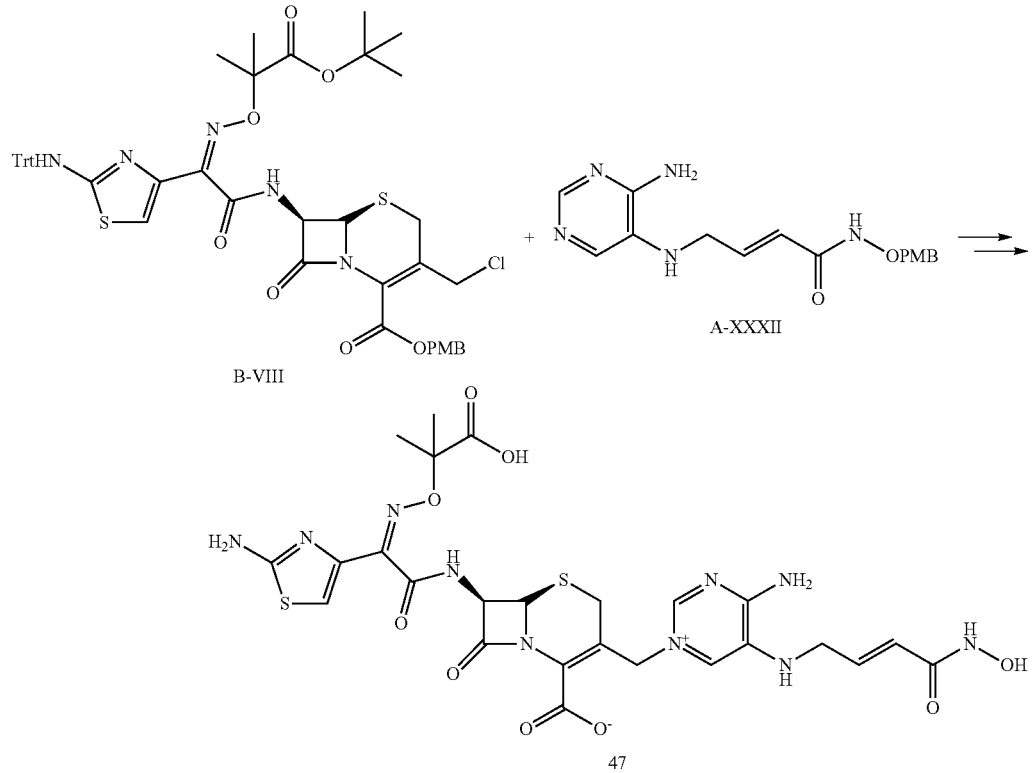

Compound 47 (1 mg, 5%) was prepared by a method similar to Example 1 by using Compound B-V and Compound A-XXXII.

$^1$H NMR (600 MHz, CD$_3$OD) δ=8.37 (s, 1H), 7.52 (s, 1H), 6.98 (s, 1H), 6.73 (m, 1H), 6.01 (m, 2H), 5.21~4.90 (m, 3H), 3.98 (m, 2H), 3.81 (m, 2H), 1.58 (s, 3H), 1.56 (s, 3H)

Example 48

Compound 48

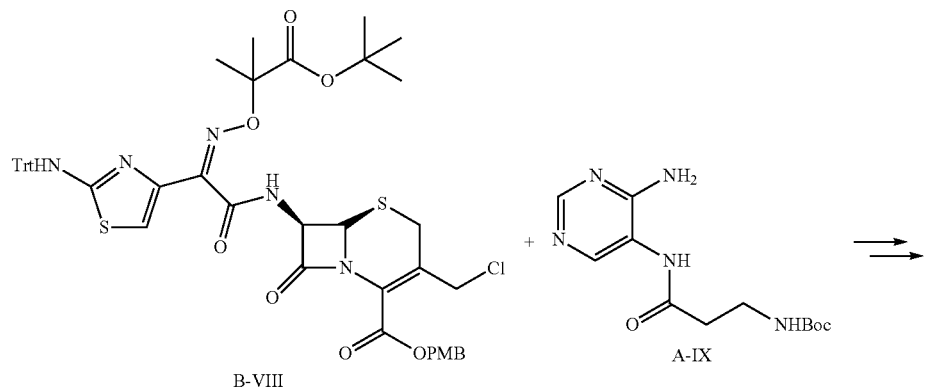

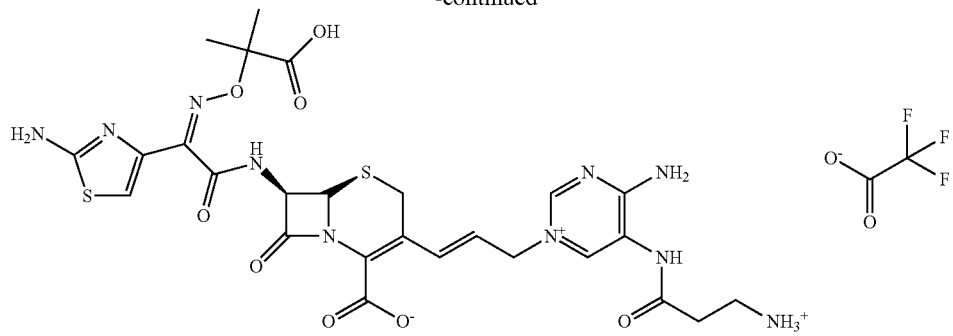
48
Compound 48 (52 mg, 58%) was prepared by a method similar to Example 1 by using Compound B-VIII and Compound A-IX.
$^1$H NMR (600 MHz, CD$_3$OD) δ 8.89 (d, J=1.8 Hz, 1H), 8.72 (d, J=1.8 Hz, 1H), 7.07 (s, 1H), 5.97 (d, J=5.4 Hz, 1H), 5.33~4.8 (m, 3H), 3.71 (d, J=18.6 Hz, 1H), 3.41 (d, J=18.6 Hz, 1H), 3.26~2.91 (m, 4H), 1.62 (s, 6H)
Example 49
Compound 49
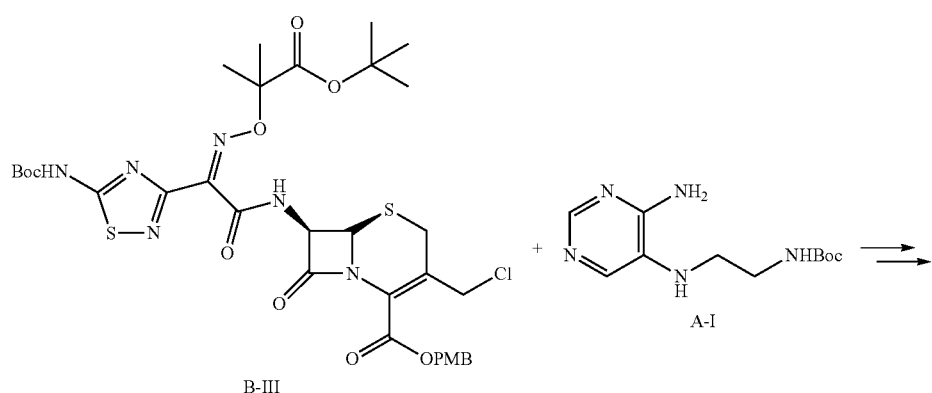
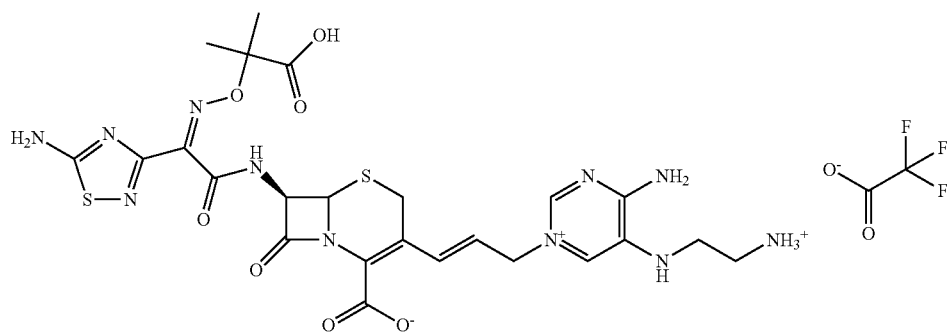
49

Compound 49 (8 mg, 9%) was prepared by a method similar to Example 1 by using Compound B-III and Compound A-I.

H NMR (600 MHz, DMSO d-$_6$) δ 9.54 (bs, 1H), 9.06 (bs, 1H), 8.44 (s, 1H), 8.21 (bs, 3H), 7.56 (s, 1H), 6.86 (d, J=16.2 Hz, 1H), 6.29 (bs, 1H), 6.05 (m, 1H), 5.76 (m, 1H), 5.13 (d, J=4.8 Hz, 1H), 4.85 (m, 2H), 3.66 (d, J=16.8 Hz, 1H), 3.49 (d, J=17.4 Hz, 1H), 3.02 (m, 4H), 1.47 (s, 3H), 1.46 (s, 3H)

Example 50

Compound 50

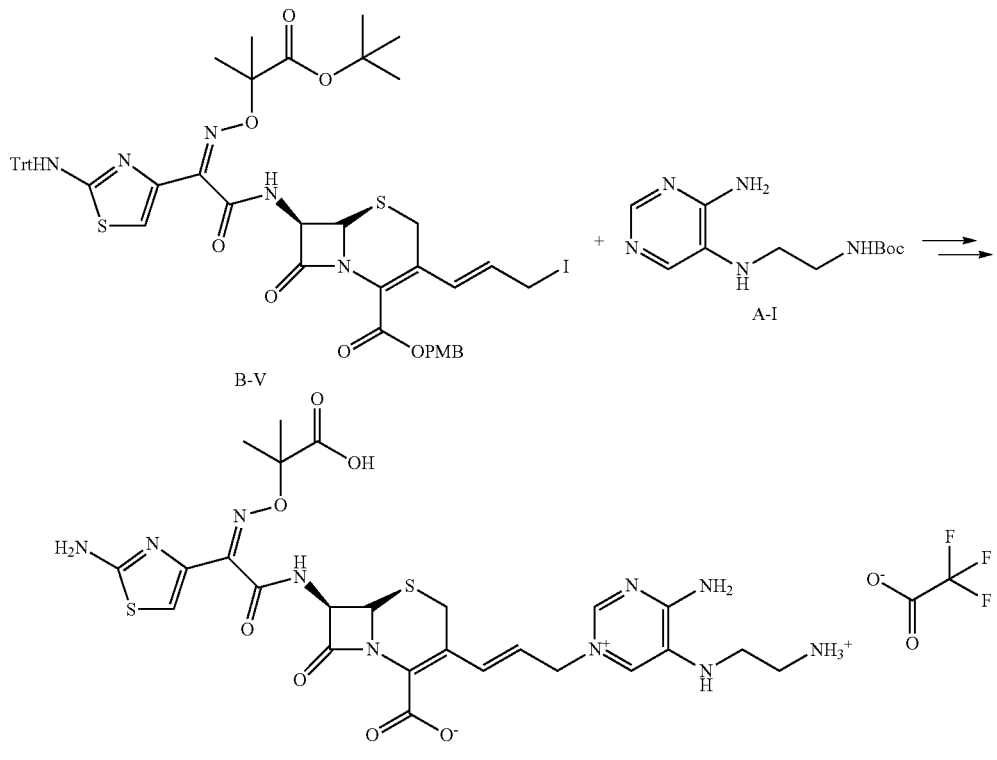

Compound 50 (3.5 mg, 7%) was prepared by a method similar to Example 1 by using Compound B-V and Compound A-I.

$^1$H NMR (600 MHz, CD$_3$OD) δ 8.31 (s, 1H), 7.53 (s, 1H), 7.05 (m, 2H), 6.22 (m, 1H), 5.90 (d, J=4.8 Hz, 1H), 5.19 (d, J=4.8 Hz, 1H), 3.80 (d, 17.4 Hz 1H), 3.64 (d, J=17.4 Hz, 1H), 3.52 (t, J=6 Hz, 2H), 3.24 (t, J=6 Hz, 2H) 1.61 (s, 3H), 1.59 (s, 3H)

Example 51

Compound 51

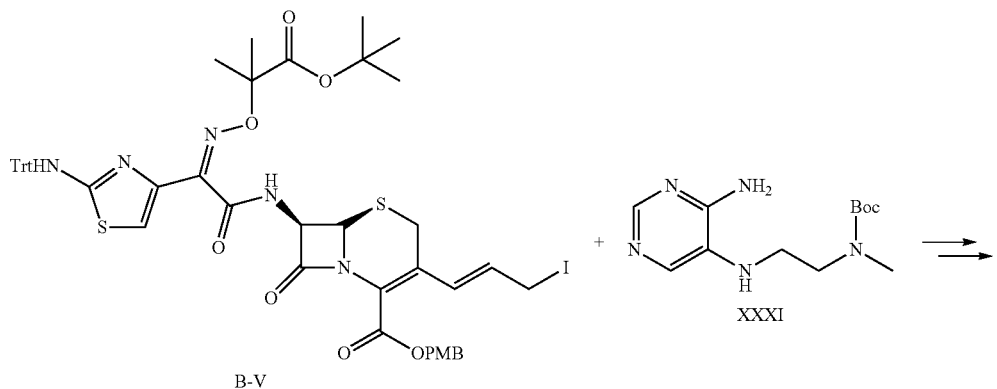

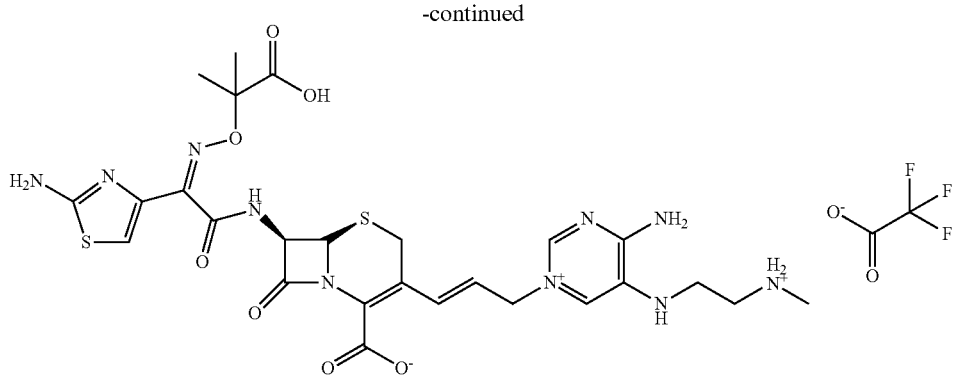
51
Compound 51 (48 mg, 60%) was prepared by a method similar to Example 8 by using Compound B-V and Compound XXXI.
$^1$H NMR (600 MHz, CD$_3$OD) δ 8.33 (s, 1H), 7.58 (s, 1H), 7.11~7.06 (m, 2H), 6.27 (m, 1H), 5.92 (d, J=4.8 Hz, 1H), 5.23 (d, J=4.8 Hz, 1H), 4.93 (m, 2H), 3.84 (d, J=18 Hz, 1H), 3.68 (d, J=18 Hz, 1H), 3.57 (br, 2H), 3.31 (m, 2H), 2.76 (s, 3H), 1.64 (s, 3H), 1.63 (s, 3H)
Example 52
Compound 52
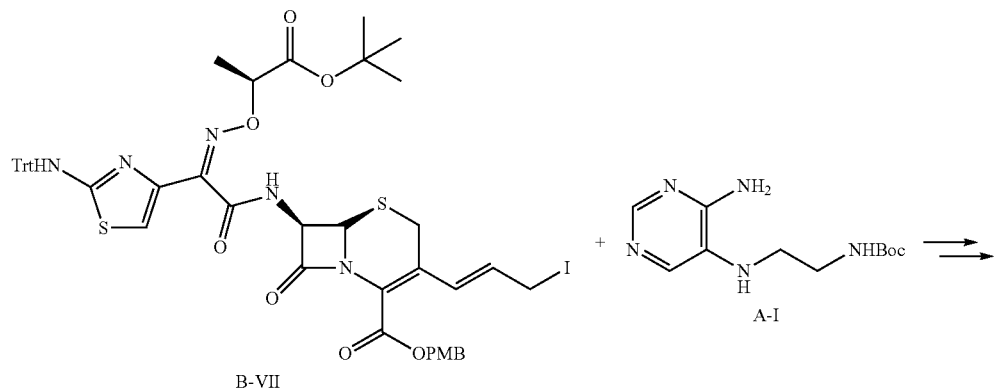
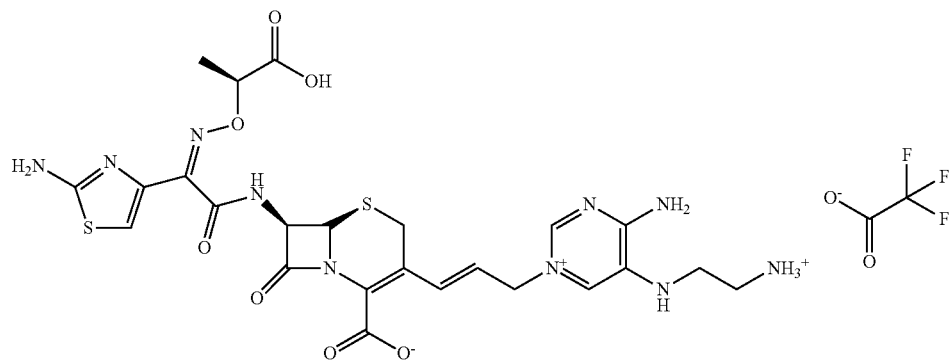
52

Compound 52 (18 mg, 30%) was prepared by a method similar to Example 8 by using Compound B-VII and Compound A-I.

$^1$H NMR (600 MHz, CD$_3$OD) δ 8.31 (s, 1H), 7.54 (s, 1H), 7.06 (m, 2H), 6.22 (m, 1H), 5.91 (d, J=5.4 Hz, 1H), 5.19 (d, J=5.4 Hz, 1H), 4.80 (m, 1H), 3.80 (d, 17.4 Hz 1H), 3.65 (d, J=17.4 Hz, 1H), 3.50 (t, J=6 Hz, 2H), 3.24 (t, J=6 Hz, 2H) 1.55 (d, J=6.6 Hz, 3H)

Example 53

Compound 53

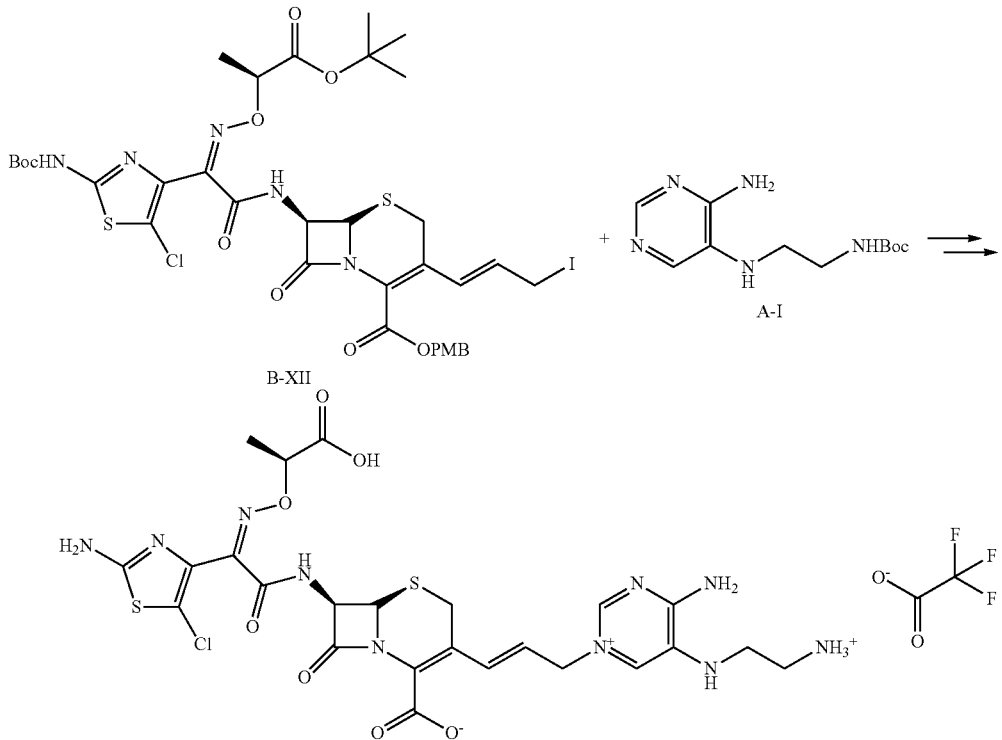

Compound 53 (30 mg, 33%) was prepared by a method similar to Example 8 by using Compound B-XII and Compound A-I.

$^1$H NMR (600 MHz, DMSO-d$^6$) δ 9.53 (d, J=7.8 Hz, 1H), 9.11 (s, 1H), 8.47 (s, 1H), 8.07 (s, 1H), 7.87 (s, 2H), 7.60 (s, 1H), 7.42 (s, 1H), 6.91 (d, J=16.2 Hz, 1H), 6.26 (m, 1H), 6.02 (br, 1H), 5.84 (dd, J=4.8 Hz, 4.8 Hz, 1H), 5.20 (d, J=4.8 Hz, 1H), 4.93 (m, 2H), 4.63 (q, J=7.2 Hz, 1H), 3.81 (d, J=18 Hz, 1H), 3.58 (d, J=18 Hz, 1H), 3.32 (m, 2H), 3.06 (br, 2H), 1.43 (d, J=7.2 Hz, 3H)

Example 54

Compound 54

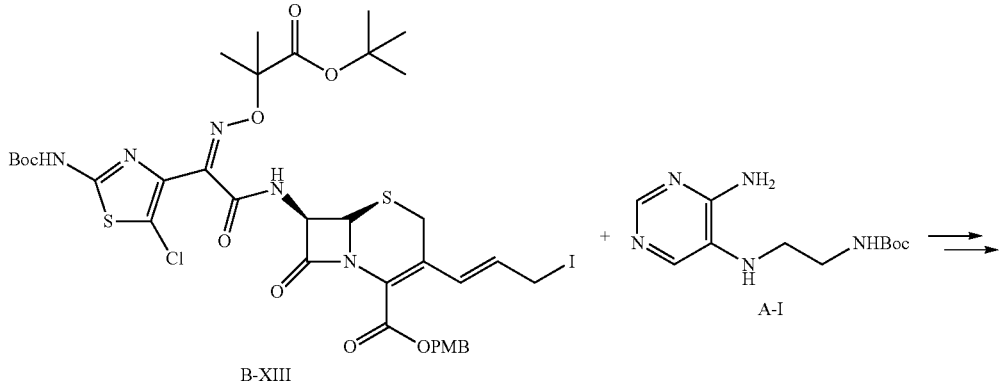

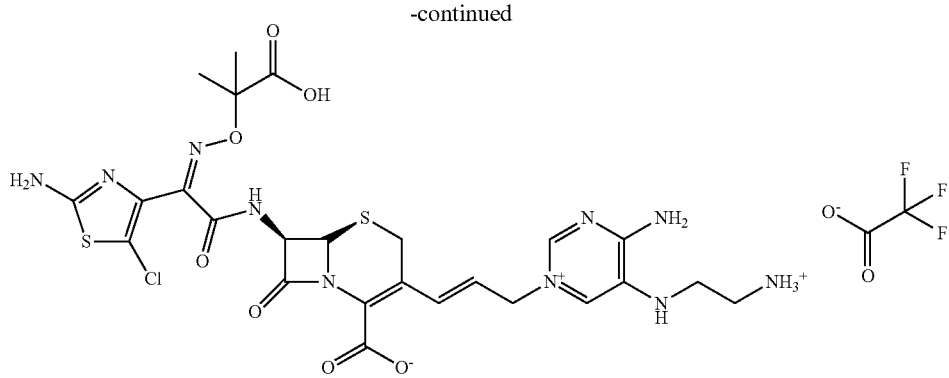
54
Compound 54 (29 mg, 30%) was prepared by a method similar to Example 8 by using Compound B-XIII and Compound A-I.
$^1$H NMR (600 MHz, DMSO d-$_6$) δ 11.77 (t, J=5.4 Hz, 1H), 11.04 (bs, 1H), 10.91 (bs, 1H), 9.45 (d, J=8.4 Hz, 1H), 9.00 (bs, 1H), 8.42 (s, 1H), 8.09 (bs, 1H), 7.82 (s, 1H), 7.70 (s, 1H), 7.57 (s, 1H), 7.42 (s, 1H), 6.90 (d, J=16.2 Hz, 1H), 6.29 (m, 1H), 6.05 (t, J=4.8 Hz, 1H), 5.82 (dd, J$_1$=8.4 Hz, J$_2$=5.4 Hz, 1H), 5.20 (d, J=5.4 Hz, 1H), 4.88 (m, 2H), 3.83 (d, J=18.0 Hz, 1H), 3.58 (m, 3H), 3.29 (m, 2H), 1.47 (s, 3H), 1.45 (s, 3H)
Example 55
Compound 55
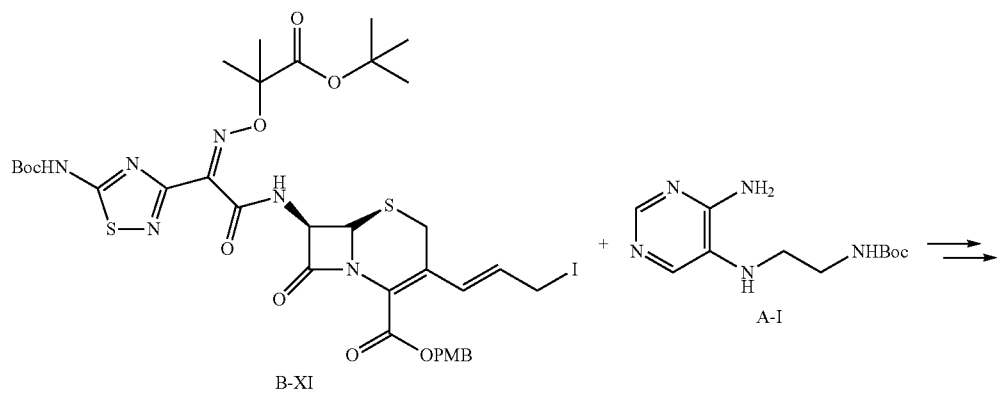
B-XI + A-I →
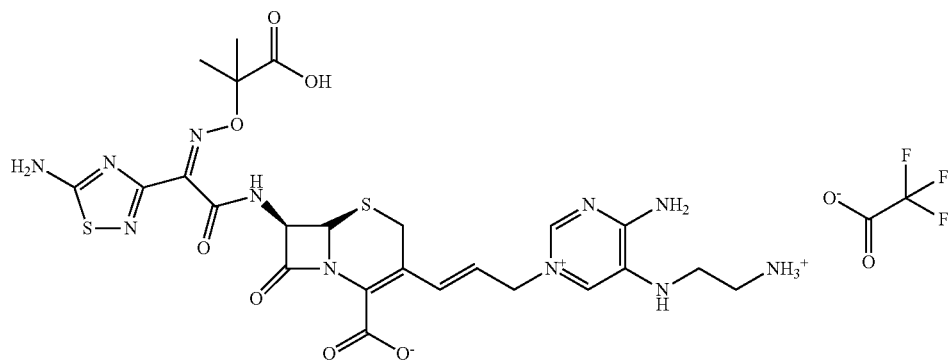
55

Compound 55 (26 mg, 29%) was prepared by a method similar to Example 8 by using Compound B-XI and Compound A-I.

$^1$H NMR (600 MHz, DMSO d-$_6$) δ 9.54 (bs, 1H), 9.06 (bs, 1H), 8.44 (s, 1H), 8.21 (bs, 3H), 7.56 (s, 1H), 6.86 (d, J=16.2 Hz, 1H), 6.29 (bs, 1H), 6.05 (m, 1H), 5.76 (m, 1H), 5.13 (d, J=4.8 Hz, 1H), 4.85 (m, 2H), 3.66 (d, J=16.8 Hz, 1H), 3.49 (d, J=17.4 Hz, 1H), 3.02 (m, 4H), 1.47 (s, 3H), 1.46 (s, 3H)

Example 56

Compound 56

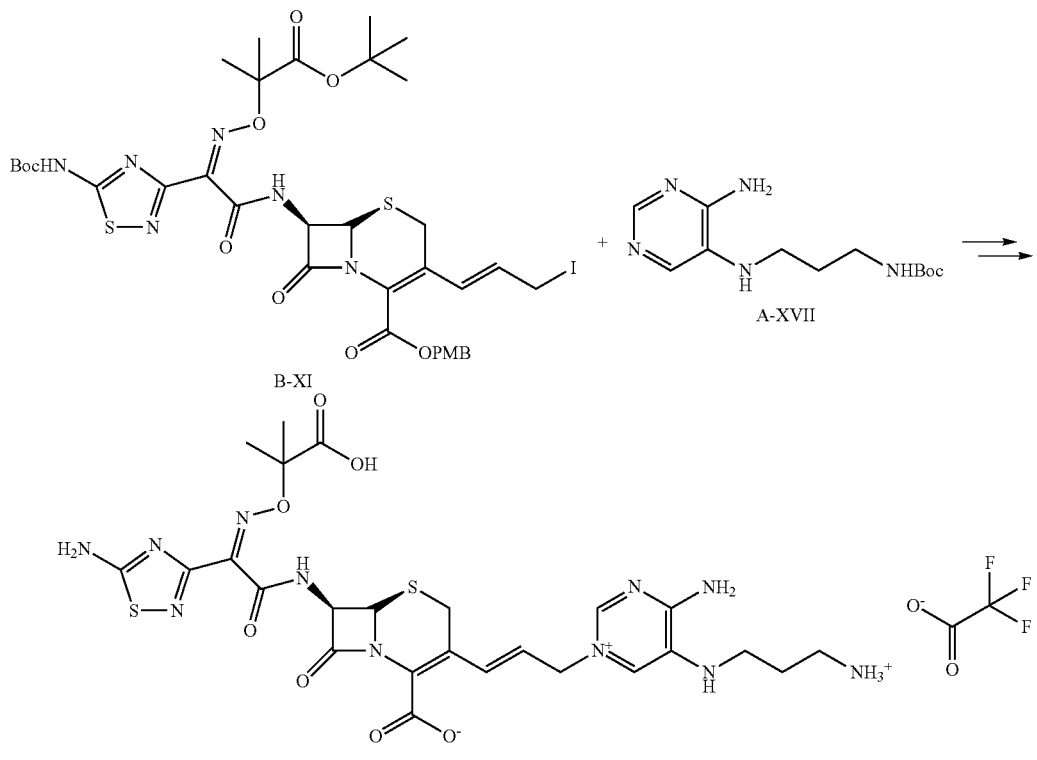

Compound 56 (38 mg, 32%) was prepared by a method similar to Example 8 by using Compound B-XI and Compound A-XVII.

$^1$H NMR (600 MHz, DMSO d-$_6$) δ 9.48 (d, J=9.0 Hz, 1H), 9.04 (bs, 1H), 8.42 (s, 1H), 8.21 (bs, 3H), 7.57 (s, 1H), 6.91 (d, J=16.2 Hz, 1H), 6.14 (m, 2H), 5.76 (bs, 1H), 5.14 (m, 1H), 4.84 (bs, 1H), 3.53 (m, 2H), 3.21 (m, 2H), 2.90 (m, 2H), 1.88 (m, 2H), 1.46 (s, 3H), 1.46 (s, 3H)

Example 57

Compound 57

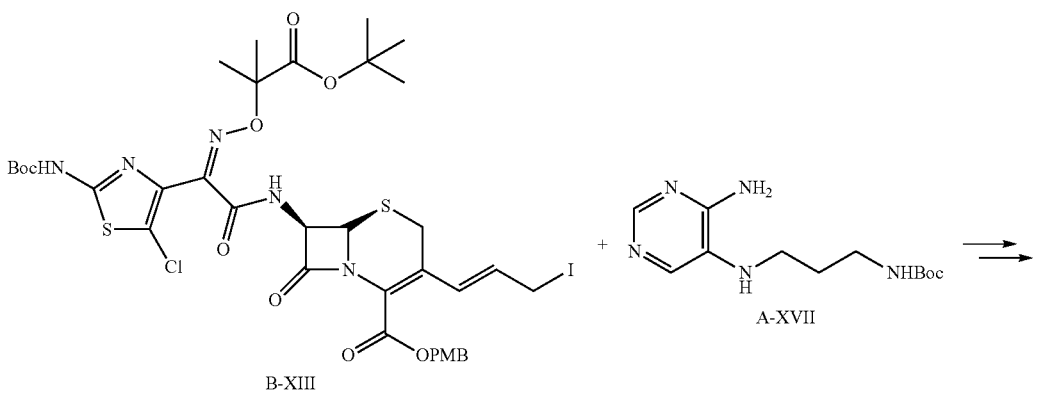

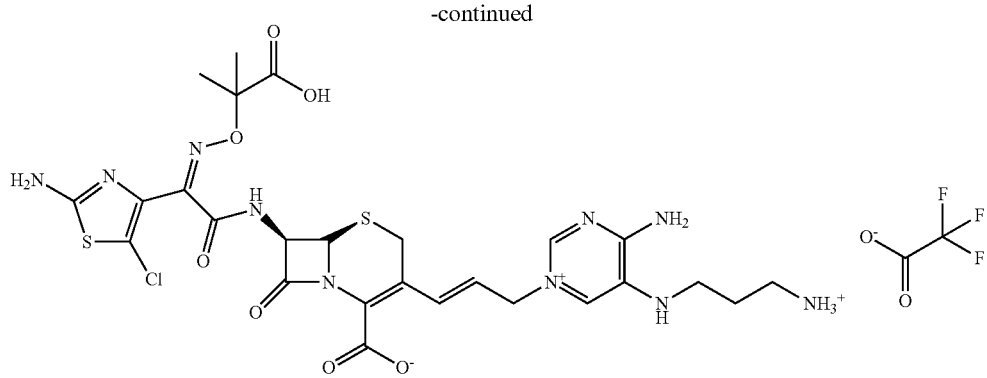
57
Compound 57 (30 mg, 25%) was prepared by a method similar to Example 8 by using Compound B-XIII and Compound A-XVI.
$^1$H NMR (600 MHz, DMSO d-$_6$) δ 9.41 (m, 1H), 9.04 (bs, 1H), 8.42 (s, 1H), 8.22 (bs, 2H), 7.58 (bs, 1H), 7.42 (s, 1H), 6.91 (d, J=15.6 Hz, 1H), 6.13 (m, 2H), 5.73 (m, 1H), 5.13 (m, 1H), 4.85 (m, 2H), 3.52 (m, 2H), 3.22 (bs, 2H), 2.89 (bs, 2H), 1.87 (m, 2H), 1.48 (s, 3H), 1.46 (s, 3H)
Example 58
Compound 58
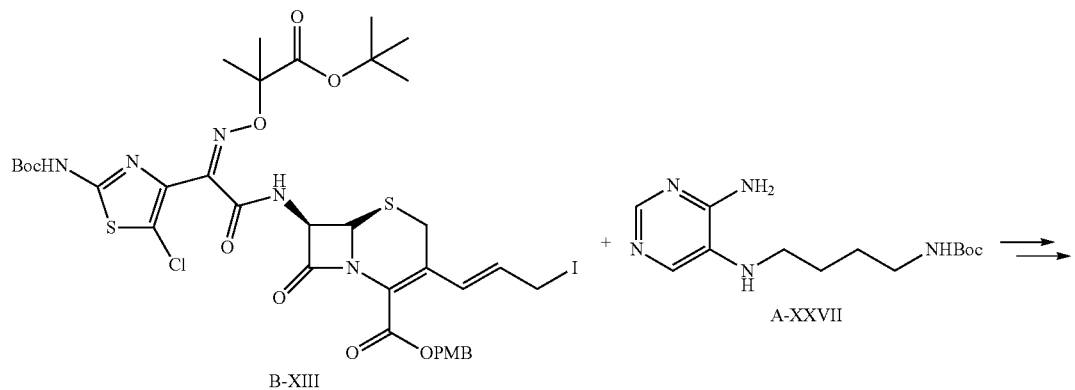
B-XIII + A-XXVII →
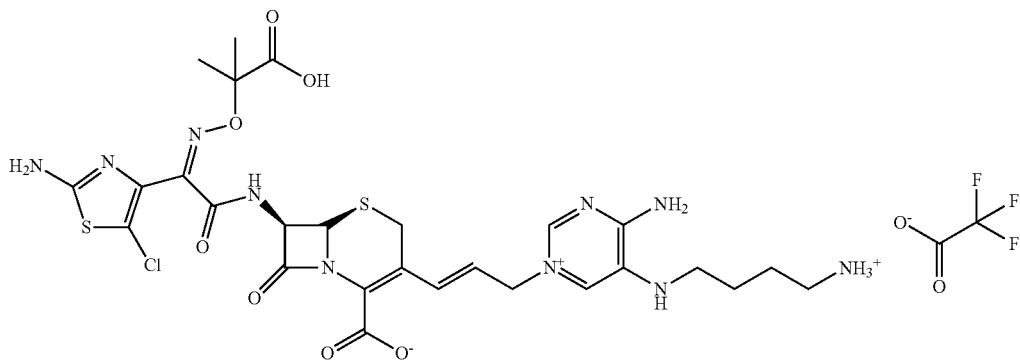
58

Compound 58 (9 mg, 24%) was prepared by a method similar to Example 8 by using Compound B-XIII and Compound A-XXVII.

$^1$H NMR (600 MHz, CD$_3$OD) δ 8.27 (s, 1H), 7.41 (s, 1H), 7.10 (d, J=15.6 Hz, 1H), 6.27 (m, 1H), 5.90 (d, J=4.8 Hz, 1H), 5.21 (d, J=4.8 Hz, 1H), 4.91 (m, 2H), 3.85 (d, J=18.6 Hz, 1H), 3.66 (d, J=18 Hz, 1H), 3.21 (br, 2H), 3.00 (br, 2H), 1.80 (br, 4H), 1.60 (s, 3H), 1.59 (s, 3H)

Example 59

Compound 59

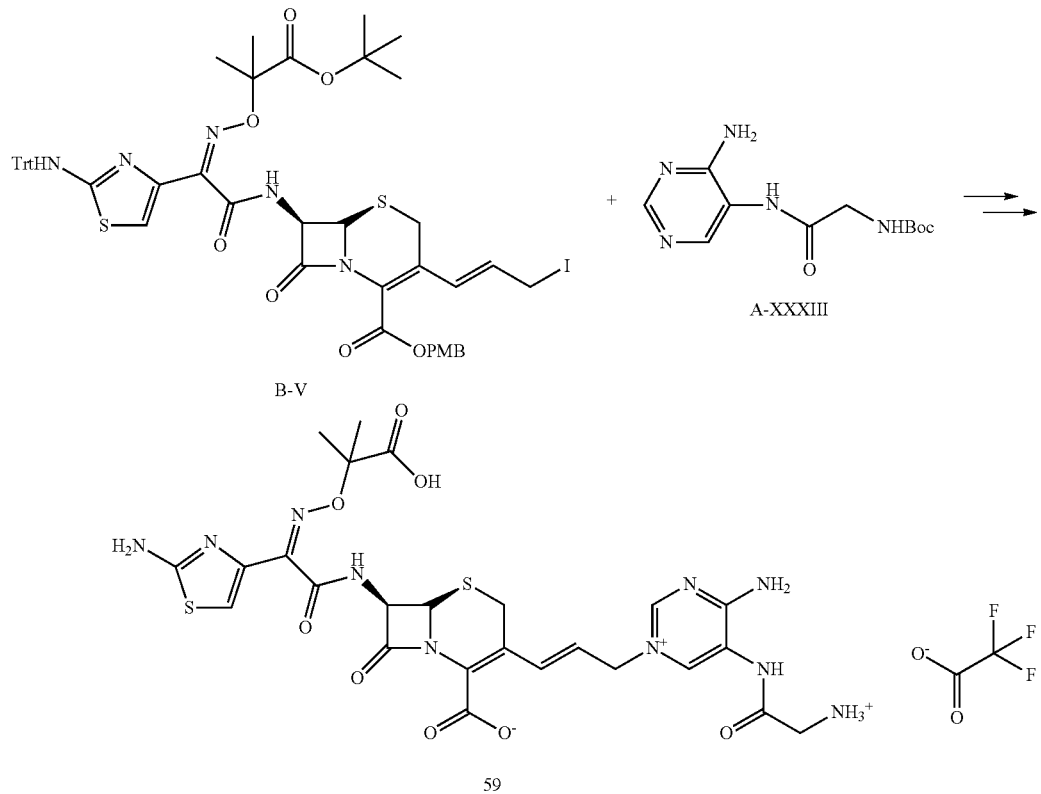

Compound 59 (47 mg, 49%) was prepared by a method similar to Example 8 by using Compound B-V and Compound A-XXXIII.

$^1$H NMR (600 MHz, CD$_3$OD) δ 8.65 (s, 1H), 8.60 (s, 1H), 7.19 (d, J=16.2 Hz, 1H), 6.97 (s, 1H), 6.20 (m, 1H), 5.92 (d, J=4.8 Hz, 1H), 5.21 (d, J=4.8 Hz, 1H), 4.93~4.83 (m, 2H), 3.98 (s, 2H), 3.80 (d, J=18 Hz, 1H), 3.66 (d, J=18 Hz, 1H), 1.62 (s, 3H), 1.6 (s, 3H)

Example 60

Compound 60

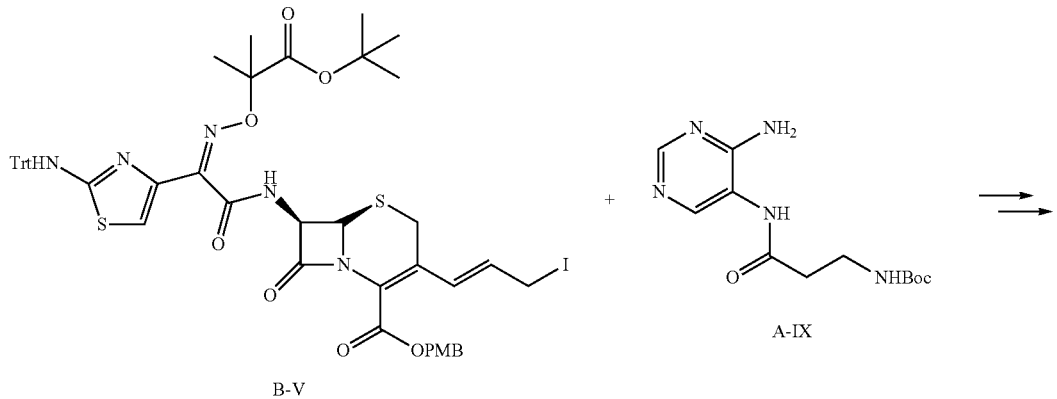

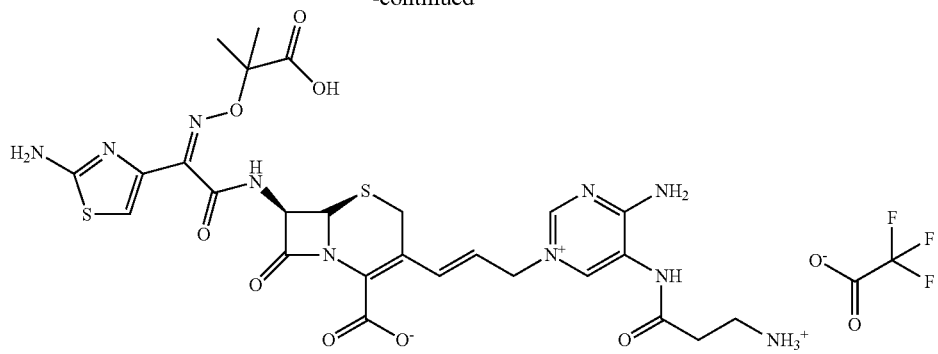
60
Compound 60 (49 mg, 53%) was prepared by a method similar to Example 8 by using Compound B-V and Compound A-IX.
$^1$H NMR (600 MHz, CD$_3$OD) δ 8.63 (s, 1H), 8.62 (s, 1H), 7.17 (d, J=16.2 Hz, 1H), 6.97 (s, 1H), 6.19 (m, 1H), 5.92 (d, J=4.8 Hz, 1H), 5.22 (d, J=5.4 Hz, 1H), 4.92~4.8 (m, 2H), 3.80 (d, J=18 Hz, 1H), 3.66 (d, J=17.4 Hz, 1H), 3.28 (m, 2H), 2.91 (t, J=6 Hz, 2H), 1.62 (s, 3H), 1.60 (s, 3H)
Example 61
Compound 61
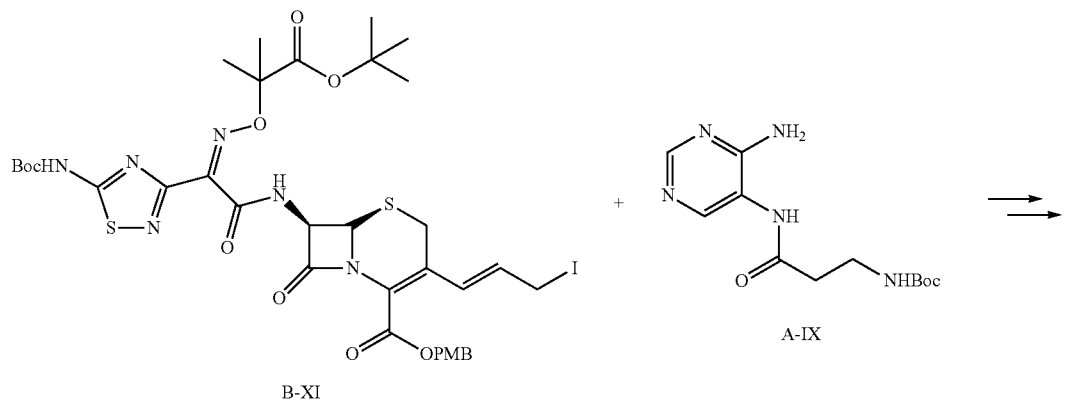
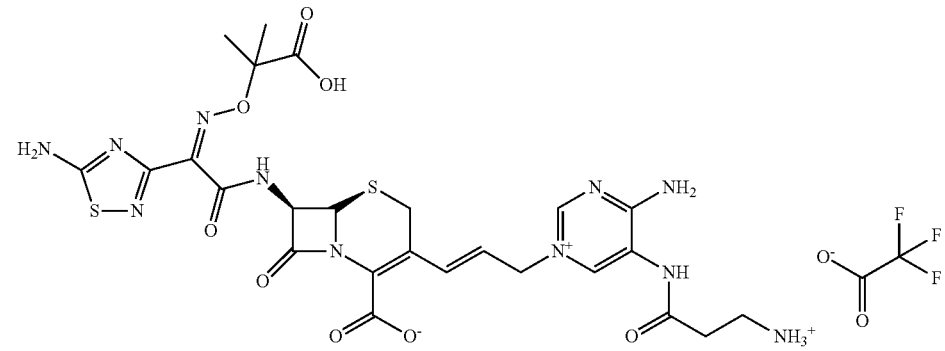
61

Compound 61 (6.8 mg, 10%) was prepared by a method similar to Example 8 by using Compound B-XI and Compound A-IX.

¹H NMR (600 MHz, CD3OD) δ 8.62 (s, 1H), 8.60 (s, 1H), 7.23 (d, J=15.6 Hz, 1H), 6.22 (m, 1H), 5.92 (d, J=4.8 Hz, 1H), 5.19 (d, J=4.8 Hz, 1H), 4.91 (m, 2H), 3.80 (d, 17.4 Hz 1H), 3.64 (d, J=17.4, 1H), 3.28 (m, 2H), 2.90 (t, J=6 Hz, 2H), 1.60 (s, 3H), 1.58 (s, 3H)

Example 62

Compound 62

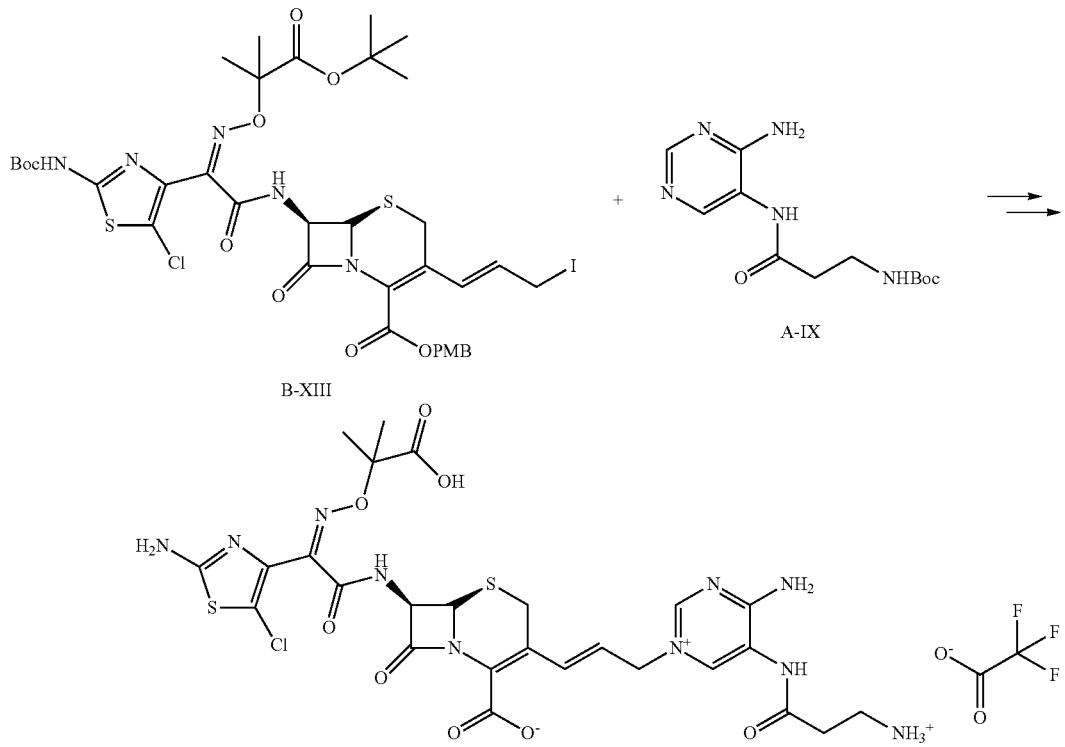

Compound 62 (11 mg, 13%) was prepared by a method similar to Example 8 by using Compound B-XIII and Compound A-IX.

¹H NMR (600 MHz, CD₃OD) δ 8.45 (s, 1H), 8.43 (s, 1H), 7.09 (d, J=16.2 Hz, 1H), 6.12 (m, 1H), 5.87 (d, J=4.8 Hz, 1H), 5.17 (d, J=5.4 Hz, 1H), 4.89 (m, 2H), 3.74 (d, J=17.4 Hz 1H), 3.61 (d, J=17.4 Hz, 1H), 3.30 (m, 2H), 2.90 (m, 2H), 1.59 (s, 3H), 1.57 (s, 3H)

Example 63

Compound 63

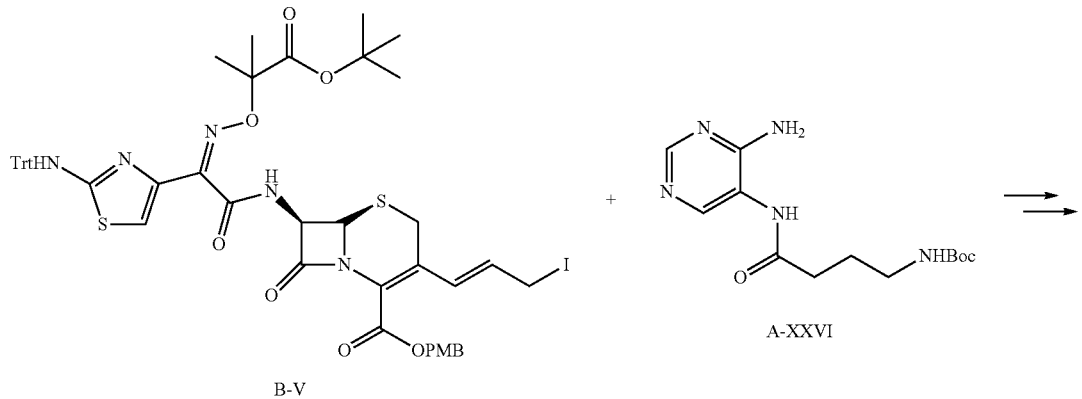

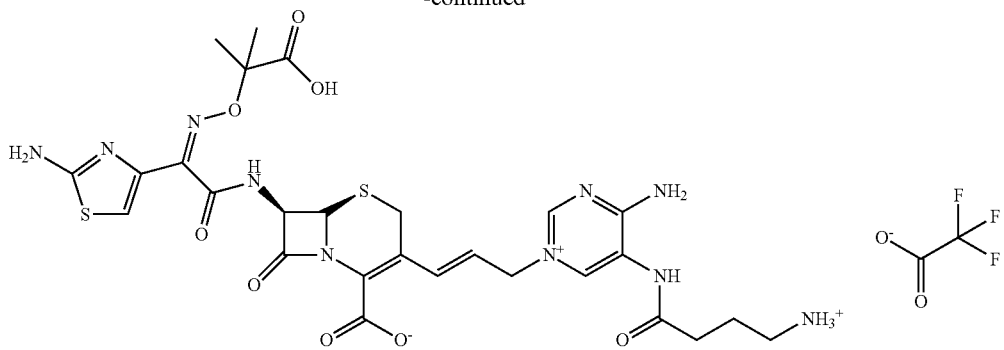
63
Compound 63 (46 mg, 57%) was prepared by a method similar to Example 8 by using Compound B-V and Compound A-XXVI.
$^1$H NMR (600 MHz, CD$_3$OD) δ 8.66 (d, J=1.8 Hz, 1H), 8.61 (d, J=1.8 Hz), 7.18 (d, J=15.6 Hz, 1H), 6.96 (s, 1H), 6.19 (m, 1H), 5.92 (d, J=4.8 Hz, 1H), 5.22 (d, J=5.4 Hz, 1H), 4.91 (m, 2H), 3.81 (d, J=18 Hz, 1H), 3.66 (d, J=18 Hz, 1H), 3.04 (t, J=7.2 Hz, 2H), 2.66 (t, J=6.6 Hz, 2H), 2.04 (m, 2H), 1.62 (s, 3H), 1.60 (s, 3H)
Example 64
Compound 64
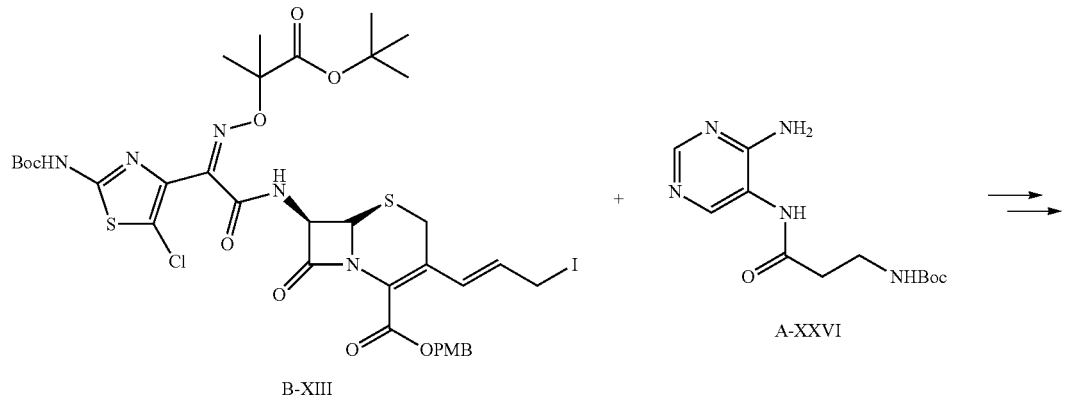
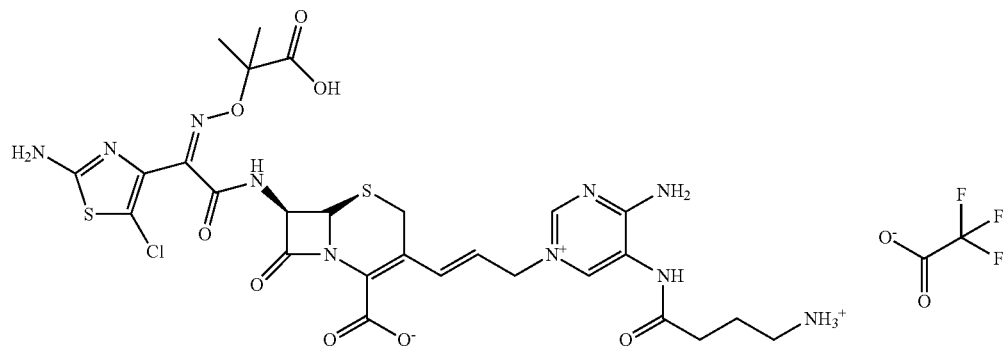
64

Compound 64 (12 mg, 14%) was prepared by a method similar to Example 8 by using Compound B-XIII and Compound A-XXVI.

$^1$H NMR (600 MHz, CD$_3$OD) δ 8.69 (s, 1H), 8.59 (s, 1H), 7.20 (d, J=16.2 Hz, 1H), 6.24 (m, 1H), 5.92 (d, J=4.8 Hz, 1H), 5.21 (d, J=4.8 Hz, 1H), 4.93 (m, 2H), 3.84 (d, J=18 Hz, 1H), 3.67 (d, J=18 Hz, 1H), 3.03 (br, 2H), 2.66 (br, 2H), 2.03 (br, 2H), 1.60 (s, 3H), 1.59 (s, 3H)

Example 65

Compound 65

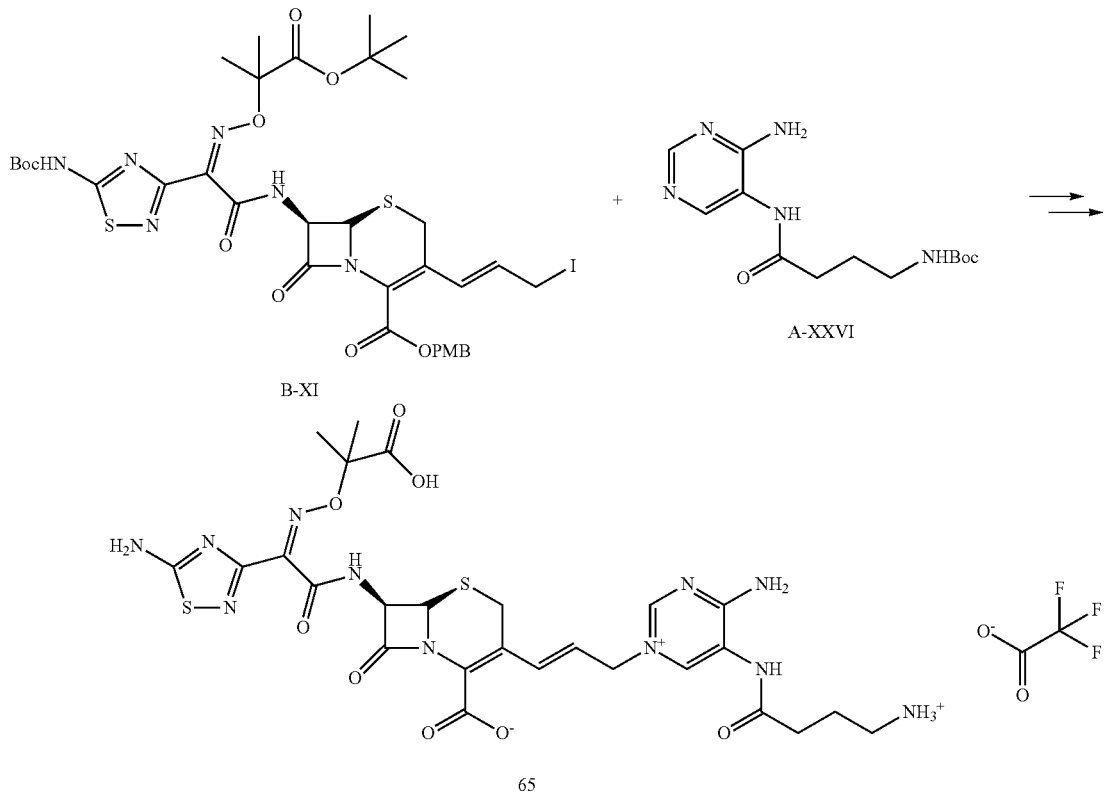

Compound 65 (39 mg, 48%) was prepared by a method similar to Example 8 by using Compound B-XI and Compound A-XXVI.

$^1$H NMR (600 MHz, CD$_3$OD) δ 8.65 (s, 1H), 8.61 (s, 1H), 7.19 (d, J=15.6 Hz, 1H), 6.22 (m, 1H), 5.93 (d, J=4.8 Hz, 1H), 5.21 (d, J=4.8 Hz, 1H), 4.92 (m, 2H), 3.82 (d, J=18 Hz, 1H), 3.66 (d, J=17.4 Hz, 1H), 3.04 (t, J=7.2 Hz, 2H), 2.66 (t, J=6.6 Hz, 2H), 2.04 (m, 2H), 1.62 (s, 3H), 1.60 (s, 3H)

Example 66

Compound 66

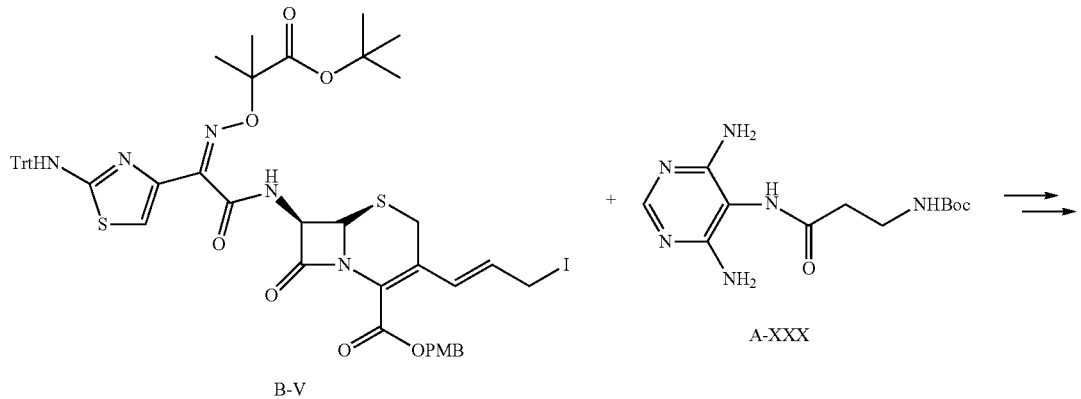

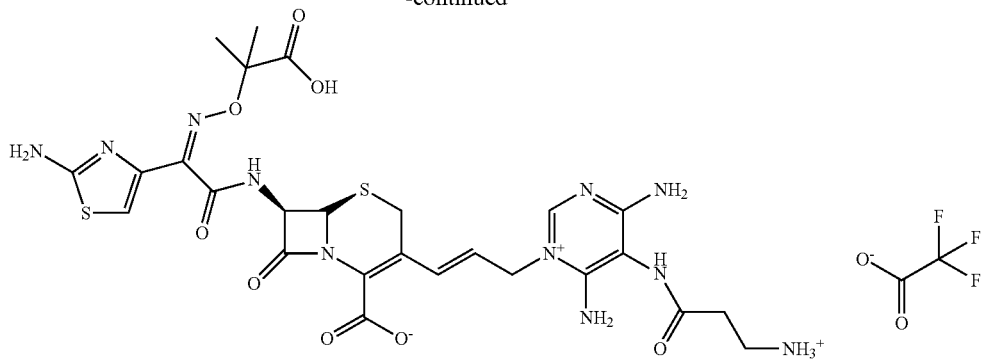
66
Compound 66 (30 mg, 32%) was prepared by a method similar to Example 8 by using Compound B-V and Compound A-XXX.
$^1$H NMR (600 MHz, CD$_3$OD) δ 8.23 (s, 1H), 7.03 (d, J=16.8 Hz, 1H), 6.98 (s, 1H), 6.13 (m, 1H), 5.91 (d, J=5.4 Hz, 1H), 5.21 (d, J=4.8 Hz, 1H), 4.90 (m, 2H), 3.81 (d, J=17.4 Hz, 1H), 3.66 (d, J=17.4 Hz, 1H), 3.29 (t, J=6 Hz, 2H), 2.93 (t, J=6 Hz, 2H), 1.62 (s, 3H), 1.60 (s, 3H)
Example 67
Compound 67
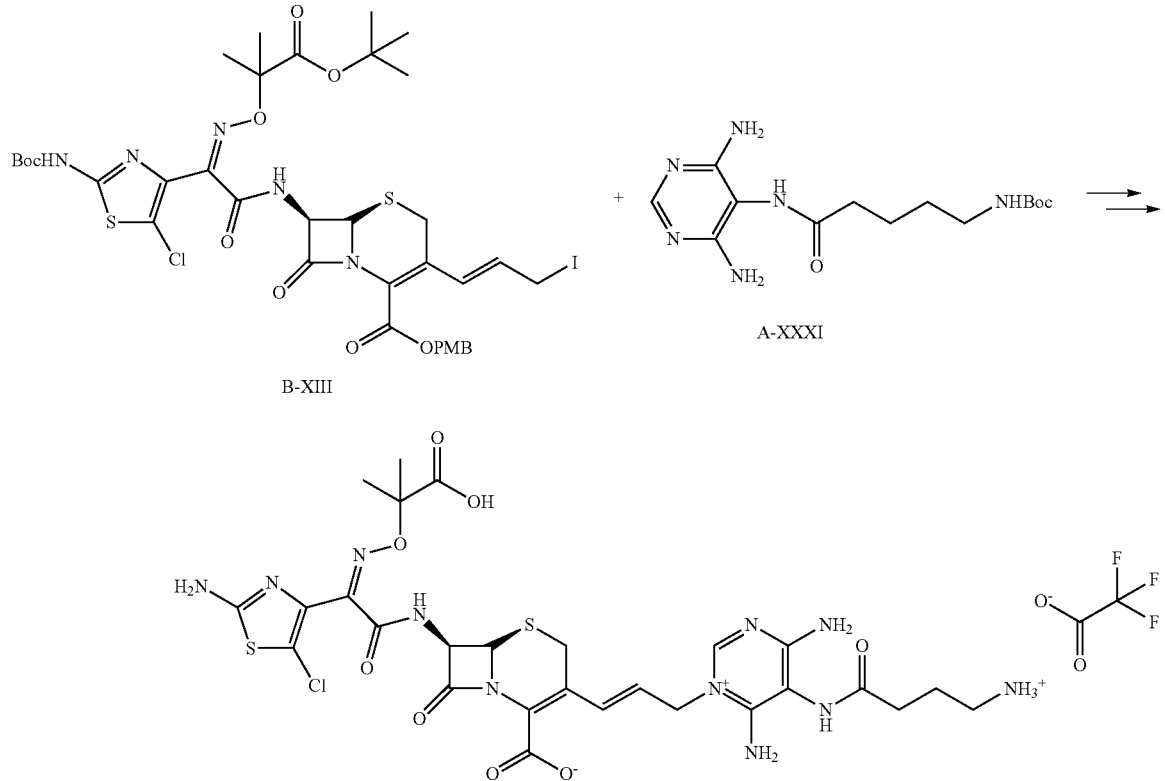
67

Compound 67 (20 mg, 18%) was prepared by a method similar to Example 8 by using Compound B-XIII and Compound A-XXXI.

$^1$H NMR (600 MHz, DMSO d-$_6$) δ 9.48 (m, 1H), 8.93 (bs, 1H), 8.36 (s, 1H), 7.97 (bs, 1H), 7.76 (bs, 1H), 7.75 (bs, 2H), 7.47 (bs, 1H), 7.42 (s, 1H), 6.92 (d, J=16.2 Hz, 1H), 6.08 (m, 1H), 5.80 (m, 1H), 5.19 (d, J=4.8 Hz, 1H), 4.82 (m, 2H), 3.80 (d, J=18.0 Hz, 1H), 3.55 (d, J=18.0 Hz, 1H), 2.83 (m, 2H), 2.44 (m, 2H), 1.82 (m, 2H), 1.48 (s, 3H), 1.46 (s, 3H)

Example 68

Compound 68

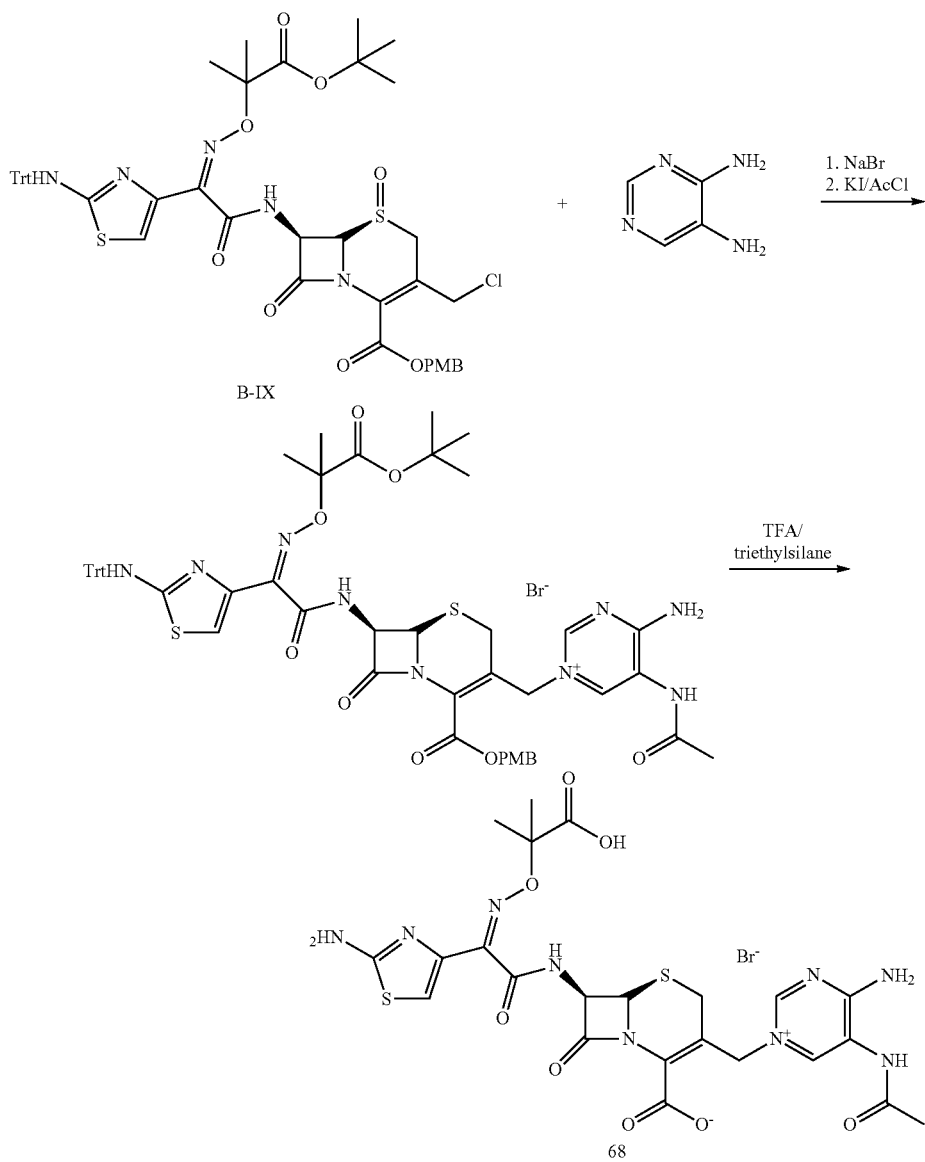

B-IX Compound (170 mg, 0.182 mmol) and 4,5-diaminopyrimidine (20 mg, 0.182 mmol) were dissolved in N,N-dimethylformamide (1.5 mL) and sodium bromide (37.5 mg, 0.364 mmol) was added. The resulting solution was stirred for 9 hours at room temperature. Potassium iodide (211 mg, 1.27 mmol) and N,N-dimethylformamide (1 mL) were added. At −40° C. acetyl chloride (71 mg, 0.91 mmol) was added while stirring, and stirred for 5 minutes at the same temperature and further stirred for 1 hour at 0° C. An aqueous solution of sodium thiosulfate pentahydrate dissolved in saline (5 mL) was added to the resulting solution at 0° C. The thus-obtained solid was dissolved in methylene chloride (15 mL) and applied to column chromatography (MC:MeOH=50:1~10:1) to yield a quaternary salt compound (78 mg (42%)). The quaternary salt compound (78 mg, 0.075 mmol) was dissolved in methylene chloride (0.5 mL). Triethylsilane (0.5 mL) and trifluoroacetic acid (1.5 mL) were sequentially added. The resulting solution was stirred for 4 hours at room temperature. Isopropylether (25 mL) was added to the resulting solution, creating a solid. The solid was filtered under reduced pressure to yield Compound 68 (50 mg, 99%) (In the middle of the reaction, due to acetyl chloride, acetylation occurred at 5 position of 4,5-diaminopyrimidine).

$^1$H NMR (600 MHz, CD$_3$OD) δ 8.79 (d, J=1.8 Hz, 1H), 8.70 (d, J=1.8 Hz, 1H), 7.08 (s, 1H), 6.00 (d, J=4.8 Hz, 1H) 5.32 (d, J=14.4 Hz, 1H), 5.27 (d, J=4.8 Hz, 1H), 4.8 (d, J=14.4 Hz, 1H), 3.71 (d, J=18.6 Hz, 1H), 3.44 (d, J=18 Hz, 1H), 1.60 (d, J=1.2 Hz, 6H)

Test Example 1

In Vitro Antibacterial Activity Test

To evaluate antibacterial activity of each of the compounds of Examples 1 to 68, in vitro antibacterial activity test was performed. The in vitro antibacterial activity was evaluated by measuring $MIC_{90}$ (ug/mL) of each of the compounds of Examples 1 to 68, which is defined as the lowest concentration of an antibiotic that will inhibit the visible growth of 90% of microorganisms after incubation as compared with a control group to which the antibiotic is not treated. $MIC_H$ values were measured by the broth microdilution method developed by the Clinical and Laboratory Standards Institute (CLSI) (see CLSI M7-A5, Methods for Dilution Antimicrobial Susceptibility Test for Bacteria that Grow Aerobically-Fifth Edition (2000): CLSI, Villanova, Pa.).

Ceftazidime (CAZ) represented by Formula B, CXA-101 represented by Formula C, and Doripenem represented by Formula D were used as comparison compounds. The test results are shown in Tables 1 and 2.

Ceftazidime represented by Formula B is a third-generation cephalosporin antibiotic and is widely used against *Pseudomonas aeruginosa*. CXA-101 represented by Formula C is a cephalosporin antibiotic which is in phase 2 clinical trials by Cubist Pharmaceuticals, Inc. Doripenem represented by Formula D belongs to a subgroup of cabapenems and is one of the antibiotics that are most widely used to treat drug-resistant Gram-negative infection.

1) Test Bacteria

In vitro antibacterial activity was measured with respect to the following 19 clinical isolates: *M. catarrhalis*; *P. aeruginosa* (5 strains); *K. pneumoniae* (6 strains); *A. baumannii* (3 strains); *E. coli* (2 strains); *A. calcoaceticus*; and *E. cloacae*. Table 1 shows the result.

2) Preparation of Test Compositions

Test compounds each (the cephalosporin derivative compounds prepared in Examples 1 to 68) were dissolved in DMSO at the concentration of 10,240 ug/mL, were diluted by two fold with DMSO, and then were diluted by twenty fold

[Formula B]

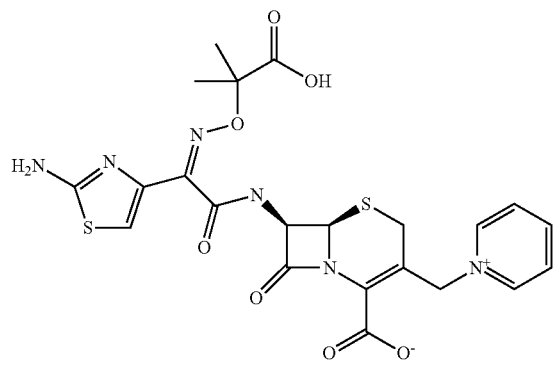

Ceftazidime

[Formula C]

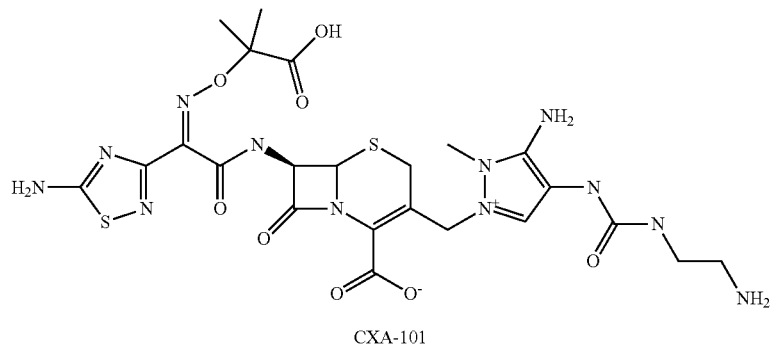

CXA-101

[Formula D]

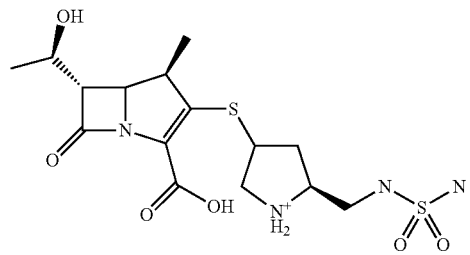

Doripenem with sterilized distilled water. The final concentration in the antibacterial activity test was in the range of 0.0626 ug/mL to 128 ug/mL, and the final concentration of DMSO used as an adjuvant was 2.5% (V/V).

TABLE 1

Antibacterial Activity of Compounds of Formula I (MIC$_{90}$, ug/mL)

| Test Bacteria | Cephalosporin derivative compounds according to the present invention | | | | | | | | |
|---|---|---|---|---|---|---|---|---|---|
| | 1 | 2 | 3 | 4 | 5 | 6 | 7 | 8 | CAZ |
| 1 M. catarrhalis | 1 | 1 | 2 | 0.25 | 0.25 | 2 | 2 | 0.5 | <0.0625 |
| 2 P. aeruginosa | 0.25 | 2 | 32 | 0.5 | 1 | 0.5 | 0.5 | 1 | 1 |
| 3 P. aeruginosa | 1 | 16 | 0.5 | 0.5 | 4 | 2 | 1 | 4 | 32 |
| 4 P. aeruginosa | 0.5 | 4 | 1 | 0.5 | 1 | 0.5 | 0.125 | 1 | 64 |
| 5 P. aeruginosa | 0.25 | 4 | 0.125 | 1 | 1 | 0.5 | 0.125 | 0.5 | 4 |
| 6 P. aeruginosa | 0.25 | 8 | 0.25 | 1 | 0.25 | 0.5 | 0.25 | 1 | 16 |
| 7 K. pneumoniae | 2 | 4 | 1 | 2 | 2 | 4 | 2 | 1 | 1 |
| 8 K. pneumoniae | 4 | | | 0.5 | <0.0625 | 2 | <0.0625 | 0.5 | 16 |
| 9 K. pneumoniae | 0.125 | | | 0.5 | 1 | 0.5 | 4 | <0.0625 | 32 |
| 10 K. pneumoniae | 128 | | | 4 | 2 | 8 | 16 | 32 | 64 |
| 11 K. pneumoniae | 0.5 | | | 1 | 0.5 | 0.125 | <0.0625 | 0.25 | 32 |
| 12 K. pneumoniae | 128 | 64 | 64 | 32 | 8 | 16 | 32 | 8 | 64 |
| 13 A. baumannii | 4 | 4 | 2 | 64 | 16 | 32 | 4 | 8 | 4 |
| 14 A. baumannii | 16 | >128 | >128 | 8 | >128 | >128 | 8 | >128 | >64 |
| 15 A. baumannii | 32 | >128 | 128 | 4 | >128 | >128 | 16 | >128 | >64 |
| 16 A. calcoacetius | 0.5 | 2 | 0.25 | 2 | 2 | 2 | 1 | 2 | 1 |
| 17 E. coli | <0.0625 | 0.25 | <0.0625 | 0.125 | <0.0625 | 0.25 | <0.0625 | 0.0625 | 0.5 |
| 18 E. coli | 2 | 4 | 1 | 0.5 | 0.5 | 4 | 0.125 | 0.5 | 8 |
| 19 E. cloacae | 2 | >128 | 2 | 1 | 0.5 | 2 | 1 | 32 | 32 |

| Test Bacteria | Cephalosporin derivative compounds according to the present invention | | | | | | | | |
|---|---|---|---|---|---|---|---|---|---|
| | 9 | 10 | 11 | 12 | 13 | 14 | 15 | 16 | 17 |
| 1 M. catarrhalis | 0.5 | 0.5 | 0.25 | 1 | 2 | 0.25 | 0.25 | 1 | 0.125 |
| 2 P. aeruginosa | 0.25 | 4 | 1 | 1 | 2 | 1 | 0.5 | 1 | 2 |
| 3 P. aeruginosa | 0.25 | 4 | 4 | 2 | 8 | 2 | 1 | 2 | 2 |
| 4 P. aeruginosa | 0.25 | 2 | 1 | 8 | 8 | 16 | 0.125 | 0.5 | 8 |
| 5 P. aeruginosa | <0.0625 | 1 | 0.5 | 1 | 2 | 0.25 | 0.5 | 0.25 | 8 |
| 6 P. aeruginosa | 0.25 | 1 | 1 | 1 | 4 | 0.25 | 0.25 | 2 | 2 |
| 7 K. pneumoniae | 0.125 | 2 | 0.5 | 2 | 2 | 2 | 8 | 8 | 4 |
| 8 K. pneumoniae | 1 | 0.25 | <0.0625 | 0.25 | 1 | 2 | 4 | 128 | 1 |
| 9 K. pneumoniae | 0.125 | <0.0625 | <0.0625 | 0.25 | 1 | 0.5 | 0.25 | 2 | 4 |
| 10 K. pneumoniae | >128 | 32 | >128 | 64 | 64 | 64 | 64 | >128 | 32 |
| 11 K. pneumoniae | 0.25 | 2 | <0.0625 | <0.0625 | 1 | 0.5 | 2 | 32 | 1 |
| 12 K. pneumoniae | 64 | 8 | 8 | 8 | 8 | 8 | 128 | 128 | 32 |
| 13 A. baumannii | 0.5 | 8 | 4 | 4 | 8 | 2 | 128 | 2 | 16 |
| 14 A. baumannii | >128 | >128 | >128 | >128 | >128 | >128 | 8 | >128 | 4 |
| 15 A. baumannii | >128 | >128 | >128 | >128 | 128 | 8 | 2 | 32 | 2 |
| 16 A. calcoacetius | 0.5 | 2 | 1 | 1 | 2 | 0.25 | 0.5 | 0.25 | 0.5 |
| 17 E. coli | <0.0625 | 0.125 | 0.125 | 0.25 | 1 | 0.25 | 2 | 1 | 1 |
| 18 E. coli | 1 | 0.5 | 0.125 | 0.25 | 2 | 1 | 16 | 4 | 4 |
| 19 E. cloacae | 2 | 0.5 | 64 | 4 | 8 | 64 | 32 | 16 | 2 |

| Test Bacteria | Cephalosporin derivative compounds according to the present invention | | | | | | | | |
|---|---|---|---|---|---|---|---|---|---|
| | 18 | 19 | 20 | 21 | 22 | 23 | 24 | 25 | 26 |
| 1 M. catarrhalis | 0.5 | 1 | 0.5 | 0.125 | 0.5 | 0.25 | <0.0625 | <0.0625 | <0.0625 |
| 2 P. aeruginosa | 1 | 2 | 4 | 4 | 2 | 1 | 0.25 | 0.25 | 0.25 |
| 3 P. aeruginosa | 2 | 2 | 1 | 4 | 2 | 2 | 0.5 | 0.5 | 0.5 |
| 4 P. aeruginosa | 0.25 | 0.5 | 2 | 32 | 1 | 0.25 | <0.0625 | <0.0625 | <0.0625 |
| 5 P. aeruginosa | 2 | 0.5 | 4 | 8 | 2 | 0.5 | 0.25 | <0.0625 | <0.0625 |
| 6 P. aeruginosa | 0.25 | 2 | 1 | 2 | 0.5 | 1 | 0.25 | 0.25 | 0.25 |
| 7 K. pneumoniae | 16 | 16 | 8 | 4 | 16 | 1 | 0.5 | 0.25 | 0.5 |
| 8 K. pneumoniae | 8 | 64 | 2 | 2 | 8 | <0.0625 | <0.0625 | <0.0625 | 0.125 |
| 9 K. pneumoniae | 4 | 1 | 0.5 | 2 | 1 | <0.0625 | <0.0625 | <0.0625 | <0.0625 |
| 10 K. pneumoniae | 64 | >128 | 16 | 8 | 64 | 64 | 2 | >128 | 0.5 |
| 11 K. pneumoniae | 4 | 16 | 1 | 2 | 2 | <0.0625 | 0.125 | <0.0625 | <0.0625 |
| 12 K. pneumoniae | 128 | 128 | 64 | 16 | 128 | 4 | 4 | 16 | 4 |
| 13 A. baumannii | 128 | 4 | 16 | 16 | 128 | 4 | 2 | 0.5 | 2 |
| 14 A. baumannii | 8 | 16 | 32 | 8 | 16 | >128 | 32 | 128 | 16 |
| 15 A. baumannii | 2 | 8 | 2 | 2 | 2 | >128 | 16 | 8 | 2 |
| 16 A. calcoacetius | 1 | 0.5 | 1 | 1 | 0.5 | 1 | 0.5 | 0.25 | 0.5 |
| 17 E. coli | 2 | 1 | 0.25 | 0.5 | 2 | <0.0625 | <0.0625 | <0.0625 | <0.0625 |
| 18 E. coli | 16 | 16 | 8 | 4 | 32 | <0.0625 | <0.0625 | <0.0625 | <0.0625 |
| 19 E. cloacae | 64 | 128 | 8 | 16 | 32 | 2 | 0.5 | 1 | 0.125 |

TABLE 1-continued

Antibacterial Activity of Compounds of Formula I (MIC$_{90}$, ug/mL)

| Test | Cephalosporin derivative compounds according to the present invention | | | | | | | | | |
|---|---|---|---|---|---|---|---|---|---|---|
| Bacteria | 27 | 28 | 29 | 30 | 31 | 32 | 33 | 34 | 35 | 47 |
| 1 *M. catarrhalis* | 0.25 | 8 | | | 1 | 0.25 | 2 | 1 | <0.0625 | 0.25 |
| 2 *P. aeruginosa* | 1 | 32 | 2 | 1 | 1 | 2 | 64 | 32 | 2 | 8 |
| 3 *P. aeruginosa* | 4 | 16 | 8 | 0.5 | 4 | 4 | 128 | 1 | 2 | 128 |
| 4 *P. aeruginosa* | 2 | 8 | 2 | 2 | 1 | 4 | >128 | 2 | 0.25 | 64 |
| 5 *P. aeruginosa* | 2 | 16 | 4 | 0.5 | 2 | 4 | 128 | 0.5 | 1 | 32 |
| 6 *P. aeruginosa* | 1 | 4 | 4 | 0.5 | 1 | 0.5 | >128 | 0.5 | 1 | 128 |
| 7 *K. pneumoniae* | 2 | 8 | 8 | 0.5 | 8 | 1 | 16 | 0.25 | 2 | 4 |
| 8 *K. pneumoniae* | | | | | | | | | | |
| 9 *K. pneumoniae* | | | | | | | | | | |
| 10 *K. pneumoniae* | | | | | | | | | | |
| 11 *K. pneumoniae* | | | | | | | | | | |
| 12 *K. pneumoniae* | 32 | 64 | 16 | 16 | 32 | 64 | 128 | 128 | 16 | 32 |
| 13 *A. baumannii* | 16 | 8 | 8 | 1 | 4 | 1 | 128 | 2 | 4 | 16 |
| 14 *A. baumannii* | >128 | >128 | 32 | >128 | 32 | 32 | >128 | 128 | 4 | >128 |
| 15 *A. baumannii* | >128 | 16 | 32 | 128 | 64 | 16 | >128 | 128 | 2 | 128 |
| 16 *A. calcoacetius* | 4 | 1 | 4 | 1 | 1 | 0.5 | 128 | 0.5 | 0.5 | 8 |
| 17 *E. coli* | 1 | >128 | 2 | 0.125 | 0.25 | <0.0625 | 16 | <0.0625 | <0.0625 | >128 |
| 18 *E. coli* | 2 | 8 | 2 | 2 | 8 | 8 | 64 | 1 | 1 | 16 |
| 19 *E. cloacae* | 16 | 128 | 8 | 4 | 16 | 128 | >128 | 16 | 0.5 | 128 |

| Test | Cephalosporin derivative compounds according to the present invention | | | | | | | | |
|---|---|---|---|---|---|---|---|---|---|
| Bacteria | 36 | 37 | 38 | 39 | 40 | 41 | 42 | 43 | 44 |
| 1 *M. catarrhalis* | | | | | | 0.125 | <0.0625 | <0.0625 | <0.0625 |
| 2 *P. aeruginosa* | 8 | 4 | 32 | 8 | 4 | 4 | 2 | 4 | 8 |
| 3 *P. aeruginosa* | 64 | 8 | 128 | 128 | 16 | 16 | 32 | 16 | 32 |
| 4 *P. aeruginosa* | >128 | 16 | >128 | 128 | 8 | 8 | 16 | 32 | 16 |
| 5 *P. aeruginosa* | 16 | 4 | 64 | 32 | 8 | 4 | 8 | 16 | 16 |
| 6 *P. aeruginosa* | | | | 4 | 32 | 128 | >128 | >128 | 128 |
| 7 *K. pneumoniae* | 0.5 | 8 | 4 | 1 | 16 | 4 | 0.5 | 0.5 | 0.5 |
| 8 *K. pneumoniae* | | | | | | 2 | 8 | 1 | 1 |
| 9 *K. pneumoniae* | | | | | | 2 | 0.5 | 0.5 | 0.5 |
| 10 *K. pneumoniae* | | | | | | 8 | >128 | 32 | 32 |
| 11 *K. pneumoniae* | | | | | | 2 | 1 | 0.5 | 1 |
| 12 *K. pneumoniae* | 16 | 16 | 64 | 8 | 8 | 2 | 2 | 1 | 1 |
| 13 *A. baumannii* | 64 | 4 | 128 | 8 | 2 | 32 | 2 | 32 | 16 |
| 14 *A. baumannii* | >128 | 128 | >128 | >128 | 128 | 32 | 64 | >128 | >128 |
| 15 *A. baumannii* | >128 | 64 | >128 | >128 | 128 | 32 | 64 | >128 | >128 |
| 16 *A. calcoacetius* | 2 | 1 | 16 | 8 | 0.25 | 1 | 0.5 | 4 | 1 |
| 17 *E. coli* | 0.5 | 4 | 8 | 1 | 4 | 1 | 0.125 | 0.25 | 0.25 |
| 18 *E. coli* | 16 | 4 | 16 | 16 | 8 | 1 | 0.5 | 0.5 | 0.5 |
| 19 *E. cloacae* | >128 | 16 | >128 | 128 | 32 | 4 | 16 | 0.5 | 0.5 |

| Test | Cephalosporin derivative compounds according to the present invention | | | | | | | | |
|---|---|---|---|---|---|---|---|---|---|
| Bacteria | 45 | 46 | 48 | 49 | 50 | 51 | 52 | 53 | 54 |
| 1 *M. catarrhalis* | <0.0625 | <0.0625 | | | <0.0625 | <0.0625 | <0.0625 | <0.0625 | <0.0625 |
| 2 *P. aeruginosa* | 4 | 4 | 8 | 2 | 2 | 2 | 0.5 | 1 | 2 |
| 3 *P. aeruginosa* | 16 | 32 | 16 | 16 | 8 | 32 | 4 | 8 | 16 |
| 4 *P. aeruginosa* | 16 | 16 | 64 | 8 | 8 | 32 | 16 | 8 | 4 |
| 5 *P. aeruginosa* | 8 | 16 | 8 | 4 | 4 | 4 | 2 | 8 | 4 |
| 6 *P. aeruginosa* | >128 | >128 | | >128 | 64 | 64 | 32 | 32 | 64 |
| 7 *K. pneumoniae* | 0.5 | 2 | 4 | 8 | 0.25 | 0.5 | <0.0625 | 1 | 1 |
| 8 *K. pneumoniae* | 0.5 | 8 | | | 0.5 | 0.5 | 4 | 1 | 1 |
| 9 *K. pneumoniae* | 0.5 | 4 | | | 0.25 | 0.25 | 1 | 1 | 0.5 |
| 10 *K. pneumoniae* | 16 | 8 | | | 16 | 32 | 128 | 2 | 2 |
| 11 *K. pneumoniae* | 0.5 | 2 | | | 0.125 | 0.5 | 4 | 2 | 1 |
| 12 *K. pneumoniae* | 1 | 4 | 16 | 32 | 0.25 | 0.5 | 8 | 2 | 1 |
| 13 *A. baumannii* | 16 | 64 | 8 | 8 | 4 | 8 | 1 | 8 | 4 |
| 14 *A. baumannii* | >128 | 64 | 128 | 64 | 64 | >128 | >128 | 64 | 128 |
| 15 *A. baumannii* | >128 | 64 | 128 | 64 | 128 | 128 | >128 | 64 | 32 |
| 16 *A. calcoacetius* | 2 | 4 | 0.5 | 2 | 0.5 | 0.5 | 1 | 2 | 1 |
| 17 *E. coli* | 0.25 | 0.5 | 2 | 4 | 0.125 | 0.125 | <0.0625 | 0.25 | 0.25 |
| 18 *E. coli* | 0.25 | 2 | 2 | 8 | <0.0625 | 0.125 | <0.0625 | 1 | 0.5 |
| 19 *E. cloacae* | 0.25 | 32 | 128 | 32 | 8 | 32 | 8 | 4 | 4 |

| Test | Cephalosporin derivative compounds according to the present invention | | | | | | | | |
|---|---|---|---|---|---|---|---|---|---|
| Bacteria | 55 | 56 | 57 | 58 | 59 | 60 | 61 | 62 | 63 |
| 1 *M. catarrhalis* | <0.0625 | <0.0625 | <0.0625 | <0.0625 | <0.0625 | <0.0625 | <0.0625 | <0.0625 | <0.0625 |
| 2 *P. aeruginosa* | 1 | 2 | 0.5 | 8 | 4 | 2 | 2 | 4 | 2 |

TABLE 1-continued

Antibacterial Activity of Compounds of Formula I (MIC$_{90}$, ug/mL)

| | | | | | | | | | | |
|---|---|---|---|---|---|---|---|---|---|---|
| 3 | P. aeruginosa | 8 | 16 | 16 | 32 | 32 | 16 | 32 | 16 | 16 |
| 4 | P. aeruginosa | 4 | 8 | 8 | 32 | 64 | 32 | 32 | 8 | 32 |
| 5 | P. aeruginosa | 1 | 8 | 4 | 16 | 16 | 8 | 2 | 8 | 4 |
| 6 | P. aeruginosa | >128 | 64 | >128 | >128 | 128 | 64 | >128 | 64 | 128 |
| 7 | K. pneumoniae | <0.0625 | 2 | 0.25 | 2 | 0.25 | 0.25 | 0.25 | 1 | 0.25 |
| 8 | K. pneumoniae | 2 | 1 | 1 | 8 | 2 | 1 | 16 | 1 | 1 |
| 9 | K. pneumoniae | 0.125 | 1 | 0.25 | 2 | 1 | 0.5 | 1 | 0.5 | 0.5 |
| 10 | K. pneumoniae | 128 | 2 | 128 | 8 | 128 | 64 | >128 | 1 | 32 |
| 11 | K. pneumoniae | 0.25 | 1 | 0.5 | 4 | 1 | 0.5 | 2 | 1 | 1 |
| 12 | K. pneumoniae | 0.5 | 2 | 1 | 4 | 2 | 0.5 | 4 | 1 | 1 |
| 13 | A. baumannii | 0.5 | 4 | 1 | 32 | 16 | 8 | 128 | 16 | 8 |
| 14 | A. baumannii | 64 | 32 | 64 | 32 | >128 | >128 | 128 | 32 | 128 |
| 15 | A. baumannii | 64 | 16 | 64 | 64 | >128 | 128 | 128 | 32 | 128 |
| 16 | A. calcoacetius | 0.125 | 1 | 0.5 | 4 | 2 | 1 | 1 | 1 | 1 |
| 17 | E. coli | <0.0625 | 0.5 | 0.125 | 0.5 | 0.25 | 0.125 | 0.125 | 0.5 | 0.125 |
| 18 | E. coli | <0.0625 | 1 | 0.125 | 2 | 0.5 | 0.25 | 0.125 | 0.5 | 0.25 |
| 19 | E. cloacae | 8 | 4 | 8 | 8 | 0.5 | 0.5 | 16 | 4 | 16 |

| | Test Bacteria | Cephalosporin derivative compounds according to the present invention | | | | |
|---|---|---|---|---|---|---|
| | | 64 | 65 | 66 | 67 | 68 |
| 1 | M. catarrhalis | <0.0625 | <0.0625 | <0.0625 | <0.0625 | |
| 2 | P. aeruginosa | 4 | 2 | 4 | 4 | 4 |
| 3 | P. aeruginosa | 32 | 32 | 16 | 32 | 16 |
| 4 | P. aeruginosa | 16 | 32 | 16 | 16 | 128 |
| 5 | P. aeruginosa | 8 | 4 | 8 | 16 | 4 |
| 6 | P. aeruginosa | 128 | >128 | >128 | >128 | |
| 7 | K. pneumoniae | 2 | 0.25 | 0.5 | 2 | 1 |
| 8 | K. pneumoniae | 2 | 16 | 0.5 | 8 | |
| 9 | K. pneumoniae | 1 | 1 | 0.5 | 4 | |
| 10 | K. pneumoniae | 8 | >128 | 16 | 8 | |
| 11 | K. pneumoniae | 2 | 2 | 0.5 | 2 | |
| 12 | K. pneumoniae | 2 | 2 | 1 | 4 | 32 |
| 13 | A. baumannii | 16 | 64 | 16 | 64 | 8 |
| 14 | A. baumannii | 32 | 64 | >128 | 64 | 128 |
| 15 | A. baumannii | 32 | 64 | >128 | 64 | 128 |
| 16 | A. calcoacetius | 1 | 0.5 | 2 | 4 | 1 |
| 17 | E. coli | 0.5 | <0.0625 | 0.25 | 0.5 | 0.5 |
| 18 | E. coli | 1 | 0.125 | 0.25 | 2 | 8 |
| 19 | E. cloacae | 8 | 32 | 0.25 | 32 | 128 |

1: M. catarrhalis 2524 2: P. aeruginosa 1912E, 3: P. aeruginosa 6065Y, 4: P. aeruginosa 37, 5: P. aeruginosa 40, 6: P. aeruginosa 43, 7: K. pneumoniae 2011E, 8: K. pneumoniae β9, 9: K. pneumoniae β10, 10: K. pneumoniae β11, 11: K. pneumoniae β13, 12: K. pneumoniae β14, 13: A. baumannii 46, 14: A. baumannii 49, 15: A. baumannii 52, 16: A. calcoaceticus ATCC15473, 17: E. coli AG100, 18: E. coli β4, 19: E. cloacae β19

As shown in Table 1, the antibacterial activities of the compounds with a siderophore group were significantly greater than those of the compounds without a siderophore group. The antibacterial activities varied depending on the kind of the siderophore group and the site at which the group is introduced. The antibacterial activity was greatly affected by the site to which the group is introduced.

For the Compounds 4, 8, 11, and 26, which exhibited antibacterial activity significantly improved by introduction of a siderophore group, antibacterial activity was then evaluated with regard to the representative drug-resistance Gram-negative bacteria: P. aeruginosa (16 clinical isolates), K. pneumoniae (38 clinical isolates), A. baumannii (6 clinical isolates). The antibacterial activity of the four compounds was compared with that of the comparison compounds, which is shown in Table 2. The numerical values in Table 2 represent the number of clinical isolates that showed the respective MIC values.

TABLE 2

Antibacterial Activity on Representative Bacteria (MIC$_{90}$, ug/mL)

| MIC(ug/mL) | >16 | 16 | 8 | 4 | 2 | 1 | 0.5 | 0.25 | 0.125 | 0.0625 | <0.0625 |
|---|---|---|---|---|---|---|---|---|---|---|---|
| P. aeruginosa (N = 16) | | | | | | | | | | | |
| Ceftazidime | 11 | 1 | 1 | 2 | 1 | | | | | | |
| CXA-101 | 7 | | 1 | 4 | 4 | | | | | | |
| Doripenem | 9 | 5 | 1 | 1 | | | | | | | |
| Compound 4 | 3 | | 1 | 1 | 2 | 1 | 2 | 5 | | 1 | |
| Compound 8 | 3 | | 1 | 3 | 2 | 2 | 2 | 1 | 2 | | |
| Compound 11 | 2 | 1 | 2 | 3 | 2 | 2 | 3 | | 1 | | |
| Compound 26 | 3 | | 1 | 3 | 2 | 1 | 3 | 2 | | 1 | |

TABLE 2-continued

Antibacterial Activity on Representative Bacteria (MIC$_{90}$, ug/mL)

| MIC(ug/mL) | >16 | 16 | 8 | 4 | 2 | 1 | 0.5 | 0.25 | 0.125 | 0.0625 | <0.0625 |
|---|---|---|---|---|---|---|---|---|---|---|---|
| *A. baumanni* (N = 6) | | | | | | | | | | | |
| Ceftazidime | 6 | | | | | | | | | | |
| CXA-101 | 6 | | | | | | | | | | |
| Doripenem | 5 | 1 | | | | | | | | | |
| Compound 4 | 3 | | | | 2 | | | | 1 | | |
| Compound 8 | 5 | | | | | | 1 | | | | |
| Compound 11 | 5 | | | | 1 | | | | | | |
| Compound 26 | 3 | | 2 | | | 1 | | | | | |
| *K. pneumomiae* (N = 38) | | | | | | | | | | | |
| Ceftazidime | 32 | 3 | | 1 | | | 2 | | | | |
| CXA-101 | 35 | 1 | | | 1 | 1 | | | | | |
| Doripenem | | 2 | 4 | | 5 | 6 | 5 | 3 | 6 | 1 | 6 |
| Compound 4 | 26 | 2 | 3 | 2 | 3 | 1 | | 1 | | | |
| Compound 8 | 35 | | 1 | | | | 1 | | | | 1 |
| Compound 11 | 35 | | 1 | | 1 | | 1 | | | | |
| Compound 26 | 22 | 4 | 4 | | 1 | 3 | 2 | 1 | | | 1 |

As shown in Table 2, the cephalosporin derivatives according to the present invention which have a siderophore group exhibited superior antibacterial spectrum compared with the comparison compounds, Ceftazidime, CXA-101, and Doripenem, and they exhibited excellent activity against, in particular, *P. aeruginosa*, suggesting that they have a great potential to be used to treat drug-resistance Gram-negative infection.

Test Example 2

In Vivo Pharmaceutical Efficacy Test

Pharmaceutical efficacy of the cephalosporin derivative compounds according to the present invention was evaluated in a whole-body infected mouse model. Tables 3 and 4 show survival rate and ED$_{50}$ values for the two compounds with excellent antibacterial activity with regard to an infected mouse by a drug-sensitive bacteria and a drug-resistant bacteria.
Test animals: 3 week old male ICR mouse, weight 18~22 g; 5 mice/group.
Lab conditions: Temperature of 23±2° C.; humidity of 55±20%.
Administration method: Inducing whole-body infection by bacterial solution followed by subcutaneous injection (0.2 mL) after 1 hour and 4 hours.

Test method: Cultured bacteria were diluted with 0.9% NaCl to prepare a bacterial solution having a concentration that is 5 to 10 times of minimal inhibitory concentration (MIC). 0.5 mL of bacterial solution was injected through abdominal cavity to induce whole-body infection. Test compounds were administered in four different amounts, which were designed considering in vitro MIC values of the test bacteria. After 1 hour and 4 hours, the four different amounts of the test compounds were subcutaneously administered. Survival rates were measured for four days and ED$_{50}$ values were calculated according to the Probit method.

TABLE 3

Efficacy on Infected Mouse by Ceftazidime-sensitive *P. aeruginosa*

| | Ceftazidime | | | | Compound 8 | | | |
|---|---|---|---|---|---|---|---|---|
| | Administered amount (mg/kg) | | | | | | | |
| | 20 | 10 | 5 | 2.5 | 20 | 10 | 5 | 2.5 |
| Survival rate | 100% | 100% | 80% | 40% | 100% | 100% | 80% | 60% |
| ED$_{50}$ (mg/kg) | | 2.50 | | | | 1.25 | | |
| (95% sd) | | (0.74~8.49) | | | | (0.09~17.5) | | |

Infecting bacteria: *P. aeruginosa* 1912E (2 × 10$^6$ CFU/mouse)

TABLE 4

Efficacy on Infected Mouse by Ceftazidime-resistant *P. aeruginosa*

| | Ceftazidime | | | | Doripenem | | | | Compound 4 | | | |
|---|---|---|---|---|---|---|---|---|---|---|---|---|
| | Administered amount (mg/kg) | | | | | | | | | | | |
| | 40 | 20 | 10 | 5 | 40 | 20 | 10 | 5 | 40 | 20 | 10 | 5 |
| Survival rate | 20% | 20% | 20% | 0% | 80% | 20% | 20% | 0% | 100% | 80% | 40% | 40% |
| ED$_{50}$ (mg/kg) | | 640 | | | | 28 | | | | 10 | | |
| (95% sd) | | (0.12~3290000) | | | | (13.8~57.8) | | | | (3.97~25.2) | | |

Infecting bacteria: *P. aeruginosa* R1023 (2 × 10$^6$ CFU/mouse)

For the whole-body infected mice by the drug-sensitive bacteria, pharmaceutical efficacy of Compound 8 was similar to that of the comparison compound, Ceftazidime. For the whole-body infected mice by the drug-resistant bacteria, the pharmaceutical efficacy of Compound 4 was much greater than that of Ceftazidime and greater than that of Doripenem that is known to be the best treating agent against *P. aeruginosa*.

As shown in the results, the compounds according to the present invention showed superior pharmaceutical efficacy in in vitro and in vivo and maintained it even in case where siderophore is introduced. In case of catechol, a typical siderophore, in vivo pharmaceutical efficacy was reported to be sharply decreased by catechol O-methyl transferase (COMT). On the other hand, the compounds according to the present invention did not show such a decrease. It suggests that the present compounds are capable of being used as a treating agent against drug-resistant bacteria that are known to be difficult to be treated.

Test Example 3

Pharmacokinetics Study

For the present compounds with superior pharmaceutical efficacy, PK values were evaluated in a rat model. Table 5 shows the results of two representative compounds.
Test animals: 9 week old SD rat, weight 290~310 g; 3 rats/sample time point
Lab conditions: Temperature of 21±2° C.; humidity of 50±20%
Administration method: Injecting test compound solution through tail vein (IV)
Test method: Blood samples were taken from jugular vein at a predetermined time period for 24 hours after administration, plasma was separated, and quantified by using LC-MS/MS.

TABLE 5

Pharmacokinetic Test Results

|  | Compound 4<br>Rat (10 mg/kg) single IV | Compound 8<br>Rat (10 mg/kg) single IV |
| --- | --- | --- |
| AUC (mg*h/l) | 40.28 | 54.60 |
| $AUC_{norm}$ (kg*h/l) | 4.03 | 5.46 |
| CL (l/h/kg) | 0.25 | 0.18 |
| $V_{ss}$ (l/kg) | 0.20 | 0.09 |
| $C_{max}$ (mg/l) | 75.80 | 196.13 |
| $C_{max,\,norm}$ (kg/l) | 7.58 | 19.61 |
| $t_{max}$ (h) | 0.02 | 0.02 |
| $t_{1/2}$ (h) | 0.62 | 0.87 |

As shown in the Table above, the cephalosporin derivatives according to the present invention maintained higher concentration in blood and exhibited an excellent pharmacokinetic profile, thereby being able to be used as a promising antibiotic.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

We claim:

1. A cephalosporin derivative represented by Chemical Formula 1, an in vivo hydrolysable ester thereof,

[Chemical Formula 1]

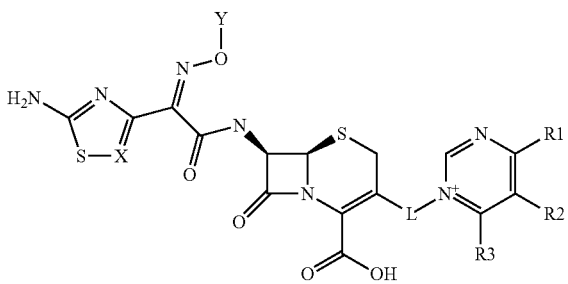

wherein X is CR, N, or C substituted by Cl (C—Cl);
Y is $C_1$-$C_2$ alkyl, $CH(CH_3)CO_2H$, or $C(CH_3)_2CO_2H$;
L is $CH_2$ or $CH=CHCH_2$;
$R_1$ is $NH_2$, $NHR_{11}$ or $NH(CH_2)_m NR_{11} R_{12}$;
$R_2$ is $NHR_{21}$, $NH(CH_2)_n COOH$, $NH(CH_2)_n NR_{21}R_{22}$, or $NHC(=O)(CH_2)_n NR_{21}R_{22}$; and
$R_3$ is hydrogen or $NH_2$,
in which R is hydrogen or $C_1$-$C_3$ alkyl;
$R_{11}$ and $R_{21}$ are independently hydrogen, $C_1$-$C_3$ alkyl, or a group selected from the group consisting of:

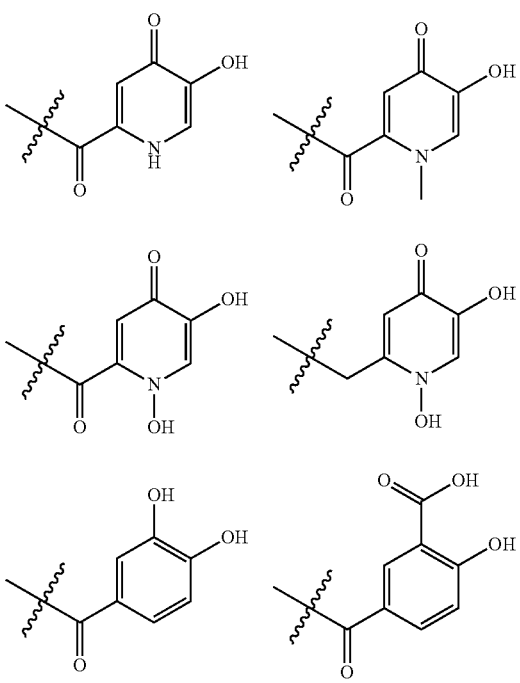

$R_{12}$ and $R_{22}$ are independently hydrogen or $C_1$-$C_2$ alkyl; and
m and n are independently an integer of 1 to 6 or an in vivo hydrolysable ester thereof, an in vivo hydrolysable phosphate ester thereof, an isomer thereof, or a pharmaceutically acceptable salt thereof.

2. The cephalosporin derivative of claim 1, which is represented by Chemical Formula 2:

[Chemical Formula 2]

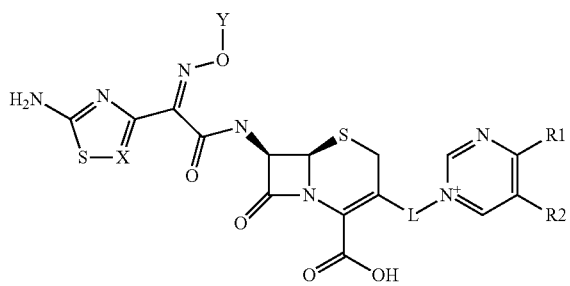

wherein X is CR, N, or C substituted by Cl (C—Cl);
Y is $C_1$-$C_2$ alkyl, $CH(CH_3)CO_2H$, or $C(CH_3)_2CO_2H$;
L is $CH_2$ or $CH=CHCH_2$;
$R_1$ is $NH_2$, $NHR_{11}$ or $NH(CH_2)_mNR_{11}R_{12}$; and
$R_2$ is $NHR_{21}$, $NH(CH_2)_nNR_{21}R_{22}$, or $NHC(=O)(CH_2)_n NR_{21}R_{22}$,
in which R is hydrogen or $C_1$-$C_3$ alkyl;
$R_{11}$ and $R_{21}$ are independently hydrogen, $C_1$-$C_3$ alkyl, or a group selected from the group consisting of:

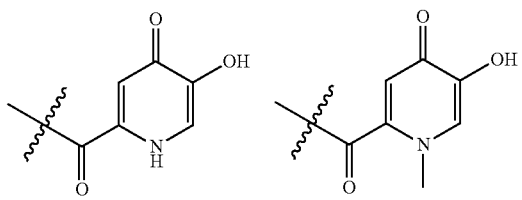

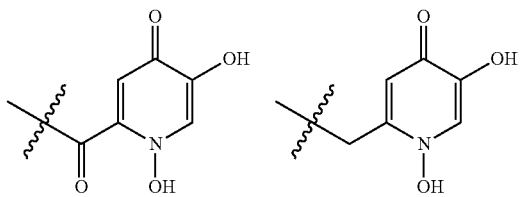

$R_{12}$ and $R_{22}$ are independently hydrogen or $C_1$-$C_2$ alkyl; and
m and n are independently an integer of 1 to 6 or an in vivo hydrolysable ester thereof, an in vivo hydrolysable phosphate ester thereof, an isomer thereof, or a pharmaceutically acceptable salt thereof.

3. The cephalosporin derivative of claim 2,
wherein X is CR, N, or C substituted by Cl (C—Cl);
Y is $CH(CH_3)CO_2H$ or $C(CH_3)_2CO_2H$;
L is $CH_2$ or $CH=CHCH_2$;
$R_1$ is $NH_2$ or $NH(CH_2)_mNH_2$;
$R_2$ is $NHR_{21}$, $NH(CH_2)_mNR_{21}$, or $NHC(=O)(CH_2)_n NR_{21}$; and
$R_3$ is hydrogen,
in which R is hydrogen or $C_1$-$C_3$ alkyl;
$R_{21}$ is a group selected from the group consisting of:

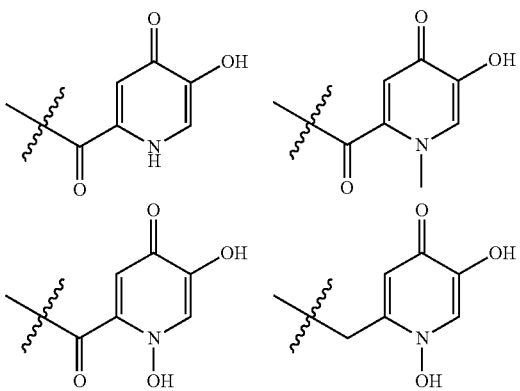

and
m and n are independently an integer of 1 to 6 or an in vivo hydrolysable ester thereof, an in vivo hydrolysable phosphate ester thereof, an isomer thereof, or a pharmaceutically acceptable salt thereof.

4. The cephalosporin derivative of claim 1, which is represented by one of the following chemical formulas:

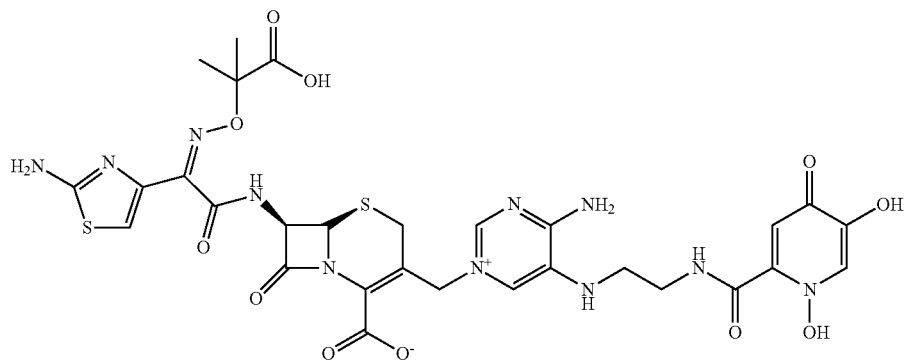

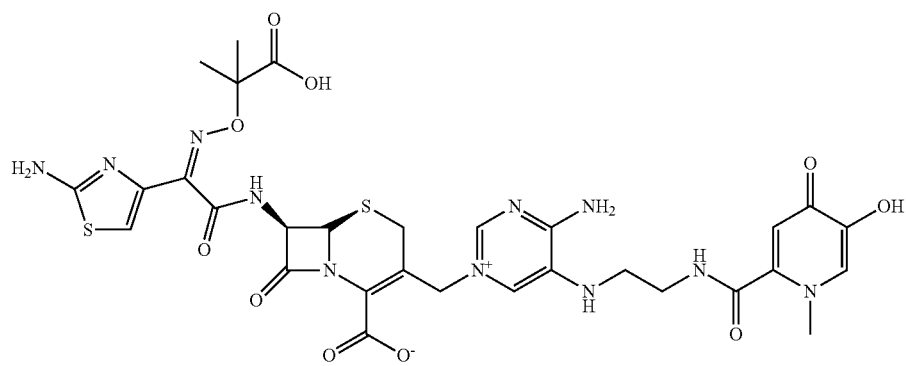
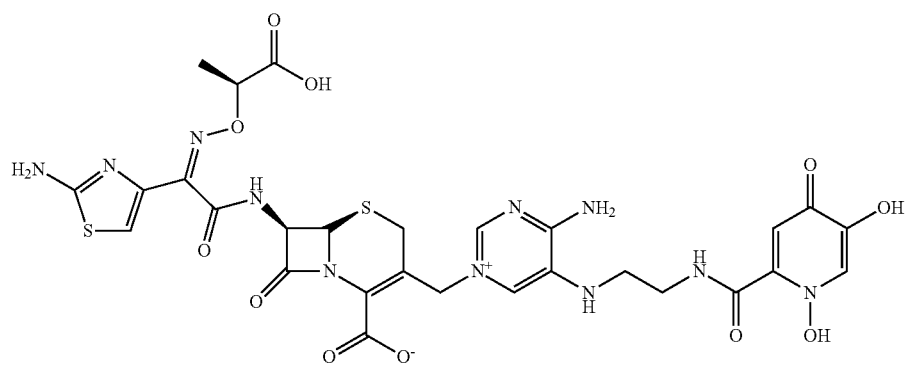
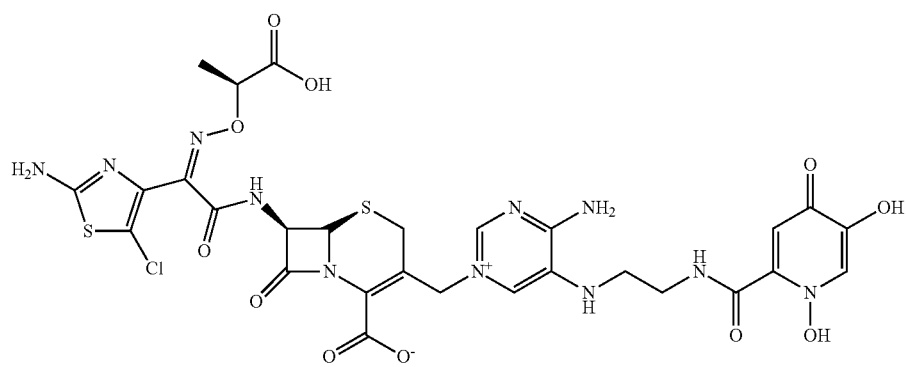
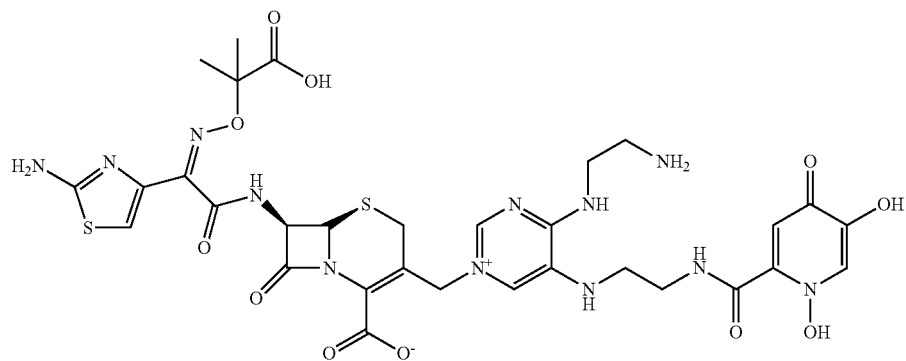

-continued
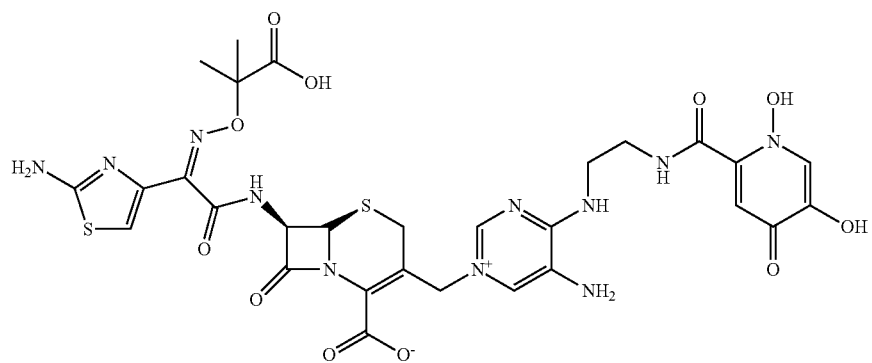
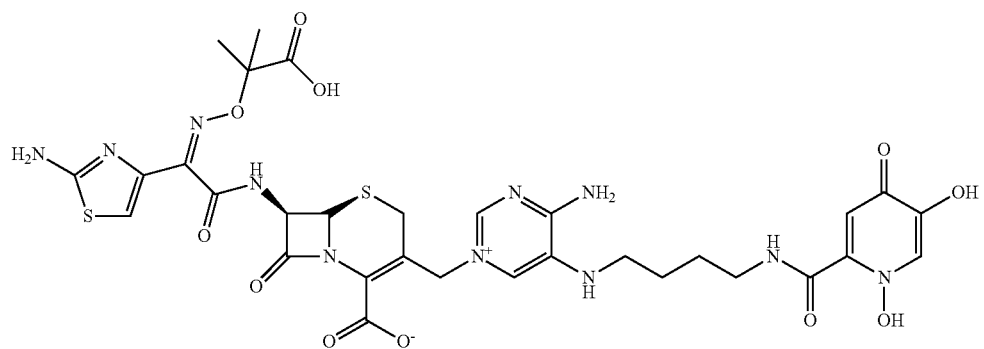
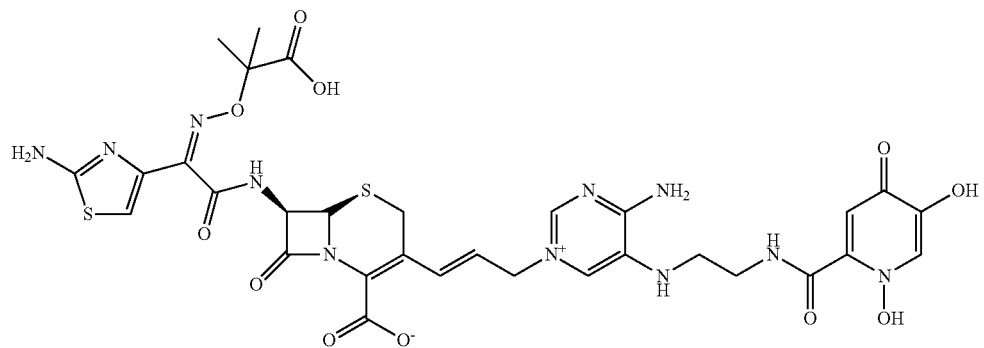
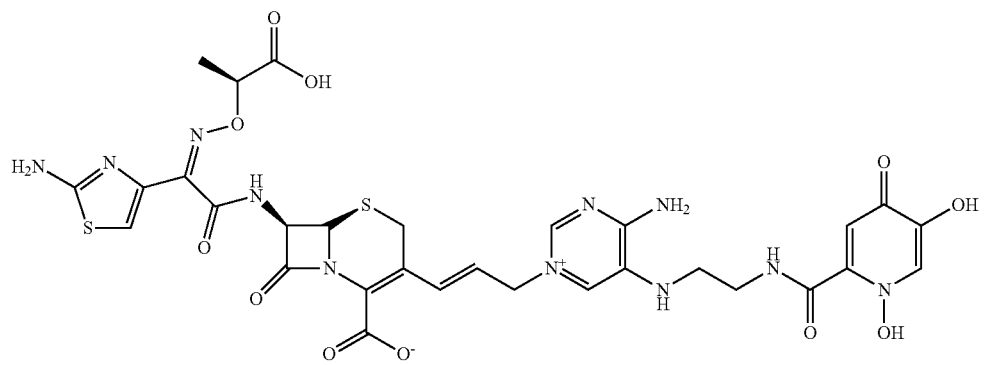

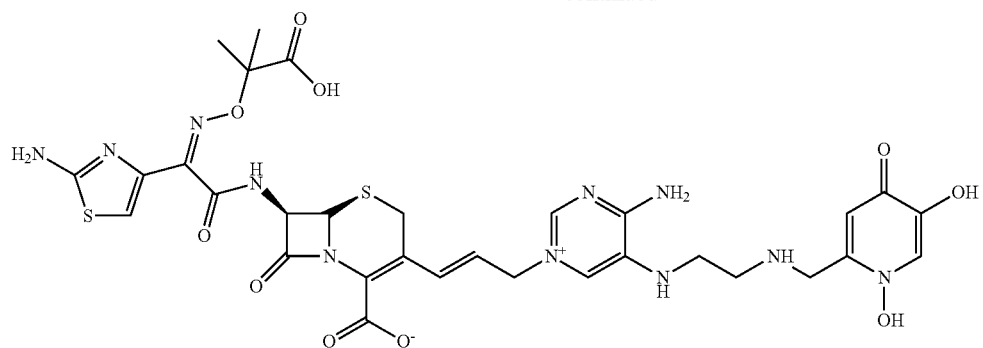
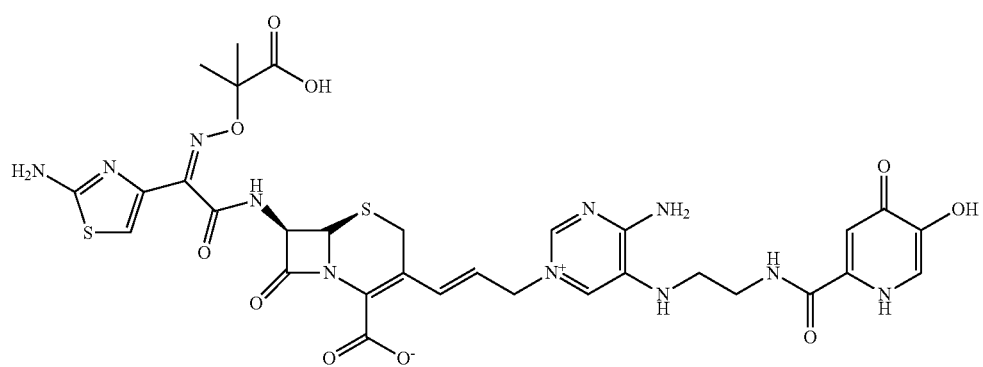
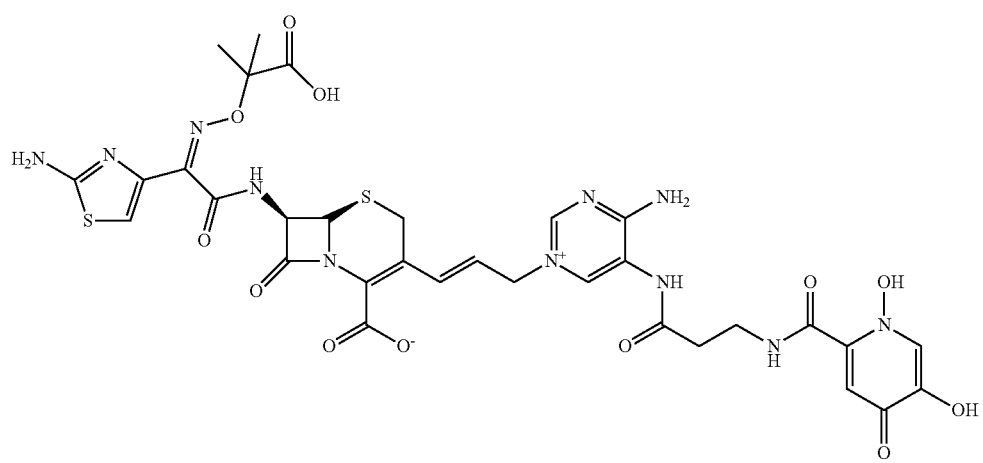
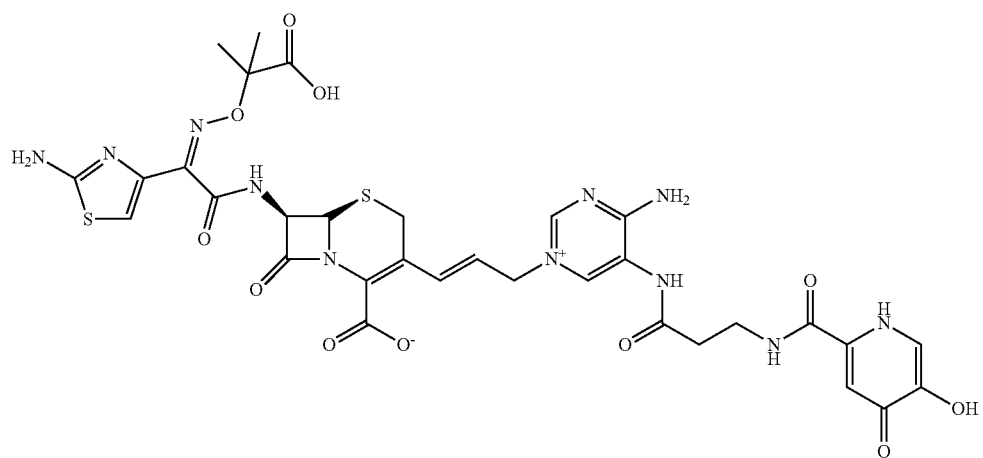

-continued
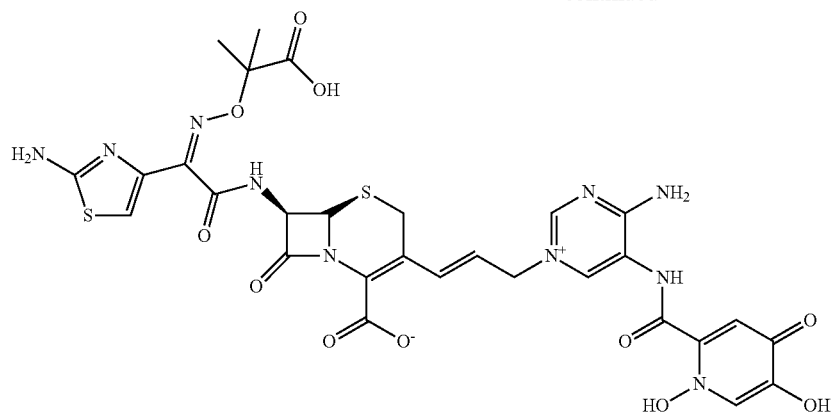
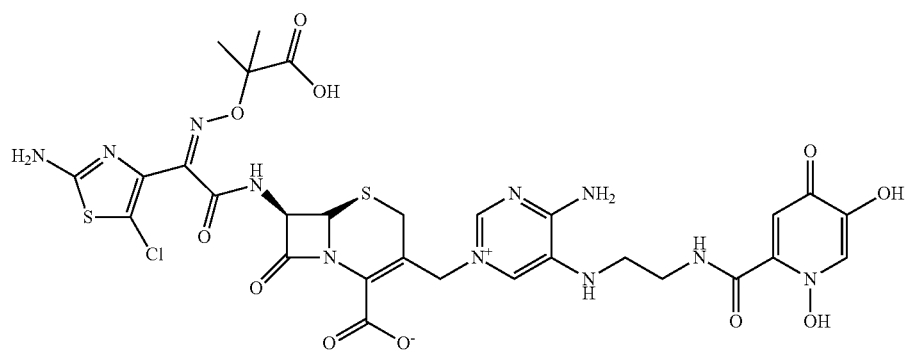
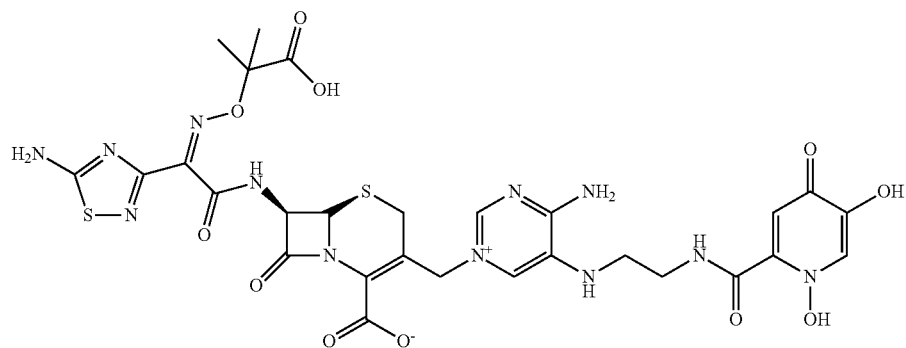
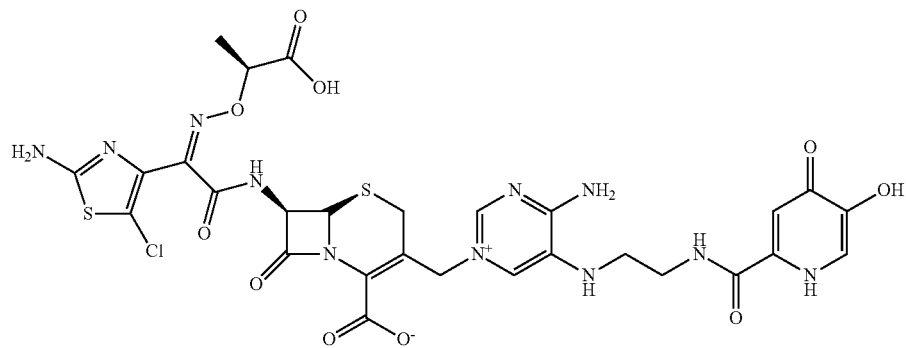

-continued
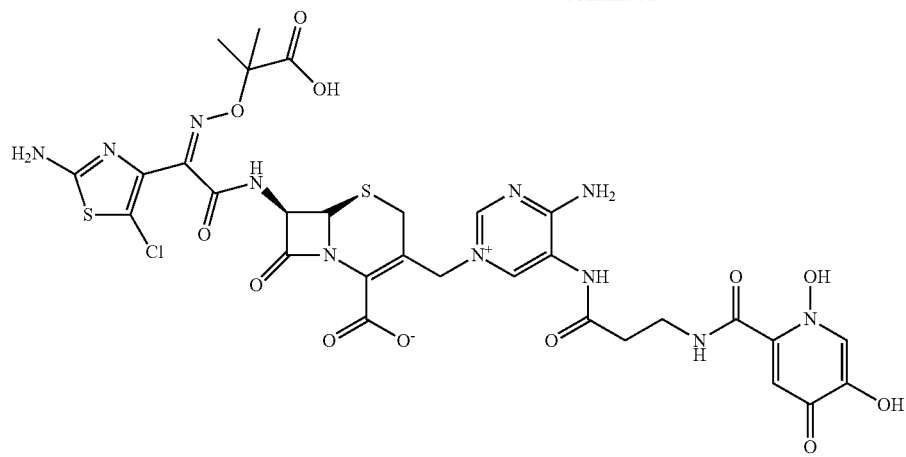
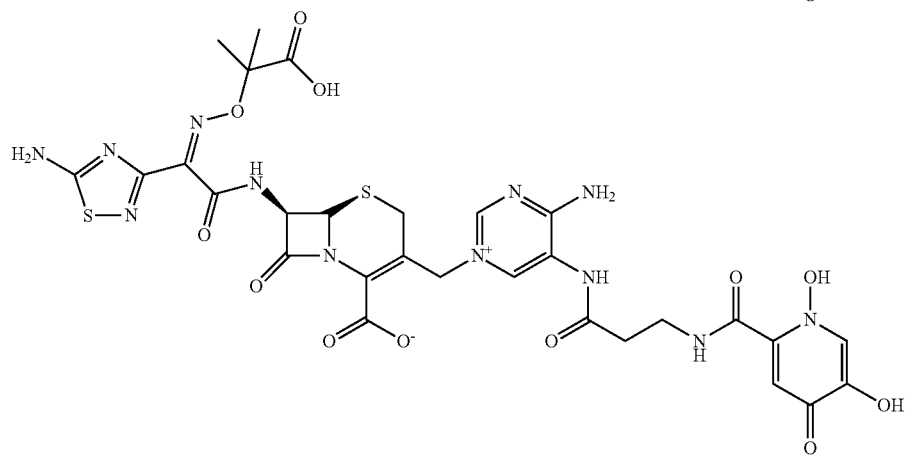
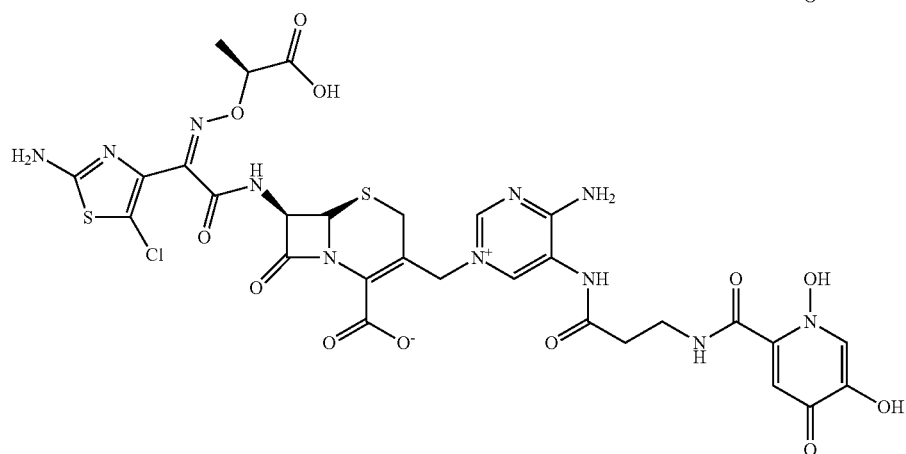
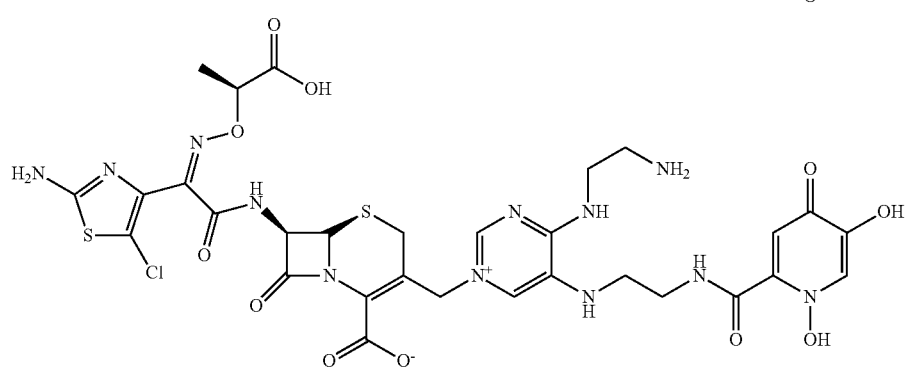

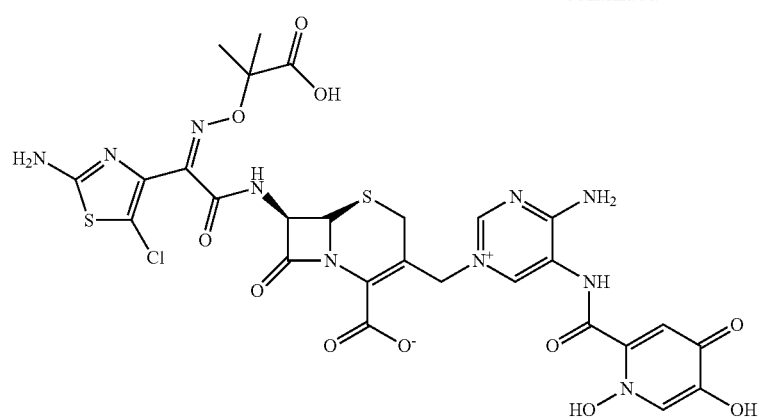
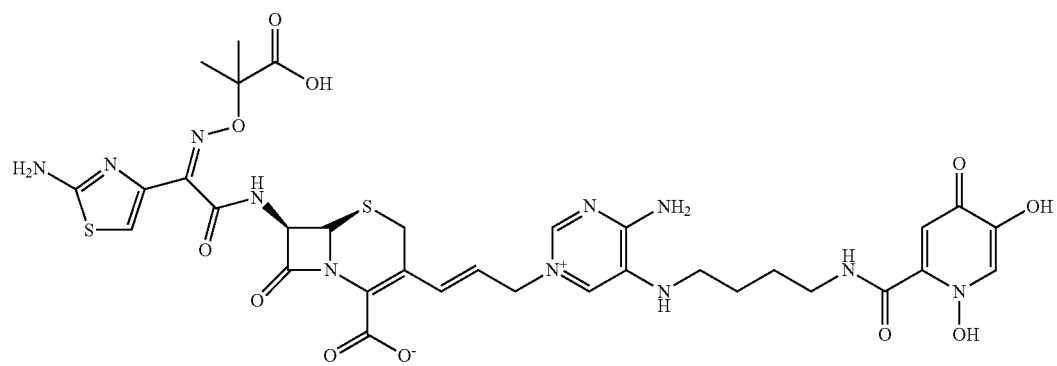
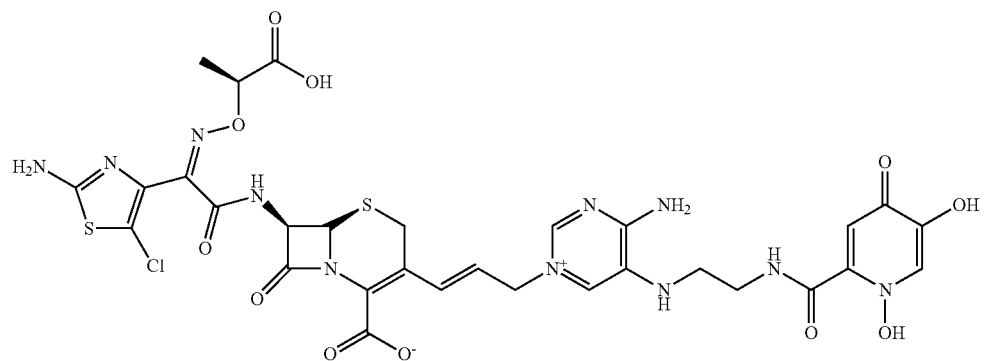
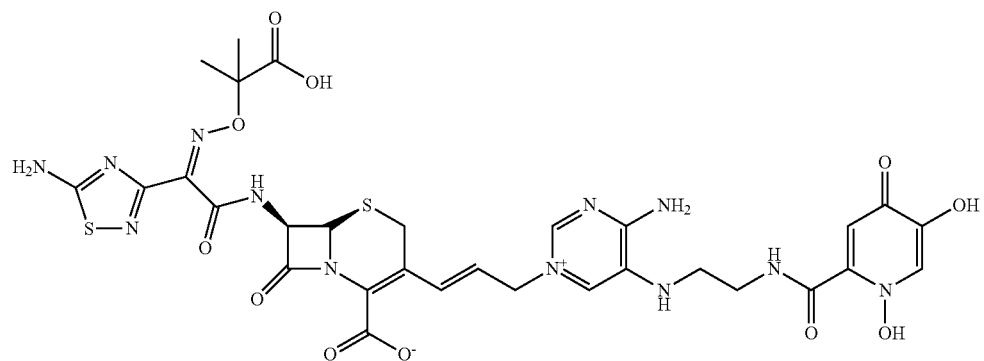

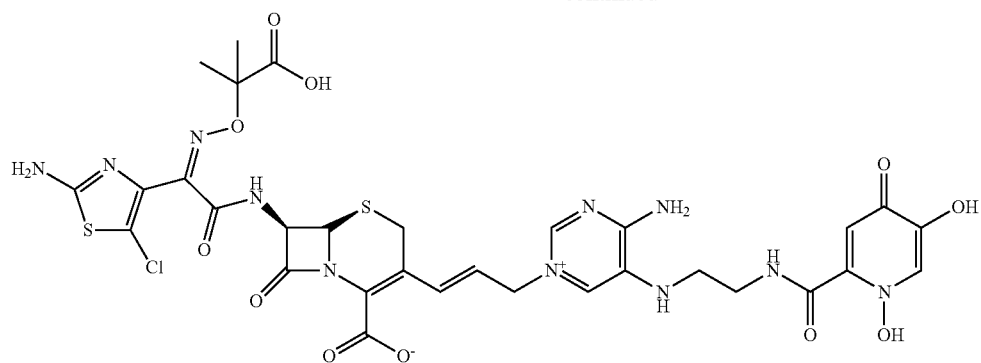
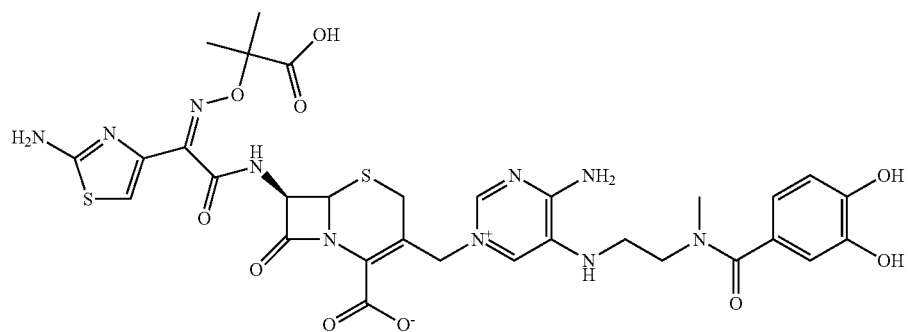
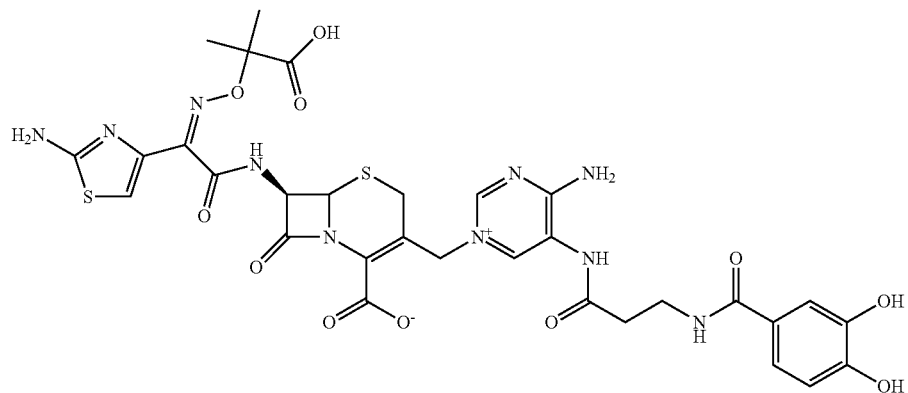
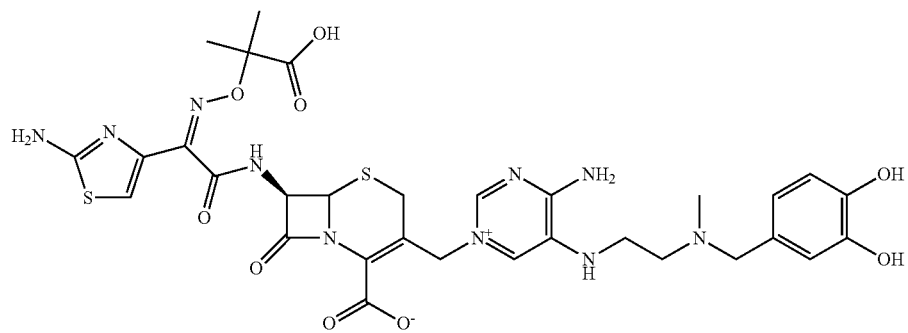

-continued
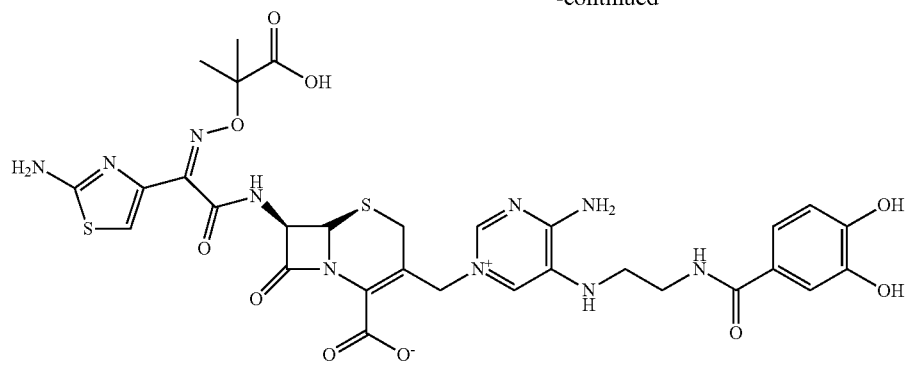
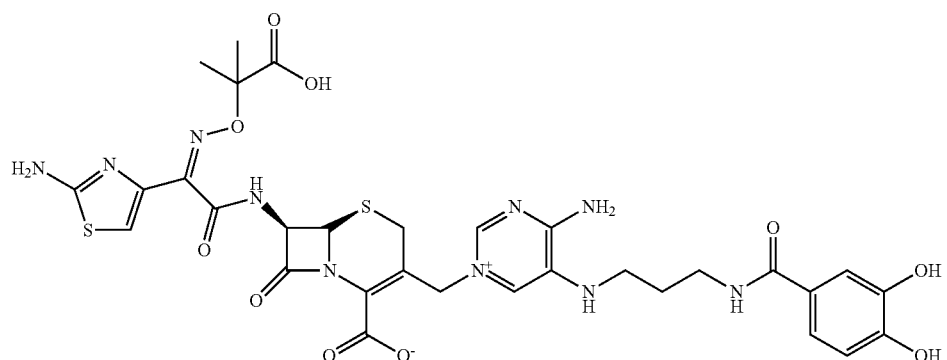
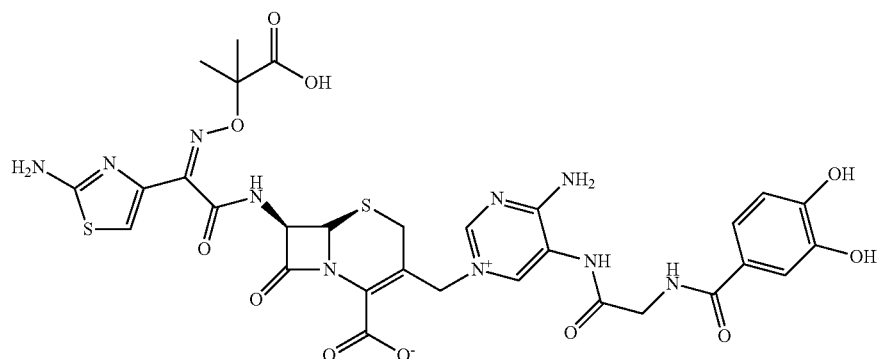
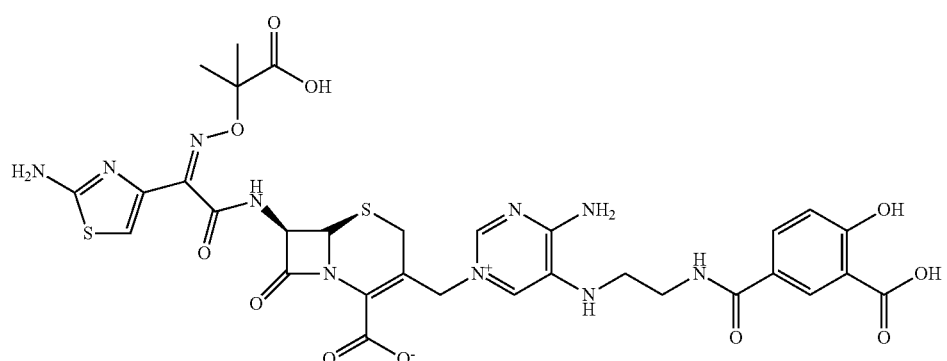

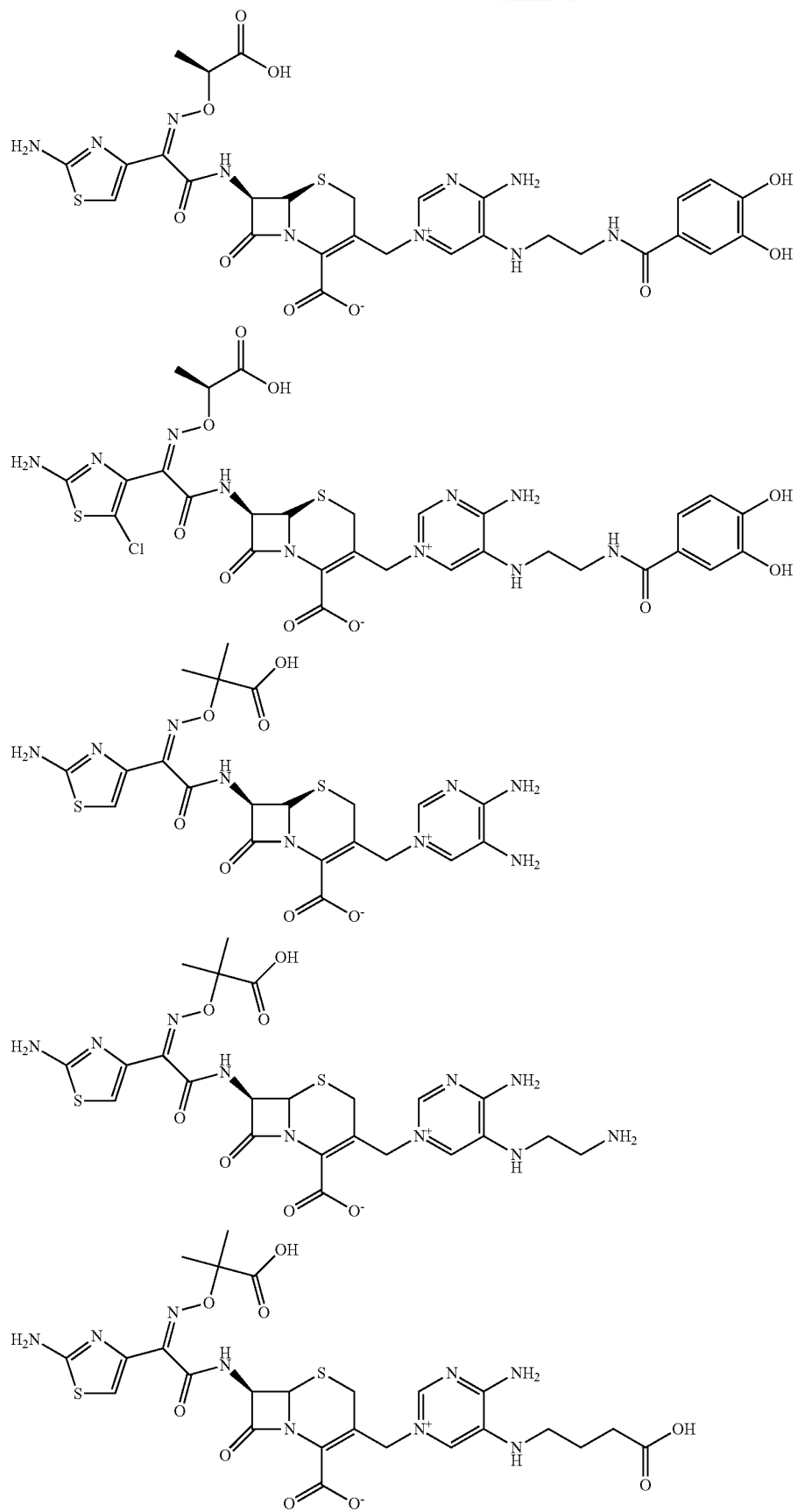

-continued
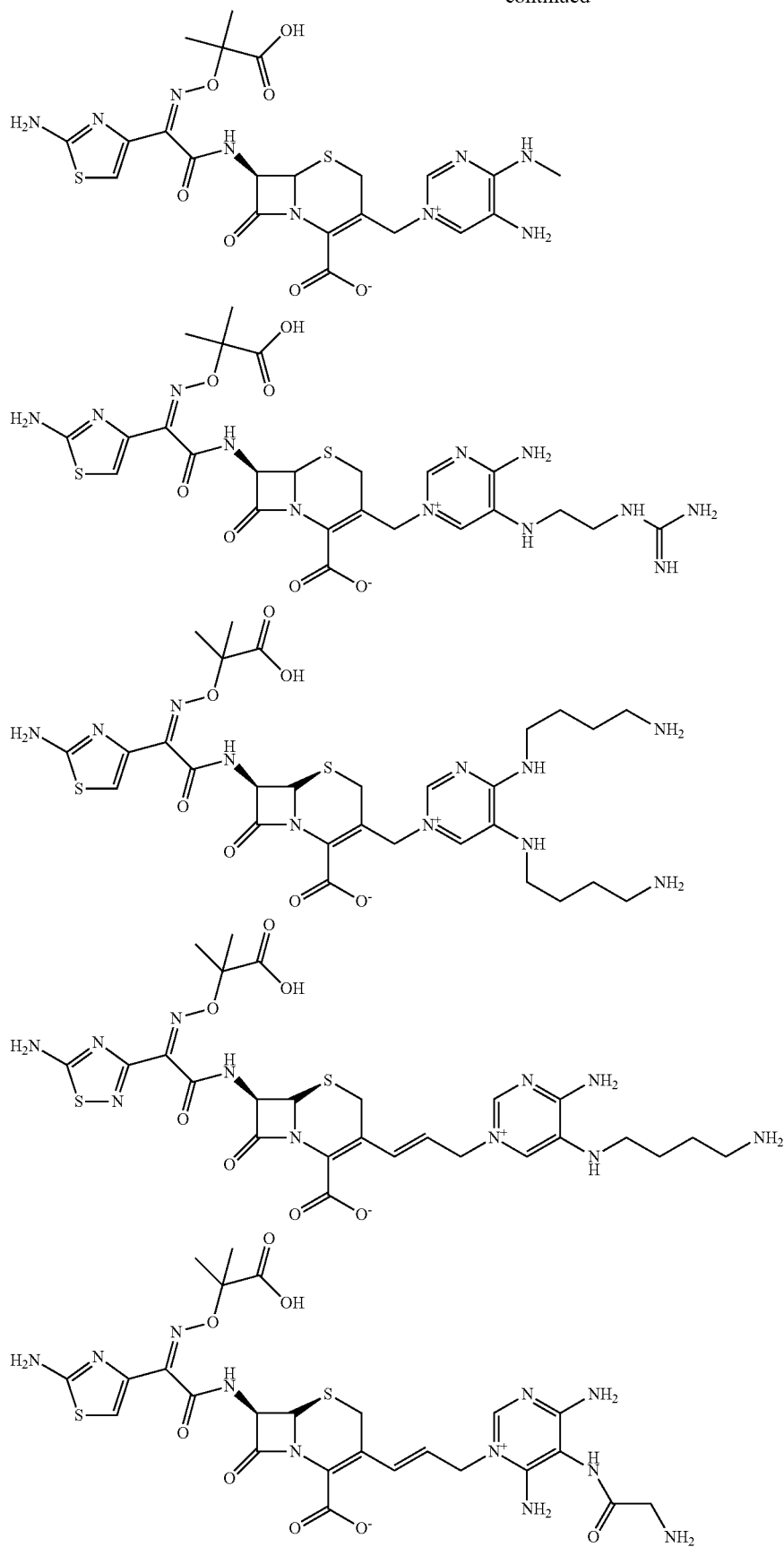

-continued
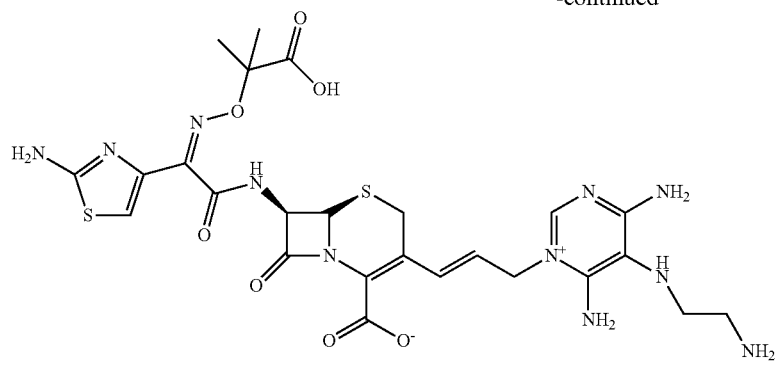
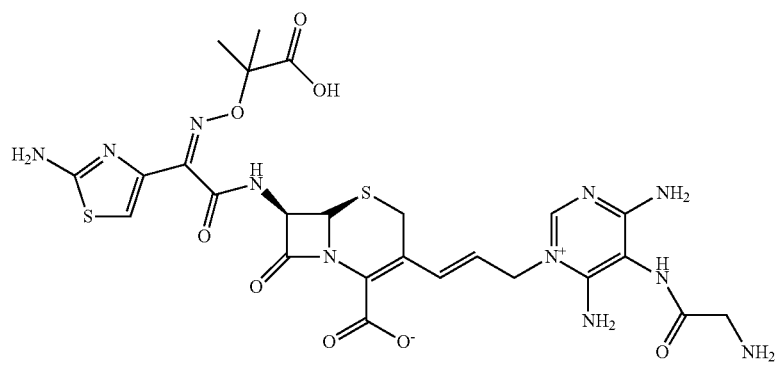
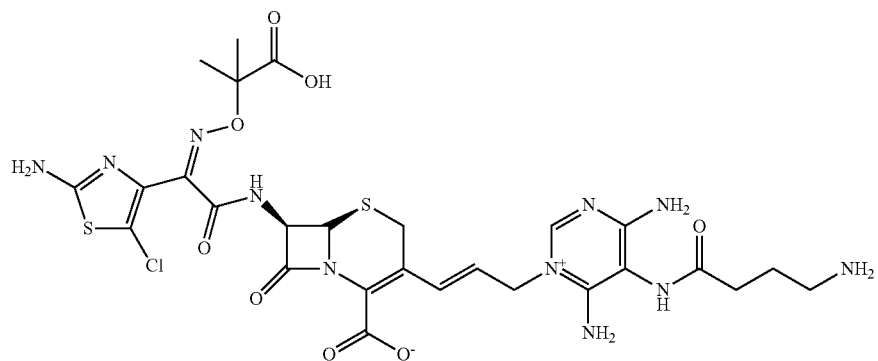
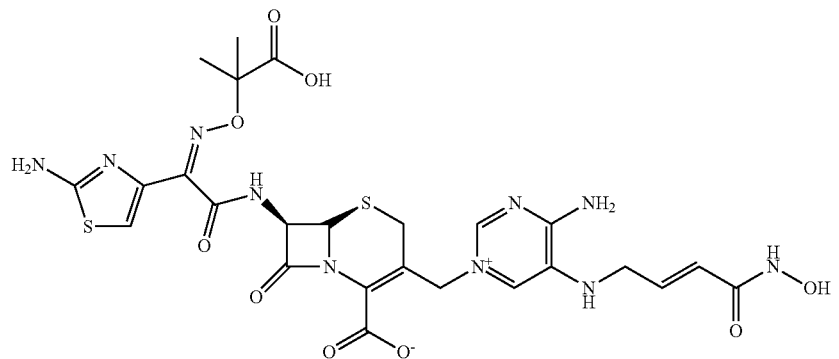

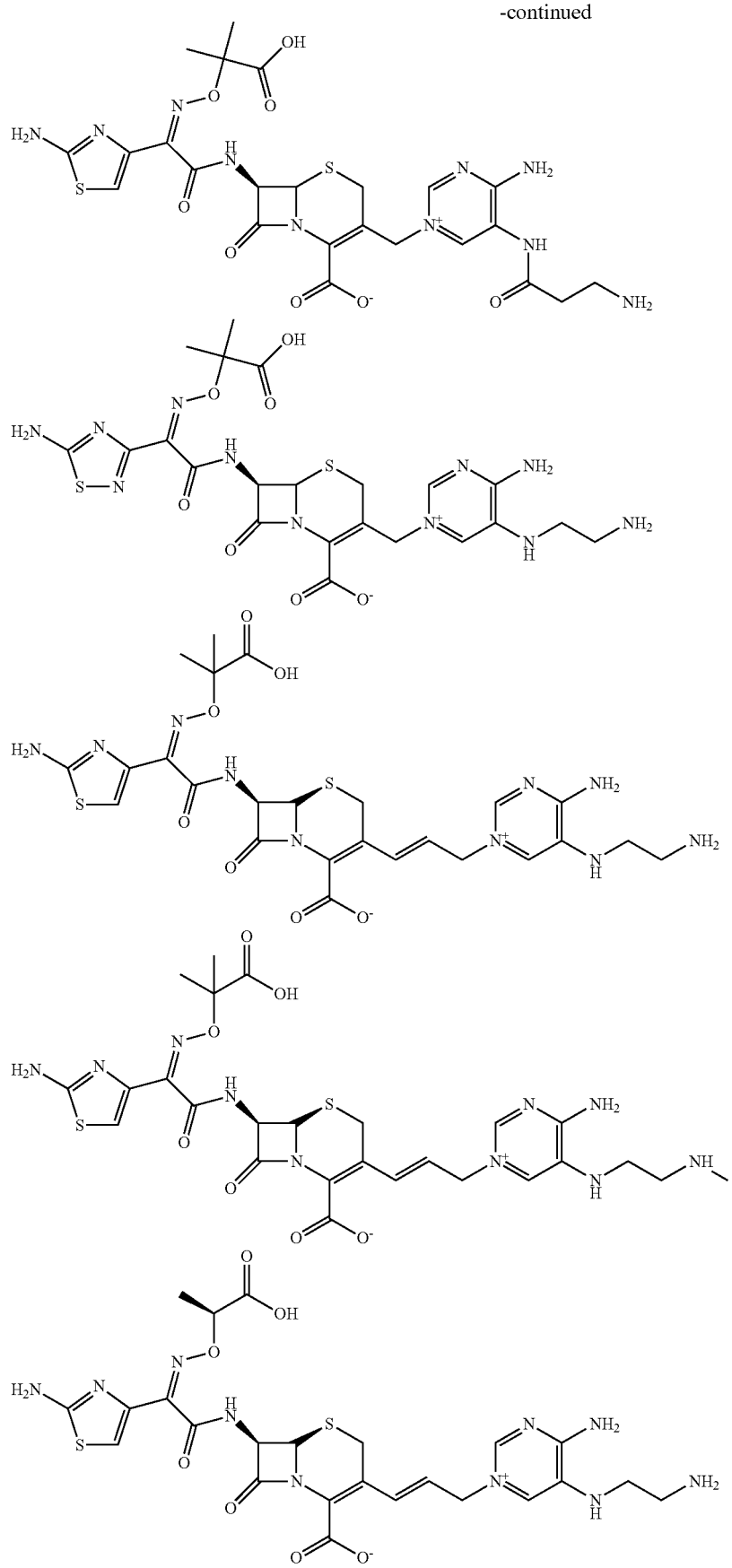

-continued
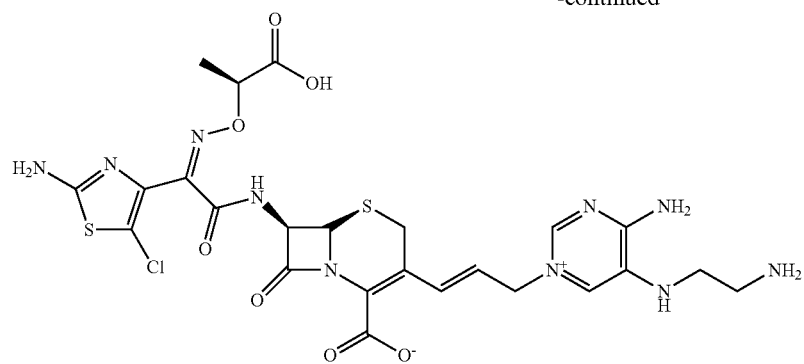
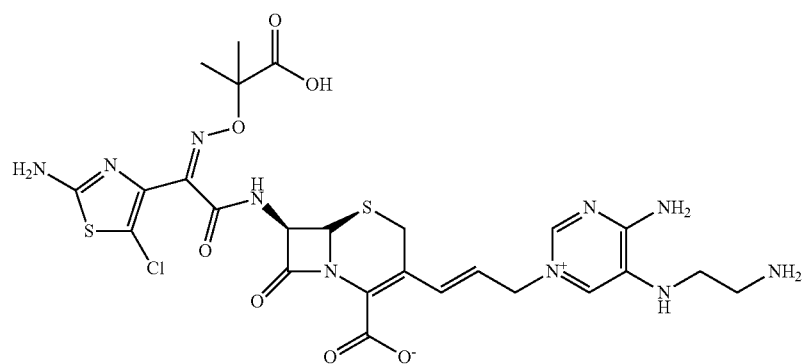
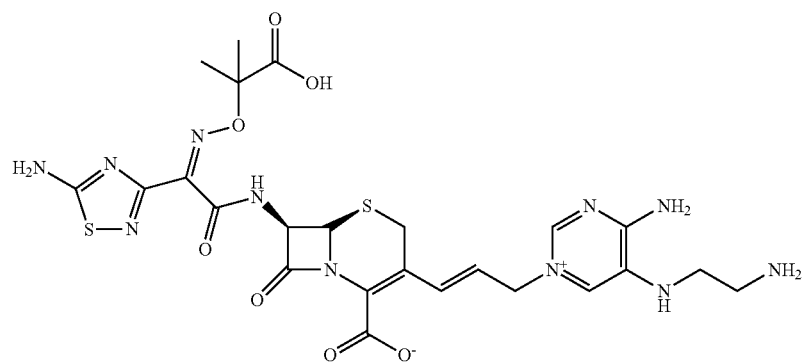
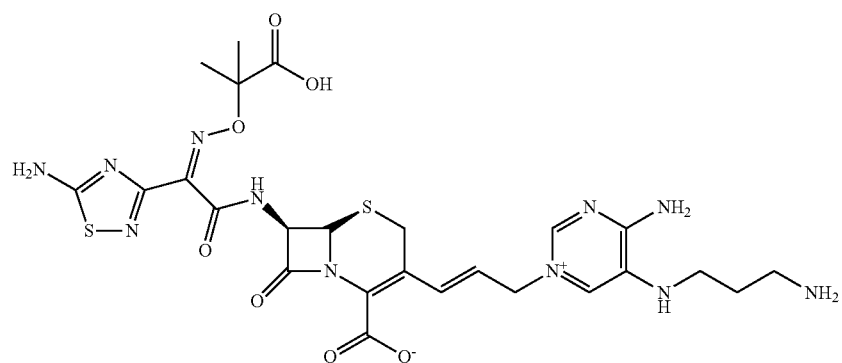

-continued
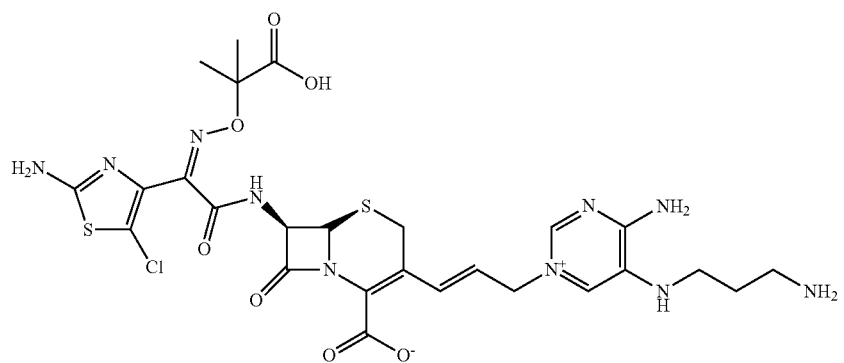
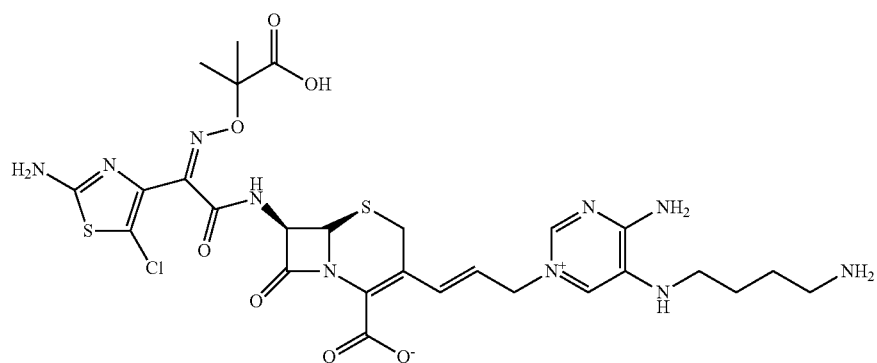
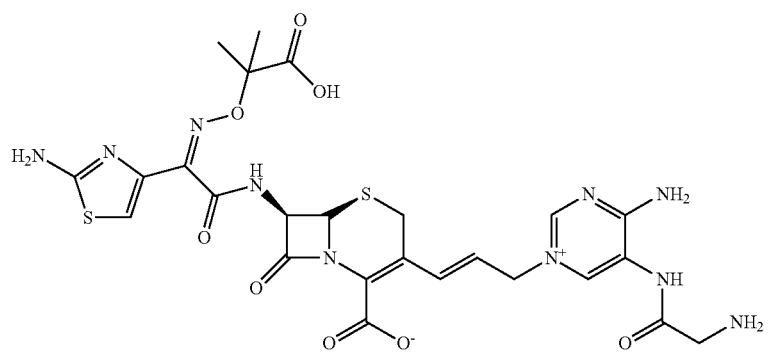
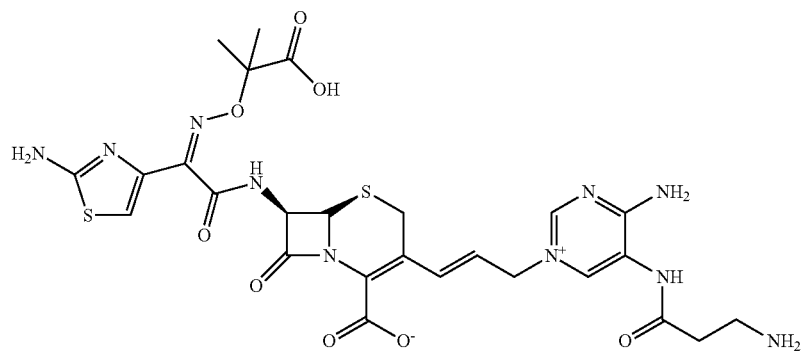

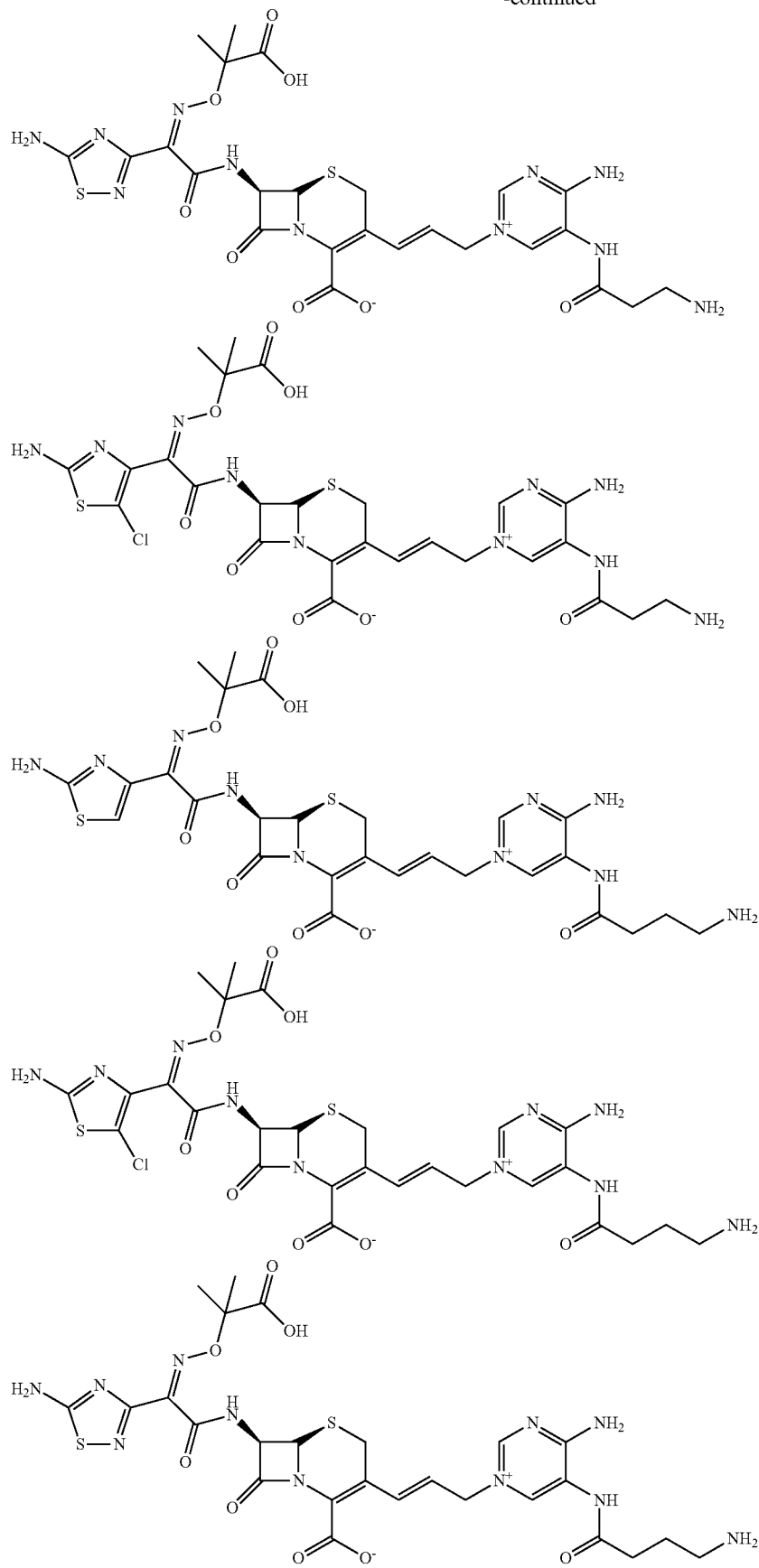

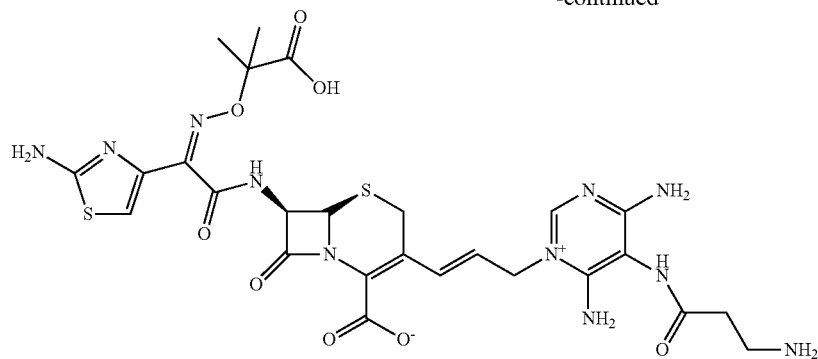
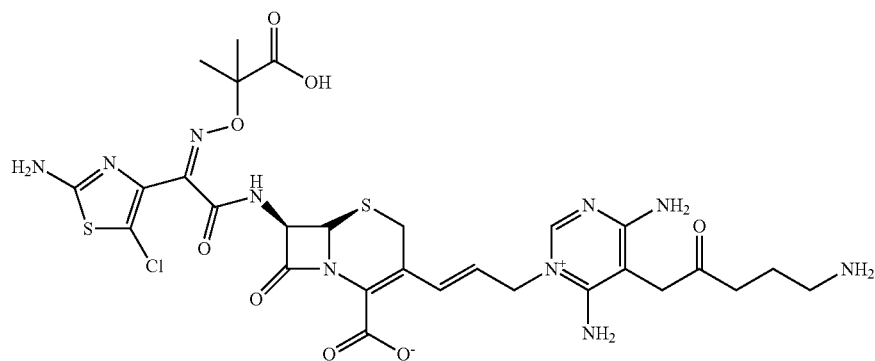
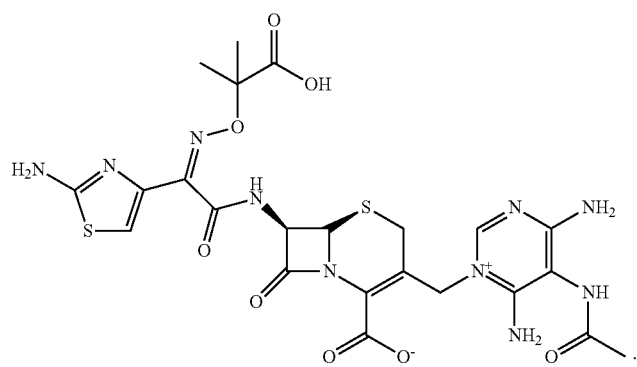
5. The cephalosporin derivative of claim 1, which is represented by one of the following chemical formulas, an in vivo hydrolysable ester thereof, an in vivo hydrolysable phosphate ester thereof, an isomer thereof, or a pharmaceutically acceptable salt thereof:
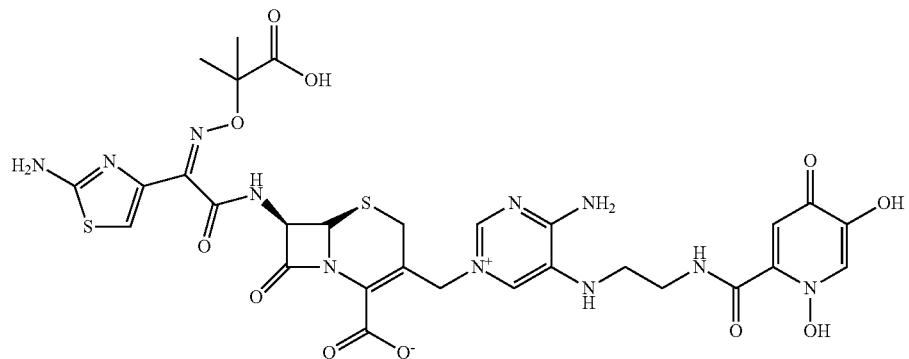

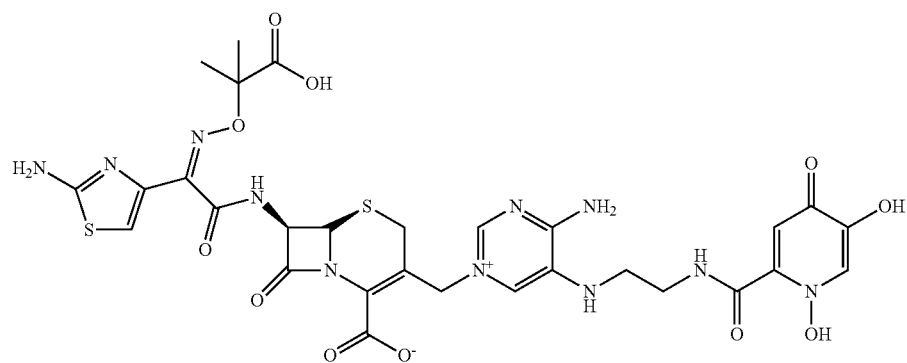
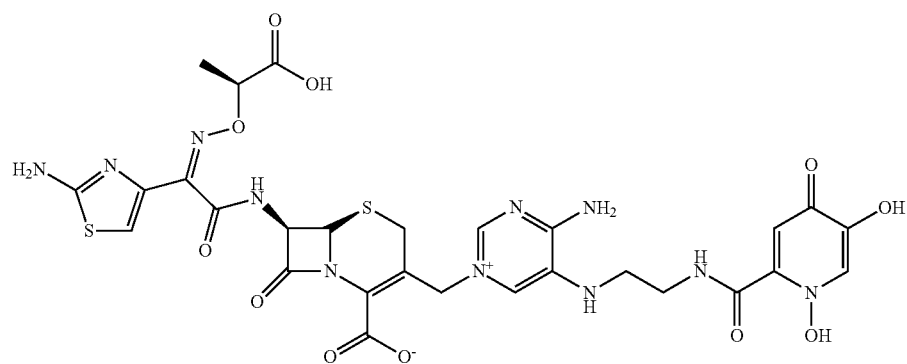
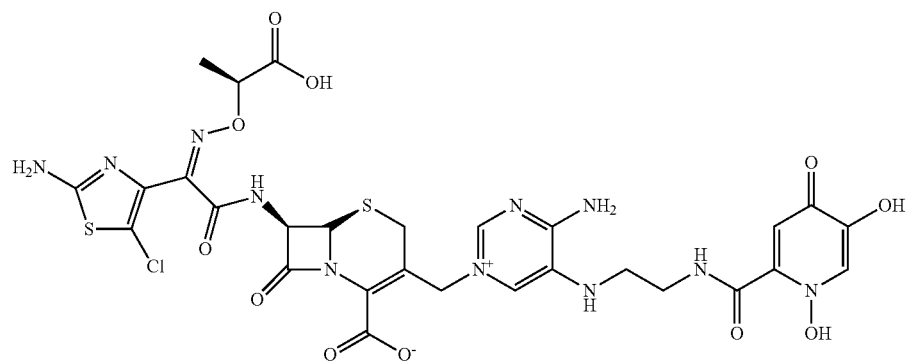
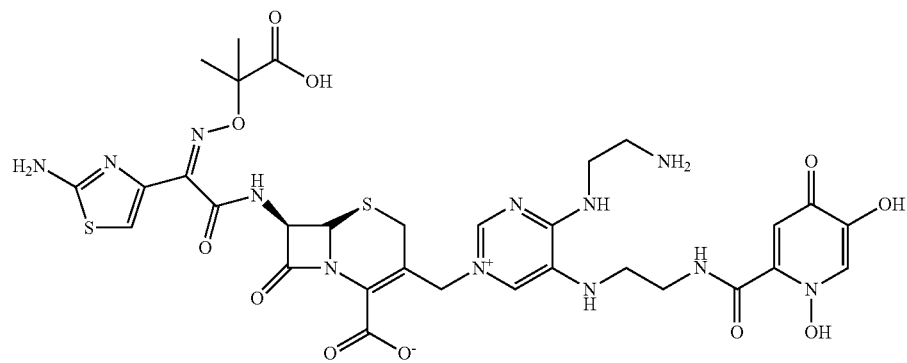

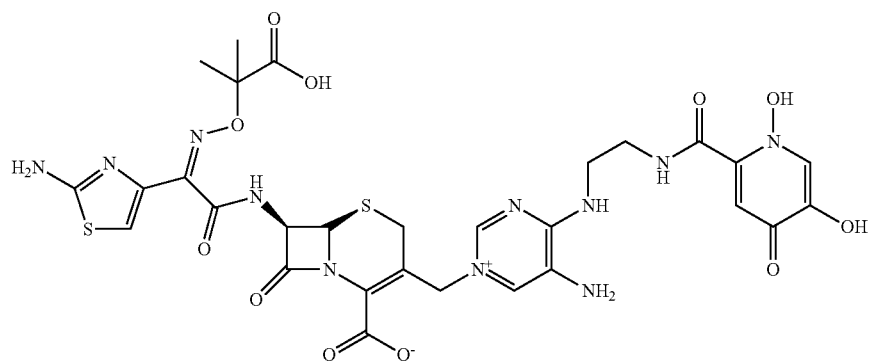
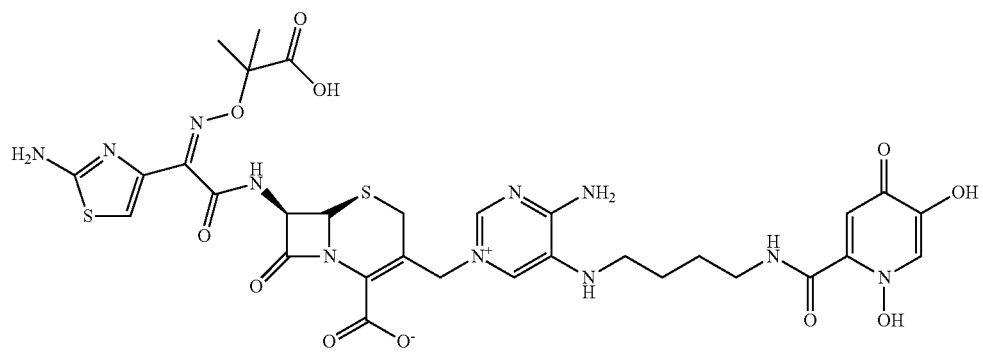
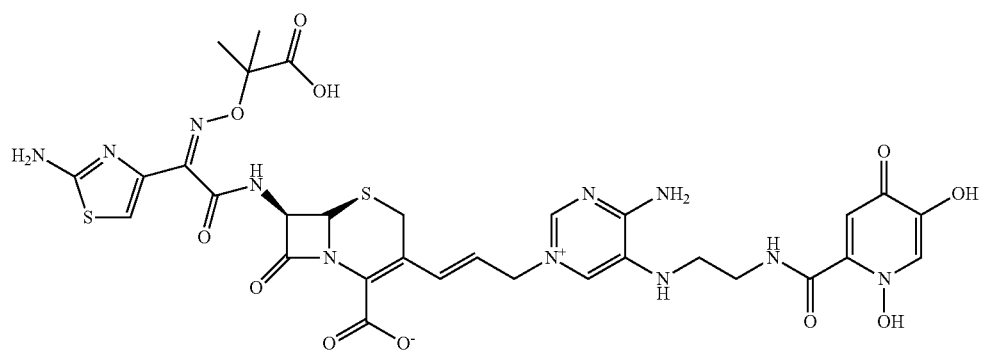
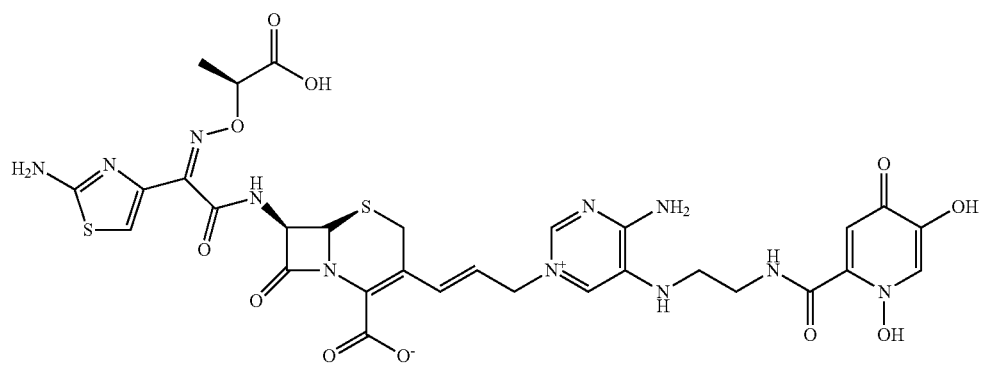

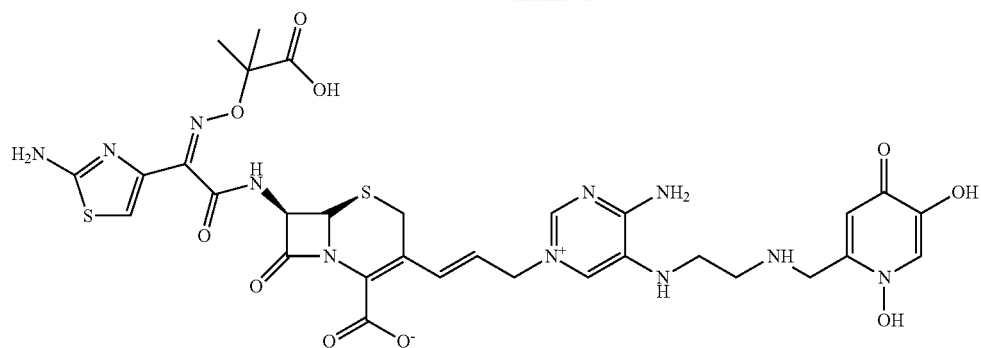
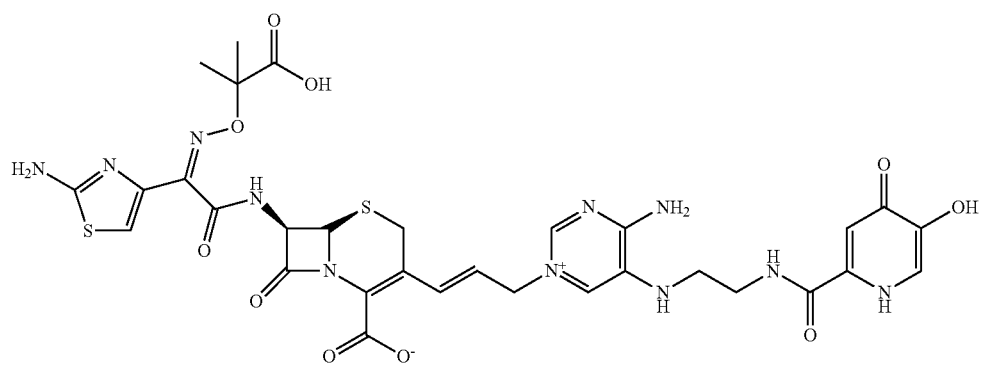
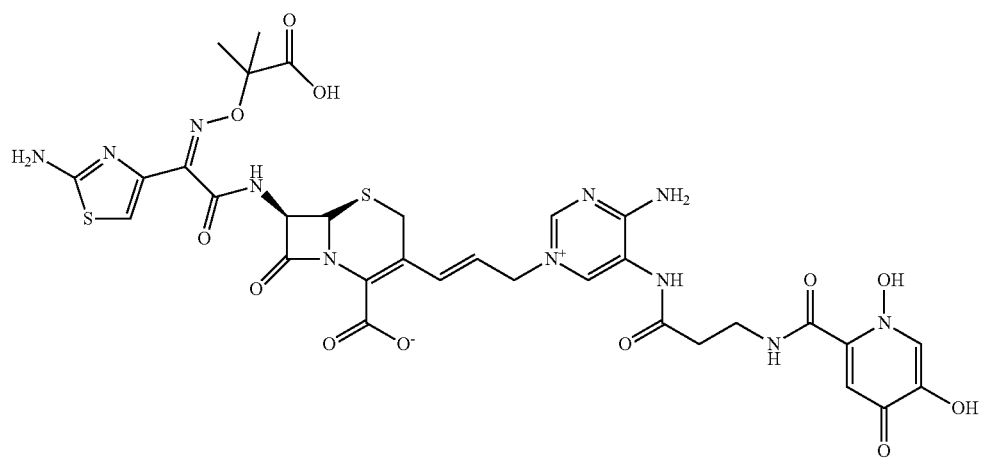
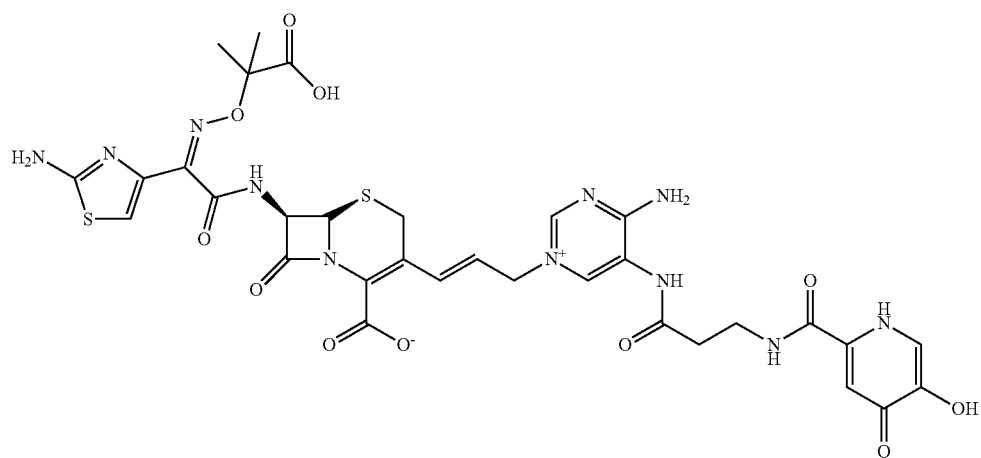

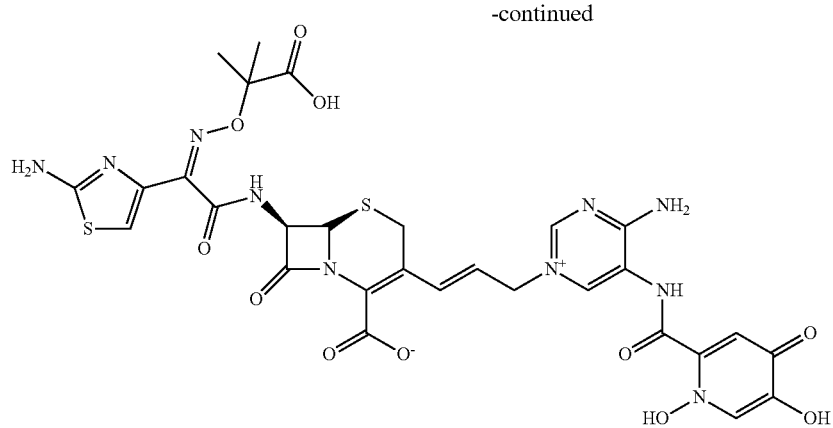
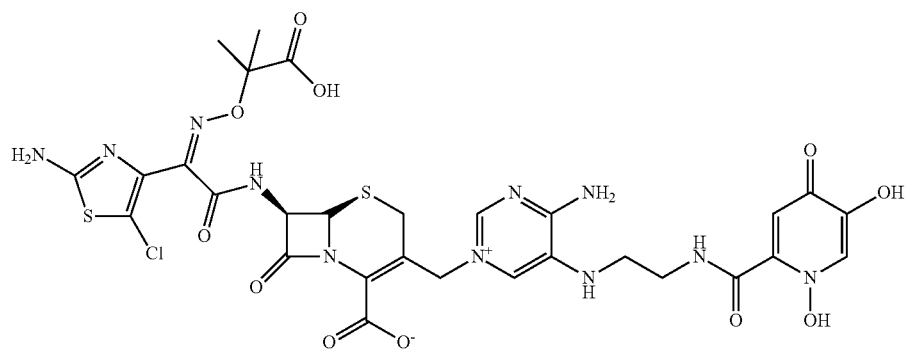
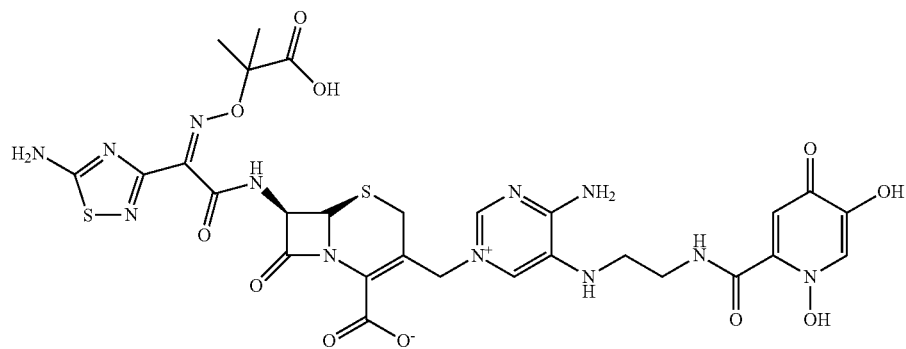
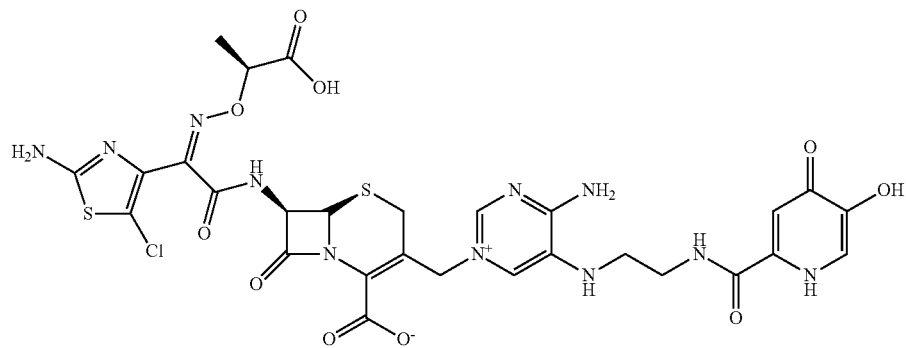

-continued
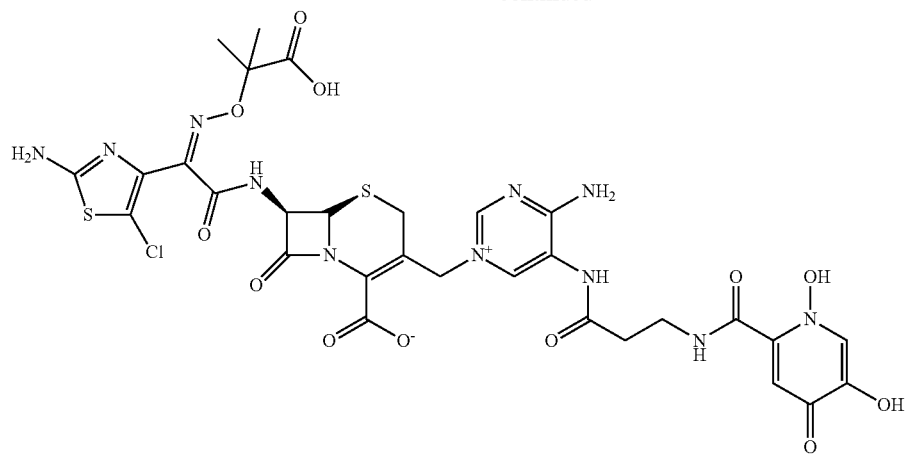
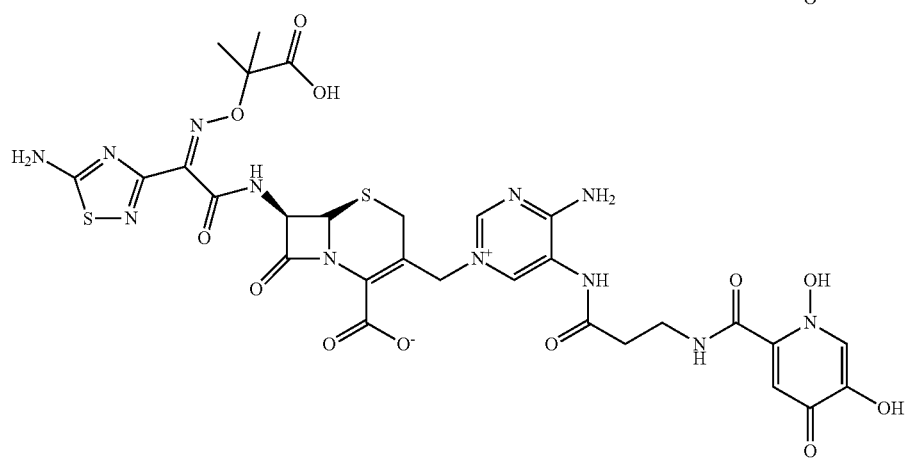
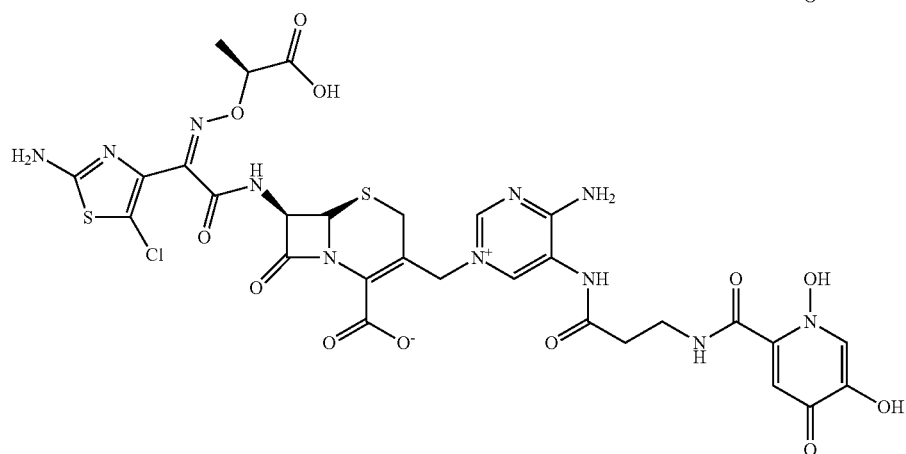
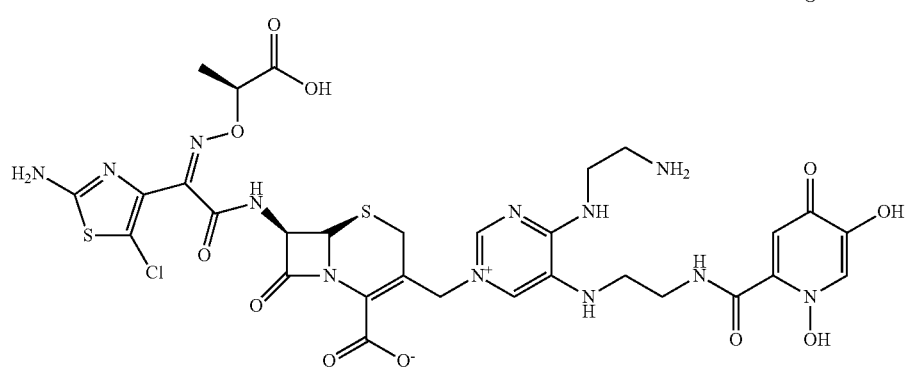

-continued
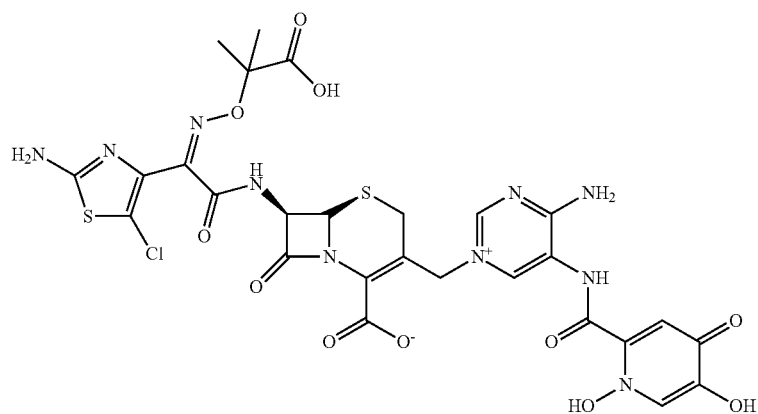
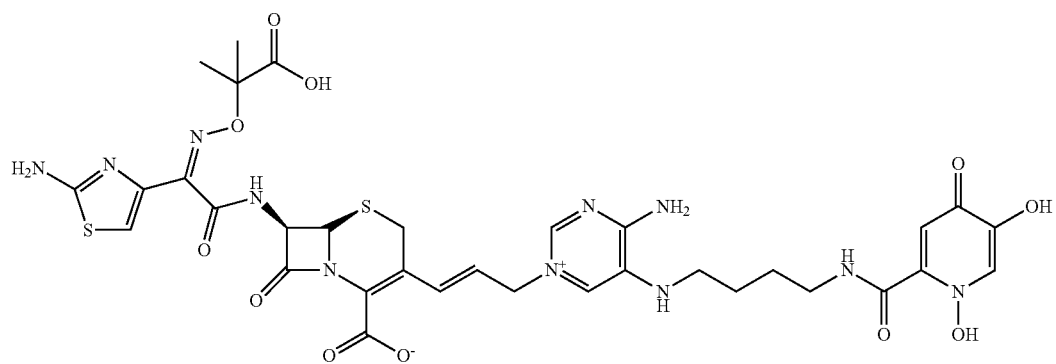
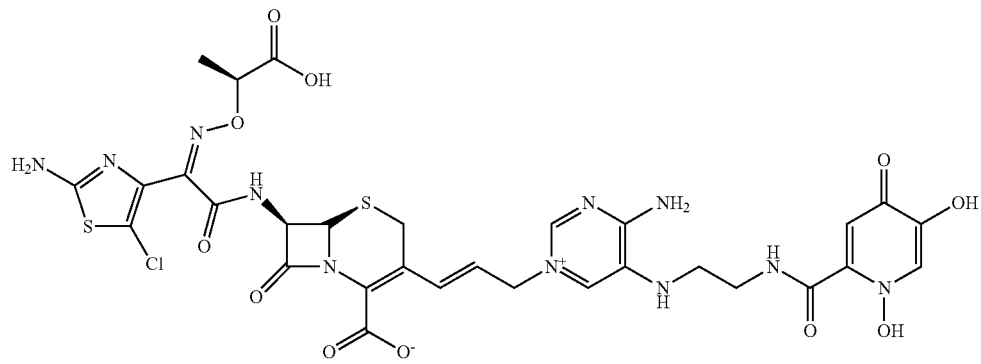
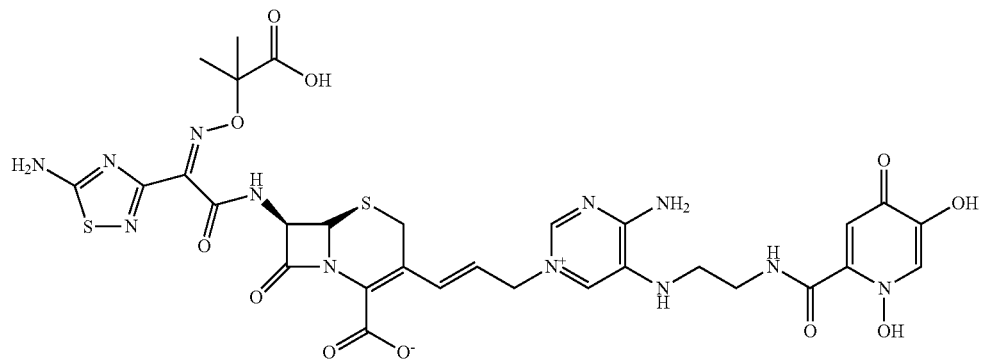

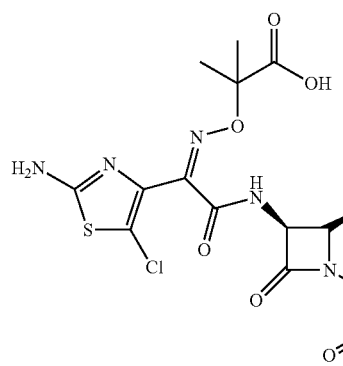

6. A pharmaceutical composition comprising the cephalosporin derivative according to claim 1, an in vivo hydrolysable ester thereof, an in vivo hydrolysable phosphate ester thereof, an isomer thereof, or a pharmaceutically acceptable salt thereof; and a pharmaceutically acceptable carrier, diluent, adjuvant, or any combination thereof, as an effective ingredient.

7. A pharmaceutical composition comprising the cephalosporin derivative according to claim 2, an in vivo hydrolysable ester thereof, an in vivo hydrolysable phosphate ester thereof, an isomer thereof, or a pharmaceutically acceptable salt thereof; and a pharmaceutically acceptable carrier, diluent, adjuvant, or any combination thereof, as an effective ingredient.

8. A pharmaceutical composition comprising the cephalosporin derivative according to claim 3, an in vivo hydrolysable ester thereof, an in vivo hydrolysable phosphate ester thereof, an isomer thereof, or a pharmaceutically acceptable salt thereof; and a pharmaceutically acceptable carrier, diluent, adjuvant, or any combination thereof, as an effective ingredient.

9. A pharmaceutical composition comprising the cephalosporin derivative according to claim 4, an in vivo hydrolysable ester thereof, an in vivo hydrolysable phosphate ester thereof, an isomer thereof, or a pharmaceutically acceptable salt thereof; and a pharmaceutically acceptable carrier, diluent, adjuvant, or any combination thereof, as an effective ingredient.

10. A pharmaceutical composition comprising the cephalosporin derivative according to claim 5, an in vivo hydrolysable ester thereof, an in vivo hydrolysable phosphate ester thereof, an isomer thereof, or a pharmaceutically acceptable salt thereof; and a pharmaceutically acceptable carrier, diluent, adjuvant, or any combination thereof, as an effective ingredient.

11. A method of treating a bacterial infection, comprising applying a pharmaceutically effective amount of the novel cephalosporin derivative of claim 1, an in vivo hydrolysable ester thereof, an in vivo hydrolysable phosphate ester thereof, an isomer thereof, or a pharmaceutically acceptable salt thereof, to a subject in need thereof.

12. A method of treating a bacterial infection, comprising applying a pharmaceutically effective amount of the cephalosporin derivative of claim 2, an in vivo hydrolysable ester thereof, an in vivo hydrolysable phosphate ester thereof, an isomer thereof, or a pharmaceutically acceptable salt thereof, to a subject in need thereof.

13. A method of treating a bacterial infection, comprising applying a pharmaceutically effective amount of the cephalosporin derivative of claim 3, an in vivo hydrolysable ester thereof, an in vivo hydrolysable phosphate ester thereof, an isomer thereof, or a pharmaceutically acceptable salt thereof, to a subject in need thereof.

14. A method of treating a bacterial infection, comprising applying a pharmaceutically effective amount of the cephalosporin derivative of claim 4, an in vivo hydrolysable ester thereof, an in vivo hydrolysable phosphate ester thereof, an isomer thereof, or a pharmaceutically acceptable salt thereof, to a subject in need thereof.

15. A method of treating a bacterial infection, comprising applying a pharmaceutically effective amount of the novel cephalosporin derivative of claim 5, an in vivo hydrolysable ester thereof, an in vivo hydrolysable phosphate ester thereof, an isomer thereof, or a pharmaceutically acceptable salt thereof, to a subject in need thereof.

16. The method of claim 11, wherein the bacterial infection results from a Gram-positive bacterium.

17. The method of claim 11, wherein the bacterial infection results from a Gram-negative bacterium.

18. The method of claim 11, wherein the Gram-positive bacterium is selected from the group consisting of *Staphylococcus, Enterococcus, Streptococcus* and acid-fast bacteria.

19. The method of claim 11, wherein the Gram-negative bacterium is selected from the group consisting of *Pseudomonas aeruginosa, Acinetobacter baumannii*, and *Klebsiella pneumoniae*.

* * * * *